US011066663B2

(12) United States Patent
Dean et al.

(10) Patent No.: US 11,066,663 B2
(45) Date of Patent: Jul. 20, 2021

(54) MULTIPLEXED DETERMINISTIC ASSEMBLY OF DNA LIBRARIES

(71) Applicant: Zymergen Inc., Emeryville, CA (US)

(72) Inventors: Erik Jedediah Dean, Lafayette, CA (US); Kedar Patel, Fremont, CA (US); Aaron Miller, Berkeley, CA (US); Kunal Mehta, Oakland, CA (US); Philip Weyman, Alameda, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 16/669,940

(22) Filed: Oct. 31, 2019

(65) Prior Publication Data

US 2020/0131508 A1 Apr. 30, 2020

Related U.S. Application Data

(60) Provisional application No. 62/753,254, filed on Oct. 31, 2018.

(51) Int. Cl.
*C12N 15/10* (2006.01)
*C40B 50/06* (2006.01)

(52) U.S. Cl.
CPC ..... *C12N 15/1068* (2013.01); *C12N 15/1093* (2013.01); *C40B 50/06* (2013.01)

(58) Field of Classification Search
CPC .. C12N 15/1068; C12N 15/1093; C40B 50/08
See application file for complete search history.

(56) References Cited

U.S. PATENT DOCUMENTS

| | | | |
|---|---|---|---|
| 5,605,793 A | 2/1997 | Stemmer | |
| 5,837,458 A | 11/1998 | Minshull et al. | |
| 6,221,597 B1 * | 4/2001 | Roberts | C12Q 1/18 435/254.1 |
| 6,368,805 B1 | 4/2002 | Borchert et al. | |
| 7,405,282 B2 * | 7/2008 | Duvick | C07H 19/00 435/320.1 |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,968,999 B2 | 3/2015 | Gibson et al. | |
| 8,993,233 B2 | 3/2015 | Zhang et al. | |
| 8,999,641 B2 | 4/2015 | Zhang et al. | |
| 9,023,649 B2 | 5/2015 | Mali et al. | |
| 9,260,723 B2 | 2/2016 | Mali et al. | |
| 9,580,701 B2 * | 2/2017 | May | C12Q 1/6827 |
| 9,580,719 B2 | 2/2017 | Retallack et al. | |
| 9,637,739 B2 | 5/2017 | Šikšnys et al. | |
| 9,677,090 B2 | 6/2017 | Donohue et al. | |
| 9,688,972 B2 | 6/2017 | May et al. | |
| 9,738,687 B2 | 8/2017 | Guay et al. | |
| 9,745,562 B2 | 8/2017 | Donohue et al. | |
| 9,790,490 B2 | 10/2017 | Zhang et al. | |
| 9,816,081 B1 | 11/2017 | Donohue et al. | |
| 9,822,372 B2 | 11/2017 | Zhang et al. | |
| 9,834,791 B2 | 12/2017 | Zhang et al. | |
| 9,840,713 B2 | 12/2017 | Zhang | |
| 9,896,696 B2 | 2/2018 | Begemann et al. | |
| 9,970,011 B2 | 5/2018 | Duffield et al. | |
| 9,982,279 B1 | 5/2018 | Gill et al. | |
| 10,011,849 B1 * | 7/2018 | Gill | C12N 9/22 |
| 2005/0090010 A1 | 4/2005 | Hayashizaki et al. | |
| 2011/0143399 A1 | 6/2011 | Evans et al. | |
| 2012/0053087 A1 | 3/2012 | Gibson et al. | |
| 2012/0270260 A1 | 10/2012 | Zhao et al. | |
| 2014/0308710 A1 | 1/2014 | Qi et al. | |
| 2014/0068797 A1 | 3/2014 | Doudna et al. | |
| 2015/0133317 A1 | 5/2015 | Robinson et al. | |
| 2015/0240261 A1 | 8/2015 | Siksnys et al. | |
| 2015/0291961 A1 | 10/2015 | Siksnys et al. | |
| 2016/0060671 A1 | 3/2016 | Hsieh et al. | |

(Continued)

FOREIGN PATENT DOCUMENTS

| | | |
|---|---|---|
| WO | WO 2006/034387 A1 | 3/2006 |
| WO | WO 2017/100377 A1 | 6/2017 |
| WO | WO 2018/005655 A2 | 1/2018 |

(Continued)

OTHER PUBLICATIONS

Makarova et al. Classification and nomenclature of CRISPR-Cas systems: Where from here? The CRISPR Journal, vol. 1, No. 5, pp. 325-336, Oct. 17, 2018. (Year: 2018).*
Karvelis et al. Methods for decoding Cas9 protospacer adjacent motif (PAM) sequences: A brief overview. Methods, vol. 121-122, pp. 3-8, Mar. 24, 2017. (Year: 2017).*
Gao et al. DNA-guided genome editing using the Natronobacterium gregori Argonaute. Nature Biotechnology, vol. 34, No. 7, pp. 768-773, May 2, 2016, including p. 1/1 of Online Methods, and p. 1/1 of an Addendum published Nov. 28, 2016. Retracted. (Year: 2016).*
Retraction Notice for Gao et al. Nature Biotechnology, vol. 34, No. 7, pp. 768-773, May 2, 2016, published in Nature Biotechnology, vol. 35, No. 8, p. 797, Aug. 2017. (Year: 2017).*

(Continued)

*Primary Examiner* — Jennifer Dunston
(74) *Attorney, Agent, or Firm* — Cooley LLP

(57) ABSTRACT

The present disclosure relates to methods of joining three or more double-stranded (ds) or single-stranded (ss) DNA molecules of interest in vitro or in vivo. The method allows the joining of a large number of DNA fragments, in a deterministic fashion. It can be used to rapidly generate nucleic acid libraries that can be subsequently used in a variety of applications that include, for example, genome editing and pathway assembly. Kits for performing the method are also disclosed.

23 Claims, 6 Drawing Sheets

Specification includes a Sequence Listing.

(56) References Cited

U.S. PATENT DOCUMENTS

2017/0316353 A1 11/2017 Frewen et al.
2017/0369879 A1 12/2017 Duffield et al.

FOREIGN PATENT DOCUMENTS

| WO | WO 2018/226880 A1 | 12/2018 |
| WO | WO 2018/226900 A2 | 12/2018 |
| WO | WO 2020/092704 A1 | 5/2020 |

OTHER PUBLICATIONS

Swarts et al. Autonomous generation and loading of DNA guides by bacterial argonaute. Molecular Cell, vol. 65, pp. 985-998, Mar. 16, 2017, including pp. 1/18-18/18 of Supplemental Information. (Year: 2017).*
Zhou et al. Universal TA cloning. Current Issues in Molecular Biology, vol. 2, No. 1, pp. 1-7, 2000. (Year: 2000).*
Stober C.B. (2004) From Genomes to Vaccines for Leishmaniasis. In: Melville S.E. (eds) Parasite Genomics Protocols. Methods in Molecular Biology™, vol. 270. Humana Press, p. 432. (Year: 2004).*
Kostylev et al. Cloning should be simple: *Escherichia coli* DH5α-mediated assembly of multiple DNA fragments with short end homologies. PLoS ONE, vol. 10, No. 9, e0137466, Sep. 2015, printed as pp. 1/15-15/15. (Year: 2015).*
PCT/US2019/059051, International Search Report and Written Opinion dated Jan. 28, 2020, 23 pages.
Atanassov, et al., "A simple, flexible and efficient PCR-fusion/Gateway cloning procedure for gene fusion, site-directed mutagenesis, short sequence insertion and domain deletions and swaps". Plant Methods (2009); 5: 14. Epub Oct. 28, 2009.
Becker and Guarente, "[12] High-efficiency transformation of yeast by electroporation." Methods in Enzymology (1991); 194: 182-187.
Coussement, et al., "One step DNA assembly for combinatorial metabolic engineering". Metabolic Engineering (May 2014); 23: 70-77. Epub Mar. 2, 2014.
Crameri, Andreas, et al., "DNA shuffling of a family of genes from diverse species accelerates directed evolution." Nature (1998); 391(6664): 288-291.
Crameri, Andreas, et al., "Molecular evolution of an arsenate detoxification pathway by DNA shuffling." Nature Biotechnology (1997); 15(5): 436-438.
Datsenko and Wanner, "One-step inactivation of chromosomal genes in *Escherichia coli* K-12 using PCR products". PNAS (Jun. 6, 2000); 97(12): 6640-6645.
De Almeida, et al. "Transgenic expression of two marker genes under the control of an Arabidopsis rbcS promoter: Sequences encoding the Rubisco transit peptide increase expression levels." Molecular and General Genetics MGG (1989); 218(1): 78-86.
De Kok, et al., "Rapid and Reliable DNA Assembly via Ligase Cycling Reaction". ACS Synthetic Biology (Feb. 21, 2014); 3(2): 97-106. Epub Jan. 15, 2014; Published Jan. 9, 2014.
Engler and Marillonnet, "Combinatorial DNA Assembly Using Golden Gate Cloning". Methods in Molecular Biology (2013); 1073: 141-156.
Engler, et al., "Golden Gate Shuffling: A One-Pot DNA Shuffling Method Based on Type IIs Restriction Enzymes". PLoS ONE (2009); 4(5): e5553. Epub May 14, 2009.
Gibson, D.G., "Enzymatic Assembly of Overlapping DNA Fragments". Methods in Enzymology (2011); 498: 349-361.
Gietz, et al., "Improved method for high efficiency transformation of intact yeast cells." Nucleic Acids Res. (Mar. 25, 1992); 20(6): 1425.
Ito, Hisao, et al., "Transformation of intact yeast cells treated with alkali cations." Journal of Bacteriology (1983); 153(1): 163-168.
Jin, et al., "Datel: A Scarless and Sequence-Independent DNA Assembly Method Using Thermostable Exonucleases and Ligase". ACS Synthetic Biology (Sep. 16, 2016); 5(9): 1028-1032. Epub Jun. 1, 2016; Published May 27, 2016.
Jones, Jonathan DG, et al. "High level expression of introduced chimaeric genes in regenerated transformed plants." The EMBO Journal (1985); 4(10): 2411-2418.
Kirchmaier, et al., "Golden GATEway Cloning—A Combinatorial Approach to Generate Fusion and Recombination Constructs". PLoS ONE (Oct. 7, 2013); 8(10): e76117.
Klein, et al., "Multiplex pairwise assembly of array-derived DNA oligonucleotides". Nucleic Acids Research (Mar. 18, 2016); 44(5): e43. Epub Nov. 8, 2015.
LeProust, et al., "Synthesis of high-quality libraries of long (150mer) oligonucleotides by a novel depurination controlled process". Nucleic Acids Research (May 2010); 38(8): 2522-2540. Epub Mar. 22, 2010.
Merryman and Gibson, "Methods and applications for assembling large DNA constructs". Metabolic Engineering (May 2012); 14(3): 196-204.
Mitchell, et al., "Versatile genetic assembly system (Vegas) to assemble pathways for expression in S. cerevisiae". Nucleic Acids Research (Jul. 27, 2015); 43(13): 6620-6630. Epub May 8, 2015.
Moore, Jeffrey C., et al., "Strategies for the in vitro evolution of protein function: enzyme evolution by random recombination of improved sequences." Journal of Molecular Biology (1997); 272(3): 336-347.
Muyrers, et al., "Rapid modification of bacterial artificial chromosomes by ET-recombination". Nucleic Acids Research (Mar. 1, 1999); 27(6): 1555-1557.
Muyrers, et al., "Techniques: Recombinogenic engineering-new options for cloning and manipulating DNA". Trends Biochem Sci. (May 2001); 26(5): 325-331.
Nakashima, Nobutaka, et al. "Bacterial cellular engineering by genome editing and gene silencing." International Journal of Molecular Sciences (2014); 15(2): 2773-2793.
Paetzold, et al., "In Situ Overlap and Sequence Synthesis During DNA Assembly". ACS Synthetic Biology (Dec. 20, 2013); 2(12): 750-755. Epub Nov. 6, 2013; Published Oct. 25, 2013.
Quan and Tian, "Circular polymerase extension cloning for high-throughput cloning of complex and combinatorial DNA libraries". Nature Protocols (Feb. 2011); 6(2): 242-251. Epub Feb. 3, 2011.
Quan, et al., "Parallel on-chip gene synthesis and application to optimization of protein expression". Nature Biotechnology (May 2011); 29(5): 449-452. Epub Apr. 24, 2011.
Ramon and Smith, "Single-step linker-based combinatorial assembly of promoter and gene cassettes for pathway engineering". Biotechnology Letters (Mar. 2011); 33(3): 549-555. Epub Nov. 24, 2010.
Rivero-Müller, et al., "Assisted large fragment insertion by Red/ET-recombination (Alfire)—an alternative and enhanced method for large fragment recombineering". Nucleic Acids Res. (May 15, 2007); 35(10): e78. Epub May 21, 2007.
Sharan, et al., "Recombineering: A Homologous Recombination-Based Method of Genetic Engineering." Nature Protocols 2009; 4(2): 206-223.
Stemmer, Willem P., "DNA shuffling by random fragmentation and reassembly: In vitro recombination for molecular evolution." Proceedings of the National Academy of Sciences (1994); 91(22): 10747-10751.
Stemmer, Willem P.C., "Rapid evolution of a protein in vitro by DNA shuffling." Nature (1994); 370(6488): 389-391.
St-Pierre, et al., "One-Step Cloning and Chromosomal Integration of DNA". ACS Synthetic Biology (Dec. 20, 2013); 2(12): 750-755. Epub Nov. 6, 2013; Published May 6, 2013.
Tear, Crystal Jing Ying, et al. "Excision of Unstable Artificial Gene-Specific Inverted Repeats Mediates Scar-Free Gene Deletions in *Escherichia coli*." Applied Biochemistry and Biotechnology (2014); 175(4): 1858-1867.
Thomason, et al., "Recombineering: Genetic Engineering in Bacteria Using Homologous Recombination." Current Protocols in Molecular Biology (Apr. 14, 2014); 106:1.16:1-39.
Trubitsyna, et al., "PaperClip: rapid multi-part DNA assembly from existing libraries". Nucleic Acids Research (Nov. 10, 2014); 42(20): e154. Epub Sep. 8, 2014.

(56) References Cited

OTHER PUBLICATIONS

Tsuge, et al., "One step assembly of multiple DNA fragments with a designed order and orientation in Bacillus subtilis plasmid". Nucleic Acids Res. (Nov. 1, 2003); 31(21): e133.

Zhang, Ji-Hu, et al., "Directed evolution of a fucosidase from a galactosidase by DNA shuffling and screening." Proceedings of the National Academy of Sciences (1997); 94 (9): 4504-4509.

Zhang, Y., et al., "A new logic for DNA engineering using recombination in *Escherichia coli*". Nature Genetics (Oct. 1998); 20(2): 123-128.

Zhang, Y., et al., "DNA cloning by homologous recombination in *Escherichia coli*". Nature Biotechnology (Dec. 2000); 18(12): 1314-1317.

Zhao, et al., "Molecular evolution by staggered extension process (StEP) in vitro recombination". Nature Biotechnology (Mar. 1998); 16(3): 258-261.

\* cited by examiner

Example of deterministic library assembly with circular-permuted payload

MULTIPLEXED DETERMINISTIC ASSEMBLY OF DNA LIBRARIES

CROSS-REFERENCE TO RELATED APPLICATIONS

This application claims the benefit of priority to U.S. Provisional Application Ser. No. 62/753,254, filed Oct. 31, 2018, which is herein incorporated by reference in its entirety for all purposes.

FIELD

The present disclosure is directed to compositions and methods for joining single-stranded and/or double-stranded nucleic acid molecules permitting in vitro or in vivo assembly of multiple nucleic acid molecules with overlapping terminal sequences in a single reaction. The disclosed methods and compositions can be useful for deterministic assembly of fragments of nucleic acid sequences and can be used for editing any DNA sequence such as, for example, plasmids, cosmid or specific genes in the genome of desired host cells or organisms.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_029_01US_SeqList_ST25.txt. The text file is about 262 KB, and was created on Oct. 31, 2019, and is being submitted electronically via EFS-Web.

BACKGROUND

Traditionally, nucleic acid assemblies such as plasmid or linear DNA are generated one at a time in a deterministic fashion and, thus, can be slow, expensive and labor-intensive. In contrast, current pooled approaches for generating libraries of complex nucleic acid assemblies can enable the generation of many assemblies at once, but often result in libraries representing all possible combinations between the sets of parts in the assembly. Such approaches are a non-deterministic and combinatorial approach to assembly and can also be time-consuming, labor intensive and expensive, especially in circumstances where a subset of sequences are the desired product of the assembly reaction.

Thus, there is a need in the art for new methods for generating complex nucleic acid assemblies, which do not suffer from the aforementioned drawbacks inherent with traditional methods for generating nucleic acid assemblies.

SUMMARY

In one aspect, provided herein is a composition comprising a mixture of polynucleotides, the mixture comprising: a first pool containing pairs of polynucleotides, wherein each pair in the first pool contains a first polynucleotide and a second polynucleotide; and a second pool of insert polynucleotides, wherein each insert polynucleotide in the second pool comprises a first assembly overlap sequence at its 5' end that is complementary to a 3' end of a first polynucleotide and a second assembly overlap sequence at its opposing 3'end that is complementary to a 5' end of a second polynucleotide in a pair of polynucleotides from the first pool. In some cases, the composition further comprises a cloning vector, wherein, for each pair in the first pool, a 5' end of the first polynucleotide and a 3' end of the second polynucleotide comprises sequence complementary to the cloning vector. In some cases, each polynucleotide from the first pool is selected such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector. In some cases, the specified threshold is between 5 and 15 contiguous nucleotides. In some cases, the composition further comprises a polymerase. In some cases, the polymerase is strand-displacing or non-strand displacing. In some cases, the polymerase is non-strand displacing and the composition further comprises a crowding agent. In some cases, the crowding agent is polyethylene glycol (PEG). In some cases, the PEG is used at a concentration of from about 3 to about 7% (weight/volume). In some cases, the PEG is selected from PEG-200, PEG-4000, PEG-6000, PEG-8000 or PEG-20,000. In some cases, the polymerase is strand displacing and the composition further comprises a single-stranded binding protein. In some cases, the single strand DNA binding protein is an extreme thermostable single-stranded DNA binding protein (ET SSB), *E. coli* recA, T7 gene 2.5 product, phage lambda RedB or Rac prophage RecT. In some cases, the composition further comprises a 5'-3' exonuclease. In some cases, the composition further comprises a ligase. In some cases, each pair in the first pool is double-stranded DNA (dsDNA) or single-stranded DNA (ssDNA). In some cases, each insert polynucleotide in the second pool is dsDNA or ssDNA. In some cases, for each pair in the first pool, the first polynucleotide and the second polynucleotide comprises sequence corresponding to a target genomic locus in a host cell. In some cases, for each pair in the first pool, the first polynucleotide and the second polynucleotide comprise coding sequence corresponding to a gene that is part of a metabolic pathway. In some cases, for each pair in the first pool, the first polynucleotide and the second polynucleotide comprise coding sequence corresponding to a functional domain or one or more proteins. In some cases, for each pair in the first pool, the first polynucleotide and the second polynucleotide are linked together in a single construct, wherein the single construct comprises one or more recognition sequences for one or more site-specific nuclease(s) between the first polynucleotide and the second polynucleotide. In some cases, the one or more recognition sequences for one or more site-specific nuclease(s) comprises a homing endonuclease recognition sequence. In some cases, the first assembly overlap sequence and the second assembly overlap sequence on each insert polynucleotide in the second pool comprises 1 or more nucleotides that are complementary to the 3' end of a first polynucleotide and the 5' end of a second polynucleotide, respectively, in a pair of polynucleotides from the first pool. In some cases, the first assembly overlap sequence and the second assembly overlap sequence on each insert polynucleotide in the second pool comprises about 25 nucleotides that are complementary to the 3' end of a first polynucleotide and the 5' end of a second polynucleotide, respectively, in a pair of polynucleotides from the first pool. In some cases, each insert polynucleotide in the second pool comprises one or more payload sequences located between the first assembly overlap sequence and the second assembly overlap sequence. In some cases, the one or more payload sequences are selected from promoters, genes, regulatory sequences, nucleic acid sequence encoding degrons, nucleic acid sequence encoding solubility tags, terminators, unique identifier sequence or portions thereof. In some cases, each pair of first and second polynucleotides in the first pool comprises sequence corresponding to a different target genomic locus in a host cell as compared to each other pair in the first pool. In some cases, each pair of first and second polynucleotides in the first pool comprises sequence corresponding to the same target genomic locus in a host cell. In some cases, each payload sequence in the insert polynucleotides in the second pool is different from the payload sequence in each other insert polynucleotide in the second pool. In some cases, each payload sequence in the insert polynucleotides in the second pool is the same as the payload sequence in each other insert polynucleotide in the second pool. In some cases, the site-specific nuclease(s) is one or more of restriction endonuclease(s), Type IIs endonuclease(s), homing endonuclease(s), RNA-guided nuclease(s), DNA-guided nuclease(s), zinc-finger nuclease(s), Transcription activator-like effector nuclease(s) (TALEN(s)) or nicking enzyme(s).

In another aspect, provided herein is a method for generating libraries of polynucleotides, the method comprising: a.) combining a first pool of polynucleotides and a second pool of polynucleotides, wherein the first pool contains pairs of polynucleotides, wherein each pair in the first pool contains a first polynucleotide and a second polynucleotide, wherein the second pool contains insert polynucleotides, wherein each insert polynucleotide in the second pool comprises a first assembly overlap sequence at its 5' end that is complementary to a 3' end of a first polynucleotide and a second assembly overlap sequence at its opposing 3'end that is complementary to a 5' end of a second polynucleotide in a pair of polynucleotides from the first pool; b.) assembling the first pool and the second pool into a library of polynucleotides, wherein each polynucleotide in the library comprises an insert polynucleotide from the second pool and a pair of first polynucleotides and second polynucleotides from the first pool, wherein the assembling is performed via in vitro cloning methods or in vivo cloning methods. In some cases, the first assembly overlap sequence and the second assembly overlap sequence on each insert polynucleotide in the second pool comprises 1 or more nucleotides that are complementary to the 3' end of a first polynucleotide and the 5' end of a second polynucleotide, respectively, in a pair of polynucleotides from the first pool. In some cases, the first assembly overlap sequence and the second assembly overlap sequence on each insert polynucleotide in the second pool comprises about 25 nucleotides that are complementary to the 3' end of a first polynucleotide and the 5' end of a second polynucleotide, respectively, in a pair of polynucleotides from the first pool. In some cases, for each pair in the first pool, the first polynucleotide and the second polynucleotide are linked together in a single construct, wherein the single construct comprises one or more recognition sequences for one or more site-specific nuclease(s) between the first polynucleotide and the second polynucleotide. In some cases, the one or more recognition sequences for one or more site-specific nuclease(s) comprises a homing endonuclease recognition sequence. In some cases, the linked single construct is produced by joining individual first and second polynucleotides via splicing and overlap-extension PCR (SOE-PCR), restriction-ligation, blunt-end ligation, overlap-based assembly method, recombination-based method, or any other enzymatic or chemical method of joining the first and second polynucleotides, or by synthesizing the single construct directly. In some cases, the method further comprises combining a cloning vector with the first pool and the second pool during step (a), wherein opposing ends of the cloning vector comprise sequence complementary to a 5'end of the first polynucleotide and a 3' end of the second polynucleotide for each pair in the first pool. In some cases, the method further comprises combining a cloning vector with the first pool prior to step (a), wherein opposing ends of the cloning vector comprise sequence complementary to a 5'end of the first polynucleotide and a 3' end of the second polynucleotide for each pair in the first pool. In some cases, the cloning vector and the 5'end of the first polynucleotide and the 3'end of the second polynucleotide in each pair from the first pool comprise one or more recognition sequences for one or more site-specific nucleases. In some cases, the method further comprises generating single-stranded complementary overhangs between the opposing ends of the cloning vector and the 5'end of the first polynucleotide and the 3'end of the second polynucleotide in each pair from the first pool by adding the one or more site-specific nucleases for the one or more recognition sequences. In some cases, the method further comprises ligating the single-stranded complementary overhangs between the opposing ends of the cloning vector and the 5'end of the first polynucleotide and the 3'end of the second polynucleotide in each pair from the first pool. The ligating can be performed using a DNA ligase. In some cases, step (b) results in a circular product comprising an insert polynucleotide from the second pool, a first and second polynucleotide from a pair from the first pool and the cloning vector. In some cases, the first pool is generated by selecting pairs of polynucleotide sequences from a larger set of such sequences such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector. In some cases, the specified threshold is between 5 and 15 contiguous nucleotides. In some cases, the assembly is an in vitro cloning method, wherein the mixture of the first pool and the second pool is heated to partially or fully denature polynucleotides present in the first and the second pools, then cooled to room temperature before assembly. In some cases, prior to step (a), the first pool of polynucleotides is generated by combining a mixture containing each first polynucleotide from the pairs of polynucleotides with a mixture containing each second polynucleotide from the pairs of polynucleotides. In some cases, each pair in the first pool is double-stranded DNA (dsDNA) or single-stranded DNA (ssDNA). In some cases, each insert polynucleotide in the second pool is dsDNA or ssDNA. In some cases, for each pair in the first pool, the first polynucleotide and the second polynucleotide comprises sequence corresponding to a target genomic locus in a host cell. In some cases, for each pair in the first pool, the first polynucleotide and the second polynucleotide comprise coding sequence corresponding to a gene that is part of a metabolic pathway. In some cases, for each pair in the first pool, the first polynucleotide and the second polynucleotide comprise coding sequence corresponding to a functional domain or one or more proteins. In some cases, each insert polynucleotide in the second pool comprises one or more payload sequences located between the first assembly overlap sequence and the second assembly overlap sequence. In some cases, the one or more payload sequences are selected from promoters, genes, regulatory sequences, nucleic acid sequence encoding degrons, nucleic acid sequence encoding solubility tags, terminators, unique identifier sequence or portions thereof. In some cases, for each pair in the first pool, the first polynucleotide and the second polynucleotide comprises sequence corresponding to a different target genomic locus in a host cell as compared to each other pair in the first pool. In some cases, for each pair in the first pool, the first polynucleotide and the second polynucleotide comprises sequence corresponding to the same target genomic locus in a host cell. In some cases, each payload sequence in the insert polynucleotides in the second pool is different from the payload sequence in each other insert polynucleotide in the second pool. In some cases, each payload sequence in the insert polynucleotides in the second pool is the same as the payload sequence in each other insert polynucleotide in the second pool. In some cases, each insert polynucleotide in the second pool is generated by: (i) performing a polymerase chain reaction (PCR) on a mixture comprising the payload sequence, a forward primer and a reverse primer, wherein the forward primer comprises from 5' to 3', a short stretch of one or more nucleotides complementary to the payload sequence, the first assembly overlap sequence, one or more recognition sequences for one or more site-specific nuclease(s), the second assembly overlap sequence and a second stretch of one or more nucleotides complementary to the payload sequence and wherein the reverse primer comprises sequence complementary to the payload sequence, wherein the PCR generates a PCR product comprising from 5' to 3', the short stretch of nucleic acid complementary to the payload sequence, the first assembly overlap sequence, the one or more site-specific nuclease recognition sequence(s), the second assembly overlap sequence and the payload sequence; (ii) circularizing the PCR product via an assembly method selected from the group consisting of splicing and overlap-extension PCR (SOE-PCR), restriction-ligation, blunt-end ligation, overlap-based assembly method, and recombination-based method, or any other enzymatic or chemical method for joining two DNA molecules; and (iii) linearizing the circularized PCR product with one or more site-specific nuclease(s) that recognizes the one or more site-specific nuclease recognition sequence(s), thereby generating the second pool of polynucleotides. In some cases, the site-specific nuclease(s) is one or more of restriction endonuclease(s), Type IIs endonuclease(s), homing endonuclease(s), RNA-guided nuclease(s), DNA-guided nuclease(s), zinc-finger nuclease(s), TALEN(s) or nicking enzyme(s).

In yet another aspect, provided herein is a method for generating libraries of polynucleotides, the method comprising: (a) amplifying via polymerase chain reaction (PCR) a first pool of polynucleotides, wherein the first pool contains pairs of polynucleotides, wherein each pair in the first pool contains a first polynucleotide and a second polynucleotide, and wherein each first polynucleotide and each second polynucleotide in a pair comprises a 5' end and a 3' end, wherein the amplifying introduces a common overlap sequence comprising one or more recognition sequences for one or more site-specific nucleases onto the 5' end of a first polynucleotide and the 3'end of a second polynucleotide in a pair from the first pool; (b) assembling each pair of first polynucleotides and second polynucleotides from the first pool into a single nucleic acid fragment by utilizing common overlap sequence, wherein the single nucleic fragment for each pair comprises a first polynucleotide and second polynucleotide separated by the common overlap sequence from the 5' end of the first polynucleotide and the 3' end of the second polynucleotide, and wherein the 3'end of the first polynucleotide and the 5' end of the second polynucleotide in the single nucleic fragment for each pair are located on opposing terminal ends of the single nucleic acid fragment, distal to the one or more site-specific nuclease recognition sequence(s); (c) combining the single nucleic acid fragments for each pair with a second pool containing insert polynucleotides, wherein each insert polynucleotide in the second pool comprises a first assembly overlap sequence at its 5' end that is complementary to the 3' end of the first polynucleotide present within the single nucleic acid fragment and a second assembly overlap sequence at its opposing 3'end that is complementary to the 5' end of the second polynucleotide present within the single nucleic acid fragment; (d) assembling the first pool and the second pool into a third pool of circularized products, wherein the assembling is performed via in vitro or in vivo overlap assembly methods, and wherein each circularized product in the third pool comprises an insert sequence from the second pool and a pair of first polynucleotides and second polynucleotides from the first pool; (e) linearizing each circularized product in the third pool via digestion by one or more site-specific nuclease(s) that recognizes the one or more site-specific nuclease recognition sequence(s) located between the first polynucleotide sequence and the second polynucleotide sequence in each of the circularized products in the third pool; and (f) assembling the linearized products into cloning vectors by in vitro or in vivo cloning methods. In some cases, the one or more site-specific nuclease recognition sequence(s) located between the first polynucleotide sequence and the second polynucleotide sequence is a homing nuclease recognition sequence. In some cases, the one or more site-specific nuclease(s) for the one or more site-specific nuclease recognition sequence(s) located between the first polynucleotide sequence and the second polynucleotide sequence is a homing endonuclease. In some cases, the common overlap sequence comprises an assembly overlap sequence of at least 1 nucleotide and the assembly in step (b) is performed by an overlap-based DNA assembly method. In some cases, the common overlap sequence comprises an assembly overlap sequence of from 10-25 nucleotides and the assembly in step (b) is performed by an overlap-based DNA assembly method. In some cases, the overlap-based DNA assembly method is selected from SOE-PCR or an in vitro overlap-assembly method (e.g., HiFi assembly). In some cases, the one or more site-specific nuclease recognition sequence(s) present in the common overlap sequence on the 5' end of the first polynucleotide is complementary to the one or more site-specific nuclease recognition sequence(s) present in the common overlap sequence on the 3' end of the second polynucleotide in each pair, and wherein the utilizing the common overlap sequences of the first and second polynucleotides in each pair in step (b) entails performing SOE-PCR. In some cases, the utilizing the common overlap sequences of the first and second polynucleotides in each pair in step (b) entails digesting the one or more site-specific nuclease recognition sequences present in the common overlap sequence on the 5' end of the first polynucleotide and the 3' end of the second polynucleotide in each pair with one or more site specific nucleases for the one or more site-specific nuclease recognition sequences to generate single-stranded overhangs on the 5' end of the first polynucleotide and the 3' end of the second polynucleotide in each pair that comprise complementary sequence; and ligating the complementary sequence present on the single-stranded overhang on the 5' end of the first polynucleotide and the 3' end of the second polynucleotide in each pair. In some cases, the assembling of step (d) is performed using an overlap-based DNA assembly method. In some cases, the overlap-based DNA assembly is selected from SOE-PCR and an in vitro overlap-assembly method (e.g., HiFi assembly). In some cases, the 3' end of the first polynucleotide and the 5' end of the second polynucleotide in the single nucleic acid fragment in each pair comprise an additional set of one or more site-specific nuclease recognition sequences and the first assembly overlap sequence and the second assembly overlap sequence in each insert polynucleotide in the second pool comprise one or more site-specific nuclease recognition sequences. In some cases, the assembling in step (d) entails digesting the additional one or more site-specific nuclease recognition sequences present on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool with one or more site specific nucleases for the additional one or more site-specific nuclease recognition sequences on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool to generate a single-stranded overhang on the 3' end of the first polynucleotide that comprises sequence complementary to sequence present on a single-stranded overhang on the 5'end of the first assembly sequence of an insert polynucleotide from the second pool and a single stranded overhang on the 5' end of the second polynucleotide that comprises sequence complementary to a sequence present on a single-stranded overhang on the 3'end of the second assembly sequence of the same insert polynucleotide from the second pool; and ligating the complementary sequence present on the single-stranded overhangs. In some cases, the cloning vectors of step (f) comprise one or more site-specific nuclease recognition sequences. In some cases, the assembling in step (f) entails digesting the one or more site-specific nuclease recognition sequences in the cloning vectors with the one or more site-specific nucleases for the one or more site-specific nuclease recognition sequences recognition sequences present in the cloning vectors, wherein the digesting generates single-stranded overhangs on opposing ends of the cloning vectors, wherein the single-stranded overhang on one of the opposing ends of the cloning vector comprises sequence complementary to an end of the linearized product generated in step (e) and the single-stranded overhang on the other of the opposing ends of the cloning vectors comprises sequence complementary to an opposing end of the linearized product generated in step (e); and ligating the complementary sequences present on the single-stranded overhangs of the cloning vectors and the linearized products from step (e). In some cases, the first pool is generated by selecting pairs of polynucleotide sequences from a larger set of such sequences such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector. In some cases, the specified threshold is between 5 and 15 contiguous nucleotides. In some cases, the first assembly overlap sequence and the second assembly overlap sequence on each insert polynucleotide in the second pool comprises 1 or more nucleotides that are complementary to the opposing terminal ends of the single nucleic acid fragment. In some cases, the first assembly overlap sequence and the second assembly overlap sequence on each insert polynucleotide in the second pool comprises about 25 nucleotides that are complementary to the opposing terminal ends of the single nucleic acid fragment. In some cases, prior to step (a), the first pool of polynucleotides is generated by combining a mixture containing each first polynucleotide from the pairs of polynucleotides with a mixture containing each second polynucleotide from the pairs of polynucleotides. In some cases, each pair in the first pool is double-stranded DNA (dsDNA) or single-stranded DNA (ssDNA). In some cases, each insert polynucleotide in the second pool is dsDNA or ssDNA. In some cases, for each pair in the first pool, the first polynucleotide and the second polynucleotide comprises sequence corresponding to a target genomic locus in a host cell. In some cases, for each pair in the first pool, the first polynucleotide and the second polynucleotide comprise coding sequence corresponding to a gene that is part of a metabolic pathway. In some cases, for each pair in the first pool, the first polynucleotide and the second polynucleotide comprise coding sequence corresponding to a functional domain or one or more proteins. In some cases, each insert polynucleotide in the second pool comprises one or more payload sequences located between the first assembly overlap sequence and the second assembly overlap sequence. In some cases, the one or more payload sequences are selected from promoters, genes, regulatory sequences, nucleic acid sequence encoding degrons, nucleic acid sequence encoding solubility tags, terminators, unique identifier sequence or portions thereof. In some cases, for each pair in the first pool, the first polynucleotide and the second polynucleotide comprises sequence corresponding to a different target genomic locus in a host cell as compared to each other pair in the first pool. In some cases, for each pair in the first pool, the first polynucleotide and the second polynucleotide comprises sequence corresponding to the same target genomic locus in a host cell. In some cases, each payload sequence in the insert polynucleotides in the second pool is different from the payload sequence in each other insert polynucleotide in the second pool. In some cases, each payload sequence in the insert polynucleotides in the second pool is the same as the payload sequence in each other insert polynucleotide in the second pool. In some cases, each insert polynucleotide in the second pool is generated by: (i) performing a polymerase chain reaction (PCR) on a mixture comprising the payload sequence, a forward primer and a reverse primer, wherein the forward primer comprises from 5' to 3', a short stretch of one or more nucleotides complementary to the payload sequence, the first assembly overlap sequence, one or more recognition sequences for one or more site-specific nuclease(s), the second assembly overlap sequence and a second stretch of one or more nucleotides complementary to the payload sequence and wherein the reverse primer comprises sequence complementary to the payload sequence or to other sequence downstream of the payload sequence, wherein the PCR generates a PCR product comprising from 5' to 3', the short stretch of nucleic acid complementary to the payload sequence, the first assembly overlap sequence, the one or more site-specific nuclease recognition sequence(s), the second assembly overlap sequence and the payload sequence; (ii) circularizing the PCR product via an assembly method selected from the group consisting of splicing and overlap-extension PCR (SOE-PCR), restriction-ligation, blunt-end ligation, overlap-based assembly method, and recombination-based method, or any other enzymatic or chemical method for joining two DNA molecules; and (iii) linearizing the circularized PCR product with one or more site-specific nuclease(s) that recognizes the one or more site-specific nuclease recognition sequence(s), thereby generating the second pool of polynucleotides. In some cases, the site-specific nuclease(s) is one or more of restriction endonuclease(s), Type IIs endonuclease(s), homing endonuclease(s), RNA-guided nuclease(s), DNA-guided nuclease(s), zinc-finger nuclease(s), TALEN(s) or nicking enzyme(s).

DETAILED DESCRIPTION

Definitions

Figure 1:
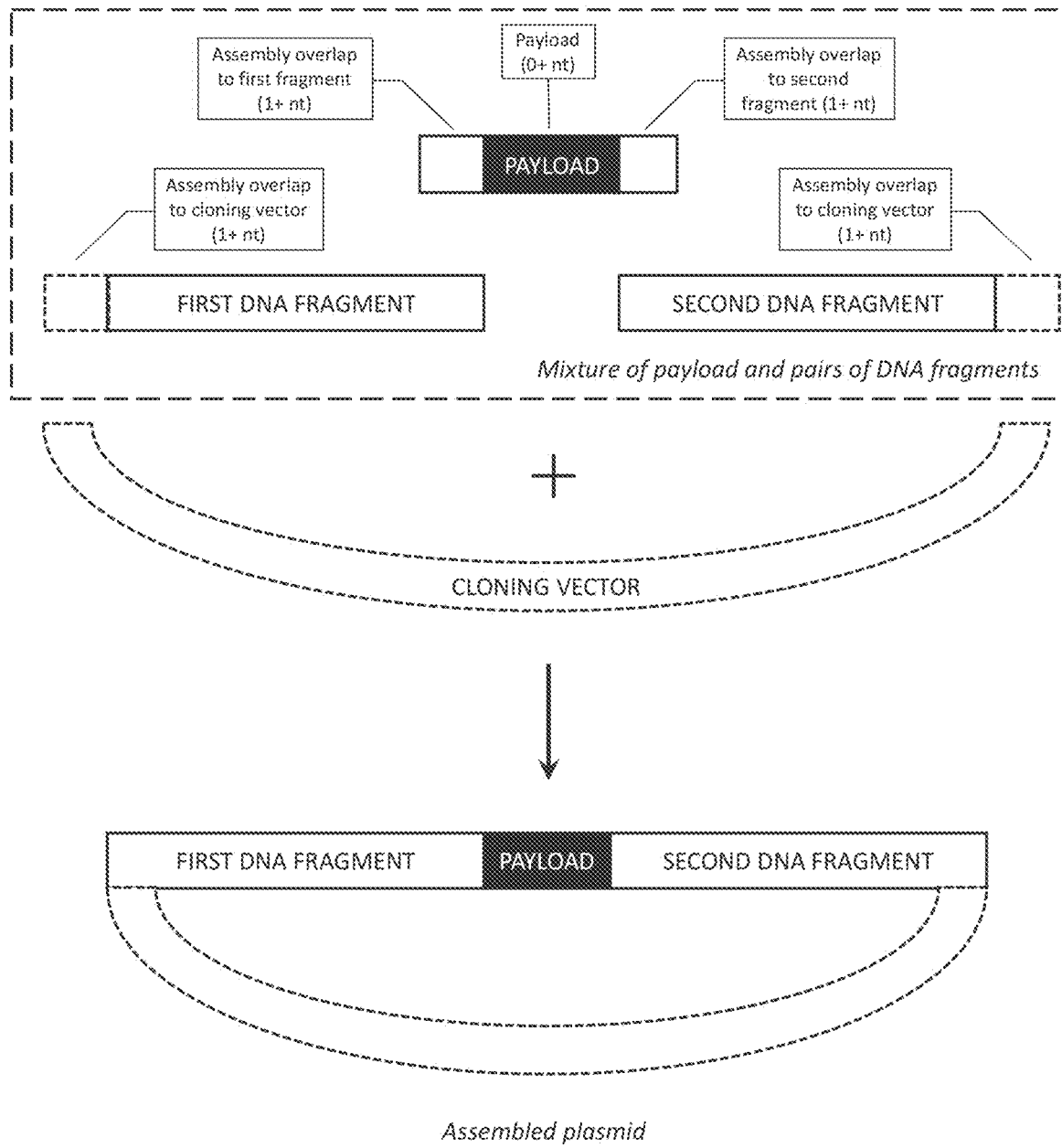
FIG. 1 depicts a method for multiplexed, deterministic assembly of DNA libraries showing an initial composition of insert polynucleotide(s) and first polynucleotides comprising a vector overlap assembly sequence and a second polynucleotide comprising a vector overlap assembly sequence, and optional cloning vector. The insert polynucleotide can comprise a payload sequence that has a length of zero nucleotides if a deletion, or nonzero if an insertion or replacement.

While the following terms are believed to be well understood by one of ordinary skill in the art, the following definitions are set forth to facilitate explanation of the presently disclosed subject matter.

As used herein, the term "a" or "an" can refer to one or more of that entity, i.e. can refer to a plural referents. As such, the terms "a" or "an", "one or more" and "at least one" can be used interchangeably herein. In addition, reference to "an element" by the indefinite article "a" or "an" does not exclude the possibility that more than one of the elements is present, unless the context clearly requires that there is one and only one of the elements.

Unless the context requires otherwise, throughout the present specification and claims, the word "comprise" and variations thereof, such as, "comprises" and "comprising" are to be construed in an open, inclusive sense that is as "including, but not limited to".

Reference throughout this specification to "one embodiment" or "an embodiment" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

As used herein, the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

As used herein, the term "prokaryotes" is art recognized and refers to cells that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

As used herein, the term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

As used herein, "bacteria" or "eubacteria" can refer to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

As used herein, a "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

As used herein, the terms "genetically modified host cell," "recombinant host cell," and "recombinant strain" are used interchangeably herein and can refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell As used herein, the term "wild-type microorganism" or "wild-type host cell" can describe a cell that occurs in nature, i.e. a cell that has not been genetically modified.

As used herein, the term "genetically engineered" may refer to any manipulation of a host cell's genome (e.g. by insertion, deletion, mutation, or replacement of nucleic acids).

As used herein, the term "control" or "control host cell" can refer to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell. In some embodiments, the present disclosure teaches the use of parent strains as control host cells (e.g., the Si strain that was used as the basis for the strain improvement program). In other embodiments, a host cell may be a genetically identical cell that lacks a specific promoter or SNP being tested in the treatment host cell.

As used herein, the term "allele(s)" can mean any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) can mean any site at which an edit to the native genomic sequence is desired. In one embodiment, said term can mean a specific place or places or a site on a chromosome where for example a gene or genetic marker is found.

As used herein, the term "genetically linked" can refer to two or more traits that are co-inherited at a high rate during breeding such that they are difficult to separate through crossing.

A "recombination" or "recombination event" as used herein can refer to a chromosomal crossing over or independent assortment.

As used herein, the term "phenotype" can refer to the observable characteristics of an individual cell, cell culture, organism, or group of organisms, which results from the interaction between that individual's genetic makeup (i.e., genotype) and the environment.

As used herein, the term "chimeric" or "recombinant" when describing a nucleic acid sequence or a protein sequence can refer to a nucleic acid, or a protein sequence, that links at least two heterologous polynucleotides, or two heterologous polypeptides, into a single macromolecule, or that rearranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence can comprise at least one nucleotide difference when compared to any other naturally occurring nucleotide sequence.

As used herein, the term "nucleic acid" can refer to a polymeric form of nucleotides of any length, either ribonucleotides or deoxyribonucleotides, or analogs thereof. This term can refer to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" can refer to any segment of DNA associated with a biological function. Thus, genes can include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" or "orthologue" is known in the art and can refer to related sequences that share a common ancestor or family member and are determined based on the degree of sequence identity.

The terms "homology," "homologous," "substantially similar" and "corresponding substantially" can be used interchangeably herein. Said terms can refer to nucleic acid fragments wherein changes in one or more nucleotide bases do not affect the ability of the nucleic acid fragment to mediate gene expression or produce a certain phenotype. These terms can also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared.

"Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Sequence homology between amino acid or nucleic acid sequences can be defined in terms of shared ancestry. Two segments of nucleic acid can have shared ancestry because of either a speciation event (orthologs) or a duplication event (paralogs). Homology among amino acid or nucleic acid sequences can be inferred from their sequence similarity such that amino acid or nucleic acid sequences are said to be homologous is said amino acid or nucleic acid sequences share significant similarity. Significant similarity can be strong evidence that two sequences are related by divergent evolution from a common ancestor. Alignments of multiple sequences can be used to discover the homologous regions. Homology can be determined using software programs readily available in the art, such as those discussed in Current Protocols in Molecular Biology (F. M. Ausubel et al., eds., 1987) Supplement 30, section 7.718, Table 7.71. Some alignment programs are BLAST (NCBI), MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," can refer to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations can contain alterations that produce silent substitutions, additions, or deletions, but do not alter the properties or activities of the encoded protein or how the proteins are made. Alternatively, mutations can be nonsynonymous substitutions or changes that can alter the amino acid sequence of the encoded protein and can result in an alteration in properties or activities of the protein.

As used herein, the term "protein modification" can refer to, e.g., amino acid substitution, amino acid modification, deletion, and/or insertion, as is well understood in the art.

As used herein, the term "at least a portion" or "fragment" of a nucleic acid or polypeptide can mean a portion having the minimal size characteristics of such sequences, or any larger fragment of the full-length molecule, up to and including the full-length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides can also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein can refer to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer can be single stranded for maximum efficiency in amplification. The primer can be an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" can refer to a DNA sequence capable of controlling the expression of a coding sequence or functional RNA. In some embodiments, the promoter sequence consists of proximal and more distal upstream elements, the latter elements often referred to as enhancers. Accordingly, an "enhancer" can be a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. A recombinant construct can comprise an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by direct sequencing, Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" or "functionally linked" can mean the sequential arrangement of any functional payload according to the disclosure (e.g., promoter, terminator, degron, solubility tag, etc.) with a further oligo- or polynucleotide. In some cases, the sequential arrangement can result in transcription of said further polynucleotide. In some cases, the sequential arrangement can result in translation of said further polynucleotide. The functional payloads can be present upstream or downstream of the further oligo or polynucleotide. In one example, "operably linked" or "functionally linked" can mean a promoter controls the transcription of the gene adjacent or downstream or 3' to said promoter. In another example, "operably linked" or "functionally linked" can mean a terminator controls termination of transcription of the gene adjacent or upstream or 5' to said terminator.

The term "product of interest" or "biomolecule" as used herein can refer to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as insulin, hepatitis B vaccine, interferon, granulocyte colony-stimulating factor, streptokinase and others.

As used herein, the term "HTP genetic design library" or "library" refers to collections of genetic perturbations according to the present disclosure. In some embodiments, the libraries of the present disclosure may manifest as i) a collection of sequence information in a database or other computer file, ii) a collection of genetic constructs encoding for the aforementioned series of genetic elements, or iii) host cell strains comprising said genetic elements. In some embodiments, the libraries of the present disclosure may refer to collections of individual elements (e.g., collections of promoters for PRO swap libraries, collections of terminators for STOP swap libraries, collections of protein solubility tags for SOLUBILITY TAG swap libraries, or collections of protein degradation tags for DEGRADATION TAG swap libraries). In other embodiments, the libraries of the present disclosure may also refer to combinations of genetic elements, such as combinations of promoter:genes, gene:terminator, or even promoter:gene:terminators. In some embodiments, the libraries of the present disclosure may also refer to combinations of promoters, terminators, protein solubility tags and/or protein degradation tags. In some embodiments, the libraries of the present disclosure further comprise meta data associated with the effects of applying each member of the library in host organisms. For example, a library as used herein can include a collection of promoter::gene sequence combinations, together with the resulting effect of those combinations on one or more phenotypes in a particular species, thus improving the future predictive value of using said combination in future promoter swaps.

As used herein, the term "SNP" refers to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or non-synonymous SNPs" refers to mutations that lead to coding changes in host cell proteins A "high-throughput (HTP)" method of genomic engineering may involve the utilization of at least one piece of automated equipment (e.g. a liquid handler or plate handler machine) to carry out at least one-step of said method.

The term "polynucleotide" as used herein encompasses oligonucleotides and refers to a nucleic acid of any length. Polynucleotides may be DNA or RNA. Polynucleotides may be single-stranded (ss) or double-stranded (ds) unless otherwise specified. Polynucleotides may be synthetic, for example, synthesized in a DNA synthesizer, or naturally occurring, for example, extracted from a natural source, or derived from cloned or amplified material. Polynucleotides referred to herein can contain modified bases or nucleotides.

The term "pool", as used herein, can refer to a collection of at least 2 polynucleotides. In some embodiments, a set of polynucleotides may comprise at least 5, at least 10, at least 12 or at least 15 or more polynucleotides.

The term "overlapping sequence", or "overlapping assembly sequence" or "assembly overlap sequence" as used herein can refer to a sequence that is complementary in two polynucleotides and where the overlapping sequence is ss, on one polynucleotide such that it can be hybridized to another overlapping complementary ss region on another polynucleotide. An overlapping sequence may be at or close to (e.g., within about 5, 10, 20 nucleotides of) the terminal ends of two distinct polynucleotides. For example, if the two distinct polynucleotides are single-stranded, then the assembly overlap sequence would be present on the 3' terminal ends of each of the single-stranded polynucleotides. Alternatively, if the two distinct polynucleotides are double-stranded, then the assembly overlap sequence of one of the polynucleotides can be present on the 3' terminal end of said polynucleotide (i.e., 3' end in reference to the top strand of the ds polynucleotide), while the complementary assembly overlap sequence on the other polynucleotide can be present at the 5' end of said polynucleotide (i.e., 5' end in reference to the top strand of the ds polynucleotide) As necessary, the assembly overlap sequence on any ds polynucleotide may be made available by removing any non-overlapping sequence. The removal can be enzymatic such as through the use of a 3'-5' exonuclease activity of a polymerase.

As used herein, the term "assembling", can refer to a reaction in which two or more, four or more, six or more, eight or more, ten or more, 12 or more, 15 or more polynucleotides, e.g., four or more polynucleotides are joined to another to make a longer polynucleotide.

As used herein, the term "incubating under suitable reaction conditions", can refer to maintaining a reaction a suitable temperature and time to achieve the desired results, i.e., polynucleotide assembly. Reaction conditions suitable for the enzymes and reagents used in the present method are known (e.g. as described in the Examples herein) and, as such, suitable reaction conditions for the present method can be readily determined. These reactions conditions may change depending on the enzymes used (e.g., depending on their optimum temperatures, etc.).

As used herein, the term "joining", can refer to the production of covalent linkage between two sequences.

As used herein, the term "composition" can refer to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

As used herein a "vector" is a suitable DNA into which a fragment or DNA assembly may be integrated such that the engineered vector can be replicated in a host cell. A linearized vector may be created restriction endonuclease digestion of a circular vector or by PCR. The concentration of fragments and/or linearized vectors can be determined by gel electrophoresis or other means.

Overview

Provided herein are methods and compositions that facilitate multiple assemblies to be produced in a single reaction in a deterministic rather than combinatorial manner. The methods and compositions provided herein impart the time, cost, and throughput benefits of multiplexed assembly while still enabling the creation of a library where all output assemblies are determined in advance. The methods and compositions provided herein allow for the creation of many plasmids or constructs in a single assembly reaction, reducing the number of total reactions required to create libraries of thousands of plasmids or constructs. The methods and compositions provided herein also allows for assembling a defined subset of desired plasmids or constructs out of a larger set of numerous possible combinations. In some cases, the methods and compositions provided herein minimizes the number of unique parts ('homology arms') that need to be amplified from genomes (or synthesized) by not including any payload or insert sequence-specific assembly overlaps. This can eliminate the need to amplify multiple copies of the same homology-arm pair designed to be combined with multiple payloads or insert sequences. Further, diversity arising from combinations of payload/insert sequence and homology arm pairs is specified by sequences on the payload/insert sequence itself. The multitude of resulting payload sequences can be produced synthetically and inexpensively. Libraries generated using the methods and compositions provided herein can be suitable for any number of applications such as, for example, any genome editing methods or any pooled pathway assembly. The genome editing methods known in the art can be those that do not require tailored sites for RCME (recombinase cassette mediated exchange) for editing the genome of a cell at multiple arbitrary locations such as, for example, scarless genomic editing.

Provided herein is a composition comprising a mixture of polynucleotides for assembly in a deterministic fashion of a library of nucleic acid constructs. The mixture can comprise n pools of polynucleotide parts (e.g., first and second polynucleotides). The n pools can be at most, at least, or exactly 2, 3, 4, 5, 6, 7, 8, 9, 10, 11, 12, 13, 14, 15, 16, 17, 18, 19 or 20 pools of polynucleotide. The n pools can each comprise an equal number of polynucleotide parts or they can comprise differing numbers of polynucleotide parts (e.g., first and second polynucleotides). In one embodiment, the mixture comprises 2 pools such that one of the two pools comprises first polynucleotides and the other of the two pools comprises second polynucleotides. Each pool of first polynucleotides can comprise a paired second polynucleotide in a separate pool of second polynucleotides. Further to any of the above embodiments, the mixture can further comprise n−1 pools of insert or bridging polynucleotides. Each insert or bridging polynucleotide can comprise sequence complementary to an element of one of the n pools of polynucleotide parts (e.g., first polynucleotide) at its 5' end and to an element of one of the other pools of polynucleotide parts (e.g., second polynucleotide) at its 3' end. The insert sequences can be designed such that the assembly results in a library of polynucleotides where each polynucleotide comprises a specific element from each of the n pools of polynucleotide parts, interspersed with a specific element from each of the n−1 pools of insert polynucleotides.

The mixture of polynucleotides can comprise: a first pool containing pairs of polynucleotides, wherein each pair in the first pool contains a first polynucleotide and a second polynucleotide; and a second pool of insert polynucleotides, wherein each insert polynucleotide in the second pool comprises a first assembly overlap sequence at its 5' end that is complementary to a 3' end of a first polynucleotide and a second assembly overlap sequence at its opposing 3'end that is complementary to a 5' end of a second polynucleotide in a pair of polynucleotides from the first pool. In one embodiment, the composition can further comprise a cloning vector, wherein, for each pair in the first pool, a 5' end of the first polynucleotide and a 3' end of the second polynucleotide comprises sequence complementary to the cloning vector. The cloning vector can be any cloning vector known in the art that is suitable for propagation in a host cell such as, for example, E. coli or S. cerevisiae. In another embodiment, the composition also comprises a polymerase, an exonuclease, a ligase or any combination thereof. The polymerase can be strand displacing or non-strand displacing. The exonuclease can be a 5'-3' exonuclease. The pairs of polynucleotides in the first pool can be double-stranded, single-stranded or a combination thereof. The insert polynucleotides in the second pool can be double-stranded, single-stranded, or a combination thereof. In one embodiment, the polymerase is non-strand displacing and the composition further comprises a crowding agent. The crowding agent can be selected from polyethylene glycol (PEG), ficoll or dextran. In one embodiment, the crowding agent is PEG. The PEG can be used at a concentration of from about 3 to about 7% (weight/volume). The PEG can be selected from PEG-200, PEG-4000, PEG-6000, PEG-8000 or PEG-20,000. In another embodiment, the polymerase is strand displacing and the composition further comprises a single-stranded binding protein. The single strand DNA binding protein can be an extreme thermostable single-stranded DNA binding protein (ET SSB), E. coli recA, T7 gene 2.5 product, phage lambda RedB or Rac prophage RecT.

In one embodiment, a composition provided herein is a mixture of the following polynucleotides: (1) one or more first polynucleotides, (2) one or more insert polynucleotides, wherein the insert polynucleotide comprises a first assembly overlap sequence at its 5' end and a second assembly overlap sequence at its opposing 3'end, and (3) one or more second polynucleotides. In another embodiment, the composition is a mixture of the following polynucleotides: (1) one or more first polynucleotides, (2) one or more insert polynucleotides, wherein the insert polynucleotide comprises a first assembly overlap sequence at its 5' end and a second assembly overlap sequence at its opposing 3'end, (3) one or more second polynucleotides and (4) a cloning vector. Each of the one or more first polynucleotides can comprise sequence at its 3' or distal end that is complementary to the first assembly overlap sequence present at the 5' or proximal end of an insert polynucleotide from the one or more insert polynucleotides. Each of the one or more second polynucleotides can comprise sequence at its 5' or proximal end that is complementary to the second assembly overlap sequence present at the 3' or distal end of an insert polynucleotide from the one or more insert polynucleotides. Each of the one or more first polynucleotides can be paired with at least one of the one or more second polynucleotides, thereby forming one or more pairs of first and second polynucleotides. Each pair of first and second polynucleotides can comprise sequence at the distal end of the first polynucleotide that is complementary to the first assembly overlap sequence on the proximal end of an insert polynucleotide from the one or more insert polynucleotides as well as sequence at the proximal end of the second polynucleotide that is complementary to the distal end of an insert polynucleotide from the one or more insert polynucleotides.

Provided herein is a method for generating libraries of polynucleotides, the method comprising: a.) combining n pools of polynucleotide parts (e.g., first and second polynucleotides) and n−1 pools of insert or bridging polynucleotides; and b.) assembling the n pools of polynucleotide parts and n−1 pools of insert polynucleotides into a library of polynucleotides, wherein each polynucleotide in the library comprises a defined combination of an individual element from each of the n pools of polynucleotide parts and bridging polynucleotides. Each insert or bridging polynucleotide in the n−1 pools of insert or bridging polynucleotides comprises a first assembly overlap sequence at its 5' end that is complementary to a 3' end of a first polynucleotide and a second assembly overlap sequence at its opposing 3'end that is complementary to a 5' end of a second polynucleotide in the n pools of first and second polynucleotides. The assembling can be performed via in vitro or in vivo overlap assembly methods. In some cases, the assembling is performed via an in vitro cloning method, wherein the mixture of the n pools of polynucleotide parts and n−1 pools of insert or bridging polynucleotides is heated to partially or fully denature any double-stranded polynucleotide parts present, then cooled at a slow rate to room temperature before being subjected to the in vitro cloning method.

Also provided herein is a method for generating libraries of polynucleotides, the method comprising: (a) combining a first pool of polynucleotides and a second pool of polynucleotides, wherein the first pool contains pairs of polynucleotides, wherein each pair in the first pool contains a first polynucleotide and a second polynucleotide, wherein the second pool contains insert polynucleotides, wherein each insert polynucleotide in the second pool comprises a first assembly overlap sequence at its 5' end that is complementary to a 3' end of a first polynucleotide and a second assembly overlap sequence at its opposing 3'end that is complementary to a 5' end of a second polynucleotide in a pair of polynucleotides from the first pool; (b) assembling the first pool and the second pool into a library of polynucleotides, wherein each polynucleotide in the library comprises an insert polynucleotide from the second pool and a pair of first polynucleotides and second polynucleotides from the first pool. The assembling can be performed via in vitro or in vivo overlap assembly methods. In some cases, the assembling is performed via an in vitro cloning method, wherein the mixture of the first pool and the second pool is heated to partially or fully denature polynucleotides present in the first and the second pools, then cooled at a slow rate to room temperature before being subjected to the in vitro cloning method. In some cases, the method further comprises combining a cloning vector with the first pool and the second pool during step (a), wherein opposing ends of the cloning vector comprise sequence complementary to a 5'end of the first polynucleotide and a 3' end of the second polynucleotide for each pair in the first pool. In some cases, the method further comprises combining a cloning vector with the first pool prior to step (a), wherein opposing ends of the cloning vector comprise sequence complementary to a 5'end of the first polynucleotide and a 3' end of the second polynucleotide for each pair in the first pool. In some cases, the cloning vector and the 5'end of the first polynucleotide and the 3'end of the second polynucleotide in each pair from the first pool comprise one or more recognition sequences for one or more site-specific nucleases. In some cases, the method further comprises generating single-stranded complementary overhangs between the opposing ends of the cloning vector and the 5'end of the first polynucleotide and the 3'end of the second polynucleotide in each pair from the first pool by adding the one or more site-specific nucleases for the one or more recognition sequences. In some cases, the method further comprises ligating the single-stranded complementary overhangs between the opposing ends of the cloning vector and the 5'end of the first polynucleotide and the 3'end of the second polynucleotide in each pair from the first pool. The ligating can be performed using a DNA ligase. In some cases, step (b) results in a circular product comprising an insert polynucleotide from the second pool, a first and second polynucleotide from a pair from the first pool and the cloning vector.

In one aspect, provided herein is a method for generating libraries of polynucleotides, the method comprising: (a) amplifying via polymerase chain reaction (PCR) a first pool of polynucleotides, wherein the first pool contains pairs of polynucleotides, wherein each pair in the first pool contains a first polynucleotide and a second polynucleotide, and wherein each first polynucleotide and each second polynucleotide in a pair comprises a 5' end and a 3' end, wherein the amplifying introduces a common overlap sequence comprising one or more recognition sequences for one or more site-specific nucleases onto the 5' end of a first polynucleotide and the 3'end of a second polynucleotide in a pair from the first pool; (b) assembling each pair of first polynucleotides and second polynucleotides from the first pool into a single nucleic acid fragment by utilizing common overlap sequence, wherein the single nucleic fragment for each pair comprises a first polynucleotide and second polynucleotide separated by the common overlap sequence from the 5' end of the first polynucleotide and the 3' end of the second polynucleotide, and wherein the 3'end of the first polynucleotide and the 5' end of the second polynucleotide in the single nucleic fragment for each pair are located on opposing terminal ends of the single nucleic acid fragment, distal to the one or more site-specific nuclease recognition sequence(s); (c) combining the single nucleic acid fragments for each pair with a second pool containing insert polynucleotides, wherein each insert polynucleotide in the second pool comprises a first assembly overlap sequence at its 5' end that is complementary to the 3' end of the first polynucleotide present within the single nucleic acid fragment and a second assembly overlap sequence at its opposing 3'end that is complementary to the 5' end of the second polynucleotide present within the single nucleic acid fragment; (d) assembling the first pool and the second pool into a third pool of circularized products, wherein the assembling is performed via in vitro or in vivo overlap assembly methods, and wherein each circularized product in the third pool comprises an insert sequence from the second pool and a pair of first polynucleotides and second polynucleotides from the first pool; (e) linearizing each circularized product in the third pool via digestion by one or more site-specific nuclease(s) that recognizes the one or more site-specific nuclease recognition sequence(s) located between the first polynucleotide sequence and the second polynucleotide sequence in each of the circularized products in the third pool; and (f) assembling the linearized products into cloning vectors by in vitro or in vivo cloning methods. In some cases, the common overlap sequence comprises an assembly overlap sequence of at least 1 nucleotide and the assembly in step (b) is performed by an overlap-based DNA assembly method. In some cases, the common overlap sequence comprises an assembly overlap sequence of from 10-25 nucleotides and the assembly in step (b) is performed by an overlap-based DNA assembly method. In some cases, the overlap-based DNA assembly method is selected from SOE-PCR or an in vitro overlap-assembly method (e.g., HiFi assembly using NEB® HiFi builder). In some cases, the one or more site-specific nuclease recognition sequence(s) present in the common overlap sequence on the 5' end of the first polynucleotide is complementary to the one or more site-specific nuclease recognition sequence(s) present in the common overlap sequence on the 3' end of the second polynucleotide in each pair, and wherein the utilizing the common overlap sequences of the first and second polynucleotides in each pair in step (b) entails performing SOE-PCR. In some cases, the utilizing the common overlap sequences of the first and second polynucleotides in each pair in step (b) entails digesting the one or more site-specific nuclease recognition sequences present in the common overlap sequence on the 5' end of the first polynucleotide and the 3' end of the second polynucleotide in each pair with one or more site specific nucleases for the one or more site-specific nuclease recognition sequences to generate single-stranded overhangs on the 5' end of the first polynucleotide and the 3' end of the second polynucleotide in each pair that comprise complementary sequence; and ligating the complementary sequence present on the single-stranded overhang on the 5' end of the first polynucleotide and the 3' end of the second polynucleotide in each pair. The assembling in step (d) can be performed via in vitro or in vivo overlap assembly methods. The assembling of step (d) can be performed using an overlap-based DNA assembly method. The overlap-based DNA assembly can be selected from SOE-PCR and an in vitro overlap-assembly method (e.g., HiFi assembly using NEB® HiFi builder). In some cases, the 3' end of the first polynucleotide and the 5' end of the second polynucleotide in the single nucleic acid fragment in each pair comprise an additional set of one or more site-specific nuclease recognition sequences and the first assembly overlap sequence and the second assembly overlap sequence in each insert polynucleotide in the second pool comprise one or more site-specific nuclease recognition sequences. In some cases, the assembling in step (d) entails digesting the additional one or more site-specific nuclease recognition sequences present on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool with one or more site specific nucleases for the additional one or more site-specific nuclease recognition sequences on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool to generate a single-stranded overhang on the 3' end of the first polynucleotide that comprises sequence complementary to sequence present on a single-stranded overhang on the 5'end of the first assembly sequence of an insert polynucleotide from the second pool and a single stranded overhang on the 5' end of the second polynucleotide that comprises sequence complementary to a sequence present on a single-stranded overhang on the 3'end of the second assembly sequence of the same insert polynucleotide from the second pool; and ligating the complementary sequence present on the single-stranded overhangs. In some cases, the assembling of step (d) is performed via an in vitro cloning method, wherein the mixture of the first pool and the second pool is heated to partially or fully denature polynucleotides present in the first and the second pools, then cooled at a slow rate to room temperature before being subjected to the in vitro cloning method. The assembling in step (f) can be performed via in vitro cloning methods or in vivo cloning methods. In some cases, the cloning vectors of step (f) comprise one or more site-specific nuclease recognition sequences. In some cases, the assembling in step (f) entails digesting the one or more site-specific nuclease recognition sequences in the cloning vectors with the one or more site-specific nucleases for the one or more site-specific nuclease recognition sequences recognition sequences present in the cloning vectors, wherein the digesting generates single-stranded overhangs on opposing ends of the cloning vectors, wherein the single-stranded overhang on one of the opposing ends of the cloning vector comprises sequence complementary to an end of the linearized product generated in step (e) and the single-stranded overhang on the other of the opposing ends of the cloning vectors comprises sequence complementary to an opposing end of the linearized product generated in step (e); and ligating the complementary sequences present on the single-stranded overhangs of the cloning vectors and the linearized products from step (e). A site-specific nuclease for use in any method or composition provided herein can be selected from a restriction endonuclease, Type IIs endonuclease(s), a homing endonuclease, an RNA-guided nuclease, a DNA-guided nuclease, a zinc-finger nuclease, a TALEN and a nicking enzyme or any combination thereof. The one or more site-specific nuclease recognition sequence(s) located between the first polynucleotide sequence and the second polynucleotide sequence can be one or more homing nuclease recognition sequence(s). The one or more site-specific nuclease(s) for the one or more site-specific nuclease recognition sequence(s) located between the first polynucleotide sequence and the second polynucleotide sequence can be a homing endonuclease.

In another aspect, provided herein is a method for generating libraries of polynucleotides, the method comprising: (a) amplifying via polymerase chain reaction (PCR) a first pool of polynucleotides, wherein the first pool contains pairs of polynucleotides, wherein each pair in the first pool contains a first polynucleotide and a second polynucleotide, and wherein each first polynucleotide and each second polynucleotide in a pair comprises a first terminal 5' end and an opposing a second terminal 3' end, wherein the amplifying introduces one or more recognition sequences for one or more site-specific nuclease(s) onto the first terminal 5' end of a first polynucleotide and the 3'end of a second polynucleotide in a pair from the first pool, wherein the one or more recognition sequences for the one or more site-specific nuclease(s) on the first terminal 5' end of the first polynucleotide is complementary to the one or more recognition sequences for the one or more site-specific nuclease(s) on the first terminal 3' end of the second polynucleotide in the pair; (b) assembling each pair of first polynucleotides and second polynucleotides from the first pool into a single nucleic acid fragment by performing a splicing and overlap extension polymerase chain reaction (SOE-PCR) utilizing the one or more complementary site-specific nuclease recognition sequence(s) on the first terminal 5' ends of the first polynucleotides and the 3' ends of the second polynucleotides within each pair, wherein the single nucleic fragment for each pair comprises a first polynucleotide and second polynucleotide separated by the one or more site-specific nuclease recognition sequence(s) from the first terminal 5' ends of the first polynucleotides and the 3' end of the second polynucleotides, and wherein the opposite second terminal 3' ends of the first polynucleotide and the 5' end of the second polynucleotide in the single nucleic fragment for each pair are located on opposing terminal ends of the single nucleic acid fragment, distal to the one or more site-specific nuclease recognition sequence(s); (c) combining the single nucleic acid fragments for each pair with a second pool containing insert polynucleotides, wherein each insert polynucleotide in the second pool comprises a first assembly overlap sequence at its 5' end that is complementary to the opposing terminal end one of the opposing 3' terminal end of the first polynucleotides present within the single nucleic acid fragment and a second assembly overlap sequence at its opposing 3'end that is complementary to the other of the opposing terminal 5' end of the second polynucleotides present within the single nucleic acid fragment; (d) assembling the first pool and the second pool into a third pool of circularized products, wherein the assembling is performed via in vitro or in vivo overlap assembly methods, and wherein each circularized product in the third pool comprises an insert sequence from the second pool and a pair of first polynucleotides and second polynucleotides from the first pool; (e) linearizing each circularized product in the third pool via addition of one or more site-specific nuclease(s) that recognizes the one or more site-specific nuclease recognition sequence(s) located between the first polynucleotide sequence and second polynucleotide sequence in each of the circularized products in the third pool; and (f) assembling the linearized products into cloning vectors by in vitro or in vivo cloning methods. The assembling in step (d) can be performed via in vitro or in vivo overlap assembly methods. In some cases, the assembling of step (d) is performed using an overlap-based DNA assembly method. The overlap-based DNA assembly can be selected from SOE-PCR and an in vitro overlap-assembly method (e.g., HiFi assembly using NEB® HiFi builder). In some cases, the 3' end of the first polynucleotide and the 5' end of the second polynucleotide in the single nucleic acid fragment in each pair comprise an additional set of one or more site-specific nuclease recognition sequences and the first assembly overlap sequence and the second assembly overlap sequence in each insert polynucleotide in the second pool comprise one or more site-specific nuclease recognition sequences. In some cases, the assembling in step (d) entails digesting the additional one or more site-specific nuclease recognition sequences present on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool with one or more site specific nucleases for the additional one or more site-specific nuclease recognition sequences on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool to generate a single-stranded overhang on the 3' end of the first polynucleotide that comprises sequence complementary to sequence present on a single-stranded overhang on the 5'end of the first assembly sequence of an insert polynucleotide from the second pool and a single stranded overhang on the 5' end of the second polynucleotide that comprises sequence complementary to a sequence present on a single-stranded overhang on the 3'end of the second assembly sequence of the same insert polynucleotide from the second pool; and ligating the complementary sequence present on the single-stranded overhangs. In some cases, the assembling of step (d) is performed via an in vitro cloning method, wherein the mixture of the first pool and the second pool is heated to partially or fully denature polynucleotides present in the first and the second pools, then cooled at a slow rate to room temperature before being subjected to the in vitro cloning method. The assembling in step (f) can be performed via in vitro cloning methods or in vivo cloning methods. In some cases, the cloning vectors of step (f) comprise one or more site-specific nuclease recognition sequences. In some cases, the assembling in step (f) entails digesting the one or more site-specific nuclease recognition sequences in the cloning vectors with the one or more site-specific nucleases for the one or more site-specific nuclease recognition sequences recognition sequences present in the cloning vectors, wherein the digesting generates single-stranded overhangs on opposing ends of the cloning vectors, wherein the single-stranded overhang on one of the opposing ends of the cloning vector comprises sequence complementary to an end of the linearized product generated in step (e) and the single-stranded overhang on the other of the opposing ends of the cloning vectors comprises sequence complementary to an opposing end of the linearized product generated in step (e); and ligating the complementary sequences present on the single-stranded overhangs of the cloning vectors and the linearized products from step (e). A site-specific nuclease for use in any method or composition provided herein can be selected from a restriction endonuclease, Type IIs endonuclease(s), a homing endonuclease, an RNA-guided nuclease, a DNA-guided nuclease, a zinc-finger nuclease, a TALEN and a nicking enzyme or any combination thereof.

In one embodiment, the first polynucleotides and the second polynucleotides in the methods and compositions provided herein comprise sequence complementary or corresponding to a target genomic locus in a host cell. The sequence complementary or corresponding to the target genomic locus present in the first and second polynucleotides can be located on the terminus of said first and second polynucleotide that opposes the terminus of said first and second polynucleotides that comprise sequence complementary to assembly overlap sequences present on an insert polynucleotide. When comprising sequence complementary or corresponding to a target genomic locus in a host cell, the first and second polynucleotides can be referred to as homology arms. In particular, each first polynucleotide can be referred to as a left homology arm, while each second polynucleotide can be referred to as a right homology arm. When comprising sequence complementary or corresponding to a target genomic locus in a host cell, generation of libraries of nucleic acid constructs through assembly of pairs of first and second polynucleotides and insert polynucleotides using the compositions and methods provided herein can be subsequently used in genome editing techniques for modifying the genome of a host cell. The host cell can be a prokaryotic cell or a eukaryotic host cell.

Polynucleotide Pairs

As described herein, the compositions and methods provided herein can comprise or utilize first polynucleotides and second polynucleotides such that each first polynucleotide is paired with a second polynucleotide. The first and second polynucleotides can be chemically synthesized (e.g., array synthesized or column synthesized) using any of the methods known in the art for synthesizing nucleic acids. The first and second polynucleotides can be amplified via an extension reaction (e.g., PCR) from existing DNA such as, for example, genomic DNA.

Each of the first and second polynucleotides can comprise functional and nonfunctional sequence or a combination thereof. The functional sequence can refer to sequence that represents a gene or a portion or domain thereof or a regulatory element or a portion thereof. As described further herein, the gene or the portion thereof can encode a protein that is part of a metabolic or biochemical pathway. Also as described further herein, the regulatory element can be a promoter, terminator, solubility tag, degradation tag or degron. The non-functional sequence can refer to sequence the does not represent a gene or portion thereof or a regulatory element or a portion thereof. The non-functional sequence can be sequence that aids in or is utilized for the assembly of said first and second polynucleotides with an insert polynucleotide as provided herein. In one embodiment, each of the first and second polynucleotides comprises a mixture of functional and non-functional sequence. In another embodiment, each of the first and second polynucleotides comprises of one or the other of functional or non-functional sequence. In embodiments where the first and second polynucleotides comprise only functional sequence, the functional sequence or a portion of the functional sequence can be utilized for the assembly of said first and second polynucleotides with an insert polynucleotide as provided herein.

The first and/or second polynucleotides can each vary in length and, in some cases, can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 200, 300, 400, 500, 600, 700, 800, 900, 950 or 1000 nucleotide bases in length and/or may be more than 1 kb or 2 kb in length. Alternatively, the first and/or second polynucleotides can be 2 kb or more, or 1 kb or more or more than 900 bases, 800 bases, 700 bases, 600 bases, 500 bases, 400 bases, 300 bases, 200 bases or 100 bases in length. The first and/or second polynucleotides length can be in the range of 100 nucleotides-2 kb for example up to 100, up to 150, up to 200, up to 250, up to 300, up to 350, up to 400, up to 450, up to 500, up to 550, up to 600, up to 650, up to 700, up to 750, or up to 800, up to 850, up to 900, up to 950, up to 1000, up to 1500, or up to 2000 nucleotides. The minimum length of the first and/or second polynucleotides may be defined by a preferable Tm that is determined empirically.

As described herein, each of the first and second polynucleotide sequences can comprise sequence that aids in the assembly of said first and second polynucleotides with an insert polynucleotide. In order to aid in said assembly, said sequence can be complementary to the assembly overlap sequences present on insert polynucleotides. The sequence complementary to the assembly overlap sequences present on insert polynucleotides can also be referred to as assembly overlap sequences. In one embodiment, the assembly overlap sequences represent the entire first and/or second polynucleotide. In another embodiment, the assembly overlap sequences represent only a portion of the first and/or second polynucleotides and the first and/or second polynucleotides further comprise additional sequence beyond the assembly overlap sequences. In one embodiment, a first polynucleotide in a pair of first and second polynucleotides as provided herein comprises an assembly overlap sequence at its distal or 3'end that is complementary to a first assembly overlap sequence present at a 5' or proximal end of an insert polynucleotide, while a second polynucleotide in said pair comprises an overlap assembly overlap sequence at its proximal or 5'end that is complementary to a second assembly overlap sequence present at a 3' or distal end of said insert polynucleotide. Further to this embodiment, the first and second polynucleotide can each comprise additional sequence beyond the assembly overlap sequences. The additional sequence of the first and/or second polynucleotides can tailor said first and/or second polynucleotides to a specific application. The specific application can be any applications that utilize nucleic acid libraries known in the art, especially those that would benefit from a pooled deterministic assembly. Exemplary uses can include, but not be limited to, genome editing and pathway assembly.

The assembly overlap sequences present on a first and/or second polynucleotide can vary in length and, in some cases, can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 nucleotides in length and/or may be up 100 nucleotides in length (e.g., up to 50, up to 30, up to 25, up to 20 or up to 15 nucleotides in length). The assembly overlap sequences length can be in the range of 15 nucleotides-100 nucleotides for example up to 20, up to 25, up to 30, up to 35, up to 40, up to 45, up to 50, up to 55, up to 60, up to 65, up to 70, up to 75, up to 80 nucleotides, up to 85 nucleotides, up to 90 nucleotides, up to 95 nucleotides or up to 100 nucleotides. The assembly overlap sequences can be the same length as an assembly overlap sequence present on an insert polynucleotide. The minimum length of the assembly overlap sequence may be defined by a preferable Tm that is determined empirically. In one embodiment, the assembly overlap sequence on a first and/or second polynucleotide comprises 1 or more nucleotides that are complementary to an end of an insert polynucleotide. In another embodiment, the assembly overlap sequence on a first and/or second polynucleotide comprises about 25 nucleotides that are complementary to an end of an insert polynucleotide.

As shown in FIG. 1, each of the pairs of first and second polynucleotides can further comprise vector overlap sequences with a cloning vector such that the first polynucleotides (i.e., the first DNA fragment in FIG. 1) may comprise a vector overlap sequence to the cloning vector at its 5' end, while the second polynucleotides (i.e., the second DNA fragment in FIG. 1) may comprise vector overlap sequences to the cloning vector at its 3' end. In embodiments, where each of the first polynucleotide and the second polynucleotide in a pair further comprise the first and second DNA fragments as provided herein, said first and second DNA fragments can be located downstream and adjacent to the vector overlap sequence to the cloning vector in the first polynucleotide and upstream and adjacent to the vector overlap sequence to the cloning vector in the second polynucleotide.

The vector overlap sequences can vary in length and, in some cases, can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 nucleotides in length and/or may be up 100 nucleotides in length (e.g., up to 50, up to 30, up to 25, up to 20 or up to 15 nucleotides in length). Alternatively, the vector overlap sequences can be 2 kb or less, or 1 kb or less or less than 900 bases, 800 bases, 700 bases, 600 bases, 500 bases, 400 bases, 300 bases, 200 bases or 100 bases. The vector overlap sequences length can be in the range of 15 nucleotides-80 nucleotides for example up to 20, up to 25, up to 30, up to 35, up to 40, up to 45, up to 50, up to 55, up to 60, up to 65, up to 70, up to 75, or up to 80 nucleotides. The minimum length of the vector overlap sequence may be defined by a preferable Tm that is determined empirically.

In one embodiment, a pool containing pairs of first and second polynucleotides is generated by selecting pairs of first and second polynucleotide sequences from a larger set of such sequences such that no polynucleotide from said pool shares common sequence with any other polynucleotide from said pool beyond a specified threshold, excluding designed overlap assembly sequences between the pairs of polynucleotides of said pool and insert polynucleotides or pools thereof as provided herein, or said pool and a cloning vector. The specified threshold is at least 1, 2, 3, 4, 5, 6, 7, 8, 9, 10, 11, 12, 13, 14, 15, 16, 17, 18, 19 or 20 contiguous nucleotides. The specified threshold is at most 1, 2, 3, 4, 5, 6, 7, 8, 9, 10, 11, 12, 13, 14, 15, 16, 17, 18, 19 or 20 contiguous nucleotides. The specified threshold between 0 and 2, between 1 and 3, between 2 and 4, between 3-5, between 4 and 6, between 5 and 7, between 6 and 8, between 7 and 9, between 8 and 10, between 9 and 11, between 10 and 12, between 11 and 13, between 12 and 14, between 13 and 15, between 14 and 16, between 15 and 17, between 16 and 18, between 17 and 19, between 18 and 20 or between 19 and 21 contiguous nucleotides. The specified threshold between 0 and 5, between 0 and 10, between 0 and 15, between 0 and 20, between 5 and 10, between 5 and 15, between 5 and 20, between 10 and 15 or between 10 and 20 contiguous nucleotides. In one embodiment, the specified threshold is 12 contiguous nucleotides. Determination of a shared common sequence beyond the specified threshold can be done using a computer program that uses either BLAST analysis or simple substring searching to determine whether components share sequence with other components. If shared sequence is found beyond the specified threshold the components would not be placed into a pool together.

Figure 2:
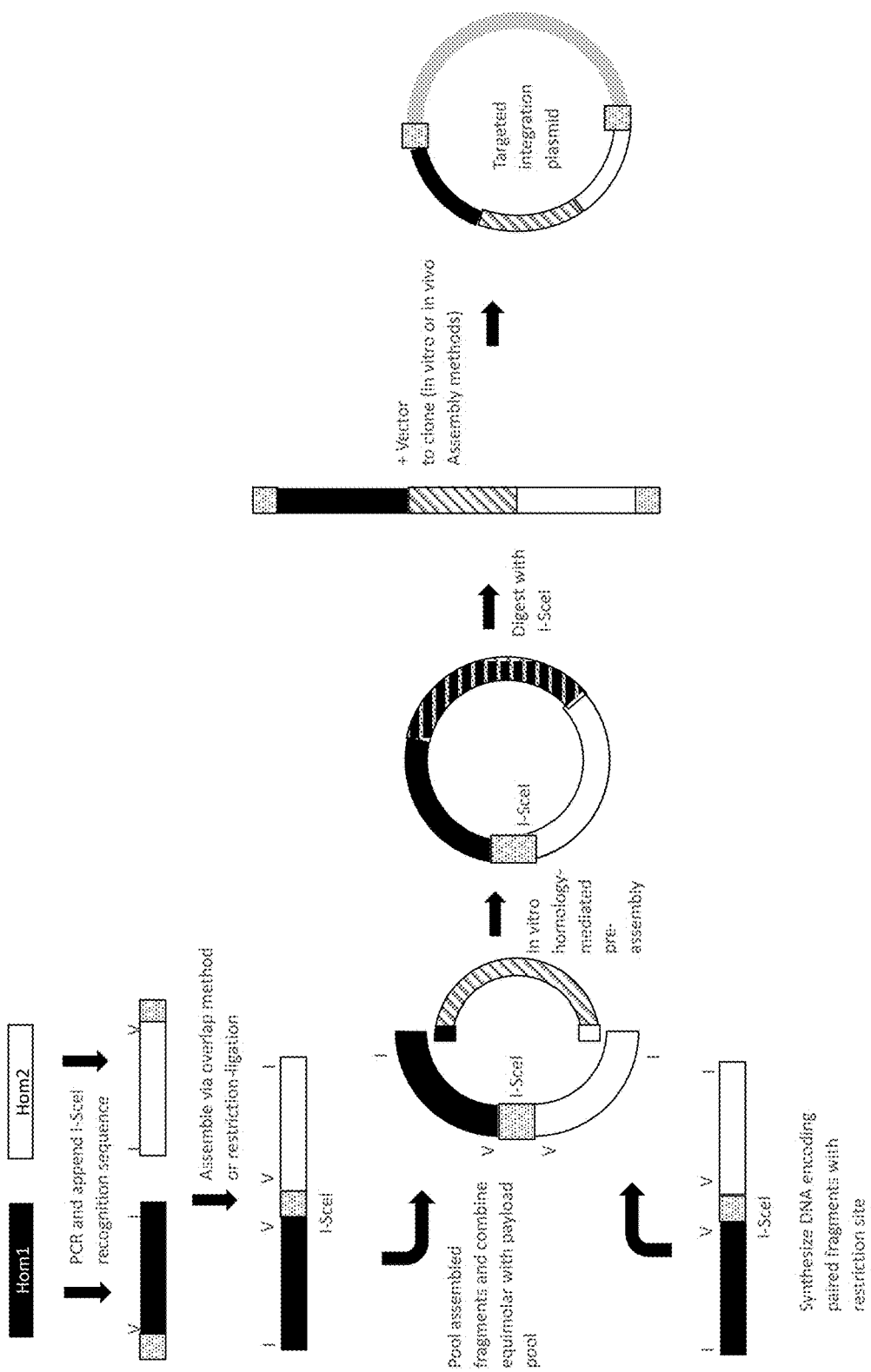
FIG. 2 illustrates an inside-out assembly method to pre-associate first and second polynucleotides for use in the method of FIG. 1 to allow for assembling insert polynucleotides (e.g., promoters) longer than a maximum synthetic oligonucleotide length.

In one embodiment, pairing of an insert polynucleotide as described herein with a desired pair of first and second polynucleotides can be facilitated by preassembling the desired pair of first and second polynucleotides using an "inside-out assembly" method as shown in FIG. 2. In this method, the first and second polynucleotides can be amplified by PCR such that the vector proximal ends of the first polynucleotides each contain one or more -unique site-specific nuclease site(s) or recognition sequence(s). The site-specific nuclease recognition sequences can be for site-specific nucleases selected from a restriction endonuclease, Type IIs endonuclease(s), a homing endonuclease, an RNA-guided nuclease, a DNA-guided nuclease, a zinc-finger nuclease, a TALEN and a nicking enzyme and any combinations thereof. In one embodiment, the vector proximal ends of the first polynucleotides each contain a single unique nuclease site or recognition sequence. In one embodiment, the unique nuclease recognition sequence is a unique restriction endonuclease site such that said restriction endonuclease site is not present in any of the polynucleotides present in a composition provided herein. In one embodiment, the unique nuclease site is a homing endonuclease sequence such as, for example, a homing endonuclease sequence specific for I-SceI or I-CeuI. A single pair of first and second polynucleotides are combined and a splicing and overlap extension polymerase chain reaction (SOE-PCR) is performed to assemble the two polynucleotides at the added unique nuclease sites (e.g. at the vector-proximal ends) leaving the ends that attach to an insert polynucleotide free. Alternatively, the entire sequence comprising the linked first and second polynucleotides can be synthesized directly using any of a variety of DNA synthesis methods known in the art. The attached first and second polynucleotides are assembled with the insert polynucleotide using an in vitro or in vivo overlap assembly method known in the art and/or provided herein, such as, for example, yeast (e.g., *S cerevisiae*) or *E. coli* homologous recombination based assembly, Gibson assembly or NEB® HiFi builder. The circularized product of the first and second polynucleotides with the insert polynucleotide can be linearized with the addition of the nuclease specific for the unique nuclease sequence (e.g., the homing endonuclease for the specific homing endonuclease sequence) resulting in the insert polynucleotide being flanked by the first and second polynucleotides which can then be assembled into the vector using Gibson assembly or other similar method.

Insert Polynucleotides/Payload Sequences

In one embodiment, an insert polynucleotide for use in a composition, kit or method provided herein comprises: (1) a first assembly overlap sequence on a 5' or proximal end of said insert polynucleotide, and (2) a second assembly overlap sequence on an opposing 3' or distal end of said insert polynucleotide. Further to this embodiment, the first assembly overlap sequence can comprise sequence complementary to sequence (e.g., an assembly overlap sequence) at a 3' or distal end of a first polynucleotide from a pair of first and second polynucleotides, while the second assembly overlap sequence can comprise sequence complementary to sequence (e.g., an assembly overlap sequence) at a 5' or proximal end of a second polynucleotide from the pair of first and second polynucleotides.

The first assembly overlap sequence and the second assembly overlap sequence on an insert polynucleotide provided herein can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length and/or may be up 100 nucleotides in length (e.g., up to 50, up to 30, up to 25, up to 20 or up to 15 nucleotides in length) that are complementary to the 3' end of a first polynucleotide and the 5' end of a second polynucleotide, respectively, in a pair of polynucleotides as provided herein. The assembly overlap sequences length can be in the range of 15 nucleotides-100 nucleotides for example up to 20, up to 25, up to 30, up to 35, up to 40, up to 45, up to 50, up to 55, up to 60, up to 65, up to 70, up to 75, up to 80 nucleotides, up to 85 nucleotides, up to 90 nucleotides, up to 95 nucleotides or up to 100 nucleotides. In one embodiment, the first assembly overlap sequence and the second assembly overlap sequence on an insert polynucleotide provided herein comprises 1 or more nucleotides that are complementary to the 3' end of a first polynucleotide and the 5' end of a second polynucleotide, respectively, in a pair of polynucleotides provided herein. In another embodiment, the first assembly overlap sequence and the second assembly overlap sequence on an insert polynucleotide provided herein comprises about 25 nucleotides that are complementary to the 3' end of a first polynucleotide and the 5' end of a second polynucleotide, respectively, in a pair of polynucleotides provided herein.

In another embodiment, the insert polynucleotide further comprises one or more payload sequences such that said one or more payload sequences are located between the first and second assembly overlap sequences. A payload sequence can be a random sequence. A payload sequence can be a marker sequence. The marker sequence can be any marker sequence known in the art. A payload sequence can be a gene or a portion thereof. The gene or portion thereof can be part of a metabolic or biochemical pathway. The gene or portion thereof can encode a protein or a domain thereof. A payload sequence can be selected from promoters, genes, regulatory sequences, nucleic acid sequence encoding degrons, nucleic acid sequence encoding solubility tags, nucleic acid sequence encoding degradation tags, terminators, barcodes, regulatory sequences or portions thereof. In some cases, the three components of the insert polynucleotide (i.e., the first assembly overlap sequence, the second assembly overlap sequence and the payload sequence) are synthesized or otherwise combined into contiguous pieces of DNA before use in an assembly method provided herein. In one embodiment, the first and second assembly overlaps are not random but designed to match specific pairs of first and second polynucleotides.

In embodiments where the pair of first and second polynucleotides comprise targeting sequences as described herein, a payload sequence present within an insert polynucleotide can result in an insertion relative to the original locus targeted by the targeting sequences on the pair of first and second polynucleotides, a deletion of sequence relative to the original locus targeted by the targeting sequences on the pair of first and second polynucleotides, or a replacement of one sequence with another. In the case of an insertion or modification, the 'payload' can be the intended final sequence. In the case of a deletion, the 'payload' can be a marker sequence or no sequence.

In one embodiment, the insert polynucleotides are used in a pooled fashion. Further to this embodiment, each insert polynucleotide in a pool of insert polynucleotides can comprise a first assembly overlap sequence that comprises sequence complementary to sequence (e.g., an assembly overlap sequence) at a 3' or distal end of a first polynucleotide from a pair of first and second polynucleotides and a second assembly overlap sequence that comprises sequence complementary to sequence (e.g., an assembly overlap sequence) at a 5' or proximal end of a second polynucleotide from the pair of first and second polynucleotides.

The pool of insert polynucleotides can contain any number of unique insert polynucleotide sequences. The number of insert polynucleotides can be at least, at most, or about 1, 5, 10, 25, 50, 75, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 3000, 4000, 5000, 6000, 7000, 8000, 9000, 10,000, 20,000, 30,000, 40,000, 50,000, 75,000, 100,000, 150,000, 200,000 or 250,000 unique insert polynucleotides with or without a payload sequence.

A payload sequence can be at most or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 150, 200, 250, 300, 350, 400, 450, 500, 600, 700, 800, 900, 1000, 2000, 3000, 4000, 5000, 6000, 7000, 8000, 9000 or 10,000 nucleotides in length. In some cases, the payload sequence can be 0 nucleotides in length. A payload sequence can be at a length such that when incorporated into an insert polynucleotide, the entire insert polynucleotide can be chemically synthesized. The synthesis can be an array-based or column based synthesis method as known in the art. In one embodiment, a payload sequence is of a length such that it can be directly included or synthesized in an insert oligonucleotide along with the first and second assembly overlaps. An insert polynucleotide that can be synthesized can be up to about 1, 5, 10, 20, 30, 40, 50, 60, 70, 80, 90, 100, 110, 120, 130, 140, 150, 160, 170, 180, 190, 200, 210, 220, 250, 300, 350, 400 or more nucleotides in length.

Figure 3:
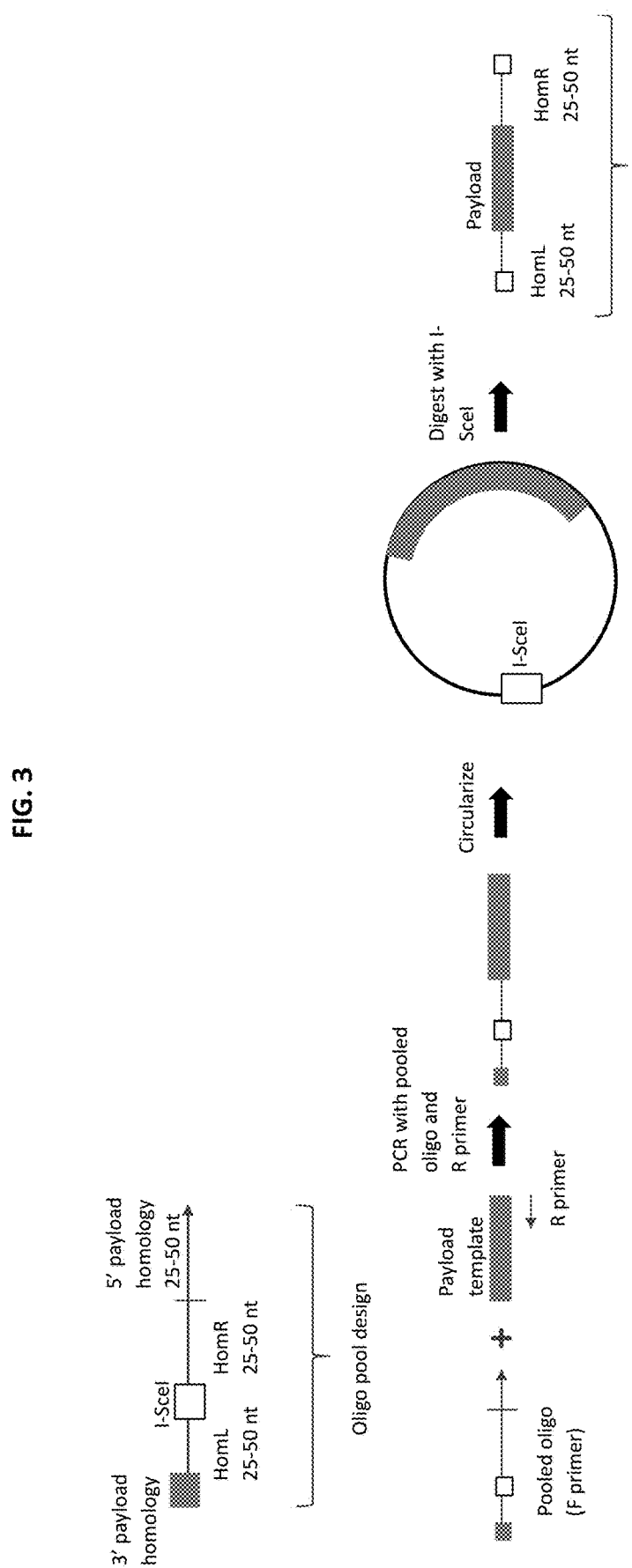
FIG. 3 illustrates adaptation of the method of FIG. 1 to allow for assembling insert polynucleotides (e.g., promoters) longer than the maximum synthetic oligonucleotide length.

In another embodiment, the insert polynucleotide can be generated in a single pool using the methods described in FIG. 3. As shown in FIG. 3, the payload sequence (e.g., the promoter sequence in FIG. 3) can be generated via PCR from three components: a pooled forward primer, a common reverse primer, and a payload template sequence (e.g., the promoter in FIG. 3). The payload sequence template can be a synthetic DNA fragment, a PCR product, or other single- or double-stranded DNA fragment. The pool of forward primers can be synthesized using array-based or column-based synthetic methods known in the art. Each forward primer in the pool can comprise (from 5' to 3'): 1) a sequence complementary to the distal or 3' end of the payload template sequence, 2) a second assembly overlap sequence comprising sequence complementary to a second polynucleotide from a pair of first and second polynucleotides, 3) one or more recognition sequences for one or more site-specific nuclease (e.g., a homing endonuclease site or recognition sequence), 4) a first assembly overlap sequence comprising sequence complementary to a first polynucleotide from a pair of first and second polynucleotides, and 5) a priming sequence that binds to the proximal end or 5' end of the payload template sequence. The common reverse primer can bind to the distal end or 3' end of the payload template sequence or to other sequence downstream of the payload sequence. PCR can be performed on the payload template sequence (e.g., the promoter in FIG. 3) using the pooled forward primers and the common reverse primer. After amplification, the PCR product can be circularized to generate a circular-permuted payload (insert) using an overlap assembly method known in the art, such as, for example, Gibson assembly, NEB® HIFI assembly, or similar methods, and then linearized using one or more site-specific nuclease(s) that recognizes the one or more site-specific nuclease recognition sequences (e.g., the homing endonuclease, I-SceI in FIG. 3). Nuclease digestion can result in a fragment suitable for use as insert polynucleotide (e.g., the "payload" part described in FIG. 1), with the large payloads flanked by first and second assembly overlap sequences (e.g., the homology arms or regions flanking the promoter sequence in FIG. 3). As shown in FIG. 3, at the ends of the payload sequences can be small partial nuclease recognition sequences (e.g., I-SceI in FIG. 3) that can be excised by the overlap assembly method utilized (e.g. 3' and 5' exonuclease activities of Gibson assembly reagents, NEB® HIFI assembly reagents, or equivalent mixtures). The product can be optionally amplified (e.g., RCA) after circularization and before linearization.

In one embodiment, each insert polynucleotide comprises a payload sequence such that each insert polynucleotide in a pool of insert polynucleotides comprises a different payload sequence from the payload sequence in each other insert polynucleotide in said pool.

In another embodiment, each insert polynucleotide comprises a payload sequence such that each insert polynucleotide in a pool of insert polynucleotides comprises the same payload sequence as the payload sequence in each other insert polynucleotide in said pool.

Cloning Methods

As described herein, a composition comprising pairs of first and second polynucleotides as well as insert polynucleotides can be assembled into a library of nucleic acids comprising first and second polynucleotides with an insert polynucleotide therebetween. Assembly of the pairs of first and second polynucleotides with the insert polynucleotides as provided herein can be performed by either in vitro or in vivo cloning methods. For the assembly of large DNA molecules, the final steps of the assembly may be conducted in vivo, such as in a yeast host cell. The balance between use of in vitro and in vivo assembly steps can be determined by the practicality of the method with regard to the nature of the nucleic acid molecules to be assembled.

In one embodiment, assembly of the pairs of first and second polynucleotides with the insert polynucleotides is performed using an in vitro cloning method. The in vitro cloning method can be any in vitro cloning method that employs overlap assembly known in the art. The in vitro cloning method used in the methods provided herein can be selected from infusion cloning (Clontech®), Golden Gate Assembly, Gateway Assembly, Gibson Assembly, and NEB® HIFI assembly or any other suitable in vitro cloning method known in the art. Infusion cloning can entail mixing a first pool of pairs of first and second polynucleotides as provided herein and a second pool of insert polynucleotides as described herein with the infusion cloning reagent and then transforming the resultant assemblies into an E. coli cloning host cell. The in vitro cloning method can be any of the overlap assembly methods described in U.S. Pat. No. 8,968,999, which is herein incorporated by reference in its entirety. The in vitro cloning method can be any of the overlap assembly methods described in US20160060671, which is herein incorporated by reference in its entirety. The in vitro cloning method can be the Gibson assembly method described in Jun Urano, Ph.D. and Christine Chen, Ph.D., Gibson Assembly® Primer-Bridge End Joining (PBnJ) Cloning, Synthetic Genomics Application Note, which is herein incorporated by reference in its entirety. In one embodiment, a composition comprising pairs of first and second polynucleotides, insert polynucleotides and a cloning vector are joined using a 5'-3' exonuclease; and a strand-displacing polymerase also present in the composition. The composition can also comprise a buffer containing a potassium salt such as potassium chloride in a concentration range of 7 mM-150 mM, for example, 20 mM-50 mM. A sodium salt (e.g., sodium chloride) in the range of 10 mM-100 mM such as 20 mM may also be used in addition to potassium salt. In some embodiments, the composition does not contain a crowding agent such as polyethylene glycol (PEG), Ficoll, or dextran. In some embodiments, the composition comprises a single stranded (ss) binding protein. A ss DNA binding protein for use in the composition may be E. coli recA, T7 gene 2.5 product, RedB (from phage lambda) or RecT (from Rac prophage), ET SSB (extreme thermostable single-stranded DNA binding protein) or any other ss DNA binding proteins known in the art could be used in the composition. The inclusion of a ss binding protein can improve the efficiency of assembly particularly for nucleic acid fragments with longer overlap sequences (e.g. at least 20 nucleotides) than would be otherwise occur in the absence of ss binding protein as measured by colony number. In some embodiments, the composition does not contain a non-strand displacing polymerase.

In another embodiment, a composition comprising pairs of first and second polynucleotides, insert polynucleotides and a cloning vector are joined using an isolated non-thermostable 5' to 3' exonuclease that lacks 3' exonuclease activity, a crowding agent, a non-strand-displacing DNA polymerase with 3' exonuclease activity, or a mixture of said DNA polymerase with a second DNA polymerase that lacks 3' exonuclease activity, and a ligase. The composition can further comprise a mixture of dNTPs, and a suitable buffer, under conditions that are effective for joining the polynucleotides and the cloning vector. In some embodiment, the composition can further comprise a crowding agent. The crowding agent can be selected from polyethylene glycol (PEG), dextran or ficoll. In one embodiment, the crowding agent is PEG. The PEG can be used at a concentration of from about 3 to about 7% (weight/volume). The PEG can be selected from PEG-200, PEG-4000, PEG-6000, PEG-8000 or PEG-20,000. In some embodiments, the exonuclease of is a T5 exonuclease and the contacting is under isothermal conditions, and/or the crowding agent is PEG, and/or the non-strand-displacing DNA polymerase is PHUSION® DNA polymerase or VENTR® DNA polymerase, and/or a Taq ligase.

In one embodiment, assembly of the pairs of first and second polynucleotides with the insert polynucleotides is performed using an in vivo cloning method. The in vivo cloning method can be any in vivo cloning method known in the art. The in vivo cloning method can be a homologous recombination mediated cloning method. The in vivo cloning method used in the methods provided herein can be selected from *E. coli* (RecA-dependent, RecA-independent or Red/ET-dependent) homologous recombination, Overlap Extension PCR and Recombination (OEPR) cloning, yeast homologous recombination, and Transformation-associated recombination (TAR) cloning and gene assembly in *Bacillus* as described in Tsuge, Kenji et al. "One step assembly of multiple DNA fragments with a designed order and orientation in *Bacillus subtilis* plasmid." Nucleic acids research vol. 31,21 (2003): e133, which is herein incorporated by reference.

Applications

The composition and assembly methods provided herein can be used to construct any desired assembly, such as plasmids, vectors, genes, metabolic pathways, minimal genomes, partial genomes, genomes, chromosomes, extrachromosomal nucleic acids, for example, cytoplasmic organelles, such as mitochondria (animals), and in chloroplasts and plastids (plants), and the like.

The compositions and assembly methods provided herein can be used to generate libraries of nucleic acid molecules, and methods to use modified whole or partial nucleic acid molecules as generated therefrom. The libraries can contain 2 or more variants, and said multiple variants, can be screened for members having desired characteristics, such as high production levels of desired products of interest, enhanced functionality of the product of interest, or decreased functionality (if that is advantageous). Such screening may be done by high throughput methods, which may be robotic/automated as provided herein.

The disclosure also further includes products made by the compositions and assembly methods provided herein, for example, the resulting assembled synthetic genes or genomes (synthetic or naturally occurring) and modified optimized genes and genomes, and the use(s) thereof.

The compositions and assembly methods provided herein can have a wide variety of applications, permitting, for example, the design of pathways for the synthesis of desired products of interest or optimization of one or more sequences whose gene products play a role in the synthesis or expression of a desired product. The compositions and assembly methods provided herein can also be used to generate optimized sequences of a gene or expression thereof or to combine one or more functional domains or motifs of protein encoded by a gene. The gene can be part of a biochemical or metabolic pathway. The biochemical or metabolic pathway can produce a desired product of interest.

The desired product of interest can be any molecule that can be assembled in a cell culture, eukaryotic or prokaryotic expression system or in a transgenic animal or plant. Thus, the nucleic acid molecules or libraries thereof that result from the deterministic assembly methods provided herein may be employed in a wide variety of contexts to produce desired products of interest. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a host cell, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others. The product of interest may also refer to a protein of interest.

Pathway Assembly

In one embodiment, the compositions and methods provided herein are used to assemble a gene or a variant thereof. The gene or variant thereof can encode a protein that is part of a metabolic or biochemical pathway. The variant can be a codon optimized version or mutated version of said gene. The metabolic or biochemical pathway can produce a product of interest as provided herein. In one embodiment, the gene sequence or variant thereof can be present as a payload sequence within an insert polynucleotide as provided herein. The pairs of first and second polynucleotides can comprise sequence such that when assembled with said insert polynucleotide can serve to facilitate targeting of and insertion into a locus in a genetic element (e.g., genome, plasmid, etc.) within a host cell using a gene editing method as provided herein. The locus can be a specific locus or a random locus. Alternatively, the pairs of first and second polynucleotides can comprise sequence such that when assembled with said insert polynucleotide can serve to facilitate further assembly of the resultant assembly with other assemblies generated using the methods provided herein. The other assemblies can comprise one or more additional genes present within the same metabolic or biochemical pathway and in this way facilitate the assembly of said metabolic or biochemical pathway. All of the genes or variants thereof can be assembled using the technique described herein of overlapping sequences on a single vector for a particular metabolic or biochemical pathway, or independent vectors for each member of said pathway can be employed by mixing the vectors for each member in successive transformation mixtures. The assembly of the first and second polynucleotides with an insert polynucleotide can be accomplished via assembly overlap sequences present in each of the polynucleotides using the assembly overlap methods provided herein. The pairs of first and second polynucleotides can further comprise vector overlap sequence as provided herein to facilitate assembly into a suitable vector. The vector can be a replicating plasmid. In some cases, the first and/second polynucleotide can further comprise sequence of a regulatory or control element that can govern an aspect of the gene or variant thereof or the protein encoded thereby such as the transcription, translation, solubility, or degradation thereof. The regulatory or control element can be a promoter, terminator, solubility tag, degradation tag or degron.

In another embodiment, the gene sequence or variant thereof is spread across a pair of first and second polynucleotides and an insert polynucleotide located therebetween or spread across a first or second polynucleotide and an insert polynucleotide located therebetween. By suitable assembly overlap segments on each of the polynucleotides, a mixture containing all of the polynucleotides can be assembled in the correct order in a single reaction mixture using overlap assembly as provided herein. The resultant will be full-length coding sequences of the gene or variant thereof. The pairs of first and second polynucleotides can further comprise sequence such that when assembled with said insert polynucleotide can serve to facilitate targeting of and insertion into a locus in a genetic element (e.g., genome, plasmid, etc.) within a host cell using a gene editing method as provided herein. The locus can be a specific locus or a random locus. Alternatively, the pairs of first and second polynucleotides can further comprise sequence that when assembled with said insert polynucleotide can serve to facilitate further assembly of the resultant assembly with other assemblies generated using the methods provided herein. The other assemblies can comprise one or more additional genes present within the same metabolic or biochemical pathway and in this way facilitate the assembly of said metabolic or biochemical pathway. All of the genes or variants thereof can be assembled using the technique described herein of overlapping sequences on a single vector for a particular metabolic or biochemical pathway, or independent vectors for each member of said pathway can be employed by mixing the vectors for each member in successive transformation mixtures. The pairs of first and second polynucleotides can further comprise vector overlap sequence as provided herein to facilitate assembly into a suitable vector. The vector can be a replicating plasmid. In some cases, the first and/second polynucleotide can further comprise sequence of a regulatory or control element that can govern an aspect of the gene or variant thereof or the protein encoded thereby such as the transcription, translation, solubility, or degradation thereof. The regulatory or control element can be a promoter, terminator, solubility tag, degradation tag or degron.

In still another embodiment, the compositions and methods provided herein are used to assemble or combine nucleic acid sequence that encode motifs or domains of a target protein. The nucleic acid sequence encoding a particular motif or domain of a target protein can be spread across a pair of first and second polynucleotides and an insert polynucleotide located therebetween or spread across a first or second polynucleotide and an insert polynucleotide located therebetween. The nucleic acid sequence encoding a particular motif or domain of a target protein can be present on a first polynucleotide, while a second motif or domain of the target protein can be present on a second polynucleotide and an insert polynucleotide can be used to join said first and second motif or domain of the target protein using assembly overlap sequences present on each polynucleotide and overlap assembly methods as provided herein. In some cases, the insert polynucleotide can comprise a portion of the first and/or second motif or domain. In some cases, the insert polynucleotide can comprise a third motif or domain of the target protein. The pairs of first and second polynucleotides can further comprise sequence such that when assembled with said insert polynucleotide can serve to facilitate targeting of and insertion into a locus in a genetic element (e.g., genome, plasmid, etc.) within a host cell using a gene editing method as provided herein. The locus can be a specific locus or a random locus. The pairs of first and second polynucleotides can further comprise vector overlap sequence as provided herein to facilitate assembly into a suitable vector. The vector can be a replicating plasmid.

Gene Editing

As described herein, a composition comprising pairs of first and second polynucleotides as well as insert polynucleotides can be assembled into a library of nucleic acids comprising first and second polynucleotides with an insert polynucleotide therebetween that can be subsequently utilized to modify the genetic content of a host cell. As provided herein, the library of nucleic acids can comprise control elements (e.g., promoters, terminators, solubility tags, degradation tags or degrons), modified forms of genes (e.g., genes with desired SNP(s)), antisense nucleic acids, and/or one or more genes that are part of a metabolic or biochemical pathway. In one embodiment, the modification entails gene editing of the host cell. The gene editing can entail editing the genome of the host cell and/or a separate genetic element present in the host cell such as, for example, a plasmid or cosmid. The gene editing method that can utilize nucleic acid assemblies generated using the methods and compositions as provided herein can be any gene editing method or system known in the art and can be selected based on the host for which gene editing is desired. Non-limiting examples of gene editing include homologous recombination, CRISPR, TALENS, FOK, or other endonucleases.

Homologous Recombination

In one embodiment, the gene editing method is a homologous recombination based method known in the art. The homologous recombination based method can be selected from single-crossover homologous recombination, double-crossover homologous recombination, or lambda red recombineering. Further to this embodiment, the first polynucleotide and the second polynucleotide in a pair of first and second polynucleotides such that each comprise sequence directed to or complementary to a desired loci in a nucleic acid element (e.g., genome, plasmid or cosmid) of a host cell and thereby direct an insert polynucleotide located therebetween to a desired locus in the genetic element (e.g., genome, cosmid or plasmid) of the host cell. Accordingly, the sequence directed to or complementary to a desired loci present in the pair can be used to determine the location(s) in the genome, cosmid or plasmid that will be targeted for editing. As exemplified in FIG. 1, the sequence directed to or complementary to a desired loci can be located at or toward the proximal or 5' end of a first polynucleotide, while in the second polynucleotide the sequence directed to or complementary to a desired loci can be located at or near the distal or 3'end. In the first polynucleotide, the sequence directed to or complementary to a desired loci can be located upstream of an assembly overlap sequence present in the first polynucleotide and downstream of a vector overlap sequence, if present. In the second polynucleotide, the sequence directed to or complementary to a desired loci can be located downstream of an assembly overlap sequence present in the second polynucleotide and upstream of a vector overlap sequence, if present.

In one embodiment, for each pair in a pool containing pairs of first polynucleotide and second polynucleotides, the sequence that is complementary to a desired loci in a pair is complementary to a different target locus in a host cell as compared to each other pair in the said pool.

In another embodiment, for each pair in a pool containing pairs of first polynucleotide and second polynucleotides, the sequence that is complementary to a desired loci in a pair is complementary to the same target locus in a host cell as compared to each other pair in the said pool.

Loop-in/Loop-Out

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. Looping out deletion techniques are known in the art, and are described in Tear et al. 2014 "Excision of Unstable Artificial Gene-Specific inverted Repeats Mediates Scar-Free Gene Deletions in *Escherichia coli*." Appl. Biochem. Biotech. 175:1858-1867. The looping out methods used in the methods provided herein can be performed using single-crossover homologous recombination or double-crossover homologous recombination. In one embodiment, looping out of selected regions can entail using single-crossover homologous recombination.

In one embodiment, a composition provided herein comprises pairs of first and second polynucleotides (e.g., left/right homology arms), insert polynucleotides and a vector such that assembly of the pairs of first and second polynucleotides with an insert polynucleotide and a vector using an in in vitro or in vivo assembly method as provided herein generates loop out vectors. In one embodiment, single-crossover homologous recombination is used between a loop-out vector and the host cell genome in order to loop-in said vector. The vector could comprise a marker that facilitates selection of looped-out clones after the loop-in step. In another embodiment, double-crossover homologous recombination is used between a loop-out vector and the host cell genome in order to integrate said vector. The insert sequence within the loop-out vector can be designed with a sequence, which is a direct repeat of an existing or introduced nearby host sequence, such that the direct repeats flank the region of DNA slated for looping and deletion. The insert sequence could further comprise a marker that facilitates selection of looped-out clones. Once inserted, cells containing the loop out plasmid or vector can be counter selected for deletion of the selection region.

In one aspect provided herein, polynucleotides or polynucleotide libraries generated using the compositions and/or methods provided herein can be used in a gene editing method that can entail the use of sets of proteins from one or more recombination systems. Said recombination systems can be endogenous to the microbial host cell or can be introduced heterologously. The sets of proteins of the one or more heterologous recombination systems can be introduced as nucleic acids (e.g., as plasmid, linear DNA or RNA, or integron) and be integrated into the genome of the host cell or be stably expressed from an extrachromosomal element. The sets of proteins of the one or more heterologous recombination systems can be introduced as RNA and be translated by the host cell. The sets of proteins of the one or more heterologous recombination systems can be introduced as proteins into the host cell. The sets of proteins of the one or more recombination systems can be from a lambda red recombination system, a RecET recombination system, a Red/ET recombination system, any homologs, orthologs or paralogs of proteins from a lambda red recombination system, a RecET recombination system, or Red/ET recombination system or any combination thereof. The recombination methods and/or sets of proteins from the RecET recombination system can be any of those as described in Zhang Y., Buchholz F., Muyrers J. P. P. and Stewart A. F. "A new logic for DNA engineering using recombination in *E. coli*." Nature Genetics 20 (1998) 123-128; Muyrers, J. P. P., Zhang, Y., Testa, G., Stewart, A. F. "Rapid modification of bacterial artificial chromosomes by ET-recombination." Nucleic Acids Res. 27 (1999) 1555-1557; Zhang Y., Muyrers J. P. P., Testa G. and Stewart A. F. "DNA cloning by homologous recombination in *E. coli*." Nature Biotechnology 18 (2000) 1314-1317 and Muyrers J P et al., "Techniques: Recombinogenic engineering—new options for cloning and manipulating DNA" Trends Biochem Sci. 2001 May; 26(5):325-31, which are herein incorporated by reference. The sets of proteins from the Red/ET recombination system can be any of those as described in Rivero-Müller, Adolfo et al. "Assisted large fragment insertion by Red/ET-recombination (ALFIRE)—an alternative and enhanced method for large fragment recombineering" Nucleic acids research vol. 35,10 (2007): e78, which is herein incorporated by reference.

Lambda RED Mediated Gene Editing

As provided herein, gene editing as described herein can be performed using Lambda Red-mediated homologous recombination as described by Datsenko and Wanner, PNAS USA 97:6640-6645 (2000), the contents of which are hereby incorporated by reference in their entirety.

To use the lambda red recombineering system to modify target DNA, a linear donor DNA substrate (either dsDNA or ssDNA) can be electroporated into *E. coli* expressing the set of proteins from the lambda red recombination system. The set of proteins from the lambda red recombination system can comprise the exo, beta or gam proteins or any combination thereof. Gam can prevent both the endogenous RecBCD and SbcCD nucleases from digesting the linear donor DNA (either dsDNA or ssDNA) introduced into a microbial host cell, while exo is a 5'-3' dsDNA-dependent exonuclease that can degrade linear dsDNA starting from the 5' end and generate 2 possible products (i.e., a partially dsDNA duplex with single-stranded 3' overhangs or a ssDNA whose entire complementary strand was degraded) and beta can protect the ssDNA created by Exo and promote its annealing to a complementary ssDNA target in the cell. Beta expression can be required for lambda red based recombination with an ssDNA oligo substrate as described at blog.addgene.org/lambda-red-a-homologous-recombination-based-technique-for-genetic-engineering, the contents of which are herein incorporated by reference.

The linear donor DNA substrate (either dsDNA or ssDNA) can be an assembly comprising a pair of first and second polynucleotides with an insert polynucleotide located therebetween generated using the methods and compositions provided herein. The pair of first and second polynucleotides can comprise genomic targeting sequences that target said donor DNA substrate to a specific locus in the genome of the host cell. These enzymes then catalyze the homologous recombination of the substrate with the target DNA sequence. This means cloning occurs in vivo, as compared to restriction enzyme cloning where the genetic changes occur in a test tube. The donor DNA substrate only requires ~50 nucleotides of homology to the target site for recombination. As described at blog.addgene.org/lambda-red-a-homologous-recombination-based-technique-for-genetic-engineering, whether a linear dsDNA or ssDNA substrate is used can depend on the goal of the experiment. dsDNA substrate may be best for insertions or deletions greater than approximately 20 nucleotides, while ssDNA substrate may be best for point mutations or changes of only a few base pairs.

dsDNA substrate can be made using the compositions and methods provided herein such that the pairs of first and second polynucleotides comprise about 50 base pairs of homology to the targeted insert site on opposing terminal ends. The dsDNA insert polynucleotide present within the substrate can include: large insertions or deletions, including selectable DNA fragments, such as antibiotic resistance genes, as well as non-selectable DNA fragments, such as gene replacements and tags.

ssDNA substrates can be also be made using the compositions and methods provided herein such that the pairs of first and second polynucleotides comprise about 50 base pairs of homology to the targeted insert site on opposing terminal ends and can have the desired alteration(s) located in the center of the sequence (i.e., within the insert polynucleotide).

ssDNA substrate can be more efficient than dsDNA with a recombination frequency between 0.1% to 1%, and can be increased to as high as 25-50% by designing substrates that avoid activating the methyl-directed mismatch repair (MMR) system. MMR's job is to correct DNA mismatches that occur during DNA replication. Activation of MMR can be avoided by: 1) using a strain of bacteria that has key MMR proteins knocked out or 2) specially design ssDNA substrates to avoid MMR: 1) *E. coli* with inactivated MMR: Using *E. coli* with inactive MMR is definitely the easier of the two options, but these cells are prone to mutations and can have more unintended changes to their genomes. 2) Designing ssDNA substrates that avoid MMR activation: In one embodiment, a C/C mismatch at or within 6 base pairs of the edit site is introduced. In another embodiment, the desired change is flanked with 4-5 silent changes in the wobble codons, i.e. make changes to the third base pair of the adjacent 4-5 codons that alter the nucleotide sequence but not the amino acid sequence of the translated protein. These changes can be 5' or 3' of the desired change.

In one embodiment, the polynucleotides or polynucleotide libraries generated using the compositions and/or methods provided herein can be used in a gene editing method that is implemented in a microbial host cell that already stably expresses lambda red recombination genes such as the DY380 strain described at blog.addgene.org/lambda-red-a-homologous-recombination-based-technique-for-genetic-engineering, the contents of which are herein incorporated by reference. Other bacterial strains that comprise components of the lambda red recombination system and can be utilized to generate the organism to be genotyped using an enrichment method provided herein (e.g., CS-seq or SG-seq) can be found in Thomason et al (Recombineering: Genetic Engineering in Bacteria Using Homologous Recombination. Current Protocols in Molecular Biology. 106:V:1.16:1.16.1-1.16.39) and Sharan et al (Recombineering: A Homologous Recombination-Based Method of Genetic Engineering. Nature protocols. 2009; 4(2):206-223), the contents of each of which are herein incorporated by reference.

As provided herein, the set of proteins of the lambda red recombination system can be introduced into the microbial host cell prior to implementation of any of the editing methods known in the art and/or provided herein. Genes for each of the proteins of the lambda red recombination system can be introduced on nucleic acids (e.g., as plasmids, linear DNA or RNA, a mini-λ, a lambda red prophage or integrons) and be integrated into the genome of the host cell or expressed from an extrachromosomal element. In some cases, each of the components (i.e., exo, beta, gam or combinations thereof) of the lambda red recombination system can be introduced as an RNA and be translated by the host cell. In some cases, each of the components (i.e., exo, beta, gam or combinations thereof) of the lambda red recombination system can be introduced as a protein into the host cell.

In one embodiment, genes for the set of proteins of the lambda red recombination system are introduced on a plasmid. The set of proteins of the lambda red recombination system on the plasmid can be under the control of a promoter such as, for example, the endogenous phage pL promoter. In one embodiment, the set of proteins of the lambda red recombination system on the plasmid is under the control of an inducible promoter. The inducible promoter can be inducible by the addition or depletion of a reagent or by a change in temperature. In one embodiment, the set of proteins of the lambda red recombination system on the plasmid is under the control of an inducible promoter such as the IPTG-inducible lac promoter or the arabinose-inducible pBAD promoter. A plasmid expressing genes for the set of proteins of the lambda red recombination system can also express repressors associated with a specific promoter such as, for example, the lacI, araC or cI857 repressors associated with the IPTG-inducible lac promoter, the arabinose-inducible pBAD promoter and the endogenous phage pL promoters, respectively.

In one embodiment, genes for the set of proteins of the lambda red recombination system are introduced on a mini-λ, which a defective non-replicating, circular piece of phage DNA, that when introduced into microbial host cell, integrates into the genome as described at blog.addgene.org/lambda-red-a-homologous-recombination-based-technique-for-genetic-engineering, the contents of which are herein incorporated by reference.

In one embodiment, genes for the set of proteins of the lambda red recombination system are introduced on a lambda red prophage, which can allow for stable integration of the lambda red recombination system into a microbial host cell such as described at blog.addgene.org/lambda-red-a-homologous-recombination-based-technique-for-genetic-engineering, the contents of which are herein incorporated by reference.

CRISPR Mediated Gene Editing

In one aspect provided herein, a genetic element (e.g., genome, cosmid, or plasmid) of a host cell can be modified by CRISPR.

The CRISPR/Cas system is a prokaryotic immune system that confers resistance to foreign genetic elements such as those present within plasmids and phages and that provides a form of acquired immunity. CRISPR stands for Clustered Regularly Interspaced Short Palindromic Repeat, and cas stands for CRISPR-associated system, and refers to the small cas genes associated with the CRISPR complex.

CRISPR-Cas systems are most broadly characterized as either Class 1 or Class 2 systems. The main distinguishing feature between these two systems is the nature of the Cas-effector module. Class 1 systems require assembly of multiple Cas proteins in a complex (referred to as a "Cascade complex") to mediate interference, while Class 2 systems use a large single Cas enzyme to mediate interference. Each of the Class 1 and Class 2 systems are further divided into multiple CRISPR-Cas types based on the presence of a specific Cas protein. For example, the Class 1 system is divided into the following three types: Type I systems, which contain the Cas3 protein; Type III systems, which contain the Cas10 protein; and the putative Type IV systems, which contain the Csf1 protein, a Cas8-like protein. Class 2 systems are generally less common than Class 1 systems and are further divided into the following three types: Type II systems, which contain the Cas9 protein; Type V systems, which contain Cas12a protein (previously known as Cpf1, and referred to as Cpf1 herein), Cas12b (previously known as C2c1), Cas12c (previously known as C2c3), Cas12d (previously known as CasY), and Cas12e (previously known as CasX); and Type VI systems, which contain Cas13a (previously known as C2c2), Cas13b, and Cas13c. Pyzocha et al., ACS Chemical Biology, Vol. 13 (2), pgs. 347-356. In one embodiment, the CRISPR-Cas system for use in the methods provided herein is a Class 2 system. In one embodiment, the CRISPR-Cas system for use in the methods provided herein is a Type II, Type V or Type VI Class 2 system. In one embodiment, the CRISPR-Cas system for use in the methods provided herein is selected from Cas9, Cas12a, Cas12b, Cas12c, Cas12d, Cas12e, Cas13a, Cas13b, Cas13c or homologs, orthologs or paralogs thereof.

CRISPR systems used in methods disclosed herein comprise a Cas effector module comprising one or more nucleic acid guided CRISPR-associated (Cas) nucleases, referred to herein as Cas effector proteins. In some embodiments, the Cas proteins can comprise one or multiple nuclease domains. A Cas effector protein can target single stranded or double stranded nucleic acid molecules (e.g. DNA or RNA nucleic acids) and can generate double strand or single strand breaks. In some embodiments, the Cas effector proteins are wild-type or naturally occurring Cas proteins. In some embodiments, the Cas effector proteins are mutant Cas proteins, wherein one or more mutations, insertions, or deletions are made in a WT or naturally occurring Cas protein (e.g., a parental Cas protein) to produce a Cas protein with one or more altered characteristics compared to the parental Cas protein.

In some instances, the Cas protein is a wild-type (WT) nuclease. Non-limiting examples of suitable Cas proteins for use in the present disclosure include C2c1, C2c2, C2c3, Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx100, Csx16, CsaX, Csx3, Csx1, Csx15, Csf1, Csf2, Csf3, Csf4, MAD1-20, SmCsm1, homologues thereof, orthologues thereof, variants thereof, mutants thereof, or modified versions thereof. Suitable nucleic acid guided nucleases (e.g., Cas 9) can be from an organism from a genus, which includes but is not limited to: *Thiomicrospira, Succinivibrio, Candidatus, Porphyromonas, Acidomonococcus, Prevotella, Smithella, Moraxella, Synergistes, Francisella, Leptospira, Catenibacterium, Kandleria, Clostridium, Dorea, Coprococcus, Enterococcus, Fructobacillus, Weissella, Pediococcus, Corynebacter, Sutterella, Legionella, Treponema, Roseburia, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Alicyclobacillus, Brevibacilus, Bacillus, Bacteroidetes, Carnobacterium, Clostridiaridium, Clostridium, Desulfonatronum, Desulfovibrio, Helcococcus, Leptotrichia, Listeria, Methanomethyophilus, Methylobacterium, Opitutaceae, Paludibacter, Rhodobacter, Sphaerochaeta, Tuberibacillus,* and *Campylobacter*. Species of organism of such a genus can be as otherwise herein discussed.

Suitable nucleic acid guided nucleases (e.g., Cas9) can be from an organism from a phylum, which includes but is not limited to: Firmicute, Actinobacteria, Bacteroidetes, Proteobacteria, Spirochates, and Tenericutes. Suitable nucleic acid guided nucleases can be from an organism from a class, which includes but is not limited to: Erysipelotrichia, Clostridia, Bacilli, Actinobacteria, Bacteroidetes, Flavobacteria, Alphaproteobacteria, Betaproteobacteria, Gammaproteobacteria, Deltaproteobacteria, Epsilonproteobacteria, Spirochaetes, and Mollicutes. Suitable nucleic acid guided nucleases can be from an organism from an order, which includes but is not limited to: Clostridiales, Lactobacillales, Actinomycetales, Bacteroidales, Flavobacteriales, Rhizobiales, Rhodospirillales, Burkholderiales, Neisseriales, Legionellales, Nautiliales, Campylobacterales, Spirochaetales, Mycoplasmatales, and Thiotrichales. Suitable nucleic acid guided nucleases can be from an organism from within a family, which includes but is not limited to: Lachnospiraceae, Enterococcaceae, Leuconostocaceae, Lactobacillaceae, Streptococcaceae, Peptostreptococcaceae, Staphylococcaceae, Eubacteriaceae, Corynebacterineae, Bacteroidaceae, *Flavobacterium*, Cryomoorphaceae, Rhodobiaceae, Rhodospirillaceae, Acetobacteraceae, Sutterellaceae, Neisseriaceae, Legionellaceae, Nautiliaceae, Campylobacteraceae, Spirochaetaceae, Mycoplasmataceae, and Francisellaceae.

Other nucleic acid guided nucleases (e.g., Cas9) suitable for use in the methods, systems, and compositions of the present disclosure include those derived from an organism such as, but not limited to: Thiomicrospira sp. XS5, *Eubacterium rectale, Succinivibrio dextrinosolvens, Candidatus Methanoplasma termitum, Candidatus Methanomethylophilus alvus, Porphyromonas crevioricanis, Flavobacterium branchiophilum, Acidomonococcus* sp., Lachnospiraceae bacterium COE1, *Prevotella brevis* ATCC 19188, *Smithella* sp. SCADC, *Moraxella bovoculi, Synergistes jonesii*, Bacteroidetes oral taxon 274, *Francisella tularensis, Leptospira inadai* serovar Lyme str. 10, *Acidomonococcus* sp. crystal structure (5B43) *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. diffcile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, Microgenomates, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens, Porphyromonas macacae, Catenibacterium* sp. CAG:290, *Kandleria vitulina*, Clostridiales bacterium KA00274, Lachnospiraceae bacterium 3-2, *Dorea longicatena, Coprococcus catus* GD/7, *Enterococcus columbae* DSM 7374, *Fructobacillus* sp. EFB-N1, *Weissella halotolerans, Pediococcus acidilactici, Lactobacillus curvatus, Streptococcus pyogenes, Lactobacillus versmoldensis,* and *Filifactor alocis* ATCC 35896. See, U.S. Pat. Nos. 8,697,359; 8,771,945; 8,795,965; 8,865,406; 8,871,445; 8,889,356; 8,895,308; 8,906,616; 8,932,814; 8,945,839; 8,993,233; 8,999,641; 9,822,372; 9,840,713; U.S. patent application Ser. No. 13/842,859 (US 2014/0068797 A1); U.S. Pat. Nos. 9,260,723; 9,023,649; 9,834,791; 9,637,739; U.S. patent application Ser. No. 14/683,443 (US 2015/0240261 A1); U.S. patent application Ser. No. 14/743,764 (US 2015/0291961 A1); U.S. Pat. Nos. 9,790,490; 9,688,972; 9,580,701; 9,745,562; 9,816,081; 9,677,090; 9,738,687; U.S. application Ser. No. 15/632,222 (US 2017/0369879 A1); U.S. application Ser. No. 15/631,989; U.S. application Ser. No. 15/632,001; and U.S. Pat. No. 9,896,696, each of which is herein incorporated by reference.

In some embodiments, a Cas effector protein comprises one or more of the following activities:

a nickase activity, i.e., the ability to cleave a single strand of a nucleic acid molecule;

a double stranded nuclease activity, i.e., the ability to cleave both strands of a double stranded nucleic acid and create a double stranded break;

an endonuclease activity;

an exonuclease activity; and/or a helicase activity, i.e., the ability to unwind the helical structure of a double stranded nucleic acid.

In aspects of the disclosure the term "guide nucleic acid" refers to a polynucleotide comprising 1) a guide sequence capable of hybridizing to a target sequence (referred to herein as a "targeting segment") and 2) a scaffold sequence capable of interacting with (either alone or in combination with a tracrRNA molecule) a nucleic acid guided nuclease as described herein (referred to herein as a "scaffold segment"). A guide nucleic acid can be DNA. A guide nucleic acid can be RNA. A guide nucleic acid can comprise both DNA and RNA. A guide nucleic acid can comprise modified non-naturally occurring nucleotides. In cases where the guide nucleic acid comprises RNA, the RNA guide nucleic acid can be encoded by a DNA sequence on a polynucleotide molecule such as a plasmid, linear construct generated using the methods and compositions provided herein.

In some embodiments, the guide nucleic acids described herein are RNA guide nucleic acids ("guide RNAs" or "gRNAs") and comprise a targeting segment and a scaffold segment. In some embodiments, the scaffold segment of a gRNA is comprised in one RNA molecule and the targeting segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

In one embodiment, an assembly comprising a pair of first and second polynucleotides with an insert polynucleotide located therebetween generated using the methods and compositions provided herein is a guide RNA (gRNA). In some cases, the methods provided herein are used to generate a library of gRNAs.

The DNA-targeting segment of a gRNA comprises a nucleotide sequence that is complementary to a sequence in a target nucleic acid sequence. As such, the targeting segment of a gRNA interacts with a target nucleic acid in a sequence-specific manner via hybridization (i.e., base pairing), and the nucleotide sequence of the targeting segment determines the location within the target DNA that the gRNA will bind. The degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 75, or more nucleotides in length. In some embodiments, a guide sequence is less than about 75, 50, 45, 40, 35, 30, 25, 20 nucleotides in length. In aspects, the guide sequence is 10-30 nucleotides long. The guide sequence can be 15-20 nucleotides in length. The guide sequence can be 15 nucleotides in length. The guide sequence can be 16 nucleotides in length. The guide sequence can be 17 nucleotides in length. The guide sequence can be 18 nucleotides in length. The guide sequence can be 19 nucleotides in length. The guide sequence can be 20 nucleotides in length.

The scaffold segment of a guide RNA interacts with a one or more Cas effector proteins to form a ribonucleoprotein complex (referred to herein as a CRISPR-RNP or a RNP-complex). The guide RNA directs the bound polypeptide to a specific nucleotide sequence within a target nucleic acid sequence via the above-described targeting segment. The scaffold segment of a guide RNA comprises two stretches of nucleotides that are complementary to one another and which form a double stranded RNA duplex. Sufficient sequence within the scaffold sequence to promote formation of a targetable nuclease complex may include a degree of complementarity along the length of two sequence regions within the scaffold sequence, such as one or two sequence regions involved in forming a secondary structure. In some cases, the one or two sequence regions are comprised or encoded on the same polynucleotide. In some cases, the one or two sequence regions are comprised or encoded on separate polynucleotides. Optimal alignment may be determined by any suitable alignment algorithm, and may further account for secondary structures, such as self-complementarity within either the one or two sequence regions. In some embodiments, the degree of complementarity between the one or two sequence regions along the length of the shorter of the two when optimally aligned is about or more than about 25%, 30%, 40%, 50%, 60%, 70%, 80%, 90%, 95%, 97.5%, 99%, or higher. In some embodiments, at least one of the two sequence regions is about or more than about 5, 6, 7, 8, 9, 10, 11, 12, 13, 14, 15, 16, 17, 18, 19, 20, 25, 30, 40, 50, or more nucleotides in length.

A scaffold sequence of a subject gRNA can comprise a secondary structure. A secondary structure can comprise a pseudoknot region or stem-loop structure. In some examples, the compatibility of a guide nucleic acid and nucleic acid guided nuclease is at least partially determined by sequence within or adjacent to the secondary structure region of the guide RNA. In some cases, binding kinetics of a guide nucleic acid to a nucleic acid guided nuclease is determined in part by secondary structures within the scaffold sequence. In some cases, binding kinetics of a guide nucleic acid to a nucleic acid guided nuclease is determined in part by nucleic acid sequence with the scaffold sequence.

A compatible scaffold sequence for a gRNA-Cas effector protein combination can be found by scanning sequences adjacent to a native Cas nuclease loci. In other words, native Cas nucleases can be encoded on a genome within proximity to a corresponding compatible guide nucleic acid or scaffold sequence.

Nucleic acid guided nucleases can be compatible with guide nucleic acids that are not found within the nucleases endogenous host. Such orthogonal guide nucleic acids can be determined by empirical testing. Orthogonal guide nucleic acids can come from different bacterial species or be synthetic or otherwise engineered to be non-naturally occurring. Orthogonal guide nucleic acids that are compatible with a common nucleic acid-guided nuclease can comprise one or more common features. Common features can include sequence outside a pseudoknot region. Common features can include a pseudoknot region. Common features can include a primary sequence or secondary structure.

A guide nucleic acid can be engineered to target a desired target sequence by altering the guide sequence such that the guide sequence is complementary to the target sequence, thereby allowing hybridization between the guide sequence and the target sequence. A guide nucleic acid with an engineered guide sequence can be referred to as an engineered guide nucleic acid. Engineered guide nucleic acids are often non-naturally occurring and are not found in nature.

In some embodiments, the present disclosure provides a polynucleotide encoding a gRNA generated using the compositions and methods provided herein. In some embodiments, the composition comprising a pair of first and second polynucleotides and an insert polynucleotide further comprises an expression vector such that assembly of the pair of first and second polynucleotides with the insert polynucleotide and expression vector generates an expression vector comprising a gRNA-encoding nucleic acid.

In another embodiment, an assembly comprising a pair of first and second polynucleotides with an insert polynucleotide located therebetween generated using the methods and compositions provided herein is a donor DNA sequence. In some cases, the methods provided herein are used to generate a library of donor DNA sequences. The donor DNA sequence can be used in combination with a guide RNA (gRNA) in a CRISPR method of gene editing using homology directed repair (HDR). The CRISPR complex can result in the strand breaks within the target gene(s) that can be repaired by using homology directed repair (HDR). HDR mediated repair can be facilitated by co-transforming the host cell with a donor DNA sequence generated using the methods and compositions provided herein. The donor DNA sequence can comprise a desired genetic perturbation (e.g., deletion, insertion, and/or single nucleotide polymorphism) as well as targeting sequences derived from the first and second polynucleotides. In this embodiment, the CRISPR complex cleaves the target gene specified by the one or more gRNAs. The donor DNA sequence can then be used as a template for the homologous recombination machinery to incorporate the desired genetic perturbation into the host cell. The donor DNA can be single-stranded, double-stranded or a double-stranded plasmid. The donor DNA can lack a PAM sequence or comprise a scrambled, altered or non-functional PAM in order to prevent re-cleavage. In some cases, the donor DNA can contain a functional or non-altered PAM site. The mutated or edited sequence in the donor DNA (also flanked by the regions of homology) prevents re-cleavage by the CRISPR-complex after the mutation(s) has/have been incorporated into the genome.

Host Cells

As provided herein, the libraries of nucleic acid constructs generated using the compositions and/or methods provided herein can be used to edit or modify a genetic element (e.g., genome, cosmid or plasmid) of a host cell or engineer the host cell via introducing (e.g., transforming or transducing) one or more genetic element(s) (e.g., plasmid or cosmid) into said host cell. The genomic engineering or editing methods can be applicable to any organism where desired traits can be identified in a population of genetic mutants. The organism can be a microorganism or higher eukaryotic organism.

Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

Suitable host cells include, but are not limited to: bacterial cells, algal cells, plant cells, fungal cells, insect cells, and mammalian cells. In one illustrative embodiment, suitable host cells include *E. coli* (e.g., SHuffle™ competent *E. coli* available from New England BioLabs in Ipswich, Mass.).

Other suitable host organisms of the present disclosure include microorganisms of the genus *Corynebacterium*. In some embodiments, preferred *Corynebacterium* strains/species include: *C. efficiens*, with the deposited type strain being DSM44549, *C. glutamicum*, with the deposited type strain being ATCC13032, and *C. ammoniagenes*, with the deposited type strain being ATCC6871. In some embodiments, the preferred host of the present disclosure is *C. glutamicum*.

Suitable host strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM12866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

In some embodiments, the host cell of the present disclosure is a eukaryotic cell. Suitable eukaryotic host cells include, but are not limited to: fungal cells, algal cells, insect cells, animal cells, and plant cells. Suitable fungal host cells include, but are not limited to: Ascomycota, Basidiomycota, Deuteromycota, Zygomycota, *Fungi imperfecti*. Certain preferred fungal host cells include yeast cells and filamentous fungal cells. Suitable filamentous fungi host cells include, for example, any filamentous forms of the subdivision Eumycotina and Oomycota. (see, e.g., Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof.

Suitable yeast host cells include, but are not limited to: *Candida, Hansenula, Saccharomyces, Schizosaccharomyces, Pichia, Kluyveromyces*, and *Yarrowia*. In some embodiments, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia piperi, Pichia stipitis, Pichia methanolica, Pichia angusta, Kluyveromyces lactis, Candida albicans*, or *Yarrowia lipolytica*.

In certain embodiments, the host cell is an algal such as, *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative, and gram-variable bacterial cells. The host cell may be a species of, but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Campylobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Mycobacterium, Neisseria, Pantoea, Pseudomonas, Prochlorococcus, Rhodobacter, Rhodopseudomonas, Roseburia, Rhodospirillum, Rhodococcus, Scenedesmus, Streptomyces, Streptococcus, Synechococcus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia,* and *Zymomonas*. In some embodiments, the host cell is *Corynebacterium glutamicum*.

In some embodiments, the bacterial host strain is an industrial strain. Numerous bacterial industrial strains are known and suitable in the methods and compositions described herein.

In some embodiments, the bacterial host cell is of the *Agrobacterium* species (e.g., *A. radiobacter, A. rhizogenes, A. rubi*), the *Arthrobacter* species (e.g., *A. aurescens, A. citreus, A. globformis, A. hydrocarboglutamicus, A. mysorens, A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. lichenformis, B. megaterium, B. clausii, B. stearothermophilus* and *B. amyloliquefaciens*. In some embodiments, the host cell will be an industrial *Clostridium* species (e.g., *C. acetobutylicum, C. tetani* E88, *C. lituseburense, C. saccharobutylicum, C. perfringens, C. beijerinckii*). In some embodiments, the host cell will be an industrial *Corynebacterium* species (e.g., *C. glutamicum, C. acetoacidophilum*). In some embodiments, the host cell will be an industrial *Escherichia* species (e.g., *E. coli*). In some embodiments, the host cell will be an industrial *Erwinia* species (e.g., *E. uredovora, E. carotovora, E. ananas, E. herbicola, E. punctata, E. terreus*). In some embodiments, the host cell will be an industrial *Pantoea* species (e.g., *P. citrea, P. agglomerans*). In some embodiments, the host cell will be an industrial *Pseudomonas* species, (e.g., *P. putida, P. aeruginosa, P. mevalonii*). In some embodiments, the host cell will be an industrial *Streptococcus* species (e.g., *S. equisimiles, S. pyogenes, S. uberis*). In some embodiments, the host cell will be an industrial *Streptomyces* species (e.g., *S. ambofaciens, S. achromogenes, S. avermitilis, S. coelicolor, S. aureofaciens, S. aureus, S. fungicidicus, S. griseus, S. lividans*). In some embodiments, the host cell will be an industrial *Zymomonas* species (e.g., *Z. mobilis, Z. lipolytica*), and the like.

In some embodiments, the host cell will be an industrial *Escherichia* species (e.g., *E. coli*).

Suitable host strains of the *E. coli* species comprise: Enterotoxigenic *E. coli* (ETEC), Enteropathogenic *E. coli* (EPEC), Enteroinvasive *E. coli* (EIEC), Enterohemorrhagic *E. coli* (EHEC), Uropathogenic *E. coli* (UPEC), Verotoxin-producing *E. coli, E. coli* O157:H7, *E. coli* 0104:H4, *Escherichia coli* 0121, *Escherichia coli* 0104:H21, *Escherichia coli* K1, and *Escherichia coli* NC101. In some embodiments, the present disclosure teaches genomic engineering of *E. coli* K12, *E. coli* B, and *E. coli* C.

In some embodiments, the host cell can be *E. coli* strains NCTC 12757, NCTC 12779, NCTC 12790, NCTC 12796, NCTC 12811, ATCC 11229, ATCC 25922, ATCC 8739, DSM 30083, BC 5849, BC 8265, BC 8267, BC 8268, BC 8270, BC 8271, BC 8272, BC 8273, BC 8276, BC 8277, BC 8278, BC 8279, BC 8312, BC 8317, BC 8319, BC 8320, BC 8321, BC 8322, BC 8326, BC 8327, BC 8331, BC 8335, BC 8338, BC 8341, BC 8344, BC 8345, BC 8346, BC 8347, BC 8348, BC 8863, and BC 8864.

In some embodiments, the present disclosure teaches host cells that can be verocytotoxigenic *E. coli* (VTEC), such as strains BC 4734 (O26:H11), BC 4735 (O157:H-), BC 4736, BC 4737 (n.d.), BC 4738 (O157:H7), BC 4945 (O26:H-), BC 4946 (O157:H7), BC 4947 (O111:H-), BC 4948 (O157:H), BC 4949 (O5), BC 5579 (O157:H7), BC 5580 (O157:H7), BC 5582 (O3:H), BC 5643 (O2:H5), BC 5644 (O128), BC 5645 (O55:H-), BC 5646 (O69:H-), BC 5647 (O101:H9), BC 5648 (O103:H2), BC 5850 (O22:H8), BC 5851 (O55:H-), BC 5852 (O48:H21), BC 5853 (O26:H11), BC 5854 (O157:H7), BC 5855 (O157:H-), BC 5856 (O26:H-), BC 5857 (O103:H2), BC 5858 (O26:H11), BC 7832, BC 7833 (O raw form:H-), BC 7834 (ONT:H-), BC 7835 (O103:H2), BC 7836 (O57:H-), BC 7837 (ONT:H-), BC 7838, BC 7839 (O128:H2), BC 7840 (O157:H-), BC 7841 (O23:H-), BC 7842 (O157:H-), BC 7843, BC 7844 (O157:H-), BC 7845 (O103:H2), BC 7846 (O26:H11), BC 7847 (O145:H-), BC 7848 (O157:H-), BC 7849 (O156:H47), BC 7850, BC 7851 (O157:H-), BC 7852 (O157:H-), BC 7853 (O5:H-), BC 7854 (O157:H7), BC 7855 (O157:H7), BC 7856 (O26:H-), BC 7857, BC 7858, BC 7859 (ONT:H-), BC 7860 (O129:H-), BC 7861, BC 7862 (O103:H2), BC 7863, BC 7864 (O raw form:H-), BC 7865, BC 7866 (O26:H-), BC 7867 (O raw form:H-), BC 7868, BC 7869 (ONT:H-), BC 7870 (O113:H-), BC 7871 (ONT:H-), BC 7872 (ONT:H-), BC 7873, BC 7874 (O raw form:H-), BC 7875 (O157:H-), BC 7876 (O111:H-), BC 7877 (O146:H21), BC 7878 (O145:H-), BC 7879 (O22:H8), BC 7880 (O raw form:H-), BC 7881 (O145:H-), BC 8275 (O157:H7), BC 8318 (O55:K-:H-), BC 8325 (O157:H7), and BC 8332 (ONT), BC 8333.

In some embodiments, the present disclosure teaches host cells that can be enteroinvasive *E. coli* (EIEC), such as strains BC 8246 (O152:K-:H-), BC 8247 (O124:K(72):H3), BC 8248 (O124), BC 8249 (O112), BC 8250 (O136:K(78):H-), BC 8251 (O124:H-), BC 8252 (O144:K-:H-), BC 8253 (O143:K:H-), BC 8254 (O143), BC 8255 (O112), BC 8256 (O28a.e), BC 8257 (O124:H-), BC 8258 (O143), BC 8259 (O167:K-:H5), BC 8260 (O128a.c.:H35), BC 8261 (O164), BC 8262 (O164:K-:H-), BC 8263 (O164), and BC 8264 (O124).

In some embodiments, the present disclosure teaches host cells that can be enterotoxigenic *E. coli* (ETEC), such as strains BC 5581 (O78:H11), BC 5583 (O2:K1), BC 8221 (O118), BC 8222 (O148:H-), BC 8223 (O111), BC 8224 (O110:H-), BC 8225 (O148), BC 8226 (O118), BC 8227 (O25:H42), BC 8229 (O6), BC 8231 (O153:H45), BC 8232 (O9), BC 8233 (O148), BC 8234 (O128), BC 8235 (O118), BC 8237 (O111), BC 8238 (O110:H17), BC 8240 (O148), BC 8241 (O6H16), BC 8243 (O153), BC 8244 (O15:H-), BC 8245 (O20), BC 8269 (O125a.c:H-), BC 8313 (O6:H6), BC 8315 (O153:H-), BC 8329, BC 8334 (O118:H12), and BC 8339.

In some embodiments, the present disclosure teaches host cells that can be enteropathogenic *E. coli* (EPEC), such as strains BC 7567 (O86), BC 7568 (O128), BC 7571 (O114), BC 7572 (O119), BC 7573 (O125), BC 7574 (O124), BC 7576 (O127a), BC 7577 (O126), BC 7578 (O142), BC 7579 (O26), BC 7580 (OK26), BC 7581 (O142), BC 7582 (O55), BC 7583 (O158), BC 7584 (O-), BC 7585 (O-), BC 7586 (O-), BC 8330, BC 8550 (O26), BC 8551 (O55), BC 8552 (O158), BC 8553 (O26), BC 8554 (O158), BC 8555 (O86), BC 8556 (O128), BC 8557 (OK26), BC 8558 (O55), BC 8560 (O158), BC 8561 (O158), BC 8562 (O114), BC 8563 (O86), BC 8564 (O128), BC 8565 (O158), BC 8566 (O158), BC 8567 (O158), BC 8568 (O111), BC 8569 (O128), BC 8570 (O114), BC 8571 (O128), BC 8572 (O128), BC 8573 (O158), BC 8574 (O158), BC 8575 (O158), BC 8576 (O158), BC 8577 (O158), BC 8578 (O158), BC 8581 (O158), BC 8583 (O128), BC 8584 (O158), BC 8585 (O128), BC 8586 (O158), BC 8588 (O26), BC 8589 (O86), BC 8590 (O127), BC 8591 (O128), BC 8592 (O114), BC 8593 (O114), BC 8594 (O114), BC 8595 (O125), BC 8596 (O158), BC 8597 (O26), BC 8598 (O26), BC 8599 (O158), BC 8605 (O158), BC 8606 (O158), BC 8607 (O158), BC 8608 (O128), BC 8609 (O55), BC 8610 (O114), BC 8615 (O158), BC 8616 (O128), BC 8617 (O26), BC 8618 (O86), BC 8619, BC 8620, BC 8621, BC 8622, BC 8623, BC 8624 (O158), and BC 8625 (O158).

In some embodiments, the present disclosure also teaches host cells that can be *Shigella* organisms, including *Shigella flexneri, Shigella dysenteriae, Shigella boydii*, and *Shigella sonnei*.

The present disclosure is also suitable for use with a variety of animal cell types, including mammalian cells, for example, human (including 293, WI38, PER.C6 and Bowes melanoma cells), mouse (including 3T3, NS0, NS1, Sp2/0), hamster (CHO, BHK), monkey (COS, FRhL, Vero), and hybridoma cell lines.

In various embodiments, strains that may be used in the practice of the disclosure including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some embodiments, the methods of the present disclosure are also applicable to multi-cellular organisms. For example, the platform could be used for improving the performance of crops. The organisms can comprise a plurality of plants such as Gramineae, Fetucoideae, Poacoideae, *Agrostis, Phleum, Dactylis, Sorgum, Setaria, Zea, Oryza, Triticum, Secale, Avena, Hordeum, Saccharum, Poa, Festuca, Stenotaphrum, Cynodon, Coix*, Olyreae, Phareae, Compositae or Leguminosae. For example, the plants can be corn, rice, soybean, cotton, wheat, rye, oats, barley, pea, beans, lentil, peanut, yam bean, cowpeas, velvet beans, clover, alfalfa, lupine, vetch, lotus, sweet clover, *wisteria*, sweet pea, sorghum, millet, sunflower, canola or the like. Similarly, the organisms can include a plurality of animals such as non-human mammals, fish, insects, or the like.

Transformation of Host Cells

In some embodiments, the constructs generated by the methods of the present disclosure may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente, Methods in Enzymology 194: 182-187 (1991). In some embodiments, transformed host cells are referred to as recombinant host strains.

Automation

In one embodiment, the compositions and methods provided herein are incorporated into a high-throughput (HTP) method for genetic engineering of a host cell. In another embodiment, the methods provided herein can be a molecular tool that is part of the suite of HTP molecular tool sets described in PCT/US18/36360, PCT/US18/36333 or WO 2017/100377, each of which is herein incorporated by reference, for all purposes, to create HTP genetic design libraries, which are derived from, inter alia, scientific insight and iterative pattern recognition. The compositions and methods provided herein can be used to generate libraries for use in high-throughput methods such as those described in PCT/US18/36360, PCT/US18/36333 or WO 2017/100377. Examples of libraries that can be generated using the methods provided herein can include, but are not limited to promoter ladders, terminator ladders, solubility tag ladders or degradation tag ladders. Examples of high-throughput genomic engineering methods that can utilize the compositions and methods provided herein can include, but are not limited to, promoter swapping, terminator (stop) swapping, solubility tag swapping, degradation tag swapping or SNP swapping as described in PCT/US18/36360, PCT/US18/36333 or WO 2017/100377. The high-throughput methods can be automated and/or utilize robotics and liquid handling platforms (e.g., plate robotics platform and liquid handling machines known in the art. The high-throughput methods can utilize multi-well plates such as, for example microtiter plates.

In some embodiments, the automated methods of the disclosure comprise a robotic system. The systems outlined herein are generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated. The robotic systems compatible with the methods and compositions provided herein can be those described in PCT/US18/36360, PCT/US18/36333 or WO 2017/100377.

Kits

Also provided by the present disclosure are kits for practicing the methods for generating nucleic acid assemblies or libraries derived therefrom as described above. The kit can comprise a mixture containing all of the reagents necessary for assembling ssDNA molecules (e.g., oligonucleotides) or dsDNA molecules. In certain embodiments, a subject kit may contain: i. a pool of first polynucleotides containing pairs of first and second polynucleotides, ii. a second pool of insert polynucleotides, and (iii) optionally, a suitable cloning vector for propagation of the generated assemblies in a suitable host cell. In some cases, the kit includes a positive control.

In one embodiment, the kits provided herein further comprise a 5'-3' exonuclease, and a strand-displacing polymerase. In another embodiment, the kits provided herein further comprise a 5'-3' exonuclease, a ligase and a strand-displacing polymerase. In a still further embodiment, the kits provided herein comprise a single-stranded (ss) binding protein. The ss binding protein can be an extreme thermostable single-stranded DNA binding protein (ET SSB), *E. coli* recA, T7 gene 2.5 product, phage lambda RedB or Rac prophage RecT.

In a separate embodiment, the kits provided herein further comprise a 5' to 3' exonuclease that lacks 3' exonuclease activity, a crowding agent, a thermostable non-strand-displacing DNA polymerase with 3' exonuclease activity, or a mixture of said DNA polymerase with a second DNA polymerase that lacks 3' exonuclease activity, and an isolated thermostable ligase, in appropriate amounts. The crowding agent can PEG, dextran or ficoll. For example, the kit may contain T5 exonuclease, PEG, PHUSION®. DNA polymerase, and Taq ligase. In another example, the kit comprises: Exonuclease III, PEG, AMPLITAQ GOLD® DNA polymerase, and Taq ligase.

Any of the kits provided herein may also contain other reagents described above and below that may be employed in the method, e.g., a mismatch repair enzyme such as mutHLS, cel-1 nuclease, T7 endo 1, uvrD, T4 EndoVII, *E. coli* EndoV, a buffer, dNTPs, plasmids into which to insert the synthon and/or competent cells to receive the plasmids, controls etc., depending on how the method is going to be implemented.

The components of the kit may be combined in one container, or each component may be in its own container. For example, the components of the kit may be combined in a single reaction tube or in one or more different reaction tubes.

In addition to above-mentioned components, the subject kit further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded.

Compositions, kits and methods for assembling pairs of polynucleotides in a first pool and insert polynucleotides in a second pool as described herein result in a product that is a dsDNA that can serve as a template for PCR, RCA or a variety of other molecular biology applications including direct transformation or transfection of a competent prokaryotic or eukaryotic host cell.

EXAMPLES

The present disclosure is further illustrated by reference to the following Examples. However, it should be noted that these Examples, like the embodiments described above, are illustrative and are not to be construed as restricting the scope of the disclosure in any way.

Example 1—Proof of Principle of Method for Multiplexed Assembly of DNA Fragments into Deterministic Library of Plasmids Objective This example describes the use of an in vitro assembly reaction as shown schematically in FIG. 1 to deterministically join a pool comprising precisely designed DNA parts comprising 4 components to generate a library of desired plasmids.

Methods/Results

Insert sequences (i.e., payloads) were synthesized on either a column or an array to generate a pool of column-synthesized payloads and a pool of array-synthesized payloads, each containing a mixture of the 7 payload sequences shown below.

>pMB070_promoter
(SEQ ID NO. 1)
ACCGTGCGTGTTGACAATTTTACCTCTGGCGGTGATACTGGTTGCATGT

ACTAAGGAGGTTGT

>b2405_promoter
(SEQ ID NO. 2)
ATGTCGGATATCTGGTGGTGAAATACTTTATGCCATGATAATTTAATA

CGATGTATTTATTATATGGAGCACTTAATT

>b0605_promoter
(SEQ ID NO. 3)
TAATGGAAACGCATTAGCCGAATCGGCAAAAATTGGTTACCTTACATC

TCATCGAAAACACGGAGGAAGTATAG

>pMB043_promoter
(SEQ ID NO. 4)
ACCGTGCGTGTTGACTATTTTACCTCTGGCGGTTAGAGTTAACATCCTA

CAAGGAGAACAAAAGC

>pMB071_promoter
(SEQ ID NO. 5)
ACCGTGCGTGTTGACTTAAATACCACTGGCGGTGATAATGGTTGCATG

TACTAAGGAGGTTGT

>b0159_promoter
(SEQ ID NO. 6)
CTCTCCCGCGTGAGAAATACGCTTCCCCGTAAGCGCATGGTAAACTAT

GCCTTCAAATCGGGCTTATCGCGAGTAAATCT

>pMB090_promoter
(SEQ ID NO. 7)
ACCGTGCGTGTTTACAATTTTACCTCTGGCGGTGATAATTAACATCCTA

CAAGGAGAACAAAAGC

Figure 4:
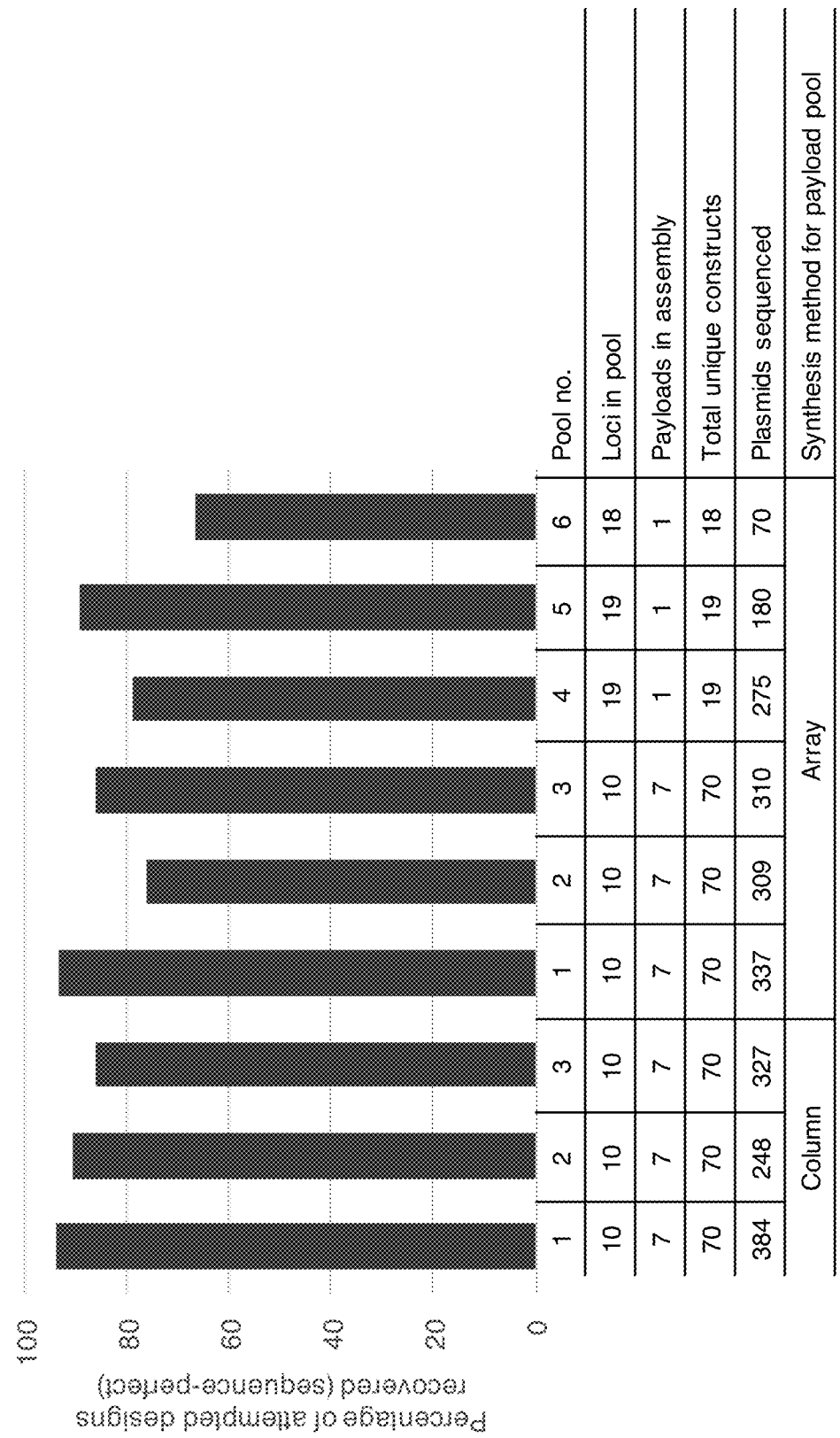
FIG. 4 illustrates assembly of deterministic libraries using the method of FIG. 1. The number of unique loci, payloads, and total possible constructs in each library is given in the table.

Separately, 6 pools comprising pairs of left and right homology arms were generated (i.e., loci pool numbers referenced in FIG. 4). Each loci pool contained a number of homology arms that each comprised sequence complementary to a separate locus in the genome of a *Escherichia coli* host cell; the number of unique loci (i.e., number of pairs of homology arms) is given below the plot for each pool in FIG. 4 (i.e., 'Loci in Pool' in Table below graph). The sequences of each homology arm in each pair from each pool are SEQ ID NOs 8-179.

The pool of column-synthesized payloads and the pool of array-synthesized payloads were each separately mixed with the specific loci pool designated in FIG. 4. It should be noted that each mixture contained a molar ratio of left homology arm:payload:right homology arm was roughly 1:10:1. There was an excess of the payload because the payload pools contained oligonucleotides corresponding to 100-500 unique left and right homology arms, while only 10-19 homology arms were assembled in a given reaction given that a certain fraction of insert oligonuclotides would be inert in the reaction. The mixture further comprised the NEB Hifi DNA assembly master mix and a cloning vector for propagation in an *E. coli* cloning strain. Each mixture contained about 0.05 pmol of the respective loci pool, 0.2-1 pmol of the respective payload pool, and 0.0125 pmol of the cloning vector, theoretically resulting in 0.0125 pmol of final assembled product. Once assembled, each of the mixtures was subjected to the NEB Hifi DNA Assembly protocol for in vitro overlap assembly and propagated in an *E. coli* cloning strain. The number of unique loci (pairs of homology arms), payloads, and total possible constructs in each library is given in the table in FIG. 4.

Following propagation, at least 100 colonies per assembly were picked separately into liquid culture and grown overnight. The liquid culture was used as template for a rolling-circle amplification (RCA) of the entire cloned plasmid. The RCA product was fragmented using a Tn5 transposase fragmentation and adapter-ligation kit (Nextera, Illumina). Sample-specific indexing barcodes were then added via PCR, and plasmids from the libraries were the pooled and column purified. Library molarity was assessed with a Tapestation instrument and plasmids from the libraries were loaded onto a MiSeq instrument (300 cycle kit) for sequencing. The number of plasmids sequenced for each assembly in shown in FIG. 4.

To determine what assembly had been generated in the pool of assemblies, algorithms were used to search for unique 20-mer sequences for each junction between parts in each unique assembly in the raw sequencing reads in order to identify which DNA sequence was assembled. The reads were then mapped to the corresponding reference sequence for each sample in order to determine the full-length products created. In the plot in FIG. 4, 'sequence-perfect' means that all four parts (vector backbone, left and right homology arms, and payload) were assembled together and there were no mutations in the plasmid. 'Correct assembly with mutations' indicates the presence of all four parts in the correct arrangement but with one or more point mutations in the plasmid. 'Misassembly' indicates plasmids with mispaired homology arms, or part(s) or portions of parts not present.

Conclusion

The results shown in FIG. 4 indicate that the process depicted in FIG. 1 can be successfully utilized to generate deterministic libraries of DNA assemblies.

Example 2—Proof of Principle of Method for Multiplexed Deterministic Assembly with Large Payloads Using Circular-Permuted Payload Objective This example describes the use of an in vitro assembly reaction as shown schematically in FIG. 1 to deterministically join a pool comprising precisely designed DNA parts including a circular-permuted payload (insert) whose preparation is described in FIG. 3.

Methods/Results

Insert was prepared by amplifying a template comprising the payload sequence (~2670 bp) using a pooled forward primer comprising, from 5' to 3' end, an assembly overlap to the right side of the payload, 53 bp of HOM2, an I-SceI restriction endonuclease recognition site, 53 bp of HOM1, and a primer binding site at the left side of the payload. The amplification product was excised from an agarose gel using a Qiagen gel extraction kit. The excised product was circularized in an NEB HiFi assembly reaction, purified via paramagnetic bead-based clean-up (e.g., an AXYPREP mag bead cleanup), and linearized using I-SceI (the 'circular permutation').

Separately, left and right homology arms that each comprised sequence complementary to a separate locus in the genome of a *Saccharomyces cerevisiae* host cell were amplified from genomic DNA.

The circular-permuted pooled payload and the set of left and right homology arms were combined with a cloning vector and assembled using an NEB HiFi reaction. The mixture contained a molar ratio of left homology arms: pooled insert:right homology arms of roughly 1:5:1. An excess of the insert was used because the pooled insert contained 54 unique sequences compared to the ten pairs of left/right homology arms used in the assembly. The mixture contained about 16 fmol of the hom arm pools, 80 fmol of the payload pool, and 2.5 fmol of the cloning vector, theoretically resulting in 2.5 fmol of final assembled product. Once assembled, the mixture was subjected to the NEB Hifi DNA Assembly protocol for in vitro overlap assembly and propagated in an *E. coli* cloning strain.

Following propagation, several colonies were picked separately into liquid culture and grown overnight. The liquid culture was used as template for a rolling-circle amplification (RCA) of the entire cloned plasmid. The RCA product was sequenced with two primers (one forward and one reverse) by Sanger sequencing. The primers were designed to bind on the cloning vector and read into the hom arms and payload.

Figure 5:
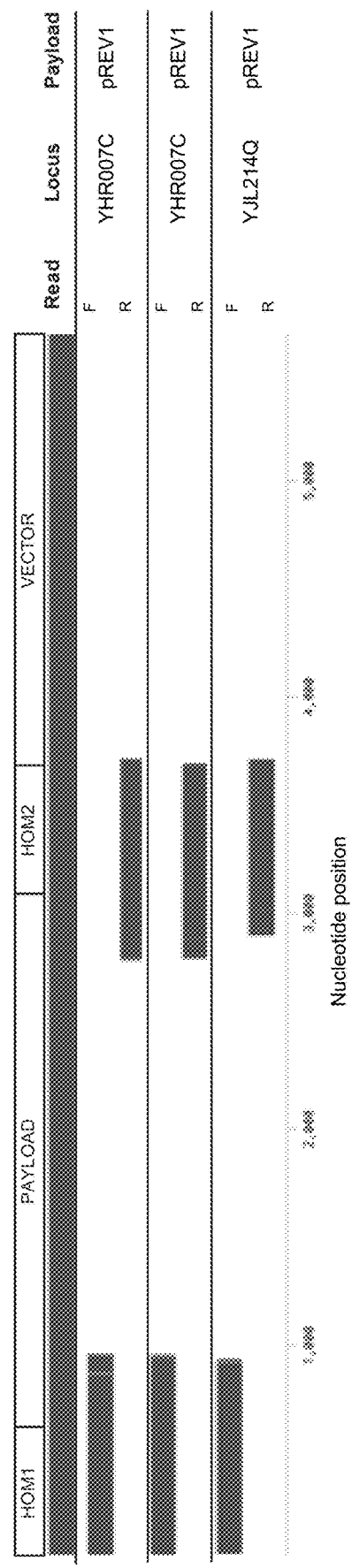
FIG. 5 illustrates the results of the successful in vitro assembly of deterministic libraries employing a pool comprising precisely designed DNA parts including a circular-permuted payload (insert). The long bars at the top indicate the structure of the plasmids to be assembled in the pool, and the shorter bars below represent Sanger sequences aligned to the corresponding reference sequence for three separate samples from the pool of assemblies. Faint vertical lines at the inner ends of the reads represent expected sequencing artifacts at the tail ends of Sanger reads.

To determine what assembly had been generated in the pool of assemblies, algorithms were used to search for unique 20-mer sequences in each unique assembly in the sequencing reads. The reads were then aligned to the corresponding reference sequence for each sample in order to verify the intended junctions were created, indicating the plasmid had assembled correctly. In FIG. 5, the long bars at the top indicate the structure of the plasmids to be assembled in the pool, and the shorter bars below represent Sanger sequences aligned to the corresponding reference sequence for three separate samples from the pool of assemblies. Faint vertical lines at the inner ends of the reads represent expected sequencing artifacts at the tail ends of Sanger reads. The data indicate that all of the intended junctions were assembled.

Conclusion

The results shown in FIG. 5 indicate that the processes depicted in FIG. 1 and FIG. 3 can be successfully utilized to generate deterministic libraries of DNA assemblies incorporating long payloads (e.g., >200 bp).

Figure 6:
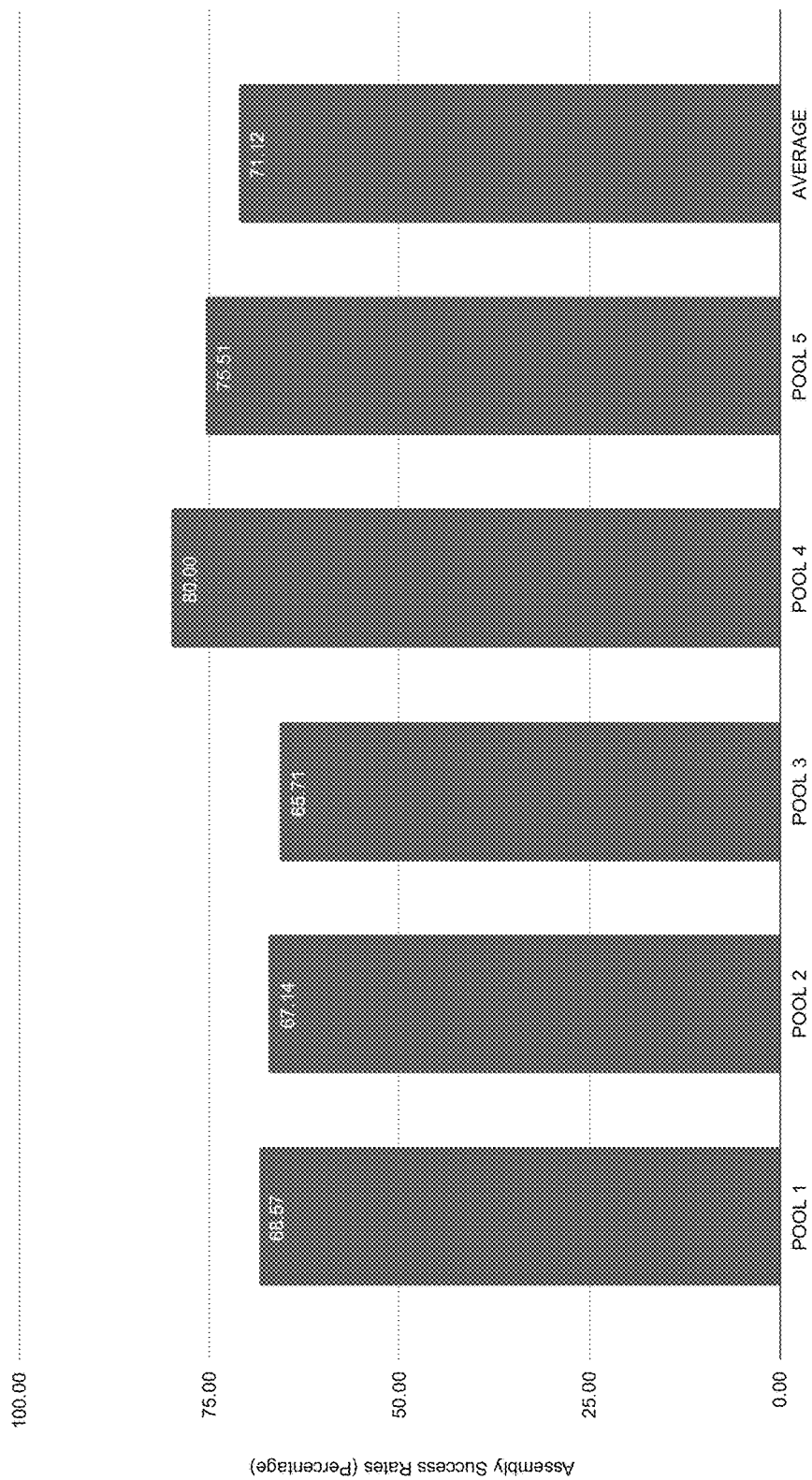
FIG. 6 illustrates total success rates for pooled assemblies for which payload containing parts were created via PCR using primers that append the assembly overlaps from templates derived from a host genome.

Example 3—Proof of Principle of Method for Multiplexed Deterministic Assembly with Large Payloads Using PCR-Amplified Payload Methods/Results FIG. 6 shows total success rates for pooled assemblies for which payload containing parts were created via PCR using primers that append the assembly overlaps from templates derived from a host genome. Amplified payloads ranged from 182-213 bp in length. PCR-amplified parts with appended 25 bp assembly overlaps were purified via magnetic bead-based protocol and subsequently normalized along with left and right parts containing homology arms to 0.25 picomoles total for payload, left and right parts separately and 0.05 picomoles of vector backbone before performing assembly using NEB's HIFI assembly master-mix and subsequently electroporated into electrocompetent cells. Success rates were calculated from the percentage of plasmids that were recovered and passed NGS-QC relative to those that were attempted to be created. Success rates were based on recovering and sequencing the following numbers of unique plasmids for each pool: pool 1: (48/70 plasmids), pool 2: (47/70 plasmids), pool 3: (46/70 plasmids), pool 4 (56/70 plasmids), pool 5: (37/49 plasmids). For pools 1:4, 7 promoter payloads were targeted to 10 Loci, and for pool 5 7 promoter payloads were targeted to 7 loci. Collectively across all five pools we 234/329 or 71.12% of plasmids were created and NGS-confirmed.

Conclusion

The results shown in FIG. 6 indicate that the process depicted in FIG. 1 can be successfully utilized with PCR-amplified insert fragments to generate deterministic libraries of DNA assemblies incorporating long payloads (e.g. >200 bp).

SEQUENCES OF THE DISCLOSURE WITH SEQ ID NO IDENTIFIERS

| Name | NUCLEIC ACID SEQ ID NO: | Description |
| --- | --- | --- |
| pMB070_promoter | 1 | Payload sequence |
| b2405_promoter | 2 | Payload sequence |
| b0605_promoter | 3 | Payload sequence |
| pMB043_promoter | 4 | Payload sequence |
| pMB071_promoter | 5 | Payload sequence |
| b0159_promoter | 6 | Payload sequence |
| pMB090_promoter | 7 | Payload sequence |
| pool_1_b3748_left | 8 | Pool 1-Left Homology Arm |
| pool_1_b3748_right | 9 | Pool 1-Right Homology Arm |
| pool_1_b0388_left | 10 | Pool 1-Left Homology Arm |
| pool_1_b0388_right | 11 | Pool 1-Right Homology Arm |
| pool_1_b4348_left | 12 | Pool 1-Left Homology Arm |
| pool_1_b4348_right | 13 | Pool 1-Right Homology Arm |
| pool_1_b1982_left | 14 | Pool 1-Left Homology Arm |
| pool_1_b1982_right | 15 | Pool 1-Right Homology Arm |
| pool_1_b4367_left | 16 | Pool 1-Left Homology Arm |
| pool_1_b4367_right | 17 | Pool 1-Right Homology Arm |
| pool_1_b2285_left | 18 | Pool 1-Left Homology Arm |
| pool_1_b2285_right | 19 | Pool 1-Right Homology Arm |
| pool_1_b2405_left | 20 | Pool 1-Left Homology Arm |
| pool_1_b2405_right | 21 | Pool 1-Right Homology Arm |
| pool_1_b0495_left | 22 | Pool 1-Left Homology Arm |
| pool_1_b0495_right | 23 | Pool 1-Right Homology Arm |
| pool_1_b1646_left | 24 | Pool 1-Left Homology Arm |
| pool_1_b1646_right | 25 | Pool 1-Right Homology Arm |
| pool_1_b3189_left | 26 | Pool 1-Left Homology Arm |
| pool_1_b3189_right | 27 | Pool 1-Right Homology Arm |
| pool_2_b3125_left | 28 | Pool 2-Left Homology Arm |
| pool_2_b3125_right | 29 | Pool 2-Right Homology Arm |
| pool_2_b3787_left | 30 | Pool 2-Left Homology Arm |
| pool_2_b3787_right | 31 | Pool 2-Right Homology Arm |
| pool_2_b1948_left | 32 | Pool 2-Left Homology Arm |
| pool_2_b1948_right | 33 | Pool 2-Right Homology Arm |
| pool_2_b2790_left | 34 | Pool 2-Left Homology Arm |
| pool_2_b2790_right | 35 | Pool 2-Right Homology Arm |
| pool_2_b3197_left | 36 | Pool 2-Left Homology Arm |
| pool_2_b3197_right | 37 | Pool 2-Right Homology Arm |
| pool_2_b3791_left | 38 | Pool 2-Left Homology Arm |
| pool_2_b3791_right | 39 | Pool 2-Right Homology Arm |
| pool_2_b4260_left | 40 | Pool 2-Left Homology Arm |
| pool_2_b4260_right | 41 | Pool 2-Right Homology Arm |
| pool_2_b0071_left | 42 | Pool 2-Left Homology Arm |
| pool_2_b0071_right | 43 | Pool 2-Right Homology Arm |
| pool_2_b1687_left | 44 | Pool 2-Left Homology Arm |
| pool_2_b1687_right | 45 | Pool 2-Right Homology Arm |
| pool_2_b1006_left | 46 | Pool 2-Left Homology Arm |
| pool_2_b1006_right | 47 | Pool 2-Right Homology Arm |
| pool_3_b0335_left | 48 | Pool 3-Left Homology Arm |
| pool_3_b0335_right | 49 | Pool 3-Right Homology Arm |
| pool_3_b1940_left | 50 | Pool 3-Left Homology Arm |
| pool_3_b1940_right | 51 | Pool 3-Right Homology Arm |
| pool_3_b0109_left | 52 | Pool 3-Left Homology Arm |
| pool_3_b0109_right | 53 | Pool 3-Right Homology Arm |
| pool_3_b3399_left | 54 | Pool 3-Left Homology Arm |
| pool_3_b3399_right | 55 | Pool 3-Right Homology Arm |
| pool_3_b2478_left | 56 | Pool 3-Left Homology Arm |
| pool_3_b2478_right | 57 | Pool 3-Right Homology Arm |
| pool_3_b0320_left | 58 | Pool 3-Left Homology Arm |
| pool_3_b0320_right | 59 | Pool 3-Right Homology Arm |
| pool_3_b4521_left | 60 | Pool 3-Left Homology Arm |
| pool_3_b4521_right | 61 | Pool 3-Right Homology Arm |
| pool_3_b2260_left | 62 | Pool 3-Left Homology Arm |
| pool_3_b2260_right | 63 | Pool 3-Right Homology Arm |
| pool_3_b4169_left | 64 | Pool 3-Left Homology Arm |
| pool_3_b4169_right | 65 | Pool 3-Right Homology Arm |
| pool_3_b2405_left | 66 | Pool 3-Left Homology Arm |
| pool_3_b2405_right | 67 | Pool 3-Right Homology Arm |
| pool_4_b3493_left | 68 | Pool 4-Left Homology Arm |
| pool_4_b3493_right | 69 | Pool 4-Right Homology Arm |
| pool_4_b0479_left | 70 | Pool 4-Left Homology Arm |
| pool_4_b0479_right | 71 | Pool 4-Right Homology Arm |
| pool_4_b2470_left | 72 | Pool 4-Left Homology Arm |
| pool_4_b2470_right | 73 | Pool 4-Right Homology Arm |
| pool_4_b1451_left | 74 | Pool 4-Left Homology Arm |
| pool_4_b1451_right | 75 | Pool 4-Right Homology Arm |
| pool_4_b1981_left | 76 | Pool 4-Left Homology Arm |
| pool_4_b1981_right | 77 | Pool 4-Right Homology Arm |
| pool_4_b0237_left | 78 | Pool 4-Left Homology Arm |
| pool_4_b0237_right | 79 | Pool 4-Right Homology Arm |
| pool_4_b2497_left | 80 | Pool 4-Left Homology Arm |
| pool_4_b2497_right | 81 | Pool 4-Right Homology Arm |
| pool_4_b4260_left | 82 | Pool 4-Left Homology Arm |
| pool_4_b4260_right | 83 | Pool 4-Right Homology Arm |
| pool_4_b1412_left | 84 | Pool 4-Left Homology Arm |
| pool_4_b1412_right | 85 | Pool 4-Right Homology Arm |
| pool_4_b4139_left | 86 | Pool 4-Left Homology Arm |
| pool_4_b4139_right | 87 | Pool 4-Right Homology Arm |
| pool_4_b2039_left | 88 | Pool 4-Left Homology Arm |
| pool_4_b2039_right | 89 | Pool 4-Right Homology Arm |
| pool_4_b4473_left | 90 | Pool 4-Left Homology Arm |
| pool_4_b4473_right | 91 | Pool 4-Right Homology Arm |
| pool_4_b3510_left | 92 | Pool 4-Left Homology Arm |
| pool_4_b3510_right | 93 | Pool 4-Right Homology Arm |
| pool_4_b1007_left | 94 | Pool 4-Left Homology Arm |
| pool_4_b1007_right | 95 | Pool 4-Right Homology Arm |
| pool_4_b3058_left | 96 | Pool 4-Left Homology Arm |
| pool_4_b3058_right | 97 | Pool 4-Right Homology Arm |
| pool_4_b2688_left | 98 | Pool 4-Left Homology Arm |
| pool_4_b2688_right | 99 | Pool 4-Right Homology Arm |
| pool_4_b1716_left | 100 | Pool 4-Left Homology Arm |
| pool_4_b1716_right | 101 | Pool 4-Right Homology Arm |
| pool_4_b3071_left | 102 | Pool 4-Left Homology Arm |
| pool_4_b3071_right | 103 | Pool 4-Right Homology Arm |
| pool_4_b2139_left | 104 | Pool 4-Left Homology Arm |
| pool_4_b2139_right | 105 | Pool 4-Right Homology Arm |
| pool_5_b2434_left | 106 | Pool 5-Left Homology Arm |
| pool_5_b2434_right | 107 | Pool 5-Right Homology Arm |
| pool_5_b2037_left | 108 | Pool 5-Left Homology Arm |
| pool_5_b2037_right | 109 | Pool 5-Right Homology Arm |
| pool_5_b2451_left | 110 | Pool 5-Left Homology Arm |
| pool_5_b2451_right | 111 | Pool 5-Right Homology Arm |
| pool_5_b1902_left | 112 | Pool 5-Left Homology Arm |
| pool_5_b1902_right | 113 | Pool 5-Right Homology Arm |
| pool_5_b4310_left | 114 | Pool 5-Left Homology Arm |
| pool_5_b4310_right | 115 | Pool 5-Right Homology Arm |
| pool_5_b0676_left | 116 | Pool 5-Left Homology Arm |
| pool_5_b0676_right | 117 | Pool 5-Right Homology Arm |
| pool_5_b1497_left | 118 | Pool 5-Left Homology Arm |
| pool_5_b1497_right | 119 | Pool 5-Right Homology Arm |
| pool_5_b0183_left | 120 | Pool 5-Left Homology Arm |
| pool_5_b0183_right | 121 | Pool 5-Right Homology Arm |
| pool_5_b3631_left | 122 | Pool 5-Left Homology Arm |
| pool_5_b3631_right | 123 | Pool 5-Right Homology Arm |
| pool_5_b3791_left | 124 | Pool 5-Left Homology Arm |
| pool_5_b3791_right | 125 | Pool 5-Right Homology Arm |
| pool_5_b0438_left | 126 | Pool 5-Left Homology Arm |
| pool_5_b0438_right | 127 | Pool 5-Right Homology Arm |

-continued

SEQUENCES OF THE DISCLOSURE
WITH SEQ ID NO IDENTIFIERS

| Name | NUCLEIC ACID SEQ ID NO: | Description |
|---|---|---|
| pool_5_b1981_left | 128 | Pool 5-Left Homology Arm |
| pool_5_b1981_right | 129 | Pool 5-Right Homology Arm |
| pool_5_b1709_left | 130 | Pool 5-Left Homology Arm |
| pool_5_b1709_right | 131 | Pool 5-Right Homology Arm |
| pool_5_b2176_left | 132 | Pool 5-Left Homology Arm |
| pool_5_b2176_right | 133 | Pool 5-Right Homology Arm |
| pool_5_b2168_left | 134 | Pool 5-Left Homology Arm |
| pool_5_b2168_right | 135 | Pool 5-Right Homology Arm |
| pool_5_b1872_left | 136 | Pool 5-Left Homology Arm |
| pool_5_b1872_right | 137 | Pool 5-Right Homology Arm |
| pool_5_b1203_left | 138 | Pool 5-Left Homology Arm |
| pool_5_b1203_right | 139 | Pool 5-Right Homology Arm |
| pool_5_b2231_left | 140 | Pool 5-Left Homology Arm |
| pool_5_b2231_right | 141 | Pool 5-Right Homology Arm |
| pool_5_b1622_left | 142 | Pool 5-Left Homology Arm |
| pool_5_b1622_right | 143 | Pool 5-Right Homology Arm |
| pool_6_b1857_left | 144 | Pool 6-Left Homology Arm |
| pool_6_b1857_right | 145 | Pool 6-Right Homology Arm |
| pool_6_b4024_left | 146 | Pool 6-Left Homology Arm |
| pool_6_b4024_right | 147 | Pool 6-Right Homology Arm |
| pool_6_b3942_left | 148 | Pool 6-Left Homology Arm |
| pool_6_b3942_right | 149 | Pool 6-Right Homology Arm |
| pool_6_b0592_left | 150 | Pool 6-Left Homology Arm |
| pool_6_b0592_right | 151 | Pool 6-Right Homology Arm |
| pool_6_b1415_left | 152 | Pool 6-Left Homology Arm |
| pool_6_b1415_right | 153 | Pool 6-Right Homology Arm |
| pool_6_b1762_left | 154 | Pool 6-Left Homology Arm |
| pool_6_b1762_right | 155 | Pool 6-Right Homology Arm |
| pool_6_b3414_left | 156 | Pool 6-Left Homology Arm |
| pool_6_b3414_right | 157 | Pool 6-Right Homology Arm |
| pool_6_b4374_left | 158 | Pool 6-Left Homology Arm |
| pool_6_b4374_right | 159 | Pool 6-Right Homology Arm |
| pool_6_b2917_left | 160 | Pool 6-Left Homology Arm |
| pool_6_b2917_right | 161 | Pool 6-Right Homology Arm |
| pool_6_b0346_left | 162 | Pool 6-Left Homology Arm |
| pool_6_b0346_right | 163 | Pool 6-Right Homology Arm |
| pool_6_b3966_left | 164 | Pool 6-Left Homology Arm |
| pool_6_b3966_right | 165 | Pool 6-Right Homology Arm |
| pool_6_b0406_left | 166 | Pool 6-Left Homology Arm |
| pool_6_b0406_right | 167 | Pool 6-Right Homology Arm |
| pool_6_b0652_left | 168 | Pool 6-Left Homology Arm |
| pool_6_b0652_right | 169 | Pool 6-Right Homology Arm |
| pool_6_b1493_left | 170 | Pool 6-Left Homology Arm |
| pool_6_b1493_right | 171 | Pool 6-Right Homology Arm |
| pool_6_b4159_left | 172 | Pool 6-Left Homology Arm |
| pool_6_b4159_right | 173 | Pool 6-Right Homology Arm |
| pool_6_b3795_left | 174 | Pool 6-Left Homology Arm |
| pool_6_b3795_right | 175 | Pool 6-Right Homology Arm |
| pool_6_b4246_left | 176 | Pool 6-Left Homology Arm |
| pool_6_b4246_right | 177 | Pool 6-Right Homology Arm |
| pool_6_b4440_left | 178 | Pool 6-Left Homology Arm |
| pool_6_b4440_right | 179 | Pool 6-Right Homology Arm |

Numbered Embodiments of the Disclosure

Other subject matter contemplated by the present disclosure is set out in the following numbered embodiments:

1. A composition comprising a mixture of polynucleotides, the mixture comprising:
a first pool containing pairs of polynucleotides, wherein each pair in the first pool contains a first polynucleotide and a second polynucleotide; and
a second pool of insert polynucleotides, wherein each insert polynucleotide in the second pool comprises a first assembly overlap sequence at its 5' end that is complementary to a 3' end of a first polynucleotide and a second assembly overlap sequence at its opposing 3'end that is complementary to a 5' end of a second polynucleotide in a pair of polynucleotides from the first pool.

2. The composition of embodiment 1, further comprising a cloning vector, wherein, for each pair in the first pool, a 5' end of the first polynucleotide and a 3' end of the second polynucleotide comprises sequence complementary to the cloning vector.

3. The composition of embodiment 2, wherein each polynucleotide from the first pool is selected such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector.

4. The composition of embodiment 3, wherein the specified threshold is between 5 and 15 contiguous nucleotides.

5. The composition of any one of embodiments 1-4, further comprising a polymerase.

6. The composition of embodiment 5, wherein the polymerase is strand-displacing or non-strand displacing.

7. The composition of embodiment 6, wherein the polymerase is non-strand displacing and the composition further comprises a crowding agent.

8. The composition of embodiment 7, wherein the crowding agent is polyethylene glycol (PEG).

9. The composition of embodiment 8, wherein the PEG is used at a concentration of from about 3 to about 7% (weight/volume).

10. The composition of embodiment 8 or 9, wherein the PEG is selected from PEG-200, PEG-4000, PEG-6000, PEG-8000 or PEG-20,000.

11. The composition of embodiment 6, wherein the polymerase is strand displacing and the composition further comprises a single-stranded binding protein.

12. The composition of embodiment 11, wherein the single strand DNA binding protein is an extreme thermostable single-stranded DNA binding protein (ET SSB), *E. coli* recA, T7 gene 2.5 product, phage lambda RedB or Rac prophage RecT.

13. The composition of any one of the above embodiments, further comprising a 5'-3' exonuclease.

14. The composition of any one of the above embodiments, further comprising a ligase.

15. The composition of any one of the above embodiments, wherein each pair in the first pool is double-stranded DNA (dsDNA) or single-stranded DNA (ssDNA).

16. The composition of any one of the above embodiments, wherein each insert polynucleotide in the second pool is dsDNA or ssDNA.

17. The composition of any one of the above embodiments, wherein, for each pair in the first pool, the first polynucleotide and the second polynucleotide comprises sequence corresponding to a target genomic locus in a host cell.

18. The composition of any one of embodiments 1-16, wherein, for each pair in the first pool, the first polynucleotide and the second polynucleotide comprise coding sequence corresponding to a gene that is part of a metabolic pathway.

19. The composition of any one of embodiments 1-18, wherein, for each pair in the first pool, the first polynucleotide and the second polynucleotide comprise coding sequence corresponding to a functional domain or one or more proteins.

20. The composition of any one of the above embodiments, wherein, for each pair in the first pool, the first polynucleotide and the second polynucleotide are linked together in a single construct, wherein the single construct comprises one or more recognition sequences for one or more site-specific nucleases between the first polynucleotide and the second polynucleotide.

21. The composition of embodiment 20, wherein the one or more recognition sequences for one or more site-specific nucleases comprise a homing endonuclease recognition sequence.

22. The composition of any one of the above embodiments, wherein the first assembly overlap sequence and the second assembly overlap sequence on each insert polynucleotide in the second pool comprises 1 or more nucleotides that are complementary to the 3' end of a first polynucleotide and the 5' end of a second polynucleotide, respectively, in a pair of polynucleotides from the first pool.

23. The composition of any one of the above embodiments, wherein the first assembly overlap sequence and the second assembly overlap sequence on each insert polynucleotide in the second pool comprises about 25 nucleotides that are complementary to the 3' end of a first polynucleotide and the 5' end of a second polynucleotide, respectively, in a pair of polynucleotides from the first pool.

24. The composition of any one of the above embodiments, wherein each insert polynucleotide in the second pool comprises one or more payload sequences located between the first assembly overlap sequence and the second assembly overlap sequence.

25. The composition of embodiment 24, wherein the one or more payload sequences are selected from promoters, genes, regulatory sequences, nucleic acid sequence encoding degrons, nucleic acid sequence encoding solubility tags, terminators, unique identifier sequence or portions thereof.

26. The composition of embodiment 17, wherein each pair of first and second polynucleotides in the first pool comprises sequence corresponding to a different target genomic locus in a host cell as compared to each other pair in the first pool.

27. The composition of embodiment 17, wherein, for each pair in the first pool, the first polynucleotide and the second polynucleotide comprises sequence corresponding to the same target genomic locus in a host cell.

28. The composition of any one of embodiments 24-27, wherein each payload sequence in the insert polynucleotides in the second pool is different from the payload sequence in each other insert polynucleotide in the second pool.

29. The composition of any one of embodiments 24-27, wherein each payload sequence in the insert polynucleotides in the second pool is the same as the payload sequence in each other insert polynucleotide in the second pool.

30. A method for generating libraries of polynucleotides, the method comprising:
(a) combining a first pool of polynucleotides and a second pool of polynucleotides, wherein the first pool contains pairs of polynucleotides, wherein each pair in the first pool contains a first polynucleotide and a second polynucleotide, wherein the second pool contains insert polynucleotides, wherein each insert polynucleotide in the second pool comprises a first assembly overlap sequence at its 5' end that is complementary to a 3' end of a first polynucleotide and a second assembly overlap sequence at its opposing 3'end that is complementary to a 5' end of a second polynucleotide in a pair of polynucleotides from the first pool; and
(b) assembling the first pool and the second pool into a library of polynucleotides, wherein each polynucleotide in the library comprises an insert polynucleotide from the second pool and a pair of first polynucleotides and second polynucleotides from the first pool, wherein the assembling is performed via in vitro cloning methods or in vivo cloning methods.

31. The method of embodiment 30, wherein the first assembly overlap sequence and the second assembly overlap sequence on each insert polynucleotide in the second pool comprises 1 or more nucleotides that are complementary to the 3' end of a first polynucleotide and the 5' end of a second polynucleotide, respectively, in a pair of polynucleotides from the first pool.

32. The method of embodiment 30 or 31, wherein the first assembly overlap sequence and the second assembly overlap sequence on each insert polynucleotide in the second pool comprises about 25 nucleotides that are complementary to the 3' end of a first polynucleotide and the 5' end of a second polynucleotide, respectively, in a pair of polynucleotides from the first pool.

33. The method of any one of embodiments 30-32, wherein, for each pair in the first pool, the first polynucleotide and the second polynucleotide are linked together in a single construct, wherein the single construct comprises one or more recognition sequences for one or more site-specific nucleases between the first polynucleotide and the second polynucleotide.

34. The method of embodiment 33, wherein the one or more recognition sequences for one or more site-specific nucleases comprises a homing endonuclease recognition sequence.

35. The method of embodiment 33, wherein the linked single construct is produced by joining individual first and second polynucleotides via splicing and overlap-extension PCR (SOE-PCR), restriction-ligation, blunt-end ligation, overlap-based assembly method, recombination-based method, or any other enzymatic or chemical method of joining the first and second polynucleotides, or by synthesizing the single-construct directly.

36. The method of any one of embodiments 30-32, further comprising combining a cloning vector with the first pool and the second pool during step (a), wherein opposing ends of the cloning vector comprise sequence complementary to a 5'end of the first polynucleotide and a 3' end of the second polynucleotide for each pair in the first pool.

37. The method of any one of embodiments 30-32, further comprising combining a cloning vector with the first pool prior to step (a), wherein opposing ends of the cloning vector comprise sequence complementary to a 5'end of the first polynucleotide and a 3' end of the second polynucleotide for each pair in the first pool.

38. The method of embodiment 36 or 37, wherein the cloning vector and the 5'end of the first polynucleotide and the 3'end of the second polynucleotide in each pair from the first pool comprise one or more recognition sequences for one or more site-specific nucleases.

39. The method of embodiment 38, further comprising generating single-stranded complementary overhangs between the opposing ends of the cloning vector and the 5'end of the first polynucleotide and the 3'end of the second polynucleotide in each pair from the first pool by adding the one or more site-specific nucleases for the one or more recognition sequences.

40. The method of embodiment 39, further comprising ligating the single-stranded complementary overhangs between the opposing ends of the cloning vector and the 5'end of the first polynucleotide and the 3'end of the second polynucleotide in each pair from the first pool.

41. The method of any one of embodiments 36-40, wherein step (b) results in a circular product comprising an insert polynucleotide from the second pool, a first and second polynucleotide from a pair from the first pool and the cloning vector.

42. The method of any one of embodiments 36-41, wherein the first pool is generated by selecting pairs of polynucleotide sequences from a larger set of such sequences such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector.

43. The method of embodiment 42, wherein the specified threshold is between 5 and 15 contiguous nucleotides.

44. The method of any one of embodiments 30-43, wherein the assembly is an in vitro cloning method, wherein the mixture of the first pool and the second pool is heated to partially or fully denature polynucleotides present in the first and the second pools, then cooled to room temperature before assembly.

45. A method for generating libraries of polynucleotides, the method comprising:
(a) amplifying via polymerase chain reaction (PCR) a first pool of polynucleotides, wherein the first pool contains pairs of polynucleotides, wherein each pair in the first pool contains a first polynucleotide and a second polynucleotide, and wherein each first polynucleotide and each second polynucleotide in a pair comprises a 5' end and a 3' end, wherein the amplifying introduces a common overlap sequence comprising one or more recognition sequences for one or more site-specific nucleases onto the 5' end of a first polynucleotide and the 3'end of a second polynucleotide in a pair from the first pool;
(b) assembling each pair of first polynucleotides and second polynucleotides from the first pool into a single nucleic acid fragment by utilizing common overlap sequence, wherein the single nucleic fragment for each pair comprises a first polynucleotide and second polynucleotide separated by the common overlap sequence from the 5' end of the first polynucleotide and the 3' end of the second polynucleotide, and wherein the 3'end of the first polynucleotide and the 5' end of the second polynucleotide in the single nucleic fragment for each pair are located on opposing terminal ends of the single nucleic acid fragment, distal to the one or more site-specific nuclease recognition sequence(s);
(c) combining the single nucleic acid fragments for each pair with a second pool containing insert polynucleotides, wherein each insert polynucleotide in the second pool comprises a first assembly overlap sequence at its 5' end that is complementary to the 3' end of the first polynucleotide present within the single nucleic acid fragment and a second assembly overlap sequence at its opposing 3'end that is complementary to the 5' end of the second polynucleotide present within the single nucleic acid fragment;
(d) assembling the first pool and the second pool into a third pool of circularized products, wherein the assembling is performed via in vitro or in vivo overlap assembly methods, and wherein each circularized product in the third pool comprises an insert sequence from the second pool and a pair of first polynucleotides and second polynucleotides from the first pool;
(e) linearizing each circularized product in the third pool via digestion by one or more site-specific nuclease(s) that recognizes the one or more site-specific nuclease recognition sequence(s) located between the first polynucleotide sequence and the second polynucleotide sequence in each of the circularized products in the third pool; and
(f) assembling the linearized products into cloning vectors by in vitro or in vivo cloning methods.

46. The method of embodiment 45, wherein the one or more site-specific nuclease recognition sequence(s) located between the first polynucleotide sequence and the second polynucleotide sequence is a homing nuclease recognition sequence.

47. The method of embodiment 45 or 46, wherein the one or more site-specific nuclease(s) for the one or more site-specific nuclease recognition sequence(s) located between the first polynucleotide sequence and the second polynucleotide sequence is a homing endonuclease.

48. The method of any one of embodiments 45-47, wherein the common overlap sequence comprises an assembly overlap sequence of at least 1 nucleotide and the assembly in step (b) is performed by an overlap-based DNA assembly method.

49. The method of any one of embodiments 45-47, wherein the common overlap sequence comprises an assembly overlap sequence of from 10-25 nucleotides and the assembly in step (b) is performed by an overlap-based DNA assembly method.

50. The method of embodiment 48 or 49, wherein the overlap-based DNA assembly method is selected from SOE-PCR or an in vitro overlap-assembly method.

51. The method of embodiment 50, wherein the one or more site-specific nuclease recognition sequence(s) present in the common overlap sequence on the 5' end of the first polynucleotide is complementary to the one or more site-specific nuclease recognition sequence(s) present in the common overlap sequence on the 3' end of the second polynucleotide in each pair, and wherein the utilizing the common overlap sequences of the first and second polynucleotides in each pair in step (b) entails performing SOE-PCR.

52. The method of any one of embodiments 45-47, wherein the utilizing the common overlap sequences of the first and second polynucleotides in each pair in step (b) entails digesting the one or more site-specific nuclease recognition sequences present in the common overlap sequence on the 5' end of the first polynucleotide and the 3' end of the second polynucleotide in each pair with one or more site specific nucleases for the one or more site-specific nuclease recognition sequences to generate single-stranded overhangs on the 5' end of the first polynucleotide and the 3' end of the second polynucleotide in each pair that comprise complementary sequence; and ligating the complementary sequence present on the single-stranded overhang on the 5' end of the first polynucleotide and the 3' end of the second polynucleotide in each pair.

53. The method of any one of embodiments 45-52, wherein the assembling of step (d) is performed using an overlap-based DNA assembly method.

54. The method of embodiment 53, wherein the overlap-based DNA assembly is selected from SOE-PCR and an in vitro overlap-assembly method.

55. The method of any one of embodiments 45-52, wherein the 3' end of the first polynucleotide and the 5' end of the second polynucleotide in the single nucleic acid fragment in each pair comprise an additional set of one or more site-specific nuclease recognition sequences and the first assembly overlap sequence and the second assembly overlap sequence in each insert polynucleotide in the second pool comprise one or more site-specific nuclease recognition sequences.

56. The method of embodiment 55, wherein the assembling in step (d) entails digesting the additional one or more site-specific nuclease recognition sequences present on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool with one or more site specific nucleases for the additional one or more site-specific nuclease recognition sequences on the 3' end of the first polynucleotide and the 5' end of the second polynucleotide in the single nucleic acid fragment in each pair and the one or more site-specific nuclease recognition sequences present in the first and second assembly sequences in each insert polynucleotide from the second pool to generate a single-stranded overhang on the 3' end of the first polynucleotide that comprises sequence complementary to sequence present on a single-stranded overhang on the 5'end of the first assembly sequence of an insert polynucleotide from the second pool and a single stranded overhang on the 5' end of the second polynucleotide that comprises sequence complementary to a sequence present on a single-stranded overhang on the 3'end of the second assembly sequence of the same insert polynucleotide from the second pool; and ligating the complementary sequence present on the single-stranded overhangs.

57. The method of any one of embodiments 45-56, wherein the cloning vectors of step (f) comprise one or more site-specific nuclease recognition sequences.

58. The method of embodiment 57, wherein the assembling in step (f) entails digesting the one or more site-specific nuclease recognition sequences in the cloning vectors with the one or more site-specific nucleases for the one or more site-specific nuclease recognition sequences recognition sequences present in the cloning vectors, wherein the digesting generates single-stranded overhangs on opposing ends of the cloning vectors, wherein the single-stranded overhang on one of the opposing ends of the cloning vector comprises sequence complementary to an end of the linearized product generated in step (e) and the single-stranded overhang on the other of the opposing ends of the cloning vectors comprises sequence complementary to an opposing end of the linearized product generated in step (e); and ligating the complementary sequences present on the single-stranded overhangs of the cloning vectors and the linearized products from step (e).

59. The method of any one of embodiments 45-58, wherein the first pool is generated by selecting pairs of polynucleotide sequences from a larger set of such sequences such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector.

60. The method of embodiment 59, wherein the specified threshold is between 5 and 15 contiguous nucleotides.

61. The method of any one of embodiments 45-60, wherein the first assembly overlap sequence and the second assembly overlap sequence on each insert polynucleotide in the second pool comprises 1 or more nucleotides that are complementary to the opposing terminal ends of the single nucleic acid fragment.

62. The method of any one of embodiments 45-61, wherein the first assembly overlap sequence and the second assembly overlap sequence on each insert polynucleotide in the second pool comprises about 25 nucleotides that are complementary to the opposing terminal ends of the single nucleic acid fragment.

63. The method of any one of embodiments 30-62, wherein, prior to step (a), the first pool of polynucleotides is generated by combining a mixture containing each first polynucleotide from the pairs of polynucleotides with a mixture containing each second polynucleotide from the pairs of polynucleotides.

64. The method of any one of embodiments 30-63, wherein each pair in the first pool is double-stranded DNA (dsDNA) or single-stranded DNA (ssDNA).

65. The method of any one of embodiments 30-43, wherein each insert polynucleotide in the second pool is dsDNA or ssDNA.

66. The method of any one of embodiments 30-65, wherein, for each pair in the first pool, the first polynucleotide and the second polynucleotide comprises sequence corresponding to a target genomic locus in a host cell.

67. The method of any one of embodiments 30-65, wherein, for each pair in the first pool, the first polynucleotide and the second polynucleotide comprise coding sequence corresponding to a gene that is part of a metabolic pathway.

68. The method of any one of embodiments 30-65, wherein, for each pair in the first pool, the first polynucleotide and the second polynucleotide comprise coding sequence corresponding to a functional domain or one or more proteins.

69. The method of any one of embodiments 30-68, wherein each insert polynucleotide in the second pool comprises one or more payload sequences located between the first assembly overlap sequence and the second assembly overlap sequence.

70. The method of embodiment 69, wherein the one or more payload sequences are selected from promoters, genes, regulatory sequences, nucleic acid sequence encoding degrons, nucleic acid sequence encoding solubility tags, terminators, unique identifier sequence or portions thereof.

71. The method of embodiment 66, wherein, for each pair in the first pool, the first polynucleotide and the second polynucleotide comprises sequence corresponding to a different target genomic locus in a host cell as compared to each other pair in the first pool.

72. The method of embodiment 66, wherein, for each pair in the first pool, the first polynucleotide and the second polynucleotide comprises sequence corresponding to the same target genomic locus in a host cell.

73. The method of any one of embodiments 69-72, wherein each payload sequence in the insert polynucleotides in the second pool is different from the payload sequence in each other insert polynucleotide in the second pool.

74. The method of any one of embodiments 69-72, wherein each payload sequence in the insert polynucleotides in the second pool is the same as the payload sequence in each other insert polynucleotide in the second pool.

75. The method of any one of embodiments 30 or 69-74, wherein each insert polynucleotide in the second pool is generated by:

(i) performing a polymerase chain reaction (PCR) on a mixture comprising the payload sequence, a forward primer and a reverse primer, wherein the forward primer comprises from 5' to 3', a short stretch of one or more nucleotides complementary to the payload sequence, the first assembly overlap sequence, one or more recognition sequences for one or more site-specific nucleases, the second assembly overlap sequence and a second stretch of one or more nucleotides complementary to the payload sequence and wherein the reverse primer comprises sequence complementary to the payload sequence or to other sequence downstream of the payload sequence, wherein the PCR generates a PCR product comprising from 5' to 3', the short stretch of nucleic acid complementary to the payload sequence, the first assembly overlap sequence, the one or more site-specific nuclease recognition sequence(s), the second assembly overlap sequence and the payload sequence;

(ii) circularizing the PCR product via an assembly method selected from the group consisting of splicing and overlap-extension PCR (SOE-PCR), restriction-ligation, blunt-end ligation, overlap based assembly method and recombination-based method, or any other enzymatic or chemical method of joining two DNA molecules; and (iii) linearizing the circularized PCR product with one or more site-specific nuclease(s) that recognize the one or more site-specific nuclease recognition sequence(s), thereby generating the second pool of polynucleotides.

76. The composition or method of any one of the above embodiments, wherein the site-specific nuclease(s) is one or more of restriction endonuclease(s), Type IIs endonuclease(s), homing endonuclease(s), RNA-guided nuclease(s), DNA-guided nuclease(s), zinc-finger nuclease(s), TALEN(s) or nicking enzyme(s).

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed:

1. A method for generating libraries of polynucleotides, the method comprising:

(a) combining a cloning vector, a first pool of polynucleotides and a second pool of polynucleotides, wherein the first pool contains pairs of polynucleotides, wherein each pair in the first pool contains a first polynucleotide and a second polynucleotide, wherein the second pool contains insert polynucleotides, wherein each insert polynucleotide in the second pool comprises a first assembly overlap sequence at its 5' end that is complementary to a 3' end of a first polynucleotide and a second assembly overlap sequence at its opposing 3' end that is complementary to a 5' end of a second polynucleotide in a pair of polynucleotides from the first pool, and wherein opposing ends of the cloning vector comprise sequence complementary to a 5' end of the first polynucleotide and a 3' end of the second polynucleotide for each pair in the first pool, wherein the first pool is generated by selecting pairs of polynucleotide sequences from a larger set of such sequences such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool, or the pairs of polynucleotides of the first pool and the cloning vector; and (b) assembling the cloning vector, the first pool and the second pool into a library of polynucleotides, wherein each polynucleotide in the library comprises an insert polynucleotide from the second pool and a pair of first polynucleotides and second polynucleotides from the first pool, wherein the assembling is performed via in vitro cloning methods or in vivo cloning methods.

2. The method of claim 1, wherein the first assembly overlap sequence and the second assembly overlap sequence on each insert polynucleotide in the second pool comprises 1 or more nucleotides that are complementary to the 3' end of a first polynucleotide and the 5' end of a second polynucleotide, respectively, in a pair of polynucleotides from the first pool.

3. The method of claim 1, wherein the first assembly overlap sequence and the second assembly overlap sequence on each insert polynucleotide in the second pool comprises about 25 nucleotides that are complementary to the 3' end of a first polynucleotide and the 5' end of a second polynucleotide, respectively, in a pair of polynucleotides from the first pool.

4. The method of claim 1, wherein the cloning vector and the 5' end of the first polynucleotide and the 3' end of the second polynucleotide in each pair from the first pool comprise one or more recognition sequences for one or more site-specific nucleases.

5. The method of claim 4, further comprising generating single-stranded complementary overhangs between the opposing ends of the cloning vector and the 5' end of the first polynucleotide and the 3' end of the second polynucleotide in each pair from the first pool by adding the one or more site-specific nucleases for the one or more recognition sequences.

6. The method of claim 5, further comprising ligating the single-stranded complementary overhangs between the opposing ends of the cloning vector and the 5' end of the first polynucleotide and the 3' end of the second polynucleotide in each pair from the first pool.

7. The method of claim 1, wherein step (b) results in a circular product comprising an insert polynucleotide from the second pool, a first and second polynucleotide from a pair from the first pool and the cloning vector.

8. The method of claim 1, wherein the specified threshold is between 5 and 15 contiguous nucleotides.

9. The method of claim 1, wherein the assembly is an in vitro cloning method, wherein the mixture of the cloning vector, the first pool and the second pool is heated to partially or fully denature polynucleotides present in the first and the second pools and the cloning vector, then cooled to room temperature before assembly.

10. The method of claim 1, wherein, prior to step (a), the first pool of polynucleotides is generated by combining a mixture containing each first polynucleotide from the pairs of polynucleotides with a mixture containing each second polynucleotide from the pairs of polynucleotides.

11. The method of claim 1, wherein each pair in the first pool is double-stranded DNA (dsDNA) or single-stranded DNA (ssDNA).

12. The method of claim 1, wherein each insert polynucleotide in the second pool is dsDNA or ssDNA.

13. The method of claim 1, wherein, for each pair in the first pool, the first polynucleotide and the second polynucleotide comprise sequence corresponding to a target genomic locus in a host cell.

14. The method of claim 1, wherein each insert polynucleotide in the second pool comprises one or more payload sequences located between the first assembly overlap sequence and the second assembly overlap sequence.

15. The method of claim 14, wherein the one or more payload sequences are selected from the group consisting of promoters, genes, regulatory sequences, nucleic acid sequence encoding degrons, nucleic acid sequence encoding solubility tags, terminators, unique identifier sequence and portions thereof.

16. The method of claim 13, wherein, for each pair in the first pool, the first polynucleotide and the second polynucleotide comprise sequence corresponding to the same target genomic locus in a host cell.

17. The method of claim 14, wherein each payload sequence in the insert polynucleotides in the second pool is different from the payload sequence in each other insert polynucleotide in the second pool.

18. The method of claim 14, wherein each payload sequence in the insert polynucleotides in the second pool is the same as the payload sequence in each other insert polynucleotide in the second pool.

19. The method of claim 1, wherein each insert polynucleotide in the second pool is generated by:
(i) performing a polymerase chain reaction (PCR) on a mixture comprising a payload sequence, a forward primer and a reverse primer, wherein the forward primer comprises from 5' to 3', a stretch of one or more nucleotides complementary to the payload sequence, the first assembly overlap sequence, one or more recognition sequences for one or more site-specific nucleases, the second assembly overlap sequence and a second stretch of one or more nucleotides complementary to the payload sequence and wherein the reverse primer comprises sequence complementary to the payload sequence or to other sequence downstream of the payload sequence, wherein the PCR generates a PCR product comprising from 5' to 3', the stretch of nucleic acid complementary to the payload sequence, the first assembly overlap sequence, the one or more site-specific nuclease recognition sequence(s), the second assembly overlap sequence and the payload sequence;
(ii) circularizing the PCR product via an assembly method selected from the group consisting of splicing and overlap-extension PCR (SOE-PCR), restriction-ligation, blunt-end ligation, an overlap based assembly method and a recombination-based method, or any other enzymatic or chemical method of joining two DNA molecules; and
(iii) linearizing the circularized PCR product with one or more site-specific nuclease(s) that recognize the one or more site-specific nuclease recognition sequences, thereby generating the second pool of polynucleotides.

20. A method for generating libraries of polynucleotides, the method comprising:
(a) combining a first pool of polynucleotides and a second pool of polynucleotides, wherein the first pool contains pairs of polynucleotides, wherein each pair in the first pool contains a first polynucleotide and a second polynucleotide, and wherein, for each pair in the first pool, the first polynucleotide and the second polynucleotide are linked together in a single construct with one or more recognition sequences for one or more site-specific nucleases located between the first polynucleotide and the second polynucleotide, wherein the second pool contains insert polynucleotides, wherein each insert polynucleotide in the second pool comprises a first assembly overlap sequence at its 5' end and a second assembly overlap sequence at its opposing 3'end that are complementary to a 3' end and 5' end, respectively, of a single construct from the first pool, wherein the first pool is generated by selecting pairs of polynucleotide sequences from a larger set of such sequences such that no polynucleotide from the first pool shares common sequence with any other polynucleotide from the first pool beyond a specified threshold, excluding designed assembly overlap sequences between the pairs of polynucleotides of the first pool and the insert polynucleotides of the second pool; and (b) assembling the first pool and the second pool into a library of polynucleotides, wherein each polynucleotide in the library comprises an insert polynucleotide from the second pool and a pair of first polynucleotides and second polynucleotides from the first pool, wherein the assembling is performed via in vitro cloning methods or in vivo cloning methods.

21. The method of claim 20, wherein the one or more recognition sequences for one or more site-specific nucleases comprises a homing endonuclease recognition sequence.

22. The method of claim 20, wherein the linked single construct is produced by joining individual first and second polynucleotides via splicing and overlap-extension PCR (SOE-PCR), restriction-ligation, blunt-end ligation, an overlap-based assembly method, a recombination-based method, or any other enzymatic or chemical method of joining the first and second polynucleotides, or by synthesizing the linked single-construct directly.

23. A method for generating libraries of polynucleotides, the method comprising:
(a) combining a first pool of polynucleotides and a second pool of polynucleotides, wherein the first pool contains pairs of polynucleotides, wherein each pair in the first pool contains a first polynucleotide and a second polynucleotide, wherein the second pool contains insert polynucleotides, wherein each insert polynucleotide in the second pool comprises a first assembly overlap sequence at its 5' end that is complementary to a 3' end of a first polynucleotide and a second assembly overlap sequence at its opposing 3' end that is complementary to a 5' end of a second polynucleotide in a pair of polynucleotides from the first pool, wherein each insert polynucleotide in the second pool is generated by:

(i) performing a polymerase chain reaction (PCR) on a mixture comprising a payload sequence, a forward primer and a reverse primer, wherein the forward primer comprises from 5' to 3', a stretch of one or more nucleotides complementary to the payload sequence, the first assembly overlap sequence, one or more recognition sequences for one or more site-specific nucleases, the second assembly overlap sequence and a second stretch of one or more nucleotides complementary to the payload sequence and wherein the reverse primer comprises sequence complementary to the payload sequence or to other sequence downstream of the payload sequence, wherein the PCR generates a PCR product comprising from 5' to 3', the stretch of nucleic acid complementary to the payload sequence, the first assembly overlap sequence, the one or more site-specific nuclease recognition sequence(s), the second assembly overlap sequence and the payload sequence;

(ii) circularizing the PCR product via an assembly method selected from the group consisting of splicing and overlap-extension PCR (SOE-PCR), restriction-ligation, blunt-end ligation, overlap based assembly method and recombination-based method, or any other enzymatic or chemical method of joining two DNA molecules; and (iii) linearizing the circularized PCR product with one or more site-specific nuclease(s) that recognize the one or more site-specific nuclease recognition sequences, thereby generating the second pool of polynucleotides; and (b) assembling the first pool and the second pool into a library of polynucleotides, wherein each polynucleotide in the library comprises an insert polynucleotide from the second pool and a pair of first polynucleotides and second polynucleotides from the first pool, wherein the assembling is performed via in vitro cloning methods or in vivo cloning methods.

* * * * *

SEQUENCE LISTING

```
<160> NUMBER OF SEQ ID NOS: 179

<210> SEQ ID NO 1
<211> LENGTH: 63
<212> TYPE: DNA
<213> ORGANISM: Artificial Sequence
<220> FEATURE:
<223> OTHER INFORMATION: pMB070_promoter

<400> SEQUENCE: 1
accgtgcgtg ttgacaattt tacctctggc ggtgatactg gttgcatgta ctaaggaggt      60
tgt                                                                    63

<210> SEQ ID NO 2
<211> LENGTH: 78
<212> TYPE: DNA
<213> ORGANISM: Artificial Sequence
<220> FEATURE:
<223> OTHER INFORMATION: b2405_promoter

<400> SEQUENCE: 2
atgtcggata tctggtggtg aaatacttta tgccatgata atttaatacg atgtatttat      60
tatatggagc acttaatt                                                    78

<210> SEQ ID NO 3
<211> LENGTH: 74
<212> TYPE: DNA
<213> ORGANISM: Artificial Sequence
<220> FEATURE:
<223> OTHER INFORMATION: b0605_promoter

<400> SEQUENCE: 3
taatggaaac gcattagccg aatcggcaaa aattggttac cttacatctc atcgaaaaca      60
cggaggaagt atag                                                        74
```

<210> SEQ ID NO 4
<211> LENGTH: 65
<212> TYPE: DNA
<213> ORGANISM: Artificial Sequence
<220> FEATURE:
<223> OTHER INFORMATION: pMB043_promoter

<400> SEQUENCE: 4

```
accgtgcgtg ttgactattt tacctctggc ggttagagtt aacatcctac aaggagaaca    60
aaagc                                                                65
```

<210> SEQ ID NO 5
<211> LENGTH: 63
<212> TYPE: DNA
<213> ORGANISM: Artificial Sequence
<220> FEATURE:
<223> OTHER INFORMATION: pMB071_promoter

<400> SEQUENCE: 5

```
accgtgcgtg ttgacttaaa taccactggc ggtgataatg gttgcatgta ctaaggaggt    60
tgt                                                                  63
```

<210> SEQ ID NO 6
<211> LENGTH: 80
<212> TYPE: DNA
<213> ORGANISM: Artificial Sequence
<220> FEATURE:
<223> OTHER INFORMATION: b0159_promoter

<400> SEQUENCE: 6

```
ctctcccgcg tgagaaatac gcttccccgt aagcgcatgg taaactatgc cttcaaatcg    60
ggcttatcgc gagtaaatct                                                80
```

<210> SEQ ID NO 7
<211> LENGTH: 65
<212> TYPE: DNA
<213> ORGANISM: Artificial Sequence
<220> FEATURE:
<223> OTHER INFORMATION: pMB090_promoter

<400> SEQUENCE: 7

```
accgtgcgtg tttacaattt tacctctggc ggtgataatt aacatcctac aaggagaaca    60
aaagc                                                                65
```

<210> SEQ ID NO 8
<211> LENGTH: 1050
<212> TYPE: DNA
<213> ORGANISM: Artificial Sequence
<220> FEATURE:
<223> OTHER INFORMATION: gene editing homology arm pool_1_b3748_left

<400> SEQUENCE: 8

```
caaatctcga agatttcttt catgcggtgg gagatataga caataccgcg gccttgcgat    60
ttcagctcgc ggatgacgcg gaacagggat tcggtttcgg tatcggtcag cgcatcggtc   120
ggttcatcca taatgatgac tttcgactca aagctcagca ctttggcgat ttcaaccatt   180
tgctggtcac cgatggaaag atcgcccacc agcttgtcgc ttttaaagcg caggttaagt   240
ttagccagca atttatccgc ttcggcatac atggttttcc agtcaatttt gccaaagcga   300
ttaacaaact cacgaccgag gaaaatgttt tcggcaatgg tcaactgcgg gatcaggttc   360
```

```
agttcctgat ggataatccc aatcccggct tcctgggaag attttggccc ggtaaatgtc    420
gtttctttcc ccagccataa aagcgtaccg gcatcgcgag tatagatgcc agtaagcact    480
ttcatcatgg tggatttacc cgcgccgttt tcgcccacca gcgccatcac gcggcccgga    540
tagacattta acgctgcgcc cgagagggct tttacgcccg ggaaggcttt atcgatgcct    600
ttaagctgaa gtaatgcttc catgacggcc tcagaacgtc acgccagcac agagaatgat    660
attcgcatac ggagaacatt ctccgctgcg aattaccgcc tgactttctg cggtttgttg    720
tttgaattgt tcatgcgtgg tgtaacgaat tcaatggta tttccctggt gttttgcag     780 ctgctcaagg tgagtgagca acgtttcgtg gagttgcgga ttatggtgtt tgatctcttc    840
cgcgataatg gccgcctcga cctgcatttc atttgtgacg acgcccagca cctgcataaa    900
agaaggtaca ccctgggtta atgccatatc gatacgcgtt gtacttttgg ggatgggtaa    960
accagcatca cacaccacca gcgtatcggt atgtcccaga cgggagatca ccgatgaaat   1020
atcagaatta agaacggtgc cttttttcat                                    1050

<210> SEQ ID NO 9
<211> LENGTH: 1047
<212> TYPE: DNA
<213> ORGANISM: Artificial Sequence
<220> FEATURE:
<223> OTHER INFORMATION: gene editing homology arm pool_1_b3748_right

<400> SEQUENCE: 9
caacctcgaa acgttttaca tggtgattaa ccatgaaaac aaaaacgccc ccttatgaag     60
aaaggaggcg tctggcgtta gatttcgacc tgagtaccca gttcgataac cctgtttggc    120
gggatttcaa attgatctgg tgcacgcagc gcattacgtt gcagcagcaa gtacagcttg    180
ccgcgcagac gcaaatacca cgggcgtttg ccgaggatca acgactcatg cgacataaag    240
aaggaggttt ccatcatccg gcaacttaat ccttccagac cgcagcggtg gaaaacttct    300
tctacgtttg gcgtttctcg ccaaccataa cttgccacca cgcgccagaa agtgggcgac    360
agttgttcaa tctgtacccg acggacgtta tggacatatg gagcgtcttc ggtgcgcaga    420
gttaacagaa tcacccgctc atgcaatacc ttgttatgtt taaggttatg catcagcgca    480
aagggaatga cgttgattgc acgcgacata taccgcgcgg tcccgggcac gcgaacaggc    540
ggtgatttct ccagcgaagc aatcatcgct tccagagagt taccatgttc atgcatccgc    600
cgcagcaagc ggaaacgctc gctcttccag gtggtcatca cgataaacat cacagtaccg    660
aggctcaatg gcaaccagcc gccggagagc agtttatcga ggttagcggt gaacaatgga    720
atatcgacac aaaggaaagc aatcaggatc agcgcaacaa aatacttatt ccagtgccag    780
ttctgacgtg ccacggtagt cgagagaata gacgtcagca ccatggttcc ggtcaccgca    840
atcccgtacg ccgccgccag gttgctggag tgctcaaagc tgacaatcac aatcacgacc    900
gcgacataga gcatccagtt cacaaacgga atatagattt gccctgactc catttcggag    960
gtgtgaataa tgcgcatcgg cgacaaatat cccagacgta ccgcctgacg cgtcaatgag   1020
aagacgccag agataaccgc ctgcgag                                       1047

<210> SEQ ID NO 10
<211> LENGTH: 1049
<212> TYPE: DNA
<213> ORGANISM: Artificial Sequence
<220> FEATURE:
<223> OTHER INFORMATION: gene editing homology arm pool_1_b0388_left

<400> SEQUENCE: 10
```

```
cgcttcgcca aagcagcgga aaatattcag cacatcagcg gtatcttctg gggttaccag    60
cgcgtttggc gttacggagg tcatcccggc attaaccagt gcgggagtgt tcggcatggc   120
gcggataatt ttccggtcat ggcccagcgc gcgggcaagc tggtcgagcg tgacacctgc   180
agcaatagaa acgaccagag agtctttatt caggctggag gtgatttcgc taagcacttt   240
aatcatgatg ccaggtttaa cggcagcaaa aatgatgtcg gcgatttgcg ccacttcttg   300
cgccgattct gcggcgttga tgccgaactg gtcatgcagg gcggcgactt tatccgggga   360
gggggtgtat acccagattt gccctggaag cacctgaccg ctggcaatca gaccgccgag   420
aatggctttt cccatattgc cgcagccaat aaaaccgatt ttcttttcca ttgcctcact   480
cctgccgtga aattcattgt tttgataatc gctggcagaa gcataaacag aactatgccg   540
gaaggcaaaa gcgcgacaca atagaggatt acccaacaaa ggatgacttt atgcaatttt   600
gggtggatgc cgacgcgtgt cccaatgtaa ttaaagagat tttgtatcgc gcggcggaac   660
gtatgcagat gccgctggta ctggtagcaa accagagttt acgcgtgccg ccatcgcgat   720
ttattcgtac gctgcgcgtc gcggcaggtt tcgacgttgc cgataacgaa attgtccggc   780
agtgtgaagc gggcgatttg gtgatcaccg cagatatacc tttggctgct gaagccatcg   840
agaaaggcgc tgcggcgctt aatccgcgcg gcgaacgtta cacgccagcg accattcgtg   900
agcgcctgac gatgcgcgat tttatggata ccttacgtgc cagtgggatc cagaccggcg   960
gaccagatag ccttttcacaa cgtgaccgcc aggcctttgc cgcggagctg gagaagtggt  1020
ggctggaagt gcaacgtagt cgtggctaa                                    1049

<210> SEQ ID NO 11
<211> LENGTH: 1046
<212> TYPE: DNA
<213> ORGANISM: Artificial Sequence
<220> FEATURE:
<223> OTHER INFORMATION: gene editing homology arm pool_1_b0388_right

<400> SEQUENCE: 11
atgacacaac ctcttttttct gatcgggcct cggggctgtg gtaaaacaac ggtcggaatg    60
gcccttgccg attcgcttaa ccgtcggttt gtcgataccg atcagtggtt gcaatcacag   120
ctcaatatga cggtcgcgga gatcgtcgaa agggaagagt gggcgggatt tcgcgccaga   180
gaaacggcgg cgctggaagc ggtaactgcg ccatccaccg ttatcgctac aggcggcggc   240
attattctga cggaatttaa tcgtcacttc atgcaaaata cgggatcgt ggtttatttg   300 tgtgcgccag tatcagtcct ggttaaccga ctgcaagctg caccggaaga agatttacgg   360
ccaaccttaa cgggaaaaacc gctgagcgaa gaagttcagg aagtgctgga agaacgcgat   420
gcgctatatc gcgaagttgc gcatattatc atcgacgcaa caaacgaacc cagccaggtg   480
atttctgaaa ttcgcagcgc cctggcacag acgatcaatt gttgattttc gagcgcctat   540
acttaacgtt catcccgtga ataaggaag aacgatgcca acgaaaccgc cttatcctcg   600
tgaagcatat atagtgacga ttgaaaaagg aaagccagga cagacggtaa cctggtacca   660
actcagagcc gatcatccta aaccagactc gttgatcagt gaacatccga ccgctcagga   720
agcgatggat gcgaaaaaac gctatgagga ccctgacaaa gagtgaccgc atcagactgc   780
tcggaaggga ttctgagtgc cactacaagg gatctgcgtc acatttttca taattcatgt   840
ttttctaata attagaatat taaacaataa caatccatta ctggaatcat ttggaatctt   900
tacattatgc cgtgcacgtc tgctgctacg cttttttgtca tttgtagcac aagtaagtgt   960
```

```
cagcagtggt gcttcacact tgcccggtaa ttaacgacga agaaaagta aggtggatga      1020 acaatgagtg cgtcgttggc gatcct                                         1046

<210> SEQ ID NO 12
<211> LENGTH: 1050
<212> TYPE: DNA
<213> ORGANISM: Artificial Sequence
<220> FEATURE:
<223> OTHER INFORMATION: gene editing homology arm pool_1_b4348_left

<400> SEQUENCE: 12
gcagttcatc attgcatttc gtgctgaggg ggatgaaaaa aatatttcga tatattctgg     60
taaagcatct ttggttaatc gagctcgaat aagtttatca ggatatagca aattttgatg    120
ttgtaatttt ttcaataacc cacaaacacc aacaaattct aaacttccgt tatagcgagt    180
aaataaaaga tctccatctt gtaatttgtg gcggtttagt tcactttctg aacattctag    240
aaaccgaata tcgttttgat ctacatggcc agcacgtaca gaactaatgc gtagtattgg    300
atgaccaaca ccactttcat ttggctttga tgaaagacca ttacgtaatt cagttaagat    360
agattcaaaa tttaacttct taaatacaga atgttgcggc tcaaaattac gccatttttc    420
tgtcaatttt ccattaactg cgccccccaa taccgcttga cgaaaacgtt tcaggatttg    480
tgggatttgc tcaaaacgtg ctttggtgct gtctacctgc gccagcagcg tatcgagttt    540
ttcagcgatg attttttgtt cggcaagtgg tgggattggt atatttatca aatcaaagct    600
tgccggctta atattattaa tatttgcacc agcagaaagt gatgaaattt tgtttcgata    660
aagagaagat tttgtgaaat gagcaataaa accagaaaat ataagttttt caggacgtaa    720
tacaccgcaa aatgcgccga aactacattc aaatggtaga tgctgatgtg cggatttacc    780
aactacggat ttgctccctg atgacattgc aataacaata tcttcaggag atatttttttg   840 actttcttta acaagatttt taggaacaaa aaccaagtcc gtagtatcaa acttgccatt    900
ctgaatattg ttcgcacgga taagaggcaa ataatcatct tttagataat ttattgcctg    960
ctctttttta tacgttactc ctcggattag agttgtgacc gtagatactg ggcgataac    1020 ccaccccctcc ggcaatttcc ccgcactcat                                   1050

<210> SEQ ID NO 13
<211> LENGTH: 1050
<212> TYPE: DNA
<213> ORGANISM: Artificial Sequence
<220> FEATURE:
<223> OTHER INFORMATION: gene editing homology arm pool_1_b4348_right

<400> SEQUENCE: 13
tccttcaccc caccaaacgc ttcttccagc aactgacgct gcaaatcggc ctcatcgctc     60
gcccccagtt cacgcatcag cgcatccagt tcagacagcg cctgtaccag ttcgcccatc    120
gcttctgccg ctaatacatc cggctccggc aggctgtcgg catcaatact gtctttatct    180
ttcagccagg agatatccag cgaatcggat tttgcggtgc ggatccactc acggctgaac    240
ttgcgccagc ggctggtagc aagatgctgg tcggtgtttt tgttctcttc gctgtcggca    300
acttccgtct cttcggcgtt aaaactccat tcaccttcag tgcgcgggct taaaccgtgc    360
gggtcttcgc catacacgcg ctcaaacggc tgcaaatgct cgtcggtaaa cggtgtgcgc    420
ttgccgaaac tcggcatatt ggtacgcagg tcatacaccc acacatcatc ggtacagttc    480
ttatcctgat tcgggttcgc caccgtccct ttggtaaaga acagcacgtt ggtcttcacg    540
ccctgagcgt aaaaaatacc ggtcggcaga cgcagaatgg tgtgcagatg acacttatcc    600
```

```
atcaggtcac gacgaatgtc ggtgcctttg ccgccttcaa acagcacgtt atccggcacc    660
accaccgccg cacgaccgcc gggatgcagc gtttcgataa tatgctgcat aaagcacaac    720
tgtttgttgc tggtcgggtg aacaaaggtg cgggtaatgt tggtgcctgc ggcgctgcca    780
aacggcgggt tagtggcgac aatatgcgcc ttcggcaggt tttcaccgtc gctacccaga    840
gtgttgccca gacggattgc gccgccgtgg tcgaggttgc cttcaatatc gtgcagcagg    900
cagttcatca gtgccagacg acgggtgccg gcaccagtt cgaggccgat aaacgcgcgg    960
tggatctgga aatcctgcgt gtcgccatca aggtcgtcca gatcattggt ttgcgactta   1020
acatagcggt cggcttcaat caaaaagccc                                    1050
```

<210> SEQ ID NO 14
<211> LENGTH: 1050
<212> TYPE: DNA
<213> ORGANISM: Artificial Sequence
<220> FEATURE:
<223> OTHER INFORMATION: gene editing homology arm pool_1_b1982_left

<400> SEQUENCE: 14

```
taagcgcatg ttaatgctga ccgtctggat gatgggcatc gcgacagcct tgattggtat     60
tcttccttca ttctcgacca ttgggtggtg ggcacctatt ttgctggtga cactgcgtgc    120
cattcaggga tttgcagtcg gcggcgaatg gggaggcgcg gcgttgcttt ccgttgaaag    180
tgcaccgaaa aataaaaaag ccttttacag tagcggtgta caagttggct acggtgtagg    240
tttactgctt tcaaccggac tggtttcatt gatcagtatg atgacgactg acgaacagtt    300
tttaagctgg ggctggcgca ttcctttcct gtttagcatc gtactggtac tgggagcatt    360
gtgggtgcgc aatggcatgg aggagtccgc ggaatttgaa caacagcaac attatcaagc    420
tgccgcgaaa aaacgcatcc cggttatcga agcgctgtta cgacatcccg gtgctttcct    480
gaagattatt gcgctacgac tgtgcgaatt gctgacgatg tacatcgtta ctgcctttgc    540
acttaattat tcaacccaga atatggggct accgcgcgaa cttttcctta atattggttt    600
gctggtaggt ggattaagct gcctgacaat tccctgtttt gcctggcttg ccgatcgttt    660
tggtcgccgt agggtttata tcacaggtac gttaatcgga acgttgagcg catttccttt    720
ctttatggcg cttgaagcac aatctatttt ctggatagtt ttcttctcca taatgctggc    780
aaacattgcg catgacatgg tggtgtgtgt gcaacaaccg atgtttaccg aaatgtttgg    840
tgccagttat cgctatagtg gcgctggagt cggttatcag gttgccagtg tggttggcgg    900 tggattttaca ccttttattg ccgctgcact catcacttac tttgccggga actggcatag    960
cgtcgccatt tatttgctgg ctggatgcct gatttccgca atgaccgctt tgttgatgaa   1020
agacagtcaa cgcgcttgat agcctggcga                                    1050
```

<210> SEQ ID NO 15
<211> LENGTH: 1050
<212> TYPE: DNA
<213> ORGANISM: Artificial Sequence
<220> FEATURE:
<223> OTHER INFORMATION: gene editing homology arm pool_1_b1982_right

<400> SEQUENCE: 15

```
atgaataata agggctccgg tctgacccca gctcaggcac tggataaact cgacgcgctg     60
tatgagcaat ctgtagtcgc attacgcaac gccattggca actatattac aagtggcgaa    120
ttacctgatg aaaacgcccg caaacaaggt cttttttgtct atccatcact gaccgtaacc    180
```

```
tgggacggta gcacaaccaa tccccccaaa acgcgcgcat ttggtcgctt tacccacgca      240
ggcagctaca ccaccacgat tactcgccct actctctttc gttcgtatct taatgaacaa      300
cttacgttgc tgtatcagga ttatggtgcg catatctcag tgcaaccctc gcagcatgaa      360
atcccttatc cttatgtcat cgatggctct gaattgacac ttgatcgctc aatgagcgct      420
gggttaactc gctacttccc gacaacagaa ctggcgcaaa ttggcgatga aactgcagac      480
ggcatttatc atccaactga attctccccg ctatcgcatt tgatgcgcg ccgcgtcgat       540 ttttccctcg cacggttgcg ccattatacc ggtacgccag ttgaacattt tcagccgttc      600
gtcttgttta ccaactacac acgttatgtg gatgaattcg ttcgttgggg atgcagccag      660
atcctcgatc ctgatagtcc ctacattgcc ctttcttgtg ctggcgggaa ctggatcacc      720
gccgaaaccg aagcgccaga agaagccatt tccgaccttg catggaaaaa acatcagatg      780
ccagcatggc atttaattac cgccgatggt cagggtatta ctctggtgaa tattggcgtg      840
ggaccgtcaa atgctaaaac catctgcgat catctggcag tgctacgccc ggatgtctgg      900
ttgatgattg gtcactgtgg cggattacgt gaaagtcagg ccattggcga ttatgtactt      960
gcacacgctt atttacgcga tgaccacgtt cttgatgcgg ttctgccgcc cgatattcct     1020
attccgagca ttgctgaagt gcaacgtgcg                                       1050

<210> SEQ ID NO 16
<211> LENGTH: 1050
<212> TYPE: DNA
<213> ORGANISM: Artificial Sequence
<220> FEATURE:
<223> OTHER INFORMATION: gene editing homology arm pool_1_b4367_left

<400> SEQUENCE: 16
cgttaagccc gacggagaga gaaatattgc gctttatgtc gcgtggctac tcaatgacac       60
aaattgccga gcagcttaaa cgcaatatca aaacgatccg tgcacataaa tttaatgtga      120
tgtcgaaact gggcgtcagt tctgacgcag ggttgttgga ggccgcagat attctgttat      180
gtatgcggca ttgcgaaaca agtaatgtgt tgcatcccta ttaatccgca tgatgccggg      240
tttacttccc cggcagtgct ttcatttcag cgtacaatcg ccacattgct gcacatccgg      300
taagcgataa cgctggcagc aagtgcggcg caccagcagg ccgtcgcgca gtaccacggt      360
acgccagagt ggattatctt caccgttcgt gagcgttttc tcaaaaaaga gggcatggcg      420
cagcgattca acagtagcct cgccgagcag ttgcttcatc tcagtgagat accagttgat      480
caaataaccg gtattactcc agataagttt gccgttgatc tctccggtcg cttctagtgc      540
ttgcacaacc ggaaccagcg cctggctgat taacgtttcc attcgatgct gcggcgaatg      600
tggtgttgcg ttttatctt cacacacatc gacccgaaa caggcgacgc gtccggtttc        660
gtgaaactca gcatggaaat gttccggcga cacatctaat gccttttcct gcgtcagtag      720
cgccagcatt aatggtggca ccatcaggcc gatataccat tgtgcccata gtgagatcag      780
cggtttgttc tcgcgatca tcatcggttg gttgcgatag atatgatcgg aatagaccgc       840
cagcagagaa cttagcacat tcggtgatga ccattgcgcc agcgtcatgg cgttaagtgg      900
ggcaggttca tccaggcgga taaactccag caaatgttca cgatgttttg cgatcgtcgc      960
ccgcacggct tgcgcaagcg tgggatcctg cggctggaga tgcgttcgcc agatgacatc     1020
ttcatagagc ggtgcggaac gataggccat                                      1050

<210> SEQ ID NO 17
<211> LENGTH: 1050
```

```
<212> TYPE: DNA
<213> ORGANISM: Artificial Sequence
<220> FEATURE:
<223> OTHER INFORMATION: gene editing homology arm pool_1_b4367_right

<400> SEQUENCE: 17
aatcgggata gtaatctaaa tgataatgat tgctaatcat agcgataggt ttacccgata    60
gcaagggatt tatctggctt gcaaatgata aaattatca tatgatattg gttatcatta   120
tcaatgaaag agatgaaatc atgttgcaac gtacgctggg cagtggctgg ggagtgttgc   180
tgccgggatt gctgattgca gggctgatgt atgcggattt atcgtcagat cagtggcgga   240
ttgtcattct gatgggatta gtattgacgc cgatgatgct gtatcacaaa cagttgcggc   300
attacatttt gctaccatcg tgcctggcac ttattgctgg catcatgctg atgataatga   360
atttgaatca gggatgaaaa atcaaggaag aaacaagaaa ggaagtaaag ataattggtg   420
cgaggggggg gacttgaacc cccacgtccg taaggacact aacacctgaa gctagcgcgt   480
ctaccaattc cgccaccttc gcacagtcat cttactttt ttgatatcgc ctcgtttggt    540
gcgaggggg ggacttgaac ccccacgtcc gtaagaacac taacacctga agctagcgcg   600
tctaccaatt ccgccacctt cgcccagtgc gagcaatatc aacgtggttt ttggtgcgag   660
ggggggact tgaaccccca cgtccgtaag gacactaaca cctgaagcta gcgcgtctac    720
caattccgcc accttcgcat accatcaatt cttaaaaaga attgctacca cggaggcgca   780
ttctagtggt tttcagcttt tcgtcaatag ttaattatcg acagaggtgt aattgctgga   840
aaaatgtcca tcaggaaact agcgtgcagg tttggtatgc atgcggggc agatgccaga    900
tgcgacgctg gcgcgtctta tctggcctac gaagggctaa cgtgcaggtt ttgtaggtcg   960
gataaggcgt tcacgccgca tccgacacgg tattcggcga gataattaac ctttcttcgc  1020
ctggcgggtc ataatggcgc gatacacctt                                    1050

<210> SEQ ID NO 18
<211> LENGTH: 1050
<212> TYPE: DNA
<213> ORGANISM: Artificial Sequence
<220> FEATURE:
<223> OTHER INFORMATION: gene editing homology arm pool_1_b2285_left

<400> SEQUENCE: 18
ctgtttcttc cccgcagatg tagcgccctg ccccggtatg gacgaacagt tcgaaatcga    60
aacctgttcc cataatgttt ttgccaagca gacccgcttc ggtggcttcg gcaatggcac   120
ggcgcagatt aactgccgct tcgatatatt cgccacgcag gaagatgtag ccacggtaag   180
cttttcagcgc aaacgcggag atgagcatac cttccaccag caggtgcggc agttgctcca   240
tcaacaggcg gtctttatag gtgcccggct ccatttcatc ggcattacac agcaggtaac   300
ggatgttcat ggattcgtct ttcggcatca ggctccattt caggccagtc gagaagcccg   360
cgccgccgcg cccttttcaga ccagcgtctt ttacctgatt aacgatttcg tccgagaca   420
gcccggtcag cgccttacgc gcgccttcgt aaccgttttt gctgcggtat tcgtccagcc   480
acactggctg tttgtcatcg cgcagacgcc aggtcagcgg atgcgtttcg ggagtacgga   540
taatgttttt catttatacc gctccagcag ttcagggatc gcttccgggg tcagatgcgc   600
gtgagtgtcc tcatcgatca tcatgtttgg ccctttatca cagttcccca ggcagcaagt   660
tggcagcagc gtaaagcggc catcaaatgt cgtttgccct ggtttgatgt tcagcttttt   720
ctcgagcgcc gcctgaatac cctgataacc gttgatatga cagaccacgc tgtcacaata   780
```

```
acggatcaca tggcgaccaa ccggctggcg aagatctga ctgtagaacg ttgccacacc      840
ttcgacgtcg cttgccggaa tacccagcac atcggcgatc gcgtggatcg caccatccgg      900
cacccagcca cgctgcttct gaacgatttt cagcgcttca atggacgccg cacgcgggtc      960
ttcgtagtgg tgcatctcgt gctcgatcgc ttcacgctct gccgcactca gctcaaaagc     1020
ctcggtttgt ggttgttgat tctcgtgcat                                       1050

<210> SEQ ID NO 19
<211> LENGTH: 1050
<212> TYPE: DNA
<213> ORGANISM: Artificial Sequence
<220> FEATURE:
<223> OTHER INFORMATION: gene editing homology arm pool_1_b2285_right

<400> SEQUENCE: 19
aattagcggt ccacatctga cataacaaaa tcgatactgc ccagataaac aatcaggtca       60
gacaccaggc tgccgcggat cgccgccgga atttgctgca aatgcgcaaa gctcggggta      120
cgaacacggg tgcggtaact catggtgctg ccgtcgctgg tcaggtagta actgttgatc      180
cctttggtcg cctcaatcat ctggaaagat tcattggcag gcatcaccgg accccacgac      240
acttgcagga agtgggtgat cagggtttcg atatgttgca gcgtgcgctc tttcggcggc      300
ggcgtggtca gcgggtgatc cgcttttgaac gggccttccg gcatgttgtt gaggcactgc     360
tcaagaatgc gcagactctg gcgcagctct tccactttaa gcattacgcg ggtgtagcag      420
tcagaaacgc caccacccac cgggatttca aagtcgaagt tttcatagcc agaataagga      480
cgcgccttac gcacgtcgaa gtcgatcccg gtagcacgca ggcccgcgcc agtggtgccc      540
cactccagcg cctctttcgc gccataggcg gcaacgccct gggaacgacc tttcagaatg      600
gtgttttgca gcgccgcttt ctcgtaagac gccagacgtt tcggcatcca gtcgaggaac      660
tcacgcagca ggcgatccca gccgcgcggc aggtcgtgcg ctacgccgcc aatacggaac      720
cacgccgggt gcatacggaa accagtgatt gcttccacca gatcgtaaat tttctgacga      780
tcggtaaagg cgaagaacac tggcgtcatt gcgccgacgt cctgaataaa ggtcgagata      840
tacagcaggt gactgttgat gcggaacagt tcggagagca taacgcgaat gacgttaacg      900
cgatccggca cggtgatccc ggccagtttc tctaccgcca gcacgtaagg catttcgtta      960
acgcagccgc cgaggtattc gatacggtca gtatacggaa tgtagctgtg ccaggactgg     1020
cgttcgccca ttttctccgc accacggtgg                                      1050

<210> SEQ ID NO 20
<211> LENGTH: 1025
<212> TYPE: DNA
<213> ORGANISM: Artificial Sequence
<220> FEATURE:
<223> OTHER INFORMATION: gene editing homology arm pool_1_b2405_left

<400> SEQUENCE: 20
gagcgaagcg agtcatcctg cacgacccac caatgtaaaa aagcgcccta aaggcgcttt       60
tttgctatct gcgatttgcg aaattgcctg atgcgcttca cttagcagac tactatttcc      120
ggcaattcct gtctcctcac ctactgtgtc aatgcagcca acagcttaac catcgcgggc      180
gtcacctgct gtgtttcata aacaatatat aaatctgcag ggatgcgctg tttgagcgga      240
cggaaaatga cacctggcca gttcatttgt gcgtagctgt ccgctatcaa tgtgatacca      300
atgcccatac tgaccatagc gagtaccgtt tgcggttcat taacttcgcg aataacaacc      360
ggtgaaaatc ccacctgctg gcaaactcgc tgcaaaaaat cccagtcagt gtaaacgggc      420
```

```
ggcattgtaa caaaatactc gtcacgtagc gcttccagcg ggacggtgga aaatgatgag      480
agatgatgct cttcaggcat cgccaccaga aacgccgatt catgcaaccg taagctggta      540
aaaccagtcg gtggttctgt cgccattcgc cagatcccgg catcaagttc gcggcgttcc      600
agcaaggcca tttgcatcgc gggcatcttt tcgcgaaaaa gaacgtcaac gttaggattt      660
tccctgagga atcgccgcat aaccgggcgc atccgtcccc acattgccgt tcccactacg      720
ccgagttcaa tccgccctgc ttctccccga cctatttgtt caatccgagc caatacatta      780
ttagcattca ccagcaatcg acgcgattct tccatcaaga ttttgcccgc gtgtgtcagt      840
acgacgctgc gcgaatggcg aataaaaagc tgcgtgccga gttgattttc cagctcttta      900
atatgaatgc tgagcggagg ctgagacata tttaaacgcg ctgctgcgcg gccaaaatgc      960
aactcttccg ctacggcaag aaaataacgg agcaacttaa gatctgttct gtatacgcgt     1020
tccat                                                                 1025

<210> SEQ ID NO 21
<211> LENGTH: 1050
<212> TYPE: DNA
<213> ORGANISM: Artificial Sequence
<220> FEATURE:
<223> OTHER INFORMATION: gene editing homology arm pool_1_b2405_right

<400> SEQUENCE: 21
aacaaagcac caataccaaa accaacgccg gaagaaaata aaatatcttt cactaattaa       60
cctttatcat aaaagcagct ctgaagagca gagccgcgaa tccttttaat gagtcaccgc      120
tcgatgcttt atcttttcag ggtcatgatt atatttaaac ccaaagaaaa atatcactgc      180
gagaaaaaga gcatatcctg caaacaccag ccagatagtt tgccagtctt ttacgccatc      240
caccgaaaag taatctactg ccatgccact cagaatcgag ccaacccatg cgccgacacc      300
atttaccatg gtcataaaga gcccctgcgc gctggcacga atgctggaat caacttcctg      360
ttcgacaaat accgaaccag aaatattgaa gaaatcgaat gcacagccat aaacaatcat      420
cgacagcagc agcaaaataa atccggttgt tgacggatcg ccataggcga agaagccaaa      480
gcgcagcgtc caggccacca tactcatcag catgacggtt ttaatgccaa atcgctttaa      540
aaagaatggg atagtcagta taaagcccac ttctgccatc tgtgaaactg acagtaaaat      600
ggagggatat ttcaccacaa aactgtcagc aaactccggg ttacgggcga atcatgtag      660 gaacggatta ccaaaaacgt tggtaatttg cagtaccgca cccagcatca tggcaaagag      720
gaaaaagatg gccatgcgtg gatttttaaa cagcacgaag gcatccagac ccagcttgct      780
ggcaagcgat gtggtcgctt ttttctccgc aaccggaatc ttcggcaaag tcagcgcata      840
agccgacagc agcaatgacg caccggacgc gatatacagc tgcagactac tcaattccag      900
atgcagcagg cttactgccc acatcgcgac aatgaacccc accgtaccaa aaacgcgaat      960
gggcgggaaa gcggtcaccg ggtcaagccc tgcctgggca agacaggaat aagagacgct     1020
gttcgataac gcaatagtcg gcataaacgc                                      1050

<210> SEQ ID NO 22
<211> LENGTH: 1050
<212> TYPE: DNA
<213> ORGANISM: Artificial Sequence
<220> FEATURE:
<223> OTHER INFORMATION: gene editing homology arm pool_1_b0495_left

<400> SEQUENCE: 22
```

| | |
|---|---:|
| cgacccggcg tggagattaa tcccatcacc gatgatgtca tcacaatacg cccttcaccg | 60 |
| tgcggtaaca tcgcgggtaa caggcgcatg gtgagctggt gtgcgccgaa aaagttggcg | 120 |
| gaaaactgct gttccatctg cgcacggctg atggtggaaa gggggccata catgccgaat | 180 |
| ccggcattgt taaagatccc atacagacaa ttatcggtca gggcgatcac ctcgtcggct | 240 |
| gcgcgatcaa cactttctgg tgaatccaga tcgatcaaca cgccggtaaa tcccatgctg | 300 |
| ttcatgcgct caacatcatc cggtttccgg caacctgcca gcacatgaaa accctggcgt | 360 |
| tttaattcga gcgcgctttc caggccaatt ccactggaac atccggtaat taagaccgat | 420 |
| ttttgcataa ctttacctgt caggatctcc gttgctttat gagtcatgat ttactaaagg | 480 |
| ctgcaactgc ttcgccatcc agtcggcaat aaacggctgg gcgtcgcggt tgggatgaat | 540 |
| accgtcatcc tgcatccatt gtggcttgag gtagacctct tccataaaaa agggcagcag | 600 |
| cggaacatca aactctttgg cgagtttggg gtaaatggcg ctaaaggctt cattataacg | 660 |
| gcgaccatag tttgcaggca gacgtatttg cattaacaat ggttcagcgt ggcggctttt | 720 |
| gacatcctgc aaaatctggc gcagcgtttg ctcggtttgc tgtggctgaa aaccacgcaa | 780 |
| accgtcattg ccgcccagtt caaccagcac ccaacgcggc tgatgctgtt tcagcagagc | 840 |
| cggaaggcgc gccagtcctt gttgcgaggt gtcgccgctg atgctggcat taactaccga | 900 |
| cgttttactc tgccacttat cattcaacaa ggcaggccag gccgcgctgg cagacattcg | 960 |
| atacccggcg ctcaggctat cacccagaat caataacgtg tccgctgcgg cggcacggaa | 1020 |
| ggttaacagg accaggaaca ggaagggcaa | 1050 |

<210> SEQ ID NO 23
<211> LENGTH: 1046
<212> TYPE: DNA
<213> ORGANISM: Artificial Sequence
<220> FEATURE:
<223> OTHER INFORMATION: gene editing homology arm pool_1_b0495_right

<400> SEQUENCE: 23

| | |
|---|---:|
| atgccagcgg aaaacattgt tgaagttcat catcttaaga agtccgtcgg tcagggggag | 60 |
| catgaactct ccatcctcac cggagttgag ctggttgtca aacgtggcga gaccatcgca | 120 |
| ctggtgggcg agtcgggatc gggtaagtca accttgctgg cgatcctcgc cgggcttgat | 180 |
| gacggcagca gtggcgaagt gagtctggtg ggacaaccgc tacataatat ggacgaagaa | 240 |
| gcgcgggcaa agttgcgcgc gaagcacgtc ggctttgttt ttcagtcatt tatgttaatt | 300 |
| cctacccctta acgcgctgga aaacgtcgag cttccggctc tgctgcgcgg tgagagtagc | 360 |
| gcggaaagtc gtaacggggc gaaagcgttg ctcgaacagt tagggctggg taaacgtctg | 420 |
| gatcatcttc cggcacagct ttccggcggt gaacagcaac gagtggcgct ggcacgagcc | 480 |
| tttaatggtc gacctgatgt gctgtttgcc gacgaaccca ccggcaacct tgaccgccag | 540 |
| acgggcgata aaattgccga cctgctgttt tccctcaacc gtgaacatgg caccacgttg | 600 |
| attatggtga cccacgacct gcaactggcg gcacgctgcg accgctgctt acggctggtg | 660 |
| aacgggcagt tgcaggagga agcatgattg cacgttggtt ctggcgcgaa tggcgttcgc | 720 |
| cgtcgctatt aattgtctgg ctggcgctaa gcctggcggt ggcctgcgtg ctggcgctgg | 780 |
| gcaatatcag cgatcgcatg gagaagggct taagccagca aagccgtgag tttatggcgg | 840 |
| gcgatcgggc gttgcgcagt tcacgcgaag tgccgcaagc gtggctggag gaagcgcaaa | 900 |
| agcgcggcct gaaagtcggc aagcagctga ctttcgccac aatgaccttt gcaggcgaca | 960 |
| caccgcagct ggcgaacgtc aaagcggtgg atgatatcta cccgatgtat ggcgatctgc | 1020 |

```
aaactaatcc ccctggcctg aaaccg                                        1046
```

<210> SEQ ID NO 24
<211> LENGTH: 1050
<212> TYPE: DNA
<213> ORGANISM: Artificial Sequence
<220> FEATURE:
<223> OTHER INFORMATION: gene editing homology arm pool_1_b1646_left

<400> SEQUENCE: 24

```
aaaatcgttg gcgtcgcgtt ggcgtggtta gcgttcgcca ttctgcgtcc aggatcggat     60
gctcgtaaaa gccgccgcca tattcgcgcg ctgcgccggg attttgtcga tcagctaagc    120
cgccatccaa cactgagtga aagcgaattt gaatcgctca cttatcatca cgtcagtcag    180
ttgagtaaca gccaggatgc gctggctcgc cgttggttat tacgctgggg tgtagtgctg    240
ctgaactgtt ctcatgttgt ctggcaattg cgcgactggg aatcgcgttc cgatccgtta    300
tcgcgagtac gggataactg tatttcactg ttgcggggag tgatgagtga gcgtggcgtt    360
cagcaaaaat cactggcggc cacacttgaa gaattacagc ggatttgcga cagccttgcc    420
cgtcatcatc aacctgccgc ccgtgagctg gcggcaattg tctggcggct gtactgctcg    480
ctttcgcaac ttgagcaagc accaccgcaa ggtacgctgg cctcttaatt acttaattac    540
accacaggca tagcgttcac cgccaccgcc cagcggttta ggttgatcgg acatattatc    600
gccgccaacg tggaccatca cgctttgtc tttgatttca tccagtgatt tcagacgagg    660
cgcgatgacg gcatcggtag ctttgccgtc attattgacg accagtgcag gcagatcgcc    720
taaatgcccg gcaccttctg gcccttcatg tttaccggta ttttgtggat caagatgccc    780
gcctgcggat tccgcggcgc tggctttgcc atctttggtg gctggctggc agcttccttt    840
ggcatgaata tggaagccat gttcaccggg gggtaatgct ttcagatcgg gcgaaaactc    900
cagacctta tcggtttcag taatggtgac gctaccaatt gactgcccta ccccttgcga    960
cgtgacgagg ttcatctcga cttttcact ggcagcttgt gcgccggttg caacaaccag   1020
cgccagaata gccagactaa acgtttcat                                     1050
```

<210> SEQ ID NO 25
<211> LENGTH: 1050
<212> TYPE: DNA
<213> ORGANISM: Artificial Sequence
<220> FEATURE:
<223> OTHER INFORMATION: gene editing homology arm pool_1_b1646_right

<400> SEQUENCE: 25

```
ttacggtacg tcgtacccca gtgccgcttt acggatacga aaccattgtt gacgggtcat     60
tttcagtgtt tctgcttcga cagctgcccg tacgcgctca attttacctg aaccgataat    120
tggcagcggc tgcgatggta aacgtaatac ccaggcgtaa accacctgtt caatcgagcc    180
cgcgtttaac tcctctgcca ccacagccag ttcatcacgc agcggctgga ataatcatc    240
attaaacaga cgaccaccac caaggcagga ccacgccatc ggacgaacac gcagttgttg    300
tagttggtcg agcgtgccat ccagcagtaa cggctgatgc accggggata tttccacctg    360
attagtggca agggtaaacg gcagacgtga ttgcaacagg gcaaattgcg caggcgtaaa    420
gttcgatacg ccaaaatgac gcactttgcc gctctgatgc agatgtttga acgcgtccgc    480
cacttcatcg gcatccatta acgggtctgg tcggtggatt aacagcaaat ccagatgatc    540
ggtcgcgaga ttaattagcg actgttcggc gctcttaatg atgtgatcgc ggtcagtgat    600
```

```
gtaatgacca atgacgtttt cttcacgcgc ggtcgtcgcg ataccgcatt tactgacgat      660
ttccatccgt tcacgcaggt gaggtgccag tttcagtgcc tcgccaaacg ccgcttcgca      720
ctgatagcca ccataaatat cagcatggtc cacggtggtc acgccgagat ccagatgctc      780
ttcaataaaa ctgaccagct ggcgggcgga catattccag tccatcaatc gccagtagcc      840
catcacaaaa cgggaaaact ccgggccttg cggcgcaata gtaatacgct gaaccataat      900
cgcttcctct tatcagatat gagaggagta tacgcaagat taggttcaaa agagtgatgg      960
ttgctccggt tcgtctgatg acgctggctt atttgcgcgt aatttgcgca ttaatcgctg     1020
ccgacaaagg cgcagcacct cttgtttttc                                      1050
```

<210> SEQ ID NO 26
<211> LENGTH: 1050
<212> TYPE: DNA
<213> ORGANISM: Artificial Sequence
<220> FEATURE:
<223> OTHER INFORMATION: gene editing homology arm pool_1_b3189_left

<400> SEQUENCE: 26

```
attgctttcg atttcggcgt gcgcgcccat acggctcagc tctggcacat gcataaagcg       60
gttttcaaag accgtttcgg tgataaaccc ggtcccttct gccaccaggt tcaacagcgt      120
gaactgggcc tgcatatcgg tcgggaatgc cggatgcggc gcggtacgta cgttaacagc      180
cttcggacgt ttgccatgca tatccaggct aatccagtct tcgccgactt cgatgtccgc      240
tccagcgtca cgcagtttcg ccagcacggc gtcgagagta tctggctgcg cgttacggca      300
gataattttg ccgcgagaaa tcgccgccgc caccaggaaa gtaccggttt cgatacgatc      360
cggcagaacg cgatagacac cgccgcctaa acgttccaca ccttcgatga cgatacgatc      420
ggtgccctga ccgctaattt tcgcacccag cgtaatcagg aagttcgcgg tatcgacgat      480
ttccggttca cgcgctgcgt tttcaataat cgtggtgcct tccgccaggg ttgcagcaca      540
catgatggtc accgttgcgc caacgctgac tttatccatc acgatatgtg cacctttcaa      600
acgaccatcg acggaagctt taacgtaacc ttcttccagt ttgatggtcg cgcctaattg      660
ttcgaggcca gaaatgtgta gatcaaccgg acgcgcaccg atcgtacaac cgccaggtag      720
tgaaacttgc ccctgaccaa agcgcgctac cagcggcccc agcgcccaga tagaagcacg      780
catggtttta accagatcgt aaggtgcgca gaatacatta acgtcgcggg catcaatatg      840
cacagaacca ttacgttcta ctttcgcacc cagctggctt agcagcttca ttgatgtatc      900
gacgtctttc agtttcggga cgttctggat ctctaccggt tcttccgcca gtagtgcggc      960
aaaaaggata ggcagagcag catttttagc gccggaaatt gtgacttcgc cctggagctt     1020
cgttggcccc tgaacacgaa atttatccat                                      1050
```

<210> SEQ ID NO 27
<211> LENGTH: 1050
<212> TYPE: DNA
<213> ORGANISM: Artificial Sequence
<220> FEATURE:
<223> OTHER INFORMATION: gene editing homology arm pool_1_b3189_right

<400> SEQUENCE: 27

```
ttagtttgtt ctcagttaac aattcatatc cgctaccggc gaatcgccca tagctcaaaa       60
gccgttcagt ttgcgatcgc gcgcccactc cgcaggggta tacgctttga tcgacacagc      120
atgaatgcgg ttatccgcaa tatattccat cagcggacca tagaccgtct gctgtttttt      180
aacccgactc atgccgtcaa acaactcacc cacggcaata acctgaaagt ggctgccatc      240
```

```
gccggaaacg tggacttcct ggagggagag agcgttcatc aacacgctct gaatttcatt        300
attttccatg ggatcttcaa tcatcagtta ataaaccagc gaaacatctt agagcaaagt        360
tgcgctggca taaataagca aaaagcctcg ctgataaatc agacaaggct cgacttgcag        420
gcaggtttgc cggacaggcg gttaacgcca tatccggcct gaaaaaattt aacgaggcag        480
aacatcagca ggcaaattat acaatttcgc cagggtatac actttgtcgt ttaccccctg        540
aagcgtcaca ttgttgccct gcttttcgc cagatcgata agatggagca gcagtgccag         600
tccccccgta tccacgcggg agacacggct aagatcgatg caggtaatcc ccttcaccgc        660
ttcctcacgc atttcccaaa gcggtagcaa aacgtcctga tccagctctc cggataacgc        720
cagcgtgtca cccgtctgca tccagctcag tgactcgctc attatttttt ctcttccaga        780
gtgattttct gttgagaaat cgatttcagt tgcgcagtca ggccgtcgat acctttggta        840
cgcagcagcg ttccccactc gttttgtttg gtggtgatca tactgacgcc ttcagcaatc        900
atgtcgtaag cctgccaatt gcccgtctgg gagtttttac gccactggaa gtccagacgc        960
accggcggac ggccattcgg gtcaataatg gtaacgcgaa taggcacaat ggttttatcg       1020
cccagcggct gttctggcgc aatctgatag                                        1050

<210> SEQ ID NO 28
<211> LENGTH: 1048
<212> TYPE: DNA
<213> ORGANISM: Artificial Sequence
<220> FEATURE:
<223> OTHER INFORMATION: gene editing homology arm pool_2_b3125_left

<400> SEQUENCE: 28
gcgcaacctc gctggcagat aaactttctt tataagagtc tggggcgatt acgattttca         60
tacctatgcc tgttaccaca tgacgccgga gggcgtttct cttattcggc ctggattcca        120
ggcccggatt gcaatacgcc atccgggcac gacgtcatta acgagtaact tcgactttcg        180 ccagttttc gtagtagcac gccagggcgc tatgatccgc cgttcctaaa ccatctgctc         240
gcagtgcctg catcatctcc ataaccgcag ctgtgagcgg cagttgtgcg ccgacgccgt        300
gagaagtatc cagcgcattc gccagatcct taatatgcag atcaatacgg aagcccggct        360
tgaagttgcg gtccatcacc atcggcgctt tggcatccag cacggtactg cccgccagtc        420
caccgcgaat tgcctgataa accaggtccg ggttaacgcc cgctttagtt gccagcgtta        480
acgcttctga catcgcggca atattcagcg ccacaatgac ctgatttgcc agtttggtga        540
cgttacctgc accgatttcc ccggtatgca ccacggaacc cgccatcgct ttcatcaaat        600
catagtattt gtcgaaaata gccttgtcgc cgcccaccat cactgacagc gtaccgtcga        660
tggctttcgg ttcaccgccg ctcaccggag catccagcat atcaatgcct ttcgctttca        720
gcgcttcgct gatttcacgg cttgccagcg gtgcgataga actcatatcg atcaataccg        780
tacctggctt cgcgccttca ataatgccat tctcacccag cgccacctct ttcacatgag        840
gggagtttgg cagcatggtt atgatgacgt cgcactgttc agcgatcgct ttagccgtag        900
acgctgtttc tgcacctgca gcaatcacgt cagcaatagc ttctgggtta cggtcagcaa        960
ccaccagcga gtaacctgct ttcagaaggt ttttactcat tggtttaccc ataatcccca       1020
ggccaataaa accaactttc atagtcat                                          1048

<210> SEQ ID NO 29
<211> LENGTH: 1050
<212> TYPE: DNA
```

<213> ORGANISM: Artificial Sequence
<220> FEATURE:
<223> OTHER INFORMATION: gene editing homology arm pool_2_b3125_right

<400> SEQUENCE: 29

```
atcaatcatc tctcttgttg cggtggtggt tattttttaa aggtatcagc cagtttctga      60
gtggcagagc ggaagacgcc gagatcgctg ccgacagcca caaacgtcgc gccccattcc     120
agataacgac gcgcatcggc ttcgaccggc gcgaggatac cgctgggttt gccgtgcgcg     180
ctggcacggt taaaaatgtg ctgaattgct ttttgtacat ccgggtgtga tgcattgccg     240
agatggccta atgccgcggc cagatcgctg gggccgacga agatgccgtc tacgccttcg     300
gtagcggcaa tggcatcgac gttatctacg ccctgctgac tttctatctg gaccagaata     360
gtgatgttct tgttcgactg agcgaaataa tccgccacgg tgccaaacat attggcgcgg     420
tgagaaacgg agacgccgcg aatgccttcc ggtgggtaac gggttgatgc caccgccagc     480
tctgcttcct cttttgtttc tacaaaagga atcaggaagt tatagaaacc gatatccaga     540
agacgcttaa taattaccgg ctcgttggtc ggcactcgca ctactggcgc gctggcgctg     600
cctttcaagg ccattaactg cggaataaac gtggagatat cgtttggcgc atgttcgcca     660
tccagcacca gccagtcaaa cccagccaaa ccaagaactt cagtgctaat cgggttagag     720
agtgctgacc agcaaccaat ttgtacctgt ttcgcagcca gtgcggcttt gaatttattc     780
gggaaaacat cgttattcat cgcttatacc tttgcttatt tctgcaattc catacgttta     840
atgtcgccaa ctacgaagag gtagcagacc atcgccatca gcgctgaaca tcccacgaaa     900
accagtgctg cattgaagga gtgcagttca cttaccaggt agccaatcac cagtggagtg     960
acaatggagg caacattgcc aaagacgtta agacgccgc cgcagaggcc aacaatctct    1020
ttcggcgcgg tgtcagaaat caccggccag                                    1050
```

<210> SEQ ID NO 30
<211> LENGTH: 1050
<212> TYPE: DNA
<213> ORGANISM: Artificial Sequence
<220> FEATURE:
<223> OTHER INFORMATION: gene editing homology arm pool_2_b3787_left

<400> SEQUENCE: 30

```
ggcgatcagt tcagcgattt ccatcgccgg gctttcgcgc aggtcatcaa tattcggttt      60
aaacgccaga ccaaagcagg cgattttcag ttcactggcg cgtttatcgg tagccgccag     120
gcaatcagcc accgccgctt tcacctgatc gataacccag aacggtttgt gatcgttcac     180
ttcgcgcgcg gtacggataa gccgcgcctg ctgggggttc tgtgccacga taaaccacgg     240
atcaacagca atgcagtgac cgcccacgcc agggccaggc tgaagaatat taacgcgagg     300
gtgacgattc gccaggcgaa tcagttccca gacgttaatc cctgatcgg cacaaatcag     360
cgacaattca ttagcaaaag cgatattcac atcgcggaag ctgttttcgg tgagcttaca     420
catttccgcc gtccgcgagt tagtgacgac acactcacct tcgaggaaaa ttttgtacag     480
ttcgctggcg cgggccgaac aaaccggcgt cataccacca atcacgcgat cgtttttaat     540
cagctcgacc attacctgtc ctggtaacac gcgttccggg cagtaagcaa tgttgacgtc     600
cgcctgctcg cccacctgct gcgggaaagt gagatccgga cgcatctctg ctaaccattc     660
tgccatcttc tcggttgacc ccaccggcga ggtggattca aggatcacca gcgcgccttt     720
tttcagcact ggcgcaatgg agcgagcagc cgattcaacg taggtcatat ctggctcatg     780
atcgcccttaa aacggcgtgg gtacagcaat cagccaggca tccgcttcaa ctggcgtcgt     840
```

```
gctcgctcgt aaaaaaccgc cttctacggc agtttttact acactcgcca aatcaggttc      900
gacgatatgg atttcgccac gattgatggt atcaaccgca tgttggttga tatcgacacc      960
aattacctgt ttttgccgtg aggcaaacgc tgctgccgtt ggcagcccga tataacccag     1020
tccgataaca gaaatggtcg caaaactcat                                      1050

<210> SEQ ID NO 31
<211> LENGTH: 1050
<212> TYPE: DNA
<213> ORGANISM: Artificial Sequence
<220> FEATURE:
<223> OTHER INFORMATION: gene editing homology arm pool_2_b3787_right

<400> SEQUENCE: 31
agtgatatcc gattattttt taacgcttcc agaatgcgag agcatgcctg accatcacca       60
tacgggttat gggcgcggct catagcttga tattcgtttt cgtcttttaa aagacgcgtc      120
acttcctcga caattcgctg cttatccgtc cctaccagac gcaccgtacc cgccgtcacc      180
gcttccggac gctcagtggt atcgcgcatc accagcacag gtttccccag cgaaggcgct      240
tcttcctgaa tgccgcctga gtcggtcaaa atcagccagg cgtggttcat cagccagaca      300
aacggtaaat actcctgggg atcgatcaga atgacatttt tcacatgccc cagaatgcga      360
ttgaccggtt ctctgacgtt cgggttgaga tgcaccggat agacaatctg gatgtcctgg      420
tgcgtggtgg cgatgtctgc cagcgcgtgg cagatttctt caaagccacg accgaaactc      480
tcacgcctgt gaccggtcac cagaatcatc tttttatcgg ggtcgataaa cgggtaattt      540
gccgccagtt ctgaacgcag cttgtcgctg ctcatcacct ggtcacgcac ccataacagt      600
gcatcaatga ctgtattacc ggtaatgaag attcggctat ccgcaacgtt ttcacgcagc      660
aagttttgcc gggaagtttc ggttggagag aagtgataca tcgccagatg cccggtcaat      720
gtacggttag cctcttccgg ccacggcgaa tagagatcgc ccgtgcgcag accagcctca      780
acgtgaccaa caggaatacg ctgataaaac gccgccaggc tggttgccag cgtcgtcgtc      840
gtatcgccgt gaaccagcac gacgtctggt ttgaactcgg caagaatagg ttttagccct      900
tccagaatcc gacaggttat ctctgtcagg ccctgtcctg gctgcattat gttgagatcg      960
tagtcaggta caatggaaaa gagtttcagc acctgatcga gcatctcccg atgctgcgca     1020
gtgacgcaaa ctttagcctc aaaaaaagga                                     1050

<210> SEQ ID NO 32
<211> LENGTH: 1050
<212> TYPE: DNA
<213> ORGANISM: Artificial Sequence
<220> FEATURE:
<223> OTHER INFORMATION: gene editing homology arm pool_2_b1948_left

<400> SEQUENCE: 32
aactggcgcg ataacctggt gcgccaggtg cagcattcac agctggagct ggtcgccaac       60
tttgccgata tctcgctacg cctgtcgcag attttaaaac tgaaccccgg cgacgtcctg      120
ccgatagaaa aacccgatcg catcatcgcc catgttgacg gcgtcccggt gctgaccagt      180
cagtatggca ccctcaacgg tcagtatgcg ttacggatag aacatttgat taacccgatt      240
ttaaattctc tgaacgagga acagcccaaa tgagtgacat gaataatccg gccgatgaca      300 acaacgcgc aatggacgat ctgtgggctg aagcgttgag cgaacaaaaa tcaaccagca      360
gcaaaagcgc tgccgagacg gtgttccagc aatttggcgg tggtgatgtc agcggaacgt      420
```

```
tgcaggatat cgacctgatt atggatattc cggtcaagct gaccgtcgag ctgggccgta      480
cgcggatgac catcaaagag ctgttgcgtc tgacgcaagg gtccgtcgtg gcgctggacg      540
gtctggcggg cgaaccactg atattctga tcaacggtta tttaatcgcc cagggcgaag      600
tggtggtcgt tgccgataaa tatggcgtgc ggatcaccga tatcattact ccgtctgagc      660
gaatgcgccg cctgagccgt tagtgatgaa taaccacgct actgtgcaat cttccgcgcc      720
ggtttctgct gcgccactgc tgcaggtgag cggcgcactc atcgccatta ttgccctgat      780
cctcgctgct gcctggctgg taaaacggtt gggatttgcc cctaaacgca ctggcgttaa      840
cggtctgaaa attagcgcca gtgcttcact gggcgcgcgt gaaagggttg tggtggtcga      900
tgtggaagat gcacggctgg tgctcggcgt taccgcaggt caaatcaatc tgctgcataa      960
acttccccct tctgcaccaa cggaagagat accgcagacc gattttcagt cggtcatgaa     1020
aaatttgctt aagcgtagcg ggagatcctg                                      1050
```

<210> SEQ ID NO 33
<211> LENGTH: 1050
<212> TYPE: DNA
<213> ORGANISM: Artificial Sequence
<220> FEATURE:
<223> OTHER INFORMATION: gene editing homology arm pool_2_b1948_right

<400> SEQUENCE: 33

```
atgcgtcgtt tattgtctgt cgcacctgtc cttctctggc tgattacgcc cctcgccttc       60
gcgcaactgc cgggtatcac cagccagccg ctgcctggcg gtggacaaag ctggtcgctc      120
ccggtgcaga cgctggtgtt catcacctcg ttgacgttta ttccggcaat tttactgatg      180
atgaccagtt tcacccgcat catcattgtt tttggtttat tgcgtaacgc gctgggaaca      240
ccctccgcgc cacctaacca ggtattgctg ggctggcac tgttttttgac ctttttttatt      300 atgtcaccgg tgatcgacaa aatttatgta gatgcgtacc agccattcag cgaagagaaa      360
atatcaatgc aggaggcgct ggaaaaaggg gcgcagccgc tgcgtgagtt tatgctgcgt      420
cagacccgtg aggcagattt agggttgttt gccagactgg cgaataccgg cccgttgcag      480
ggacctgaag ccgtgccgat gcgcatttg ctcccggcct acgtgaccag cgagttgaaa      540 accgcattc agataggctt cacgatttc atcccttttt tgattatcga cctggtgata      600
gccagcgtgt tgatggcatt ggggatgatg atggttcccc cagccaccat tgctctgccc      660
tttaaactga tgctgtttgt actggtggat ggctggcaat gctggtcgg ttcgctggcg      720 cagagctttt acagctagag aggcaaaatg acacctgaat cggtcatgat gatgggact      780 gaagcgatga agtcgcgct ggcactggct gccccgctat tgttggtagc gttggtcacg      840
ggccttatca tcagtatttt gcaggccgcc acgcagatta cgaaatgac gctgtcgttt      900 attccgaaaa tcatcgccgt atttatcgcc attattattg ccggaccgtg gatgctcaat      960
ctgttgctgg attacgtccg caccttgttc actaacctgc cgtatatcat cgggtagccg     1020
tactatgttg caggtgacaa gcgaacaatg                                      1050
```

<210> SEQ ID NO 34
<211> LENGTH: 1050
<212> TYPE: DNA
<213> ORGANISM: Artificial Sequence
<220> FEATURE:
<223> OTHER INFORMATION: gene editing homology arm pool_2_b2790_left

<400> SEQUENCE: 34

```
ccacgggatc aaggccgata tctttggcca tttccgaacc ggcgatagag agcgtagcgc       60
```

```
ggtcgccgta gttgaaggat gtgacgataa acaacatcac cactatccag taacgagcat    120
ttgtgcgttt ttccacactg ctcgcagcct gacttaaaga actcattgtt gcactcctga    180
aaattcgcgt tagccacgct cactctggac tgcgacatcg ccaggaaatc agaggtgacg    240
tagggtgttt tttgccgttt ttataggtcg ttcgccgaat acggcgcgtg tttatatctg    300
gcaatagcag tataaaaagc gcgccatagc ggctcaccgt gcaacaacac aacattaatg    360
cgttcaatga ggcccgattt tggcattagc cctggacggt ggaatccact tcacggaaat    420
gaaaacaaga acaagaaagg aagggttaaa acgaagaaat aagaagagt atgaaatgga     480 tcgcttgact ccaggcaaac gccagtaaaa atccgcgcta tgaagcagtt tttactggca    540
tttgcctgaa aagattcgat tcagcaccgc taaaacgaca tttaccgctc gctgaacata    600
tcaggacaac agcgtgcccc actgttcgac ccacggattt gattccgttt ccggttccgg    660
gttctcactg gcgtcaatca acagcatttc gccaacccgc tgagcgctct gttcctgcaa    720
caaggcatcg aactgtttgc cgccattgca gaaattcaca taactactgt cgccgagcgc    780
aatcacgcca taacgcagat tcggctggaa gcccagacta tctttgattc cctgaaagag    840
tggcacaatg ctatcaggaa ggtcgccctg cccggtcgtg gacgtaacca ccagaacata    900
cttatcctga tagggcagcc agtcgcttaa ttcaggatct tcaaataccg ttgctttgtg    960
gccctgcgcg gtcagaatcg cttccgcttc ttcggccact aacagtgaat tcccgtacat   1020
ggtgccgaca aaaataccaa tttccgccat                                     1050

<210> SEQ ID NO 35
<211> LENGTH: 1050
<212> TYPE: DNA
<213> ORGANISM: Artificial Sequence
<220> FEATURE:
<223> OTHER INFORMATION: gene editing homology arm pool_2_b2790_right

<400> SEQUENCE: 35
accgttttct ccctggatta ggaacttatc tctccatcct gacccgatgg cgcactgaac     60
tcaacccttt cattttcagg aagcagaccg cgccagccaa attgtgataa cgcctgcatc    120
caggtgtcgt ccaggcccgc gtgaatagtc agcggctcgc cagtaaaagg atgcgtcaat    180
gacaactgac tggcatgtag cattaaccgc tggaggccaa aatgctcagc accgctgcga    240
ttctggcgta aatcgccatg tttgctatcg ccaataatcg gatgacgcaa atgggcaaga    300
tgtcggcgaa gctgatgttt gcgtccggtt ttcggctcca gttccaccag gccgtagcgc    360
gtggtcgggt aacgtccggt cgctaccggc atttctacgg tcgccagacc gcgataatgc    420
gtcactgctg gctgcgggcc tttatcttcg cgggcaaatt tatcagcgat tttgtccagt    480
tcttccacca gtggataatc cagcaccgct tcttccatca accagccgcg cacaatcgca    540
tggtaacgtt tctggatttg gtgctgttca aactgttgtg ccagcagccg tccggcctcg    600
ctggataatc ccatcaacaa cacaccagaa gtgggtcggt ccagacgatg agcagtaaaa    660
acatgctggc ctatctggtc acgcacggtt tgcatgacca ctactttctc gtcgcgatcc    720
agccagctgc ggtgaaccag ccagccgagg ggtttattta ccgcaaccag ccattcatcc    780
tgatagagta tttccagcat tagctcgcat catccgcaaa aagagcatcc agttttccca    840
gctcagccag aataagcgcg cgttgcggat ggtccgtcgc cagcgccatt tcataatagg    900
gtgcaacggc aaaagcgccc ggtaacggct gttttgttatc taacaaatcg tgcattcgcg    960
ggatcagcac ccactgcaac cactccagtg gttccatggt gtccataaag aacggttggg   1020
```
tactattaaa ttgatgcggc tggggttcat                                    1050

<210> SEQ ID NO 36
<211> LENGTH: 1050
<212> TYPE: DNA
<213> ORGANISM: Artificial Sequence
<220> FEATURE:
<223> OTHER INFORMATION: gene editing homology arm pool_2_b3197_left

<400> SEQUENCE: 36
ttacggcttt ctgaaaatct tcagcggacc ggcgagtata cctgaagaaa ggacgttaga    60
tgcttttagc tacggcactg ttaattgttg gtttactttt ggtcgtttac agtgccgacc   120
gcctggtttt tgccgcgtct attctttgcc gaacctttgg catcccgccg ctgatcatcg   180
gcatgacggt ggtcagtatt ggtacatcgt taccagaagt catcgtctcg cttgccgcgt   240
ctctgcacga caacgcgat ttagccgttg gtacagccct cggctcaaac attatcaata   300
tattgctgat cctcggtctg gctgcgctgg ttcgtccttt taccgtccat tctgatgttc   360
tacgccgtga attacccttacctg ctgtcctgtg gaacccgttta ttaacctg  gtactctatg   420
acggacaact tagtcgcagc gatggtatct ttctcctctt tctggctgtg ctatggctgc   480
tgttcattgt taaacttgca cgtcaggctg aacgtcaggg gactgacagc ctgaccagag   540
agcagcttgc agagctgccg cgtgacggcg gattgcccgt cgcgttttta tggctcggca   600
ttgcgcttat catcatgcca gtggccacgc ggatggtggt tgataacgcc acggtgctgg   660
cgaattactt tgccatcagc gagttgacga tgggtctgac ggcaattgct atcggaacca   720
gcctgccgga actggcaacc gcaatagcgg gggttcgcaa aggtgaaaac gacattgctg   780
tcggaaatat cattggcgca aacatttta atattgtcat cgtgttgggt ttacccgcgc   840
tgataacgcc aggagagatt gatccactgg cgtacagtcg tgactacagc gtgatgttgc   900
tggtgagcat tattttgcg ttgctgtgct ggcggcgctc cccgcaaccg ggccgtggtg   960
taggggtatt attaactggc ggatttatcg tatggctggc gatgttgtac tggttatcgc  1020
caatactcgt tgaataactg gaaacgcatt                                   1050

<210> SEQ ID NO 37
<211> LENGTH: 1043
<212> TYPE: DNA
<213> ORGANISM: Artificial Sequence
<220> FEATURE:
<223> OTHER INFORMATION: gene editing homology arm pool_2_b3197_right

<400> SEQUENCE: 37
atgtcgcacg tagagttaca accgggtttt gactttcagc aagcaggtaa agaagtcctg    60
gcgattgaac gtgaatgcct ggcggagctt gatcaataca tcaatcagaa tttcacgctt   120
gcctgtgaaa agatgttctg gtgtaaaggg aaagttgtcg tcatggggat gggaaaatcg   180
ggcatattg gcgaaaaat ggcggcaacg tttgccagca ccggtacacc ttcattttc   240
gtccatcctg gtgaagccgc gcatggtgat ttaggcatgt ttaccccaca ggatgtggtg   300
attgctatct ctaactctgg tgaatccagc gaaatcacgg ccttaattcc agtgcttaag   360
cgtcttcacg taccgttaat ctgcatcacc ggtcgcccgg agagcagcat ggcgcgcgcc   420
gcagatgtgc atctgtgtgt taaagtagcg aaagaagcct gtccgttagg gctggcaccg   480
accagcagca ccaccgccac gctggttatg ggcgatgccc tcgctgtcgc gctgttaaaa   540
gcacgcggct ttactgctga agattttgcg ctctcacacc caggcggcgc actgggtcgt   600
aaacttctgc tgcgcgtaaa cgatattatg catacggggcg atgagatccc gcatgttaag   660

```
aaaacggcca gtctgcgtga cgcgttgctg gaagttaccc gcaaaaatct tggtatgact     720
gtcatttgcg atgacaatat gatgattgaa ggcatcttta ccgacggtga tttacgccgt     780
gtcttcgata tgggcgtgga tgttcgtcag ttaagtattg ccgatgtgat gacgccgggg     840
ggaatacgtg tgcgccctgg cattctggcc gttgaggcac tgaacttaat gcagtcccgc     900
catatcacct ccgtgatggt tgccgatggc gaccatttac tcggtgtgtt acatatgcat     960
gatttactgc gtgcaggcgt agtgtaaaga ttcaaggata acaacaatg agcaaagcag      1020 gtgcgtcgct tgcgacctgt tac                                             1043
```

<210> SEQ ID NO 38
<211> LENGTH: 1047
<212> TYPE: DNA
<213> ORGANISM: Artificial Sequence
<220> FEATURE:
<223> OTHER INFORMATION: gene editing homology arm pool_2_b3791_left

<400> SEQUENCE: 38

```
gcgctcgctc tctttggtgg tgtagcgatc ttcaccgtgg aactcaccaa agtgttcccc     60
cgcagggcaa ccgtgcagcg gaatgtaatg aaacaccgcc atgatttccg cttctttcag    120
aaagttaatc aacgcgctcc ggtcatcaat atcccgcagt ttaatgtaga acatatgcgc    180
gttctgcacg cagccatcgg gaatcgacgg cagctcgata cgcccggctt cgccagagg     240 cgctaacgca tcgtagtagt tttgccacag cgccagacgt tgctggttga tacgatccgc    300
tgcttccagt tgcgcccaca ggtatgcagc ttgcagatcg gacatcaaat agctggagcc    360
aatatcgcgc caggtatatt tatcgacctg accacggaag aactggctgc ggttagtgcc    420
cttttcacgg atgatctcgg ctcgttcgat taacgcttta tcgttaatca gcgtcgcgcc    480
gccttcaccg cccgccgtgt agttttggt ttcatggaag ctaaagcagc caatatgacc     540
aatggttccc agtgcacgcc ctttgtaagt ggacatcacg ccctgagcgg catcttctac    600
cacaaacaaa ttatgctttt cgccaacgc cataatggtg tccatttcgc aggccacacc     660
cgcgtaatgg accggcacga taacgcgcgt tttgtcggtg atcgccgctt caatcagcgt    720
ttcgtcgatg ttcatggtgt ccgggcgaac atccacaaaa acgattttg cgccacgcag     780 cacaaaggca ttggcggtgg agacaaaggt gtagctcggc atgatcactt catcgccagg    840
ctggatatcg agcagcagcg ccgccatctc cagcgaagcg gtgcaggacg gcgtcagtaa    900
cactttggcg ctgccaaaac gttgctccag ccactgctgg cagcgacggg taaaaccgcc    960
atcgccacac agtttgccgc tacccattgc cgactgcata tagtcgagtt cggttcccac   1020
caccggcggt gcgttaaatg gaatcat                                        1047
```

<210> SEQ ID NO 39
<211> LENGTH: 1048
<212> TYPE: DNA
<213> ORGANISM: Artificial Sequence
<220> FEATURE:
<223> OTHER INFORMATION: gene editing homology arm pool_2_b3791_right

<400> SEQUENCE: 39

```
gtgatcacct gtataaccag tacgcggtgc tttctacatt cgcaccactt tgtatgtatc    60
gtttaagcgc ggcggtgttg cccatttggg tcgccacccg caaagttgtt ttaccgcgag    120
catacgccca gtttagcgcc gtttgcatca gctcagcacc tgcaccgcgt ccagccagca    180
ggccaattcg cgcatctgtc gcattgagtt cccgtaaaga gacatagccg cgaatatcgc    240
```

```
cggacgccgc acgtaaaatc agacattgat gatcaaaggt gccgcgcacg gcattttcaa      300
tccactgtgc ataaaagcga ctgctggcgt caggcgcata ccacggcgca cgaaaacggc      360
tttgcgcaaa tgcggcgctg gctaactgac gtaatgcggg aatatcggtc tcttgtgcca      420
ctacagcacc gctatcactg gcattgttca cgggtagcgc caaatcaact tcaccttcta      480
ccagggagaa tcccagctgt tgcagggcat ccagttcacc cgtatttgat gccgcaattt      540
tggcctgcac ccgtgaccac ggcgctaacg cgtctggcgt caggagcggt gcttcagacg      600
taatgcgcac gatggcgctg ttaacaccaa agaaggcgtt ttcccaggtt agtggctcaa      660
tactggcgcg gacgggcacg aagtaactcc agcagatatt ggccgtagcc agttttcgct      720
aatgaactgg cagcacgctt cacaccctcg tcatcgagcc agccgttacg ccaggcaatc      780
tcttccaggc aggcaatctt aaagccctgg cgttttttcca ccgtctgtac aaaggtgctg      840
gcttcaatca ggctgtcgtg agtgccggta tccagccagg caaatccgcg cccgagcagt      900
tcaacggtca ggttgcccgc ctcgaggtac atctggttga tggaggtaat ctccagttca      960
ccacgctccg acggcttcac ctgctttgcg tactccacga ctttactgtc gtagaaataa     1020
agcccggtca ccgcccagtt tgacttcg                                         1048
```

<210> SEQ ID NO 40
<211> LENGTH: 1050
<212> TYPE: DNA
<213> ORGANISM: Artificial Sequence
<220> FEATURE:
<223> OTHER INFORMATION: gene editing homology arm pool_2_b4260_left

<400> SEQUENCE: 40

```
gttcagcact tcaacggttt gaccggacat ggtggttaac acatcgcccg gacgataggc       60
tcgtccgcca ggcatgtttt cgcagcctgc caacacgccg ataacgttaa tcggcagttg      120
tagctccgcg accatccgca tcacgccgta aaccgctgcc gcaccgcaca tatcgtactt      180
catctcatcc atgccttctg aaggcttgat cgagataccg ccggagtcga aggttaaacc      240
tttacccacc agcacgattg ggcgtgcatc ttccgacgcg ttgcctttgt actcaatcac      300
cgacatcagc gattcgtttt gcgaaccctg accaccgcc agataggaat gcatccccag      360 ctcttttcatc tgctgttcgc cgataacgcg ggtgatgaca ttcttgctgt agctgtcagc      420
cagctggcgc gcttgtgaag cgaggtaagc ggcgttacag atattcggcg gcatattgcc      480
gagatctttt gctgctttaa tcccggcggc aatcgccaga ccgtgctgga tcgcgcgctc      540
accgctggtc agttcacggc gggtcggcac gttgaacacc atcttacgca gcggacgacg      600
cggttcgctc ttgttcgttt tcagctgatc gaaactgtag agcgtctctt ttgccgtctc      660
gacagcctga cgcactttcc agtagttgtt acgcctttta acgtgcagct cagtcagaaa      720
gcagaccgct tccattgagc cagtatcatt cagcgtatta atggttttct gaataacctg      780
cttgtactga cgctcatcca gctcacgttc tttgccgcaa ccaataagga gaattcgctc      840
ggaaagtaca ttcggaacat ggtgcagcaa caatgtctgc cccggttttc cttccagttc      900
gccccgacgt agcagggcgc tgatgtaccc atcgctgatt ttatcgagct gttctgcaat      960
cggagaaagg cgacgtggtt cgaagacgcc cacgacgatg caggcactcc gctgtttctc     1020
cgggctaccg cttttttacac taaactccat                                     1050
```

<210> SEQ ID NO 41
<211> LENGTH: 1049
<212> TYPE: DNA
<213> ORGANISM: Artificial Sequence

```
<220> FEATURE:
<223> OTHER INFORMATION: gene editing homology arm pool_2_b4260_right

<400> SEQUENCE: 41
tttacgggcg tatttaaagt gataatcata agatatctgg tgcgggagac gctcaaaagc      60
cagctggcga tactcttcat cttgcttttg atcttcttct gtcaaaagtt agtgaggatc     120
ctcggcgcag cggttgacgg cgatattccg gcgaatctgg tgctctccct tctcgggttg     180
ggcgtgccga aaatggcgca gcttatcctg ccattaagcc tgttcctcgg gctgctgatg     240
acgctgggca aactgtatac cgaaagtgaa attacggtaa tgcatgcctg cggcctgagc     300
aaagcggttc tggtgaaagc ggcaatgatc cttgcggtat tcacggcaat cgtagcggcg     360
gttaacgtga tgtgggcggg accgtggtca tcgcgtcatc aggatgaagt gttagcagaa     420
gcgaaagcga accctggcat ggcggcgctg gcgcaagggc aattccagca agcgactaat     480
ggcagctcgg tgctgttcat cgaaagcgtt gacggcagcg atttcaaaga tgtgttcctc     540
gcgcaaattc gaccaaaagg taatgcacgt ccttctgtgg tggtggccga ttccggacat     600
ttaacccagc tgcgcgacgg ctcccaggtc gtcactctca accagggaac gcgcttcgaa     660
ggcactgcat tgttacgtga tttccgcatt acggacttcc aggattatca ggcgatcatt     720
ggtcaccagg cggtggcgct cgacccgaac gataccgacc agatggacat gcgcacattg     780
tggaacactg acaccgatcg tgctcgcgca gaactgaact ggcgtatcac gttggtattc     840
accgtgttta tgatggcact tatggtcgta ccgctgagcg tggttaaccc acgtcaggga     900
cgcgtactgt cgatgctgcc agccatgctg ctgtatctac ttttcttcct gatccagacc     960
tccctgaaat cgaacggcgg taaaggtaag ctggacccga cgctgtggat gtggaccgtt    1020
aacctgattt atctggcttt agcgattgt                                      1049

<210> SEQ ID NO 42
<211> LENGTH: 1050
<212> TYPE: DNA
<213> ORGANISM: Artificial Sequence
<220> FEATURE:
<223> OTHER INFORMATION: gene editing homology arm pool_2_b0071_left

<400> SEQUENCE: 42
ggactggaaa taccagcaat gattctggct ggctactatg tcaaacgtta tggtaagcgg      60
cgaatgatgg tcatagcagt ggcggcagga gtactgtttt acaccggatt gattttcttt     120
aatagccgta tggcgttgat gacgctgcaa ctttttaacg ctgtatttat cggcattgtt     180
gcgggtattg ggatgctatg gtttcaggat ttaatgcctg gaagagcggg ggcagctacc     240
accttattta ctaacagtat ttctaccggg gtaattctgg ctggcgttat tcagggagca     300
attgcacaaa gttgggggca ctttgctgtc tactgggtaa ttgcggttat ttctgttgtc     360
gcattatttt taaccgcaaa ggttaaagac gtttgatgac gtggacgata gcggaaagcc     420
cggtcatttg accgggcaag gggattaatt cataaacgca ggttgttttg cttcataagc     480
ggcaatggcg tcgtcgtgct gcaaggtaag cccaatactg tccagaccgt tcatcatgca     540
gtggcggcgg aaggcatcga tggtaaagcg ataggttttc tctcccgctt tcacctcttg     600
cgcttccaga tccacgtcga aatggatccc cggattagct tcaccagcg caaacagttc      660 gtccacttct gcatcgctta atttcaccgg cagcagctgg ttgttaaagc tattgccgta     720
gaagatgtca gcaaaactcg gcgcaatcac cactttaaaa ccgtagtcgg tcaatgccca     780
gggcgcgtgc tcacgcgaag agccacagcc gaagtttct cgtgccagca aaatggaagc      840
```

```
gccctgatac tgcgggaagt tcagcacgaa gtccgggttt ggctgttggc cttttttcatc    900 cagaaaacgc cagtcgttaa acagatgcgc gccaaaaccc gtacgggtca ctttctgcaa    960
aaactgtttc gggatgattg catcggtatc gacattggcg gcatccagcg gaaccaccag    1020
gcctgtgtgt tgataaaatt tctctgccat                                     1050
```

<210> SEQ ID NO 43
<211> LENGTH: 1050
<212> TYPE: DNA
<213> ORGANISM: Artificial Sequence
<220> FEATURE:
<223> OTHER INFORMATION: gene editing homology arm pool_2_b0071_right

<400> SEQUENCE: 43

```
ggtgtgctcc ttatttaatg ttgcgaatgt cggcgaaatg tccggtcaca gcagcagcgg    60
cagccattgc cgggctgacc agatgcgtgc gcccgccgcg ccctggcgg ccttcaaagt     120 tacggttgct ggtggaggca caacgttcgc ccggattcag acggtcgttg ttcatcgcca    180
gacacattga gcagccaggc aagcgccatt caaaaccggc ttcaataaag attttatcca    240
gaccttccgc ttccgcctgg cttttaccg ggccagagcc gggaaccacc agtgcctgca     300
cgcctggcgc gacttttcgc cctttggcga tctccgctgc cgcgcgtaaa tcttcaatgc    360
gcgagttggt acaggaaccg ataaacactt tgtcgatagc cacttcggtc agcggaatac    420
ccggtttcag ccccatatag gccagcgctt tttctgccga cgcgcgttca accggatcgg    480
caaacgaagc cggatcggga atattgtcgt tcacggaaat cacctggccg ggattggtgc    540
cccaggtgac ctgcggtgaa atttcttctg cttgcagagt gacaacggta tcgaaagttg    600
cgccttcgtc ggtttgcagg gttttccagt aggcaacggc gtcgtcgaaa tctttgcctt    660
tcggcgcatg cagacggcct ttgacatagt taaaggtggt ttcgtccggt gcaaccagac    720
cggcttttgc gcccatttcg attgccatat tgcacagggt catacgacct tccatgctta    780
aatcacggat tgcttcgccg caaaactcca ccacatgccc ggtgccgcct gcgctaccgg    840
ttttaccgat aattgccagc acgatatctt tgcggtaat gcccggcgcg gctttgccct     900
ggacttcaat tttcatggtt tttgcgcggc cctgtttcag ggtttgcgtt gccagtacgt    960
gttcaacttc ggaagtgccg ataccaaagg ccagtgcgcc aaacgcgccg tgggtggcgg    1020
tatgcgagtc gccgcagaca atggtcatcc                                     1050
```

<210> SEQ ID NO 44
<211> LENGTH: 1050
<212> TYPE: DNA
<213> ORGANISM: Artificial Sequence
<220> FEATURE:
<223> OTHER INFORMATION: gene editing homology arm pool_2_b1687_left

<400> SEQUENCE: 44

```
aatgttcagc ccgagcatct cttggtcagg cacatcggta atcaactcgc tgacggaatg    60
ccagacaata tcttcccgcg ccagattcag cactttgag tccaccgtct ctaccgaaag     120
cgcccgcgcc tcaaccataa acggcgcgtt acgcagcgca gagtcaaaag agtcatattt    180
gacgttcacc agacggcgca ctttaggcaa gcgtgtaata tccagccgcg cttcggtaat    240
aaaggccagc gtcccttctg aacccgtcag aatgcgcgtc aggtcgaact cggtcatctc    300
atcgttaaag acatgacgca gatcgtaacc ggtaagaaag cggttaagtt tggggaagtt    360
gtcgataatt aactggcgtt gctgacggca acgttgataa accgtgttat aaattcgccc    420
gattgtggta ttggatttac ccagcgtttc cgccaattcg acgggtaaag gttgcgtatc    480
```

```
gagaatatcg ccccccaaca acaccgcgcg tacgccaagt acgtgatctg acgttttgcc      540
atagaccagc gatccctgac cggatgcatc ggtattgatc atcccaccga gcgttgcccg      600
gttgctggtc gaaagttccg cgcaaaaaa gtagccgaac ggtttcaggt actgattgag      660
ttgatctttt atcaccccgg cctcaacgcg cacccagccc tcttcagggt taatttcgat      720
gatgcggttc atatggcggg acatatcaac aataatcccc tggttgagcg cctgaccgtt      780
agtgccggtg ccgccgccgc gggggtaaa gatcagcgat gaatagcgtt cctgcgcggc      840
aagacgggcg atcagcgcca catctgcggt tgaacgcgga ataccaccg catcggggag      900 aagttggtaa atactgttgt cggtcgacat tgtcagacga tcggcataac ttgtcgccgt      960
atcgccggta aaaccttgtt gctccagctc ttgcaaaaaa ttaagcacca gttgaacgac     1020
gccgggtgcc tgggaaatct gtggaatcat                                      1050

<210> SEQ ID NO 45
<211> LENGTH: 979
<212> TYPE: DNA
<213> ORGANISM: Artificial Sequence
<220> FEATURE:
<223> OTHER INFORMATION: gene editing homology arm pool_2_b1687_right

<400> SEQUENCE: 45
tatattgacc ctttcctgcg gtctgtgatg taggtcgata cactattctt tcaggctgct       60
gcaatagcgc actgaaaggt gatgtttgtt tactctatgg atttcgtgtt gcaggaaggc      120
ggcaagcgag tgaactccag gagcttacaa tagtaagtga ctgggggtgaa cgaacgtagc    180 cgcagcacat gcaacttgaa atacgacgag taaatcgttt gcgtgttgcc tgagttgttg     240
taccacattt ttttctaaca cgcccatcag aattaagggc agaatcggcc tgttaaaaac     300
cgctgaaatt gctcatcatt atgcaggtga gtttcgcgtg ttcacgtcgc gtcgacgatt      360
tgacgcacaa aaaaggtgaa aagtagttat ggtaaatgtt cgtcagccca gggatgtcgc     420
acaaattctg ctttcggtgc tgttttttagc catcatgatt gtggcatgtc tgtggattgt   480
tcaacccttt attctcggct ttgcatgggc cggtacggtg gttatcgcca cctggccggt      540
attgttacgt ttgcaaaaga tcatgtttgg ccgccgctct ctcgccgttc tggtgatgac     600
gctgttatta gtgatggtgt ttatcatccc tattgctttg ctggttaaca gtatcgtcga     660
cggcagcggc ccgctaatta aagccatttc cagcggtgac atgacgttac ccgatctggc     720
gtggcttaat accattccgg tgattggcgc gaagctgtat gcaggctggc acaacttgct     780
ggatatgggg gggacggcga tcatggcgaa agtccgccct tatattggca ccaccaccac     840
ctggttcgtt gggcaggcgg cgcatatcgg gcgctttatg gtgcattgtg cgctgatgct     900
tctcttcagt gccctgctgt actggcgcgg tgaacaggtg gcacaaggca ttcgccattt     960
tgcaacccgt ctggcaggc                                                  979

<210> SEQ ID NO 46
<211> LENGTH: 1050
<212> TYPE: DNA
<213> ORGANISM: Artificial Sequence
<220> FEATURE:
<223> OTHER INFORMATION: gene editing homology arm pool_2_b1006_left

<400> SEQUENCE: 46
ggccggaatg gtatgaatca gcgcaccaaa tttcggtgaa aagcccaaca gcatggcgat      60
gacggcagca gcaacaaaca ccagcgtcga gtagactttg gtcacggcca tcacaccgat    120
```

| | |
|---|---|
| attttcagca taggtggtca cgccgctacc gccgacagag ccggaaagca tcgttgccag | 180 |
| accatcgcct acgaatgccc gccccatata cgggtccata ttgcgtccgg tcatcccggc | 240 |
| gactgccttg agatgaccta agttttccgc caccagaatc accgccacgg gcgcaatcag | 300 |
| catcattgcc tgaccattaa aagcaggagt ggaaaaatgt ggcagaccga accaggcagc | 360 |
| atggctgacg agagtaaaat cgacggcttt tcccagccct aaaacgttgg tcatcacgcc | 420 |
| atacagcaga caggcgacaa ttaatcctac gagaatcaat aaccgctgga tcatgccacg | 480 |
| ggtaaacacc gccaccagcc caatacacag caccgtcatt accgccatcc agctatcaaa | 540 |
| ggccgaagcc gatacacttt tcactgcgat aggcgctaag ttcaggccaa tcgccatcac | 600 |
| caccgcaccc gtcaccaccg gcggcatcag tcgttcaatc cagcgcgtac cgattttcat | 660 |
| caccaccagg ccaatgacgg tataaaccag cccacaggcg ataatcccgc ccagcgcaat | 720 |
| gctgatattc gggttaatgc cctgaccgtt aaagcccgtc gcggcgatca ccacgccgac | 780 |
| aaaagccgcg ctggagccga gataactggg gacgcgcccg ccggtaataa agaaaaacag | 840 |
| taacgtgccg atccccgaca ttaaaatgga agattgggga tccagcccca tcagaatcgg | 900 |
| cattaacacc gtcgcgccaa acatcgccac cgcgtgttga acgcccatta ctgccgtctg | 960 |
| agcaaacggc aatcgttcat ccggcgcgac cacgccgctc tctgtagagg tcgattttaa | 1020 |
| ctgccagtga ggaaaaccga acattgccat | 1050 |

<210> SEQ ID NO 47
<211> LENGTH: 1044
<212> TYPE: DNA
<213> ORGANISM: Artificial Sequence
<220> FEATURE:
<223> OTHER INFORMATION: gene editing homology arm pool_2_b1006_right

<400> SEQUENCE: 47

| | |
|---|---|
| cagctgtctc cttaaggagg ttaacaagca gggcgcatca gcgcgtgata actgcgatcg | 60 |
| aaccacacca gcccgtaggg tgtggtgtga cgatgaatcg cttcgatggc gcaaaacaga | 120 |
| atgtcgtggg tgccgacgct caccacctgg ctgatacggc agtcaaacga aaccagagcc | 180 |
| tcttccagtt gcgggcatcc ggtcaccccc gtctgccagc gggcggcggc aaagcggtgt | 240 |
| tccatgggcg ttttgccgcc aaaaaggttt gaaagcggct cctgcccggc gctaagtgta | 300 |
| tttacacaca gcgttcgatt ttcattgaat gccggccaga cggacgcccc acgattcagg | 360 |
| cacaccagta atgtgggcgg cgtatcggtc acactgcaga cggcgctggc ggtgaacccg | 420 |
| gcgcgcccgg ctggaccgtc cgtggtgata atattgaccg ccgcgcccat gcaggacatc | 480 |
| gcatcgcgaa aagtttgttg atcgacaatg ttcatagttt gctccttaca acagcccgca | 540 |
| ggcttcttca aaggacagac gtggcaggcg cgcataaagc ttgctgctat cgccatagcc | 600 |
| gatattaatc agcagattgc tcttcagcgt gctgcccgta aaaaaggcgt cgtccacgtg | 660 |
| ttgacggtca aagcccgaca tcgggccggt atccagtccc agcgcccggc aggcgacgat | 720 |
| cagataggcc gcctgcatgg aactgttgcg aaacgctgtt tcttcggcaa gttgtgggct | 780 |
| ggaggtaaac caactgcggg catcaccgtg gggaaacagt agtggtaacc gttcataaaa | 840 |
| ttcactgtcc caggcgacga tagcggtgac gggcgcggtc agggtttttt gcagattgcc | 900 |
| gctggaaagt gccgggcgca gacgttcttt tccttctgcc gtgcgggtaa acacgatccg | 960 |
| tgccggagaa cagttagctg atgtcggccc ccatttcatc agggcataaa tctcccgtaa | 1020 |
| cgtctcatcg ctgacgggtg tctc | 1044 |

<210> SEQ ID NO 48
<211> LENGTH: 1050
<212> TYPE: DNA
<213> ORGANISM: Artificial Sequence
<220> FEATURE:
<223> OTHER INFORMATION: gene editing homology arm pool_3_b0335_left

<400> SEQUENCE: 48

```
atgatcaaag cccatgaaat tcagggctgc atcgcgctgg aaaactcctt taaccgcgtc      60
ggcctcgacc acgttctgtt agtgaaagtg gcttccaccg ccgtggtcgc cgaaatgctc     120
ggcctgaccc gcgaggaaat tctcaacgcc gtttcgctgg cgtgggtgga cggtcagtcg     180
ctgcgcacct atcgccatgc gccgaacacc ggcacgcgta atcctgggc ggcgggcgat      240
gccacttccc gcgcggtacg tctggcactg atggcgaaaa cgggcgaaat gggttacccg     300
tcagccctga ctgcgccggt gtggggcttc tacgacgtct cctttaaagg tgaatcgttc     360
cgcttccagc gcccgtacgg ttcctacgtt atggaaaatg tgctgttcaa aatctccttc     420
ccggcggagt tccactccca gacggcagtt gaagcagcga tgacgctcta tgaacagatg     480
caggcagcag gcaaaacggc ggcggatatc gaaaaagtga ccattcgcac ccacgaagcc     540
tgtattcgca tcatcgacaa aaaagggccg ctcaataacc cggcagaccg cgatcactgc     600
attcagtaca tggtggcgat cccgctgcta ttcgggcgct taacggcggc agattacgag     660
gacaacgttg cgcaagataa acgcattgac gccctgcgcg agaagatcaa ttgctttgaa     720
gatccggcat ttaccgctga ctaccacgac ccggaaaaac gcgccatcgc caatgccatt     780
acccttgagt tcaccgacgg cacacgattt gaagaagtgg tggtggagta ccccattggt     840
catgctcgcc gccgtcagga tggtattccg aaactggtcg ataaattcaa aatcaatctc     900
gcgcgccagt tcccgactcg ccaacagcag cgcattctgg aggtttctct cgacagagct     960
cgcctggaac agatgccggt caatgagtat ctcgacctgt acgtcattta agtaaacggc    1020
ggtaaggcgt aagttcaaca ggagagcatt                                     1050
```

<210> SEQ ID NO 49
<211> LENGTH: 1050
<212> TYPE: DNA
<213> ORGANISM: Artificial Sequence
<220> FEATURE:
<223> OTHER INFORMATION: gene editing homology arm pool_3_b0335_right

<400> SEQUENCE: 49

```
atgtctttta gcgaattttta tcagcgttcg attaacgaac cggagcagtt ctgggccgag      60
caggcccggc gtattgactg gcagacgccc tttacgcaaa cgctcgatca cagcaatccg     120
ccgtttgccc gttggttttg tgaaggccga accaacttgt gccacaacgc catcgaccgc     180
tggctggaga acagccaga ggcgctggcg ctgattgccg tctcttcgga aacagaagaa      240
gagcgcacct ttacctttcg tcagctgcat gacgaagtga acgcggtggc ctcaatgttg     300
cgttcattgg gtgtgcagcg cggcgatcgg gtgctggtgt atatgccgat gattgccgaa     360
gcgcatatta ctctgctggc ctgcgcgcgc attggcgcta ttcactcggt ggtgtttggt     420
ggatttgcct cgcacagcgt ggcggcgcga attgatgacg ctaaaccggt gctgattgtc     480
tcggctgatg ccggagcgcg cggtggcaaa atcattccct ataaaaaatt gctcgacgat     540
gcgataagtc aggcgcagca ccagccacgc catgtttttgc tggtggatcg cgggctggcg     600
aaaatggcgc gcgtcagcgg gcgggatgtc gatttgcgt cgttgcgcca tcaacacatc      660
ggcgcgcggg taccggtggc gtggctggaa tccaacgaaa cctcctgcat tctctacact     720
```

```
tccggcacga ccggcaaacc taaaggcgtg cagcgtgacg tcggcggata tgcggtggcg    780
ctggcgacct cgatggacac cattttttggc ggcaaagcgg gcagcgtgtt cttttgcgca    840
tcggatatcg gctgggtggt ggggcattcg tatatcgttt acgcgccgct gctggcgggg    900
atggcgacta tcgtttacga aggattgccg acctggccgg actgcggcgt gtggtggaca    960
atcgtcgaga aatatcaggt tagccggatg ttctcagcgc cgaccgccat tcgcgtgctg   1020
aaaaaattcc ctaccgctga aattcgcaaa                                    1050
```

<210> SEQ ID NO 50
<211> LENGTH: 1050
<212> TYPE: DNA
<213> ORGANISM: Artificial Sequence
<220> FEATURE:
<223> OTHER INFORMATION: gene editing homology arm pool_3_b1940_left

<400> SEQUENCE: 50

```
aatgtctgat aacgatccgc gcgtggtggc gctggtcatt cgccagtgga taaataacga     60
tcatgagtaa cctgacaggc accgataaaa gcgtcatcct gctgatgacc attggcgaag    120
accgggcggc agaggtgttc aagcacctct cccagcgtga agtacaaacc ctgagcgctg    180
caatggcgaa cgtcacgcag atctccaaca agcagctaac cgatgtgctg gcggagtttg    240
agcaagaagc tgaacagttt gccgcactga atatcaacgc caacgattat ctgcgctcgg    300
tattggtcaa agctctgggt gaagaacgtg ccgccagcct gctggaagat attctcgaaa    360
ctcgcgatac cgccagcggt attgaaacgc tcaactttat ggagccacag agcgccgccg    420
atctgattcg cgatgagcat ccgcaaatta tcgccaccat tctggtgcat ctgaagcgcg    480
cccaagccgc cgatattctg gcgttgttcg atgaacgtct gcgccacgac gtgatgttgc    540
gtatcgccac ctttggcggc gtgcagccag ccgcgctggc ggagctgacc gaagtactga    600
atggcttgct cgacggtcag aatctcaagc gcagcaaaat gggcggcgtg agaacggcag    660
ccgaaattat caacctgatg aaaactcagc aggaagaagc cgttattacc gccgtgcgtg    720
aattcgacgg cgagctggcg cagaaaatca tcgacgagat gttcctgttc gagaatctgg    780
tggatgtcga cgatcgcagc attcagcgtc tgttgcagga agtggattcc gaatcgctgt    840
tgatcgcgct gaaaggagcc gagcagccac tgcgcgagaa attcttgcgc aatatgtcgc    900
agcgtgccgc cgatattctg gcgcgacgatc tcgccaaccg tggtccggtg cgtctgtcgc    960
aggtggaaaa cgaacagaaa gcgattctgc tgattgtgcg ccgccttgcc gaaactggcg   1020
agatggtaat tggcagcggc gaggatacct                                    1050
```

<210> SEQ ID NO 51
<211> LENGTH: 1050
<212> TYPE: DNA
<213> ORGANISM: Artificial Sequence
<220> FEATURE:
<223> OTHER INFORMATION: gene editing homology arm pool_3_b1940_right

<400> SEQUENCE: 51

```
atgtctgata atctgccgtg gaaaacctgg acgccggacg atctcgcgcc accacaggca     60
gagtttgtgc ccatagtcga gccggaagaa accatcattg aagaggctga acccagcctt    120
gagcagcaac tggcgcaact gcaaatgcag gcccatgagc aaggttatca ggcgggtatt    180
gccgaaggtc gccagcaagg tcataagcag ggctatcagg aaggactggc ccaggggctg    240
gagcaaggtc tggcagaggc gaagtctcaa caagcgccaa ttcatgcccg gatgcagcaa    300
ctggtcagcg aatttcaaac taccccttgat gcacttgata gtgtgatagc gtcgcgcctg    360
```

```
atgcagatgg cgctggaggc ggcacgtcag gtcatcggtc agacgccaac ggtggataac        420
tcggcactga tcaaacagat ccaacagttg ttgcagcaag aaccgttatt cagcggtaaa        480
ccacagctgc gcgtgcaccc ggatgatctg caacgtgtgg atgatatgct cggcgctacc        540
ttaagtttgc atggctggcg cttgcggggc gatcccaccc tccatcctgg cggctgtaaa        600
gtctccgccg atgaaggcga tctcgacgcc agtgtcgcca ctcgctggca agaactctgc        660
cgtctggcag caccaggagt ggtgtaatga ccacgcgcct gactcgctgg ctaaccacgc        720
tggataactt tgaagccaaa atggcgcagt tgcctgcggt acgtcgctac gggcgattaa        780
cccgcgctac cgggctggtg ctggaagcca ccggattaca attgccgctc ggcgcaacct        840
gtgtcattga gcgccagaac ggcagcgaaa cgcacgaagt agaaagcgaa gtcgttggct        900
ttaacggtca acggctgttt ttaatgccgc tggaggaagt cgaaggtgtc ctgcccggcg        960
cgcgtgttta tgccaaaaac atttcggcag aagggctgca aagcggcaag cagttgccgc       1020
tcggtccggc gttattaggt cgcgttctgg                                        1050
```

<210> SEQ ID NO 52
<211> LENGTH: 1050
<212> TYPE: DNA
<213> ORGANISM: Artificial Sequence
<220> FEATURE:
<223> OTHER INFORMATION: gene editing homology arm pool_3_b0109_left

<400> SEQUENCE: 52

```
cagcacaggc gaggggcaaa aaacgaaacg ggaaagcaga ttccgaggtt ttttatttcg         60
ttgcagcgaa agacaagaaa tttgcgaggc gttacgaaga aagttgggga aggggagatt       120
atccgcccgc gatggagcgg ataaatctgt caactattag cgaaaacgca ttgaaaggtc       180
gagtgcttgt acgtgtttag ttagcgcacc gacggagata aagtccacgc ccgtttcggc       240
aaattcacgc agtgttttgt cagtgacgtt gccagacact tccagtagcg ccttgccgtt       300
ggtgcgtttg acggcttcgc gcatctgttc tgtttcgaag ttatccagca tgatgatatc       360
ggctcctgct ttcagggctt catcaagttc ttccagattc tctacttcga cttctactgg       420
cgcatccggg tgcagccagg acgcttttc gaccgcctgg cgcactgagc cggaggcaat       480
aatatggttt tctttgatca ggaaggcatc agaaagcccc agacggtgat tcgctccgcc       540
gccgcaaagt accgcgtatt tcagagctga acgcaggccg ggtaaggttt tgcgcgtatc       600
caacaactgc gtgttggtgc cttccagcaa ttcgacatag tggcgtacct tactggcaac       660
tcctgaaagg gtttgcacaa aattaagcgc agtgcgttcg cccgttaaca gcacgcggga       720
tgggccttca agttcgaaca aggattgatt ggcattgatg acatcgccgt catccacatg       780
ccagattatg gtgacatcgt cgcctgccag ttgaataaac acctcttcaa cccagcgttt       840
gccgcaaaag acgccattct cgcgggtgat caccgtggca tgagagcgag aattttccgg       900
taaaagtttt gccgtaatat cattgttggc atcgactgtt ccgcctaaat cttcccgcag       960
cgcctgggcc accgcgccgg ggatatcgag attaatgcgt tccagcagct cgtcacgtcg      1020
ggtgtcaggg ttatagcggc gaggcggcat                                        1050
```

<210> SEQ ID NO 53
<211> LENGTH: 1050
<212> TYPE: DNA
<213> ORGANISM: Artificial Sequence
<220> FEATURE:
<223> OTHER INFORMATION: gene editing homology arm pool_3_b0109_right

<400> SEQUENCE: 53

```
gttaaaactc cagatagcta acgaatcata aggtagaaac atgctactct gaaccgggta      60
ttagcaccac atataaggag atcctgcatg ttgttagaac aggggtggct ggttggcgcg     120
cgccgcgttc cctcaccaca ttacgattgc cgcccggatg acgaaacacc caccctgctg     180
gtggtgcaca atattagcct gccgccaggc gagtttggcg gtccgtggat cgacgcatta     240
ttcactggaa ctattgatcc gcaggcacat cctttctttg ctgagatcgc ccatttgcgc     300
gtctccgctc actgtttgat cgccgtgat ggtgaaatag tccagtatgt tccttttcgat     360
aaacgtgcat ggcatgcggg agtctctcag tatcaggggc gcgaacgctg caatgatttt     420
tctattggga ttgagcttga aggcaccgat acgctggcgt ataccgatgc gcagtatcaa     480
cagcttgcgg cggttacgcg ggcactgatt gattgctatc cggatatcgc taaaaacatg     540
acgggccatt gtgatattgc gccggatcgg aaaaccgatc ccggtcctgc atttgattgg     600
gcacggtttc gtgtgctggt cagcaaggag acaacatgac gctatttaca accttactgg     660
tgttaatttt cgagcgcctg tttaagttgg gcgagcactg gcagcttgat catcgtcttg     720
aagcgttctt tcggcgggtg aaacattttt ctctcgggcg cacgttaggc atgaccatta     780
ttgcgatggg cgtgacttt ttactgttac gcgcattgca gggagtattg ttcaacgttc     840
ccacgctact ggtgtggctg ctgattggtt tgctgtgtat tggcgcaggt aaagttcgtc     900
ttcattatca tgcttatctg acagctgctt cacgtaatga tagccatgcc cgtgccacga     960
tggctggcga actcaccatg attcacggcg tcccggcagg ctgcgacgaa cgtgagtatt    1020
tgcgtgagct gcaaaatgca ttgctgtgga                                      1050
```

<210> SEQ ID NO 54
<211> LENGTH: 1048
<212> TYPE: DNA
<213> ORGANISM: Artificial Sequence
<220> FEATURE:
<223> OTHER INFORMATION: gene editing homology arm pool_3_b3399_left

<400> SEQUENCE: 54

```
gtcgcggcgc tcttttttgt ccgggcgtcg gtccgggtgc ggcatggtta aggcattaag      60
tttacgtgcc agcgccattt tttcgcgttt ctctacactt tccgcagtct cttcatacag     120
caaggctgcc tcgctggcgg ggcgacgctg ttcagtaatc gcctttacaa tcaccgtgcg     180
ttcgtcattt ccctggcgca gagtgagcgt ggcattcagc tcgacgattt tgctcggctt     240
gctgcgctgc ccgttgtaat gcaccttacc gccttcaatc atttcacggg ccagcgcgcg     300
ggttttataa aaacgggcag cccatagcca tttatccagt cgaacctcaa cagcaggttt     360
ctctttcatg gcgtctcctt cacattagcg aggggatcag gcggcggtag tcattcagtg     420
acggatggcg ttgatactgt ttctcggcaa tcccggaatc aggattagtc acgccgaggc     480
agtaacgaat accaaattgc gcggcagcat cgagaatcgc ttcgctgtca tcaataaaca     540
gcgttctttc agctttcaga cccgtagctt cggccaccgc atgccataac cgctgatcct     600
ctttcggata accaaatgtg tgggtggaaa gtaataaatc aaggtgtgcg tccagaccgg     660
tatgctcaag ttttaccgcc aggttgtgcg gatgcgcatt ggtgagcaaa attcgctgct     720
taccgctggc tttcagtgcc tcaagaaacg gaatggtatc ttcacgcagt acggcacgcg     780
gtcccatctc ggtggtcatc gcacagatat ccagacccag ttgctcactc cagtaatcaa     840
gacagtacca gttagcgta tgctgtacgt cgtgatattg ctggcgcata tattccatcg     900
cttcctgtgg cgtaaccccg ttttcgcgc cccatgtttc aggcaccagc ttttgccaga     960
```

```
aatagttatc gaaggcgagg tcgagcaacg tgccgtccat atccagcaga acggtatcta    1020
cgtcctgcca ggcaatgttg atatgcat                                      1048

<210> SEQ ID NO 55
<211> LENGTH: 1034
<212> TYPE: DNA
<213> ORGANISM: Artificial Sequence
<220> FEATURE:
<223> OTHER INFORMATION: gene editing homology arm pool_3_b3399_right

<400> SEQUENCE: 55
gagggaaatc tccagagtga agcaatttgc gcgacagggt agcataacct gccgcgcaaa      60
cgtgttattc gataaggctt tctgaagggg tgatcagttg cgggttcagg cagctttcat     120
aataggcctg aatctccatc atgcgagtgc gatgacgctg gtaacgacgc caggcctgta     180
cgccattgta aatggcgcta cccagcatcg tcagtagcag caatgtggtg ctgagatagc     240
gccacaggcc ggaacgatcc gggatcggat gaaggccaat atgctgcgta ccattggcgt     300
cagtgaagat ttttgtgacg ataccctcgg cgttaaacgg cgtatgcatc agcatttgtg     360
ccagtttctg gaaagcgttc cactgttctt cggcgggta gtcgtaaagt gatgccgaag      420
gccagggctg atcaacaaaa tcgctgcctt cgtcgctgac aatcaggaat ccgccggggg     480
ccggactgtt tagtgattgt gccgctcgcg ccgtttcatg cgtgataaac ggcgcggtgg     540
aggttgccac caggttatcc agcgattccg cactcaccgg gcgtaataac acattcacgc     600
catcgagctt cccggcgttg gcgcgttta ccagcgcgtc ccagtcttta ctgttgccga      660
gattgaccag cgcatttttc agtcgcacac agtcatcttt ggcagaacat aaatccgctg     720
tcttcagtac aatgtcgcca aaatcatcaa gcaataccat gccggatttt tgaattgctg     780
aacgtaatga ggcactgacg cgagattcat cttccggttt agggtgcagc tggcgattaa     840
ctgcttcagt caatgccgtc gctttgttga ccagttcaga ttctggtaat ggcaatgagc     900
gggcgtcgtt ccagatgatc tgcgagcagt caaacggtaa aaaaggtgaa ttggttttcg     960
cgctccaggt tccggaagtt cgaatattac acattcccgt accgctaata cgcaatgtat    1020
cgcctacccg cacg                                                     1034

<210> SEQ ID NO 56
<211> LENGTH: 1031
<212> TYPE: DNA
<213> ORGANISM: Artificial Sequence
<220> FEATURE:
<223> OTHER INFORMATION: gene editing homology arm pool_3_b2478_left

<400> SEQUENCE: 56
gtgccgcttc caggtaggct tcatcaccac tgacctgacg cttatagcgt gagtcagaac      60
tacaggcagc gagtaataaa acaagcgaaa cacccgcaac ctttgccagg cgcgactttt     120
gaacagagta agccatcaaa tctccctaaa ctttacagca aaccggcatg cttaagcgcc     180
gctctgaccg tctcacgacc actgtcggtg attggtgtca ttggcaggcg cagcgtatcg     240
gtcgccacaa gacccagttc cttacatgcc catttcaccg ggattggatt gggttcgaca     300
aatagtttgt tgtgtaatgg catcagacgc tgattaataa cgcgtgcctc ggcaaaatgc     360
ccttctgctg ccagtttgca catctgggcc atatcacgcg ctgcgacgtt agccgtaacg     420
gaaataaccc catgaccgcc caattgcatg aagtccagcg cgctcgcatc atcgccgctc     480
agcagaacaa aatcatctga aaccagctct ttgatctggt ttacacgcgt taagttccct     540
```

| | |
|---|---|
| gttgcctctt tgattccgat aatattttt actttcgcca gacggcccac cgtttccggg | 600 |
| agcagatcgc agccagtacg ggacggcaca ttatacagaa tttgcggcag gtcagtatgc | 660 |
| tcagcgatgg ctttgaaatg ctgatacaaa ccttcttgcg acggacgatt gtagtaaggg | 720 |
| gttaccgtca ggcagccgac gataccactg tcattgaagc gctgcgtcag gctaatggct | 780 |
| tccgcagtag cgttagcgcc ggtcccggca attaccggaa tgcgcccatc agccagatcc | 840 |
| agcgtcatca tcaccacatc agcatgttcg tcatgattta aggtagcgga ctcgccagtg | 900 |
| gtgccaacag aaacgatcgc cgaagtaccg ctggcgacat gataatcaat cagttttttc | 960 |
| aagctagccc gacagacatt acctttttca tccatcggag taacaatcgc gacaatactt | 1020 |
| cccgtgaaca t | 1031 |

<210> SEQ ID NO 57
<211> LENGTH: 1050
<212> TYPE: DNA
<213> ORGANISM: Artificial Sequence
<220> FEATURE:
<223> OTHER INFORMATION: gene editing homology arm pool_3_b2478_right

<400> SEQUENCE: 57

| | |
|---|---|
| gggccatcct ctgtgcaaac aagtgtctca atggtacgtt tggtatggca ttaaaagcaa | 60 |
| gcagacagaa ccgttctgat tgttgtatgc atgttttttt tatgctttcc ttaagaacaa | 120 |
| ctcaccccctt aaaggaataa ccagtttgac actgtcatcg caacattatc tggtgatcac | 180 |
| tgcgttgggt gccgatcgcc ctggaattgt gaacaccatc acccgtcatg tcagtagttg | 240 |
| cggctgtaat attgaagaca gtcgcctggc gatgctggga gaagagttca cgtttattat | 300 |
| gctgctttcc ggttcatgga atgccattac tctgattgaa tcaacgttac cgttgaaagg | 360 |
| tgccgaactg gatcttttaa tcgtgatgaa gcgcacgacg gcgcgtccgc gtccgccaat | 420 |
| gccagcatct gtctgggttc aggtcgatgt ggcagactcc ccgcatttaa ttgaacgctt | 480 |
| cacagcactt ttcgacgcgc atcatatgaa cattgcggag ctggtgtcgc gcacgcaacc | 540 |
| tgctgaaaat gaacgggctg cgcagttgca tattcagata accgcccaca gccccgcatc | 600 |
| tgcggacgca gcaaatattg agcaagcgtt caaagcccta tgtacagaac tcaatgcaca | 660 |
| aggcagtatt aacgtcgtca attattccca acatgatgaa caggatggag ttaagtaatg | 720 |
| aatccactga agccggtga tatcgcaccg aaatttagct tgccggatca agacggagaa | 780 |
| caagttaatt tgaccgactt ccagggacag cgtgttctgg tttatttcta cccgaaagcc | 840 |
| atgaccccg gctgtaccgt acaggcctgc ggcttacgcg ataacatgga tgagttgaaa | 900 |
| aaagcgggcg ttgatgtgct gggtatcagc accgataaac ccgaaaaact ctcccgtttt | 960 |
| gcggaaaaag agctgcttaa ctttacgctc ctgtctgatg aggaccacca ggtgtgcgaa | 1020 |
| caattcggcg tctggggtga aaagtccttc | 1050 |

<210> SEQ ID NO 58
<211> LENGTH: 1050
<212> TYPE: DNA
<213> ORGANISM: Artificial Sequence
<220> FEATURE:
<223> OTHER INFORMATION: gene editing homology arm pool_3_b0320_left

<400> SEQUENCE: 58

| | |
|---|---|
| atgatggtgg tattaaacag caggcgattg tgcagttatt gctggaacac ggtgccagcc | 60 |
| cgcatctgac cgataaatat ggcaaaacgc cactggaact ggcgcgggaa cggggctttg | 120 |
| aagagattgc gcagttactg attgccgcag gtgcataaac cgggaggctt gctatcaaca | 180 |

```
caccagaaag acggtgtgtg tgggcgctaa ctgcggatgc ggattttctg gcgcagcggg      240
ggcaaggaca ggttgaacag gtctttgcca gagcggtaaa tatcgcactc ccggctcgcc      300
agcagttgct gacgctgctt tgtgaagagt acgacaatgc gccaaacagt tgtcggttgg      360
cactcactca ctttgatgat ctgttccggc atggtgataa ggttcagttt gacgatcaag      420
gtattacggt tggtcaacat cttcatatag agatgagtcg ttgtcggcgt tggctgtccc      480
caaccttgca aatgaccgct gtgaattttc accttatcgc ctggctacag tggcacgaca      540
ttattcatca gcacctgggg gaaaatgaaa ccctgtttaa ttatcgcggc gataatccgt      600
tttatcaggc gttaaataaa gaattacata ttaaacgacg ggcagttatt caggccgtaa      660
acgataaaca aaatatcgcc tcagcggtcg ccagtatgat ggggttaggg attggcctta      720
cgccatcagc cgacgattat ttaacaggtc tggcgcttat tttatttatt cccgggcatc      780
cggcggaaaa atacaaagag gaattttatc tcggtctgca acgcggcaaa aataatacca      840
cattattaag tgccataacg ctggaagccg cattacaaca acgctgccgg gaaaatattc      900
atcgttttat tcacaacatt atttatgaca tccctgggaa cgcaactcag gcaatagaaa      960
aaattaaaca tattggctcc agttccggct gcgacatgct gtatggcatg gccgatggtt     1020
gtgcgctgag ccaaacctac ggagggaatt                                       1050

<210> SEQ ID NO 59
<211> LENGTH: 1046
<212> TYPE: DNA
<213> ORGANISM: Artificial Sequence
<220> FEATURE:
<223> OTHER INFORMATION: gene editing homology arm pool_3_b0320_right

<400> SEQUENCE: 59
atgtcagtta aaatagtcat taaaccgaat acctattttg attctgtctc gctgatgtct       60
atctccacgc gtgcaaataa actcgacggc gtcgagcagg catttgtggc gatggcgacc      120
gaaatgaata aaggcgtgct gaagaattta ggactgctga cgccggagct ggagcaggcg      180
aaaaacggcg acctgatgat tgtcatcaat ggtaaatcgg gtgcggacaa cgagcagtta      240
ctggtggaga ttgaagaact gttcaacacc aaagcgcaaa gcggctcgca cgaggcgcgt      300
tacgccacta ttggcagcgc caaaaagcat atcccggaaa gtaacctggc ggtgatttcg      360
gtcaacggtc tgtttgccgc tcgcgaagcg cgtcaggcgc tgcaaaacga tctcaacgtg      420
atgctgtttt ccgataacgt ctcagttgaa gatgaactgg cgctcaagca actggcccac      480
gaaaaagggc tgctgatgat ggggccagac tgtggcacgg cgattatcaa cggcgcggcg      540
ctctgttttg gtaacgccgt gcgtcgcggc aacatcggta ttgttggcgc atccggcacc      600
ggcagtcagg agttgagcgt ccgcattcat gaatttggcg cggcgtttc gcaactgatt      660 ggcaccggcg ggcgcgacct gagcgagaaa atcggcggcc tgatgatgct cgacgccatc      720
gggatgctga aaaacgatcc gcaaactgaa atcattgcgc ttatctccaa accgcctgcg      780
cctgcggtgg cccgcaaagt gctggaacgt gcgcgcgcct gccgcaagcc ggtggtcgtc      840
tgcttcctcg atcgtggcga aacgccagtg gatgagcagg ggctacagtt tgcccgcggc      900
accaaagagg cagcgctaaa agcggtgatg ctctccggcg tgaaacagga aaatctcgac      960
ctgcatacgc ttaaccagcc gttgattgcg gatgtgcgtg cgcgtctgca accgcagcag     1020
aaatacattc gtggcctgtt ctgcgg                                          1046

<210> SEQ ID NO 60
```

<211> LENGTH: 1050
<212> TYPE: DNA
<213> ORGANISM: Artificial Sequence
<220> FEATURE:
<223> OTHER INFORMATION: gene editing homology arm pool_3_b4521_left

<400> SEQUENCE: 60

```
ccggagattg ctcaattttt aaatcacggc tggcaacgct ggcattaccc attaccgcaa      60
caatttctgc aacctgtgcg ctgtcagttt ttgccatttc gttggcttct gcgcaagtaa     120
tataggtttc tgacggcaaa ccgttttaa tattgtagtc ctgcgcccag gtcattggtg      180
cgaaaacaaa caggcccgcc agtaaagcaa atttttcat catcattcct tatttcattt      240
tacccagaat tgcaccaccc gtaccgccaa tcacggcacc tttaatcgcc ccttcgaggc     300
cattgccggt cagaacgcca gtgacagcac caacggcggc acccactttt gcacctttac     360
gcgcattttt accgtcgcgg cctttttctg ttactgcacc aacaccagcg ccaacagctg     420
cacctttcag tacgccatta acaccattgc cagtaagtaa accaacgcct gcgcctagca     480
atgcaccttt cgtggtgcgg ttcatatccg ccatcgctgg cgtggagcag aacaatgctg     540
agataagccc gaaggcaagt atttttttct tcaacttaga tgtccggtat taagtaagtt     600
gcacacacaa taatttcgtc ttcaattaag atctgcttaa ctaaagaacg ctcgctatta     660
ttcagataat tcaaaatgag cgtggctgtg atgataggaa ttatgttttt tacgtgaatg     720
agaataatct taaatgagga ataactcatt gattgacaat attttattc aagaagtgtc      780
attgactgtt aacgcaatgt tgtaaaggta agataatctg atttatcaat attattgtgt    840
gatttttatg tgagcagaag atattcatca gcaacgatta cattagtcat tttatttgc      900
cgacggcctc attgtcgaaa gataagcgta cgacagtatt atcagaaaag agtgattttt    960
tatccaacta cacttcagcg cactgcgtgt aaaaatgcc tctttcttat gcgggatatc     1020
atcatttcat catgatgtct ttggtgagcg                                      1050
```

<210> SEQ ID NO 61
<211> LENGTH: 1049
<212> TYPE: DNA
<213> ORGANISM: Artificial Sequence
<220> FEATURE:
<223> OTHER INFORMATION: gene editing homology arm pool_3_b4521_right

<400> SEQUENCE: 61

```
gtgaacacaa tacacctgcg ctgtctcttc aggatgaatc ccctggtctg gtgcctgcgg      60
gctgatgttg cagcagagct taggtcactt agacgctact atcatttatc caatggcatg     120
gaatcgaaat cagtcgatac ccgcagtata tatcgtgaac tgggtgcaac gctgagttac     180
aacatgcgcc tggggaacgg tatggaaatg aaccctggct gaaggcggct gtgcgcaaag     240
aatttgtcga tgataaccgg gtgaaggtga ataatgacgg taatttcgtc aatgatttgt     300
cgggcagacg tggaatatac caggcagcta ttaaagcctc attcagcagt acgtttagcg     360
gacatctcgg ggtggggtat agccatggtg ccggtgtgga atccccgtgg aacgcggtgg     420
ctggtgtgaa ctggtcgttc tgaccatcaa cgattaaact gcgcttcggc gcagttttcg     480
tttacaggat gttgaagggg aaaattctgg ggcaaaaaaa gcccgccagt tacggcggga     540
aacctcatcc tatgggagaa caatgaataa tgaaattgcg gggttatcat ctcccagtat     600
atccatacta acaataaggt tatttactca accaggcata acatttgt tttgtgcgtg       660
ggaacagcct aaggtgtaa aggggaggt ggaaatagca atgaggagta tcagcaagaa      720
tactcgccgc tttaccacaa cgtggatgag agggatgaaa aactcaaggc agagataact    780
```

```
ctgccttgaa gataaatgcg cttttacagc gggcttattt cagctcttct gcttccggta        840
aggtcacgtt cagctcaaga atagaaatat cgccatcttt ttgctcaagc tgtacggtta        900
ccatctcagg atcaatttgt acgtatttac aaatgacctc aagaatatct ttacgcaact        960
gcggcagata atgcggttct gcatcgctgc gacggcgttc agcaacaata atctgcagcc       1020
gttcttttgc aatgttggct gtgttttc                                           1049
```

```
<210> SEQ ID NO 62
<211> LENGTH: 1050
<212> TYPE: DNA
<213> ORGANISM: Artificial Sequence
<220> FEATURE:
<223> OTHER INFORMATION: gene editing homology arm pool_3_b2260_left

<400> SEQUENCE: 62
acgtccgaca atggtcagct tgccattatg catctcaccg cgatcgcgcg tagcgtacca         60
gccttcgtca ttaaccagtg aaaccagttg cccgttacgc cagtaacctt ctgccatact        120
ggcagcccgc agccacactt cattattaac gattttcact tcccgacccg gcagcggcga        180
accaacgtct gccaggccgt cggcttcttt cgcacacacc gtggaggcaa actcggtcag        240
accatagccg caaaagcaac gaatcccctg ctcgcgcgcc tgttccgtca actcgaccgg        300
gatagccgcg ccgccaagta acaccgcttt cagggaaacg gaactacggt taaccagcaa        360
acgccagagt tgtgttggca ccagtgaagc gtgagtacag cctgccagca tttgctccaa        420
tggctgttta tcacgtaccg tcatccgcgc accagcgtat aaccagcgcc acataattcc        480
ctgaccggag acgtgaaaca gcggtaaaga gagcaaccaa tcatcgtgat cgccaaacgg        540
aatcagcgat aacacacctt gcgcactggc aagatgggcc tgataagtat ggacagcggc        600
tttcggcaaa ccggtagaac ccgaggtcaa cgtcattgag cacagacgcg tcggctgcca        660
cgtagcggca tgtgcgcctt caaccagctg aatgtgcagc gacgttaatg ccggaaacgt        720
gttttcccca tccggcacca gagcaaattg cagcgtcaga ttgggcagca attcttcaag        780
caacggttgc ggcagctgag ggttcacggg caacacccgc gccccgcatt gcagtaacgc        840
cagccaggcg agcagcgttt gcggcgtatt ccacgcccgc aacatcacgc cgctgccctc        900 aaccacccc tgcaccgcaa atccggaggc taattcatcg acgcgagcac aaagctcgcg        960
ccagttgagt tgctcgtcat taagacgtaa ggcgatggtt tctccccgca cttgccgcca       1020
gtgacgccac ggccagtcag agaagatcat                                         1050
```

```
<210> SEQ ID NO 63
<211> LENGTH: 1050
<212> TYPE: DNA
<213> ORGANISM: Artificial Sequence
<220> FEATURE:
<223> OTHER INFORMATION: gene editing homology arm pool_3_b2260_right

<400> SEQUENCE: 63
aacaaccgct ccagtgcatc aacttccacg acaggcagcg tgctacccgg ccagcgacgt         60
acctgctgcg cctgcatcag atccagcgtg tccagccctg gaatggtgtc ggcgttaac         120 caggcggcaa tccgcgccag ttgcgttaag cctaagctcg attcaatgga gaactgatc        180 accgccgtca gcccagcgc gtgcgccgcc tgtacctgct cgcgtacttt ttccagactg        240
cccgtgagcg tgggtttgat aactaccgcg cgcacgcccc cttcagccac aaaggcaaaa        300
tccggctcgc gcaggctttc atcccaggca atggcaatgc cggtttcacg ggcaaacgct        360
```

```
cgcgaatcat cgcgggtttt gcacggctct tcgagaaacg cgatgcggtc gcgataatcc      420
gggttaacgt atttggcaaa ctgctgacct ttcagcggtg tccaggcgcg atttgcgtca      480
agacgcaaat gcagatccgg aattgcctcc agcaacagat tcaccaccat gccgtcgcgc      540
accgcttcgt acaatcccac tttgaccttc gccactttct cgcctggcat atctgcaagt      600
ttgaggatca gatcgtccgg atcgccatta cacagcggtg ccgcacggta gttggctgct      660
tgcggcaacg tatctgtcag ttctgccaat gcacagctta cgccaaaggc cacggaaggc      720
atctgcggta gctcgcaatc gcctgccagc cagttattta cccaggcaag cagcacactt      780
tgcgcctctt cccaggtttc ctgactgaag cccggcagtg gggagatctc cccccaccct      840
tcgcgctcgc cttcacgcag gcaaacatac agcccgtcgc gggttttttaa ccgcctgtcg      900 cgcagaacca ccccgcgtc catgggatc tgccagcgt ataccgcgc gctacgcatt       960 acggattccg tttgaatttg ctgaagtcag gctgacgttt ctggttgaag gcgttgcgac     1020
cttcctgacc ttcttccgtc atgtagaaca                                     1050
```

<210> SEQ ID NO 64
<211> LENGTH: 1047
<212> TYPE: DNA
<213> ORGANISM: Artificial Sequence
<220> FEATURE:
<223> OTHER INFORMATION: gene editing homology arm pool_3_b4169_left

<400> SEQUENCE: 64

```
tggaatgggc cgatgtggtg gtgattggtc ccggtctggg ccagcaagag tgggggaaaa       60
aagcactgca aaaagttgag aattttcgca aaccgatgtt gtgggatgcc gatgcattga      120
acctgctggc aatcaatccc gataagcgtc acaatcgcgt gatcacgccg catcctggcg      180
aggccgcacg gttgttaggc tgttccgtcg ctgaaattga agtgaccgc ttacattgcg       240 ccaaacgtct ggtacaacgt tatggcggcg tagcggtgct gaaaggtgcc ggaaccgtgg      300
tcgccgccca tcctgacgct ttaggcatta ttgatgccgg aaatgcaggc atggcgagcg      360
gcggcatggg cgatgtgctc tctggtatta ttggcgcatt gcttgggcaa aaactgtcgc      420
cgtatgatgc agcctgtgca ggctgtgtcg cgcacggtgc ggcagctgac gtactggcgg      480
cgcgttttgg aacgcgcggg atgctggcaa ccgatctctt ttccacgcta cagcgtattg      540
ttaacccgga agtgactgat aaaaaccatg atgaatcgag taattccgct ccctgatgag      600
caggcaacat tagacctggg cgagcgggta gcgaaagcct gcgatggcgc aaccgtaatc      660
tatctgtatg gcgatttagg cgcaggtaaa accacctta gccggggctt tttacaggct      720
ctgggtcatc agggtaatgt caaaagcccc acttatacgc tggtcgaacc ctatacgctc      780
gacaacttaa tggtctatca ctttgatttg taccgccttg ccgatcccga ggagctggag      840
tttatgggga tccgcgatta ttttgccaac gatgccatct gcctggtgga gtggccacaa      900
caaggtacag tgttcttcc tgaccccggat gtcgaaatac acattgatta tcaggcacaa      960
ggccgtgagg cgcgcgtgag tgcggtttcc tctgcgggtg aattgttgct ggcgcgttta     1020
gccggttaac cttttgaaagg tggcggg                                        1047
```

<210> SEQ ID NO 65
<211> LENGTH: 1050
<212> TYPE: DNA
<213> ORGANISM: Artificial Sequence
<220> FEATURE:
<223> OTHER INFORMATION: gene editing homology arm pool_3_b4169_right

<400> SEQUENCE: 65

```
atgatgtatc gcatcagaaa ttggttggta gcgacgctgc tgctgctgtg cacgccggtg      60
ggtgccgcga cgctctctga tattcaggtt tctaacggta atcaacaggc gcggataacg     120
ttgagtttta ttggcgatcc tgattatgcg tttagccatc aaagcaaacg caccgtggcg     180
ctcgatatca aacaaacggg cgtgattcag ggactgccgt tgttgttcag cggcaataat     240
ctggtgaagg cgattcgctc tggaacgcct aaagatgcac aaacgctacg gctggtggtc     300
gatcttaccg aaaacggtaa aaccgaagcg gtgaagcggc agaatggcag caattacact     360
gtcgtcttta cgattaacgc cgatgtgccg ccaccgcctc ctccgccgcc cgtggttgcg     420
aaacgcgttg aaacgcctgc ggttgtcgca ccgcgcgtca cgaaccggc gcgcaatccg      480 tttaaaacgg aaagtaaccg cactacgggt gttatcagca gtaatacggt aacgcgtccg     540
gcagcgcgcg cgacggctaa cactggcgat aaaattatca tcgctattga tgccggacac     600
ggcggtcagg accctggcgc tatcggcccc ggtggtacgc gggagaaaaa tgtcaccatc     660
gccatcgcgc gtaaattgcg tactttgctc aatgacgatc cgatgtttaa aggcgtttta     720
acccgtgacg gggattactt tatctcggtg atggggcgca gtgatgtggc acgtaagcaa     780
aacgccaatt cctcgtgtc gattcacgct gatgccgcac cgaaccgcag tgcgactggc      840
gcttccgtat gggtgctctc taaccgtcgc gccaacagtg aaatggccag ctggctggag     900
cagcacgaga aacagtcgga gctgctgggt ggggcgggtg atgtgctggc gaacagtcag     960
tctgacccct atttaagcca ggcggtgctg gatttacagt tcggtcattc ccagcgggta    1020
gggtatgatg tagcgaccag tatgatcagt                                    1050
```

<210> SEQ ID NO 66
<211> LENGTH: 1025
<212> TYPE: DNA
<213> ORGANISM: Artificial Sequence
<220> FEATURE:
<223> OTHER INFORMATION: gene editing homology arm pool_3_b2405_left

<400> SEQUENCE: 66

```
gagcgaagcg agtcatcctg cacgacccac caatgtaaaa aagcgcccta aaggcgcttt      60
tttgctatct gcgatttgcg aaattgcctg atgcgcttca cttagcagac tactatttcc     120
ggcaattcct gtctcctcac ctactgtgtc aatgcagcca acagcttaac catcgcgggc     180
gtcacctgct gtgtttcata aacaatatat aaatctgcag ggatgcgctg tttgagcgga     240
cggaaaatga cacctggcca gttcatttgt gcgtagctgt ccgctatcaa tgtgataccca    300 atgcccatac tgaccatagc gagtaccgtt tgcggttcat taacttcgcg aataacaacc     360
ggtgaaaatc ccacctgctg gcaaactcgc tgcaaaaaat cccagtcagt gtaaacgggc     420
ggcattgtaa caaaatactc gtcacgtagc gcttccagcg ggacggtgga aaatgatgag     480
agatgatgct cttcaggcat cgccaccaga aacgccgatt catgcaaccg taagctggta     540
aaaccagtcg gtggttctgt cgccattcgc cagatcccgg catcaagttc gcggcgttcc     600
agcaaggcca tttgcatcgc gggcatcttt tcgcgaaaaa gaacgtcaac gttaggattt     660
tccctgagga atcgccgcat aaccgggcgc atccgtcccc acattgccgt tcccactacg     720
ccgagttcaa tccgccctgc ttctccccga cctatttgtt caatccgagc aatacatta     780 ttagcattca ccagcaatcg acgcgattct tccatcaaga ttttgcccgc gtgtgtcagt     840
acgacgctgc gcgaatggcg aataaaaagc tgcgtgccga gttgatttc cagctcttta     900 atatgaatgc tgagcggagg ctgagacata tttaaacgcg ctgctgcgcg gccaaaatgc     960
```

```
aactcttccg ctacggcaag aaaataacgg agcaacttaa gatctgttct gtatacgcgt    1020
tccat                                                                1025

<210> SEQ ID NO 67
<211> LENGTH: 1050
<212> TYPE: DNA
<213> ORGANISM: Artificial Sequence
<220> FEATURE:
<223> OTHER INFORMATION: gene editing homology arm pool_3_b2405_right

<400> SEQUENCE: 67
aacaaagcac caataccaaa accaacgccg gaagaaaata aaatatcttt cactaattaa      60
cctttatcat aaaagcagct ctgaagagca gagccgcgaa tccttttaat gagtcaccgc     120
tcgatgcttt atcttttcag ggtcatgatt atatttaaac ccaaagaaaa atatcactgc     180
gagaaaaaga gcatatcctg caaacaccag ccagatagtt tgccagtctt ttacgccatc     240
caccgaaaag taatctactg ccatgccact cagaatcgag ccaacccatg cgccgacacc     300
atttaccatg gtcataaaga gcccctgcgc gctggcacga atgctggaat caacttcctg     360
ttcgacaaat accgaaccag aaatattgaa gaaatcgaat gcacagccat aaacaatcat     420
cgacagcagc agcaaaataa atccggttgt tgacggatcg ccataggcga agaagccaaa     480
gcgcagcgtc caggccacca tactcatcag catgacggtt ttaatgccaa atcgctttaa     540
aaagaatggg atagtcagta taaagcccac ttctgccatc tgtgaaactg acagtaaaat     600
ggagggatat ttcaccacaa aactgtcagc aaactccggg ttacgggcga aatcatgtag     660
gaacggatta ccaaaaacgt tggtaatttg cagtaccgca cccagcatca tggcaaagag     720
gaaaaagatg gccatgcgtg gattttaaaa cagcacgaag gcatccagac ccagcttgct     780
ggcaagcgat gtggtcgctt ttttctccgc aaccggaatc ttcggcaaag tcagcgcata     840
agccgacagc agcaatgacg caccggacgc gatatacagc tgcagactac tcaattccag     900
atgcagcagg cttactgccc acatcgcgac aatgaacccc accgtaccaa aaacgcgaat     960
gggcgggaaa gcggtcaccg ggtcaagccc tgcctgggca agacaggaat aagagacgct    1020
gttcgataac gcaatagtcg gcataaacgc                                    1050

<210> SEQ ID NO 68
<211> LENGTH: 1050
<212> TYPE: DNA
<213> ORGANISM: Artificial Sequence
<220> FEATURE:
<223> OTHER INFORMATION: gene editing homology arm pool_4_b3493_left

<400> SEQUENCE: 68
agtgtcagaa acgcacagca taatgcggcg catctggcta cgttgatcaa gcgacagctt      60
gtcgtagctt tccacatcgg tggtcaacat acctttcagg cggttgagcg cgttaatggt     120
attcgacgga tggcagtgga actccgcagg ttgcgttgcg ccagcttccg gagccggtac     180
taactgatca gcaccggtag cctgtttgag cagcgcagga tgctgctcaa agtaagcttc     240
gacgttgttg atggcatcac gggtacgggt gatttcgtag ccagtggcat tcatgttcac     300
cacgaagcct gctggcgcga cgccaatcaa taccaacata accagaccaa tgcctttctg     360
accatcgttc gcgccgtgcg aaaacgccac gccgatagcg gaaaggatca gcgcaatacg     420
cgtccagaac ggcggctttt tcttgccgtc tttcttttca cgctccgctg gggtcaggtg     480
gatacgggcg cgtttcttgg tgccgctcca gtagcgacgc agcaagaaaa tcagaccgcc     540
agcaaacacc aggccgacaa taggggaaac gatcagagaa ccgaaaatac ttaatacttt     600
```

```
cgggatattg agtgcatcca ccactgacgt cccggtcatc aacgcattgg ttaaaccaat      660
cccgatgatc gcgccaatca gcgtatgaga gctggatgca ggtaaaccaa agtaccaggt      720
acccaggttc cagataatcg ccgccagcaa catagagaac accatggcaa ggccatgaga      780
cgatcccata ttaagcagca gatccgtcgg cagcatatgc acaatggcat aggcaacact      840
cagaccaccc agcaaaacac ccaaaaagtt gaataccgcc gccataacca cggcgagctg      900
agaacgcatc gcgcgggtat agataacggt tgccacggcg ttggctgtgt catggaaacc      960
attgatggct tcgtagaaca gcacaaaagc cagtgcaagc aataataaca gcccggtatg     1020
caaatccagg ccagcaaaca aatgtagcat                                      1050

<210> SEQ ID NO 69
<211> LENGTH: 1050
<212> TYPE: DNA
<213> ORGANISM: Artificial Sequence
<220> FEATURE:
<223> OTHER INFORMATION: gene editing homology arm pool_4_b3493_right

<400> SEQUENCE: 69 ttgcccctg tatggatttc actcaaaaaa taattatctt atataattca ggcaaatact       60
tccttttagt aatattgatg ctggtgcgac cactgaggaa tctttacaat tcacgcccgt      120
tttttctaag aggagcgcaa cgtggaaagg tttgatgcca ttattatagg cgctggtgcg      180
gcgggtatgt tctgttctgc gctggcaggt caggcaggac gccgggttct gctgatcgat      240
aatggtaaaa aaccagggcg caaaatcctt atgtctggcg gtgggcgctg caactttacc      300 aaccctttatg tcgaaccagg cgcttatctg agccagaatc cgcatttttg taagtctgca      360
ctcgcacgtt ttacccagtg ggatttcatt gatctggtca ataaacacgg catcgcctgg      420
cacgagaaaa cgttagggca actcttctgc gatgactccg cgcagcagat tgtcgacatg      480
ctggtggatg agtgcgagaa gggcaatgtg accttcagat tgcgtagcga agtgctgagt      540
gtggcgaagg atgaaacagg cttcacgctt gatctgaacg gcatgactgt cggttgcgaa      600
aagctggtca tcgcgactgg tgggctgtca atgccggggc tgggcgcgtc gccgtttggt      660
tataagattg ccgaacaatt tggcctcaac gtgctgccga cccgcgcggg tctggtgcca      720
ttcactctgc ataaaccgtt gctcgaagag ttacaggtgc tggcgggcgt ggcggtgcct      780
tccgtgatta ccgctgaaaa cggcaccgtt ttccgtgaga acttactctt cacccaccgc      840
ggcttgtctg gaccggcggt gttgcagatt tcaagctact ggcaaccggg ggaatttgtc      900
agcatcaatc tgctaccgga tgtggacctc gaaaccttcc tgaatgagca gcgtaacgca      960
catccgaatc aaagcctgaa aaacacactg gcggttcatc taccgaagcg gttggttgaa     1020
cgcttacagc aactcgggca aatcccggat                                     1050

<210> SEQ ID NO 70
<211> LENGTH: 1050
<212> TYPE: DNA
<213> ORGANISM: Artificial Sequence
<220> FEATURE:
<223> OTHER INFORMATION: gene editing homology arm pool_4_b0479_left

<400> SEQUENCE: 70
cataccgata cgtcctggaa gcagctcctg agcgtagacc agaatggcag agaatgccga       60
agcgaggata aatccaataa tcaccgttaa aaccccgtc cagtgcaggc tggcgtaggg       120
taaaatcagc gtaaacggcg caacgccgag gatagagccg caaatcacat atttccgccc      180
```

```
aattttatcc cctacaggcc cgccgatcac cgtacctgcc gcaacggcaa acaggaaggc      240
aaacagatga agctgagcat tctggataga taatccgaat ttttgcatca gataaaaggt      300
gtaatagctg ctgatgctcg ccatatagaa atatttcgag aaaatgagga ttaacagaat      360
gctgaccgcc agtacaactt tattgcgcgg cagtggattg ataatcgtcg ctttgggttt      420
tcctttattc attcggtgct gtgccgagta ccaacggctg atttgcgcca acaccacgat      480
cgccagcagt gccgcaagca caaaccaggc aacgttgcct ttgccataag gcgcgataat      540
caccgccgcc agcaagggtc ccagggaact gccaaagttg ccgccgacct gaaagataga      600
ttgcgccagg ccatgccgcc cgccggaagc catacgggcc acgcgagaag attccggatg      660
aaagaccgat gaaccggtac cgaccagcgc cgccgccagc agaactgcgc caaaactgcc      720
cgccagcgca agcagcacca gaccgcttaa ggtaaagcac atgccaattg gcaacgacca      780
tggcatcgga tatttatcgg tccagtagcc gaccactggt tgcagtagcg aagaggcgag      840
ctggaaggtg agggttatca tgccaatctg cataaatgtc agagaaaatt ctgactgaag      900
cagcggataa atcgccagaa tcagcgattg gatcatgtcg ttcagcagat gtgagaggct      960
gatagcacct aaaataccaa acgatgttcg ggccttggtc gttgacgcag ccgcgcccgc     1020
cacaggctgg ggttgttcac tcattgccat                                      1050

<210> SEQ ID NO 71
<211> LENGTH: 1050
<212> TYPE: DNA
<213> ORGANISM: Artificial Sequence
<220> FEATURE:
<223> OTHER INFORMATION: gene editing homology arm pool_4_b0479_right

<400> SEQUENCE: 71
aggaaagtca cttttcagg gttgcgatgt aaagaatgat cttatttgtg attattacca       60
gactaacata cctgtatgcg tcgtctgaag gaagtctcaa cgccgaatac agaatttcta     120
atctggatgc agatttatct tcaccggacg cagacttgtc tatgatgtcg cgtcatacta     180
tttttcaaca cgttgaaatc aggtcaggga gagaagtatg aaattattgc agcggggcgt     240
ggcgttagcg ctgttaacca catttacact ggcgagtgaa actgctctgg cgtatgagca     300
ggataaaacc tacaaaatta cagttctgca taccaatgat catcatgggc attttttggcg   360 caatgaatat ggcgaatatg gtctggcggc gcaaaaaacg ctggtggatg gtatccgcaa     420
agaggttgcg gctgaaggcg gtagcgtgct gctactttcc ggtggcgaca ttaacactgg     480
cgtgcccgag tctgacttac aggatgccga acctgatttt cgcggtatga atctggtggg     540
ctatgacgcg atggcgatcg gtaatcatga atttgataat ccgctcaccg tattacgcca     600
gcaggaaaag tgggccaagt cccgttgct ttccgcgaat atctaccaga aaagtactgg     660
cgagcgcctg tttaaaccgt gggcgctgtt taagcgtcag gatctgaaaa ttgccgttat     720
tgggctgaca accgatgaca cagcaaaaat tggtaacccg gaatacttca ctgtatatcga    780 atttcgtaag cccgccgatg aagcgaagct ggtgattcag gagctgcaac agacagaaaa    840
gccagacatt attatcgcgg cgacccatat ggggcattac gataatggtg agcacggctc    900
taacgcaccg ggcgatgtgg agatggcacg cgcgctgcct gccggatcgc tggcgatgat    960
cgtcggtggt cactcgcaag atccggtctg catggcggca gaaaacaaaa aacaggtcga   1020
ttacgtgccg ggtacgccat gcaaaccaga                                    1050

<210> SEQ ID NO 72
<211> LENGTH: 1032
```

<212> TYPE: DNA
<213> ORGANISM: Artificial Sequence
<220> FEATURE:
<223> OTHER INFORMATION: gene editing homology arm pool_4_b2470_left

<400> SEQUENCE: 72

```
ccaagcgtcg tctggaggtg ttgtatcagt gttcgcaggc gctgaacact agccagattg      60
atgtgcattg tttccgccat attttgcaga ttgttcgcga caatgaagcg gctgaatatc     120
tggagttaaa tgtcggtgaa aactggcgga ttagcgaagg gcaaccaaac ccggaattgc     180
cgatgcagat tttaccggtg acaatgcaag agacggttta cggcgaactg cactggcaaa     240
atagtcacgt tcatcatca gaaccgctgc ttaacagcgt ttcgtcgatg ctgggacgcg     300
gtttgtactt taatcaggcg cagaagcatt ttcagcaatt attgttgatg gaagaacgtg     360
cgaccatcgc ccgcgaattg cacgactcgc tggctcaggt actttcttac ttacgtatcc     420
agttgacgtt actgaagcgt tcgataccgg aagataacgc caccgcacaa agtatcatgg     480
ccgattttc ccaggcgttg aatgatgctt atcggcagtt acgcgagctg ttgactactt     540
tccgcctgac gctgcagcag gcggatctcc cctccgcatt gagggaaatg ctggatacgt     600
tacaaaatca aaccagcgcc aaactgaccc tcgactgccg tctgccaacc ctggcactgg     660
atgcgcaaat gcaggtgcat ttgttgcaaa ttattcgcga agcggtgctg aatgcgatga     720
agcacgccaa cgccagcgaa atcgccgtca gttgcgtcac cgcgccggac ggcaatcaca     780
cggtttatat ccgtgataac gggattggta tcggtgaacc gaaagaaccc gaaggtcatt     840
atggtctgaa tatcatgcgc gaacgcgcgg aacggctagg tgggacgctg acttttttcac     900
aaccttccgg cggcggcacg ttagtgagta ttagctttcg ctctgcggag ggtgaggaaa     960
gtcagttaat gtaatgcctc ctactgacca aagaatactt gcacttaagg ttcagtataa    1020
aagggcatga ta                                                        1032
```

<210> SEQ ID NO 73
<211> LENGTH: 1050
<212> TYPE: DNA
<213> ORGANISM: Artificial Sequence
<220> FEATURE:
<223> OTHER INFORMATION: gene editing homology arm pool_4_b2470_right

<400> SEQUENCE: 73

```
atggcgaatt tctttattga tcgccccatt tttgcctggg tgctggcaat cctgttgtgt      60
ctgacaggta ccctggcgat tttttcattg cccgttgaac aatacccgga tctcgcgcca     120
ccgaatgtgc gagtgaccgc taactatccc ggcgcatcgg cccagacgct ggaaaacacc     180
gtgacccagg ttatcgagca aaatatgacc ggcctcgata atctcatgta tatgtcatct     240
cagagcagtg gcaccggtca ggcatctgtc actttaagtt ttaaagcagg caccgatccg     300
gacgaagccg tgcagcaagt acaaaaccag ctgcaatcag ccatgcgaaa gttaccgcag     360
gcggtgcaaa atcagggcgt gacggtgcgt aaaaccggcg ataccaacat tctgaccatt     420
gccttcgtct ctaccgatgg ttcgatggat aaacaggata ttgctgatta tgttgccagt     480
aatattcagg acccgttaag ccgcgtgaat ggcgtcgggg atatcgatgc ctatggttcg     540
caatattcca tgcgtatctg gctggacccg gcgaaactca acagtttcca gatgacggct     600
aaagatgtca ctgatgccat tgagtcacag aacgcgcaga ttgcggttgg gcaacttggt     660
ggtacacctt ccgtcgataa gcaggcgctc aacgccacca ttaacgccca gtcactgctg     720
caaacaccag aacagttccg cgatatcacc ttgcgggtca atcaggacgg ctcagaggta    780
```

| | |
|---|---|
| aggctgggcg atgtcgccac cgtcgaaatg ggggcggaga aatacgatta tcttagccgc | 840 |
| ttcaatggta agccagcctc cgggctgggg gtaaaactgg cctccggcgc taacgaaatg | 900 |
| gcgacagcgg agctggtgct caatcgtctc gacgagctgg cgcagtattt cccgcatgga | 960 |
| ctggaataca aggtggcgta tgaaaccacc tcgtttgtta aagcctccat tgaagacgtg | 1020 |
| gtgaaaacgc tgctggaagc tatcgctctg | 1050 |

<210> SEQ ID NO 74
<211> LENGTH: 1039
<212> TYPE: DNA
<213> ORGANISM: Artificial Sequence
<220> FEATURE:
<223> OTHER INFORMATION: gene editing homology arm pool_4_b1451_left

<400> SEQUENCE: 74

| | |
|---|---|
| ccagttcacc acggtgtgtc cagcggctgt ctattccctg gtaatggcgt tgcagggtaa | 60 |
| tcacgccgcc cgcatgtgac gggttaagtt gtggtgccat gggtattgac tggtactggg | 120 |
| tcgtttctcg ctctccggca tacatcatca cactcatatc atcccgcgaa ctcaggctac | 180 |
| gctcatagcg caaccagcc tgagtttgct tgatggtttt tcgcgtgtcg tactgttctg | 240 |
| cacgaggcgc ttgttgtgga ttagccttcc attctgcttt ggttagccca cctgggtcat | 300 |
| ctgctttgat atccacacta ttgaaaatca gacttaattt gctggcttca tcaatgcgta | 360 |
| cgcccagttt ggcattggct aaattttct gtgcgccact atggtcacga tagccgtggg | 420 |
| tcgtaaaacg cgtggttgag acggtgtaat cgacatcgcc aggctgtgtg ccgtctcccg | 480 |
| ttgcgcccgt tgctttcagc ccatagcgcc agctgccaaa actgccgtag taactactgg | 540 |
| cttcaatggt tggtggctgt tgtccggtct gggtggtgac attcattacc ccaccagacg | 600 |
| cgttgccata cagggcagag aaggggccac gcagcacttc cacattttgc acactgctta | 660 |
| aatcgatgtt ggatgtttgc ccttgcccgt cgggcatggt ggcgggaata ccgtccacat | 720 |
| acaggcgaat accgcgaata ccgtaagtgg agcgggagcc aaatccgcga atcgacagct | 780 |
| gtaaatcttg cgcatagttc tgccggtttt gtacctgcaa accaggcacg ccggtcagtg | 840 |
| attcggacaa gttaatgcgc ggtgttgcca ggcgcatctc ctcgccatcc accacgctta | 900 |
| ctgctgctgg ggtatccagt tctgaaaacca cctgcggtgc ggcactgaca atcatagtct | 960 |
| gttcatcagc ggcaaaaaca acggggggaaa ggacaagcag tgcgggcaaa acggtctgtc | 1020 |
| ggacggaaaa aatcttcat | 1039 |

<210> SEQ ID NO 75
<211> LENGTH: 1050
<212> TYPE: DNA
<213> ORGANISM: Artificial Sequence
<220> FEATURE:
<223> OTHER INFORMATION: gene editing homology arm pool_4_b1451_right

<400> SEQUENCE: 75

| | |
|---|---|
| gaaaaaagcc aggttaagaa tgggaaaacg ccgtcatggt aatgaaattg taaatttatg | 60 |
| gaaaatgaaa cggcacaata cgttaagtaa ttgagaaaat tgtagtcgta acggcaagaa | 120 |
| atgctccaca tttgagaaaa taatgattac cattcccatt tataacaaga gcgtaacgat | 180 |
| gattacgctt agcgaagcat tgtgaagcag caaaaatatc ggttcatcaa agggagtcgt | 240 |
| catgcatttta cgtcatctgt tttcatcgcg cctgcgtggt tcattactgt taggttcatt | 300 |
| gcttgttgtt tcatcattca gtacgcaggc cgcagaagaa atgctgcgta aagcggtagg | 360 |
| taaaggtgcc tacgaaatgg cttatagcca gcaagaaaac gcgctgtggc tcgccacttc | 420 |

```
gcaaagccgc aaactggata aaggtggcgt ggtttatcgt cttgatccgg tcactctgga      480
agtgacgcag gcgatccata acgatctcaa gccgtttggt gccaccatca ataacacgac      540
tcagacgttg tggtttggta acaccgtaaa cagcgcggtc acggcgatag atgccaaaac      600
gggcgaagtg aaaggccgtc tggtgctgga tgatcgtaag cgcacggaag aggtgcgccc      660
gctgcaaccg cgtgagctgg tagctgacga tgccacgaac accgtttaca tcagtggtat      720
tggtaaagag agcgtgattt gggtcgttga tggcgggaat atcaaactga aaccgccat      780 ccagaacacc ggtaaaatga gtaccggtct ggcgctggat agcgaaggca aacgtcttta      840
caccactaac gctgacggcg aattgattac catcgacacc gccgacaata aaatcctcag      900
ccgtaaaaag ctgctggatg acggcaaaga gcacttcttt atcaacatta gccttgatac      960
cgccaggcag cgtgcattta tcaccgattc taaagccgca gaagtgttag tggtcgatac     1020
ccgtaatggc aatattctgg cgaaggttgc                                      1050

<210> SEQ ID NO 76
<211> LENGTH: 1050
<212> TYPE: DNA
<213> ORGANISM: Artificial Sequence
<220> FEATURE:
<223> OTHER INFORMATION: gene editing homology arm pool_4_b1981_left

<400> SEQUENCE: 76
ggtgtcagga gttattgcga tataagcatc ttttatgatt gctgctgaac gtttaatcga       60
gggtggtaag gataaacggt agacattatt ataacaatcc actaatgccc tggctttatc      120
ttcacctttg ggtccatgaa cgatcactat tggtatatct gtttcacttt aaattttgc      180 tattagattt tctgcaatcg ataatgaaaa tgtacgttcc tgcgagctac cttctaaatt      240
gaacgcaatg taagatccta acgatcgcat ttcctcgcgc acctcatcga gtacatcctc      300
acttagtggc aattcatata ttggcctgac tgctggaaaa cccgcctcac gcatcataaa      360
tgcccatgtc ataggtacgg gagcccggag tttctgatcc atactggacg cgttcttgca      420
caaaggggag aagcaattca tggttatacc aacaacctga aaattcgttt ttgctttcaa      480
ctgactgata ataacatcg ttttcaggtt cttttacgc atcccctcaa tgcaaagatc       540
cggcgtaccg tattgctgtg ttatgttctt tgctaaatct tttatttctt ttaatgttgc      600
gtgatcctgc atagtcattg tgactaatgt taatttagtc tgttcaagtt taagcgcatt      660
aaagacttct aaaattaattg tcgacgttac aattaaaaga tgcttaattt tatgcaattc     720
aagcgcccga ataacaggaa agatggccat agcatcgcca atctgatcgg gaatatggat      780
gacaacaaag tctgtttttt caatattgaa attataagct ttataatcgt agtaactaaa      840
tgcaatacgt ctcaacaatg atgctaaaaa catacctaac ctcgcctccc tactggttat      900
aatgcaatgc agtctatcag actcatcagg gtgccatttt gtgcatatgc ggacttttat      960
gtttcatatc tctaacctgt gggtcctctg cttaatcctt aaacaacacc agcaactcct     1020
gcgctttcat cttccatcga atttttcatg                                      1050

<210> SEQ ID NO 77
<211> LENGTH: 1036
<212> TYPE: DNA
<213> ORGANISM: Artificial Sequence
<220> FEATURE:
<223> OTHER INFORMATION: gene editing homology arm pool_4_b1981_right

<400> SEQUENCE: 77
```

```
atggactcca cgctcatctc cactcgtccc gatgaaggga cgctttcgtt aagtcgcgcc      60
cgacgagctg cgttaggcag cttcgctggt gccgtcgtcg actggtatga ttttttactc     120
tatggcatca ccgccgcact ggtgtttaat cgcgagtttt ccccgcaagt aagcccggcg     180
atgggaacgc tcgccgcatt tgctaccttt ggcgtcggat ttcttttccg tccgctcggc     240
ggtgtcattt tcggtcactt tggcgaccga ctgggacgta agcgcatgtt aatgctgacc     300
gtctggatga tggcatcgc gacagccttg attggtattc ttccttcatt ctcgaccatt      360
gggtggtggg cacctatttt gctggtgaca ctgcgtgcca ttcagggatt tgcagtcggc     420
ggcgaatggg gaggcgcggc gttgcttccc gttgaaagtg caccgaaaaa taaaaaagcc     480
ttttacagta gcggtgtaca agttggctac ggtgtaggtt tactgctttc aaccggactg     540
gtttcattga tcagtatgat gacgactgac gaacagtttt taagctgggg ctggcgcatt     600
cctttcctgt ttagcatcgt actggtactg ggagcattgt gggtgcgcaa tggcatggag     660
gagtccgcgg aatttgaaca acagcaacat tatcaagctg ccgcgaaaaa acgcatcccg     720
gttatcgaag cgctgttacg acatcccggt gctttcctga agattattgc gctacgactg     780
tgcgaattgc tgacgatgta catcgttact gcctttgcac ttaattattc aacccagaat     840
atggggctac cgcgcgaact tttccttaat attggtttgc tggtaggtgg attaagctgc     900
ctgacaattc cctgttttgc ctggcttgcc gatcgttttg gtcgccgtag ggtttatatc     960
acaggtacgt taatcggaac gttgagcgca tttcctttct ttatggcgct tgaagcacaa    1020
tctatttttct ggatag                                                   1036
```

<210> SEQ ID NO 78
<211> LENGTH: 1050
<212> TYPE: DNA
<213> ORGANISM: Artificial Sequence
<220> FEATURE:
<223> OTHER INFORMATION: gene editing homology arm pool_4_b0237_left

<400> SEQUENCE: 78

```
cacaccgacg ttcagggagg tttcaaccac acctttggct acatcggagt tacgaatcac      60
accgttcggg gtggcgttca gcagacgaat aaaggtatcg cgagatttcg caatcagggc     120
agctttatcg ttcgctacag agtccagcaa caaggccaga ttttttctctt tttctgccag    180
ctcgttttc aggatctcct gataggtatt caccagagat tcaggacgt cgactttatc      240
agctgcgaca gcaatggtcg caaaggcttc acgcgggatg gcgttacgca gtgtgccgcc     300
gttgaaatcg ataaggcgca gatccagttc ttccgcatga cccgccagga agcgcaccag     360
cagtttgttg gcattaccca gcccaacgtg gatttccccg ccggagtgac cgccttcag     420
accttttaag gttaacttga aggtttcaaa accagctgga accgcttcac gatctaaatg     480
caggttggag gtgaagtcga tacccccgc acaacccatg tagatttcac cttcttcttc     540
ggagtcggtg ttaatcagaa tatcagcctg caaccagttg ccctgtaagc cgaacgcacc     600
gtccataccg gcttcttcgg tcatggtcag cagcacttcc agcgggccgt gaaccacgtt     660
ttcgtcagcc agaaccgcca gcgcagaggc cataccaatg ccgttatccg cacccagcgt     720
ggtgccgcgc gctttaaccc attcgccatc aatataaggc tggataggat ctttcgtgaa     780
gtcatgcacg gtgtcgttat tttctgcgg caccatatcg aggtgggcct gtaagacgac     840
cggtttacga ttttccatac ctgcggtagc aggtttacga atcaggatat tacctacctg     900
atcgcgttcg acatggaaac ctttctcttt tgcccaacca acaatgtatt cagcgagttg     960
ctcttcatga taggacgggt gaggaataga acagattttg gcaaaatat cccacagcgg     1020
```
ctgtggagat aattgagaca gttcagacac         1050

<210> SEQ ID NO 79
<211> LENGTH: 1039
<212> TYPE: DNA
<213> ORGANISM: Artificial Sequence
<220> FEATURE:
<223> OTHER INFORMATION: gene editing homology arm pool_4_b0237_right

<400> SEQUENCE: 79
catgtgaaat actggttttt agtgcgccag atctctataa tctcgcgcaa cctatttcc      60
cctcgaacac tttttaagcc gtagataaac aggctgggac acttcacatg agcgaaaaat    120
acatcgtcac ctgggacatg ttgcagatcc atgcacgtaa actcgcaagc cgactgatgc    180
cttctgaaca atgaaaggc attattgccg taagccgtgg cggtctggta ccgggtgcgt     240
tactggcgcg tgaactgggt attcgtcatg tcgataccgt ttgtatttcc agctacgatc    300
acgacaacca gcgcgagctt aaagtgctga acgcgcaga aggcgatggc gaaggcttca    360
tcgttattga tgacctggtg ataccggtg gtactgcggt tgcgattcgt gaaatgtatc     420
caaaagcgca ctttgtcacc atcttcgcaa accggctgg tcgtccgctg gttgatgact     480
atgttgttga tatcccgcaa gatacctgga ttgaacagcc gtgggatatg ggcgtcgtat    540
tcgtcccgcc aatctccggt cgctaatctt ttcaacgcct ggcactgccg ggcgttgttc    600
ttttttaactt caggcgggtt acaatagttt ccagtaagta ttctggaggc tgcatccatg    660
acacaggcaa acctgagcga aaccctgttc aaacccgct ttaaacatcc tgaaacctcg     720
acgctagtcc gccgctttaa tcacggcgca caaccgcctg tgcagtcggc ccttgatggt    780
aaaaccatcc ctcactggta tcgcatgatt aaccgtctga tgtggatctg gcgcggcatt    840
gacccacgcg aaatcctcga cgtccaggca cgtattgtga tgagcgatgc cgaacgtacc    900
gacgatgatt tatacgatac ggtgattggc taccgtggcg gcaactggat ttatgagtgg    960
gccacccagg cgatggtgtg gcaacaaaaa gcctgtgcgg aagacgatcc gcaactcagt    1020
ggtcgtcact ggctgcatg                                                1039

<210> SEQ ID NO 80
<211> LENGTH: 1050
<212> TYPE: DNA
<213> ORGANISM: Artificial Sequence
<220> FEATURE:
<223> OTHER INFORMATION: gene editing homology arm pool_4_b2497_left

<400> SEQUENCE: 80
aataccggaa gcaccgatga caccataaag cagcagcgaa acgccgccca tcaccggcaa     60
tgggatcatc tggatagcgg cagccagttt accgacgcag gaaagcagga tagcgaaaat    120
cgccgccccg ccgataaccc aggtactgta aacacgggtg atcgccatca cgccaatgtt    180
ttctccgtaa gtagtatttg gcgtagagcc aaagaagccg gaaatcacgg tcgacaagcc    240
attagcaaac atcgaacggt gcagacctgg atcgcgcagc agatctttt tgacgatatt    300
agccgttact accaggtgcc ctacgtgttc ggcaataacc actaacgccg ctggcagaat    360
agtcagaatg gcaaaccact cgaagcgcgg cgtatagagg gttggcagcg caaaccagtg    420
agcattaata atcggcgtgg tatcgacaat tcccattgcg aaagagagcg cgtaccccac    480
cagcacgcca attaaaatcg ggataattgc caggaaacca cgaaacagca cggaacctaa    540
aaccgtgacc gccagggtgg taatagagat gatgatggtt ttggagtctg gcgtttgccc    600

```
ttcagccggg agtaaacccg ccataccggc agctacgccc ccagctcca gaccgatgac    660 ggcaacgatt gcgcccattg ccgcaggtgg aaacagcacg tccagccagc cggtccccgc    720
tttcttcacg ataaaagaaa ccaggcagaa cagcacgccg cacataataa agccgcccag    780
cgcgacttca taccctaacg gcaacagtaa caataccggt gaaataaagg caaagctgga    840
accaagataa gccggaattt tccctttaca gatgaagaga tacagcagcg ttccaatacc    900
gttaaataac agtacagtcg ccgggttaat atgaaataag acgggcacca ggacggttgc    960
accaaacatg gcgaacaaat gttgcaaact aagcgggatt gtctgtaaaa gtggcggtct   1020
ttcactcacc ccgatagcac ggcgcgtcat                                    1050
```

<210> SEQ ID NO 81
<211> LENGTH: 1050
<212> TYPE: DNA
<213> ORGANISM: Artificial Sequence
<220> FEATURE:
<223> OTHER INFORMATION: gene editing homology arm pool_4_b2497_right

<400> SEQUENCE: 81

```
agtattatcc tctgtattat gtgttatagg cgctttactc aaaaaaaagc cgactcttaa     60
agtcggcttt aattattttt attctttatt tcgtaccaaa gattttgtca ccggcatcgc    120
cgaggcccgg aataatgtat ccgtgctcgt tcagtccctg atcaatcgat gcggtataca    180
gttcgacgtc cgggtgcgct ttttccagcg cagcgatacc ttctggcgca gctaccagca    240
ccagaacttt gatgctgctg cagcccgctt ttttcagcag gtcgatggtc gcgataacgg    300
aaccaccggt tgccagcatt gggtcaacga tcagcgccat acgctcatcg atgttagaaa    360
ccagtttctg gaagtacggt accggctcca gcgtttcttc attacggtac ataccgacaa    420
cgctgatgcg cgcgctcgga acgttttcca gcacaccgtc catcatacca agacccgcac    480
gcagaattgg cacaacggta attttcttac ctttgatctg gtcgatttct accgggccgt    540
tccagccttc gatagttact ttttccgttt cgaggtcggc ggtcgcttcg taagtcagca    600
ggctacccac ttcggaagcg agttcgcgaa agcgcttggt gctgatatct tgctcacgca    660
tcagtcccag cttgtgtttg acgagtgggt gtttgacttc cacgatcttc atactctttc    720
tcctttgagg ggcagccaca aaaaaaatcg acggattata cctccttcct tcaaggcggc    780
aatattcttt tcgttgactt tagtcaaaat gataacggtt tgagataaag ttattttata    840
ttcagatggt tatgaaagaa gattattcca tccgaaaact aacctttacc ctggcacaag    900
tcttctttcg ccgcgcgcct ggggaaaaga cgtgcaaaaa ggttgtgtaa agcagtctcg    960
caaacgtttg ctttccctgt tagaattgcg ccgaattttta tttttctacc gcaagtaacg   1020
cgtggggacc caagcagtga ccgataaaac                                    1050
```

<210> SEQ ID NO 82
<211> LENGTH: 1050
<212> TYPE: DNA
<213> ORGANISM: Artificial Sequence
<220> FEATURE:
<223> OTHER INFORMATION: gene editing homology arm pool_4_b4260_left

<400> SEQUENCE: 82

```
gttcagcact tcaacggttt gaccggacat ggtggttaac acatcgcccg gacgataggc     60
tcgtccgcca ggcatgtttt cgcagcctgc caacacgccg ataacgttaa tcggcagttg    120
tagctccgcg accatccgca tcacgccgta accgctgcc gcaccgcaca tatcgtactt    180
catctcatcc atgccttctg aaggcttgat cgagataccg ccggagtcga aggttaaacc    240
```

-continued

```
tttacccacc agcacgattg ggcgtgcatc ttccgacgcg ttgcctttgt actcaatcac        300
cgacatcagc gattcgtttt gcgaaccctg accgaccgcc agataggaat gcatcccag        360 ctctttcatc tgctgttcgc cgataacgcg ggtgatgaca ttcttgctgt agctgtcagc      420
cagctggcgc gcttgtgaag cgaggtaagc ggcgttacag atattcggcg gcatattgcc        480
gagatctttt gctgctttaa tcccggcggc aatcgccaga ccgtgctgga tcgcgcgctc        540
accgctggtc agttcacggc gggtcggcac gttgaacacc atcttacgca gcggacgacg        600
cggttcgctc ttgttcgttt tcagctgatc gaaactgtag agcgtctctt ttgccgtctc        660
gacagcctga cgcactttcc agtagttgtt acggccttta acgtgcagct cagtcagaaa        720
gcagaccgct tccattgagc cagtatcatt cagcgtatta atggttttct gaataacctg        780
cttgtactga cgctcatcca gctcacgttc tttgccgcaa ccaataagga gaattcgctc        840
ggaaagtaca ttcggaacat ggtgcagcaa caatgtctgc cccggttttc cttccagttc        900
gccccgacgt agcagggcgc tgatgtaccc atcgctgatt ttatcgagct gttctgcaat        960
cggagaaagg cgacgtggtt cgaagacgcc cacgacgatg caggcactcc gctgtttctc        1020
cgggctaccg cttttacac taaactccat                                          1050
```

```
<210> SEQ ID NO 83
<211> LENGTH: 1049
<212> TYPE: DNA
<213> ORGANISM: Artificial Sequence
<220> FEATURE:
<223> OTHER INFORMATION: gene editing homology arm pool_4_b4260_right

<400> SEQUENCE: 83
tttacgggcg tatttaaagt gataatcata agatatctgg tgcgggagac gctcaaaagc        60
cagctggcga tactcttcat cttgcttttg atcttcttct gtcaaaagtt agtgaggatc        120
ctcggcgcag cggttgacgg cgatattccg gcgaatctgg tgctctccct tctcgggttg        180
ggcgtgccgg aaatggcgca gcttatcctg ccattaagcc tgttcctcgg gctgctgatg        240
acgctgggca aactgtatac cgaaagtgaa attacggtaa tgcatgcctg cggcctgagc        300
aaagcggttc tggtgaaagc ggcaatgatc cttgcggtat tcacggcaat cgtagcggcg        360
gttaacgtga tgtgggcggg accgtggtca tcgcgtcatc aggatgaagt gttagcagaa        420
gcgaaagcga accctggcat ggcggcgctg gcgcaagggc aattccagca agcgactaat        480
ggcagctcgg tgctgttcat cgaaagcgtt gacggcagcg atttcaaaga tgtgttcctc        540
gcgcaaattc gaccaaaagg taatgcacgt ccttctgtgg tggtggccga ttccggacat        600
ttaacccagc tgcgcgacgg ctcccaggtc gtcactctca accagggaac gcgcttcgaa        660
ggcactgcat tgttacgtga tttccgcatt acggacttcc aggattatca ggcgatcatt        720
ggtcaccagg cggtggcgct cgacccgaac gataccgacc agatggacat gcgcacattg        780
tggaacactg acaccgatcg tgctcgcgca gaactgaact ggcgtatcac gttggtattc        840
accgtgttta tgatggcact tatggtcgta ccgctgagcg tggttaaccc acgtcaggga        900
cgcgtactgt cgatgctgcc agccatgctg ctgtatctac ttttcttcct gatccagacc        960
tccctgaaat cgaacggcgg taaggtaag ctggacccga cgctgtggat gtggaccgtt        1020
aacctgattt atctggcttt agcgattgt                                          1049
```

```
<210> SEQ ID NO 84
<211> LENGTH: 1050
<212> TYPE: DNA
```

<213> ORGANISM: Artificial Sequence
<220> FEATURE:
<223> OTHER INFORMATION: gene editing homology arm pool_4_b1412_left

<400> SEQUENCE: 84

```
aatgactgct ggtgtttatt tagggggcgtt tccacgacat attccggcac agaatgcggt      60
tctggacgtc acctttgaat tccctcgcgg acgagccaca aaagatcgac tctattttg      120
tgtaccgatg ctggatctgg tggttccgga agagggggag ctccgacagg ccgtggcgat     180
gctggaaaca ttacgcgaag agcaaggcag cgttctggtc cattgtgcat tgggattatc     240
gcgcagtgcg ctggtggtgg cggcatggtt gttatgttac ggacactgta aaaccgttaa     300
tgaagcgatt agctatattc gagccagacg cccgcagatt gtgctgacag acgagcacaa     360
agcgatgctg agattatggg aaaacaggta agtggattga gatgtggact gaatatctac     420
agtccacatc aagaccgtgt ccggttatgc agaaacaatg ctgtcgatgg ctgcttttgc     480
gtcagactgt gctttcgctg ccatttccgg accgtatgcg atcccttcgg cgaagacaaa     540
tttcacatcg gtaatgccga taaagccgag gaacgtggac agatacggcg tcaccaggtc     600
cgttggtcca tctttgtgga tcccgccgcg gctggtaata cgatggctt ttttacccgt      660
taccagacct tccggaccgt tctcggtata gcggaaagta acgcctgcgc gggcaaccag     720
gtcaaaatag tttttcaact gagtcgagat gttgaagtta tacatcggtg ccgcaataac     780
gataacgtcg tgggctttca gctcggcaat caactcatcg gaaagtgcca gagcttcctg     840
ctgacgcgga gtcagcggcg catcgctcgg acgcagagcg ccaaccagtt cgccatccag     900
taccggaatc ggatttgcag ccaggtcgcg aacggtgatt tcatcagcgg agtgcttttc     960
gcgccattgt tcaacaaaat aatcggacaa ctgattagac tgagagtacc ctgccaggat    1020
gctggattta agaactaata ccttgctcat                                       1050
```

<210> SEQ ID NO 85
<211> LENGTH: 1050
<212> TYPE: DNA
<213> ORGANISM: Artificial Sequence
<220> FEATURE:
<223> OTHER INFORMATION: gene editing homology arm pool_4_b1412_right

<400> SEQUENCE: 85

```
gaatttattg aacaacgcat agaaagccgc gatgtggtac tctatatcta tcatttaaaa      60
gaaaattaat caggcagact actgcccact aacgttatga cagaacaaca aaaattgacc    120
tttacggcct tgcagcagcg gctggattcg ctgatgctgc gtgacagact gcgtttttct    180
cgccgtctgc acggcgtgaa gaaggttaaa aatcctgatg cacaacaggc cattttccag    240
gagatggcga aagagattga ccaggcggca gggaaagtcc tgctgcgtga agcggcacga    300
ccggaaatta cttatcctga caatttaccg gttagtcaga aaaacagga cattctcgaa     360
gcgattcgtg atcaccaggt ggtgatcgtc gccggggaaa cgggttctgg taaaacgact    420
cagttaccga aaatctgtat ggagctgggg cgcgggatta aggactgat cggccatacc      480
cagccgcgtc gtctggcggc aagaacagtg gcgaaccgta ttgcggaaga gctgaaaacg    540
gagccgggcg gttgcatcgg ttacaaagtg cgtttcagcg atcacgtaag tgataacacg    600
atggtcaagc tgatgaccga cggtatcctg ctggcggaga tccagcaaga ccgcctgctg    660
atgcagtacg acactatcat tattgacgaa gcgcacgaac gcagcctgaa tatcgatttt    720
ttgctcggct atttgaaaga gttgctgccg cggcgtcctg acctaaaaat cattatcact    780
tccgcgacta tcgacccgga acgcttttcg cgccacttta ataatgcgcc gattattgaa    840
```

```
gtctccggtc ggacctatcc ggtggaagtg cgctatcgcc cgattgttga agaagccgat    900
gacaccgagc gcgatcagtt gcaggcgatt tttgacgccg tagacgaact gagtcaggaa    960
agccatggcg acattctgat ctttatgagc ggcgagcggg aaatccgcga taccgccgat   1020
gcgctgaaca agctgaactt acgccatacc                                    1050
```

<210> SEQ ID NO 86
<211> LENGTH: 1050
<212> TYPE: DNA
<213> ORGANISM: Artificial Sequence
<220> FEATURE:
<223> OTHER INFORMATION: gene editing homology arm pool_4_b4139_left

<400> SEQUENCE: 86

```
aacagtggtg tcgttaccga tgactttgaa gcatacctgg ttaaccactt ccggaacaac     60
cgggtttact ttagctggca tgatggaaga gcccgcctgc agttccggca ggttgatctc    120
gttcaggccg gcacgtgggc ctgaagagag caagcgcagg tcgttacaga ttttggacat    180
cttcacagcc aggcgtttca gcgcgccgtg aaccataaca taagcgccgc agtcagaggt    240
cgcttcgatc aggtcttcag ccggtacgca tgggaagcca gtaacttcag ccagtttttt    300
cactgccagc ggagagtact cttcggcgt gttcagacca gtaccgattg ctgttgcacc    360
aaggttaact tccagcagca gttcagcggt acgttgatg ttttcactt cttctttcag    420 caggatgctg aaagcgcgga attcctgacc gagggtcatc ggtactgcgt cctgcagctg    480
ggtacgaccc atttttcagga tgtcctggaa ttcgacagct ttacgttcaa agccttcacg    540
cagttggtta atcgcatcta ccagcttaat cagggaagag taaactgcga tacggaaacc    600
ggtcgggtag gcgtcgttag tggactgaca ttttgttaaca tggtcgttcg ggttcaggta    660
ctgatattca ccttttttggt gacccatcag ttccagaccg atattggcca gcacttcgtt    720
ggtgttcatg tttacggaag tacctgcgcc gccctggtag acgtctaccg ggaactgatc    780
catgcatttt ccgttgttca ggacttcatc acatgcggca atgatggcat tcgctacact    840
tttaggaatg gtttgcagct cttttgtttgc catagctgcg gctttttttaa ccattaccat    900 accgcgaaca aattcaggaa tatcactgat tttgttgttg ctgatataga agttttcaat    960
cgctctcaga gtgtgaacac catagtaggc atcagctgga acttccctgg tacccaacag   1020
atcttcttcg atacgaatgt tgtttgacat                                    1050
```

<210> SEQ ID NO 87
<211> LENGTH: 1041
<212> TYPE: DNA
<213> ORGANISM: Artificial Sequence
<220> FEATURE:
<223> OTHER INFORMATION: gene editing homology arm pool_4_b4139_right

<400> SEQUENCE: 87

```
ttttacccct taattattaa tttgtgaaat agatcaccgc tttgggatta ctaccaaaaa     60
tagttgcgca aacatcttga aattttgcta atgaccacaa tataagctaa acgcgattcg    120
caacccattc aggtagccgg ggttaaccgg ctgctattac aggagaaacc tttgcgctgg    180
ttacctttta ttgccatttt cctttatgtc tatattgaga tttcaatctt tattcaggtt    240
gcccatgtat tgggggtatt gctgaccctc gtgctggtta tattcacgtc agttatcggt    300
atgtcactgg tacgtaacca gggctttaag aatttcgtgc tgatgcagca aaaaatggcg    360
gcgggtgaaa acccagcggc ggagatgatt aaaagtgttt cgctgatcat tgctggtttg    420
```

```
ctgcttttat taccgggctt ttttaccgac ttcctcggtc ttctactttt attgccgccg      480
gtgcaaaagc atctgacagt gaagttgatg ccgcatttgc gcttttctcg catgcctggc      540
ggcggtttta gcgccgggac cggtggcggt aatacttttg atggtgagta ccagcgaaag      600
gatgatgagc gcgaccgcct tgatcataaa gacgatcgcc aggattaatg tcgaaacgcc      660
ggattatgtg gttatgccat tttccggcgt ttttcgtttt ggcagcaaca gccataaccc      720
cgccagcatg atcagcgcat agagactttt ccagccgacc attgccagta acagaacgca      780
taacagcccg ccaaccaccg ccagtagtcg ataacgtcct tgcaataatt tacagcctgc      840
cagcatgcat aacagataaa tcataataaa gatgccattg cataaataa taagagcgtc       900 cagattgatc tctaaagcat gaatcaccaa agtgctcacc acacagcagc cgagcaccgc      960
attgagggca ttattcggga tatggcgaga agagaggcgt gccaggtagt ggtcaggatt      1020
atgttgcgcc tgcgaccaga c                                                1041

<210> SEQ ID NO 88
<211> LENGTH: 1044
<212> TYPE: DNA
<213> ORGANISM: Artificial Sequence
<220> FEATURE:
<223> OTHER INFORMATION: gene editing homology arm pool_4_b2039_left

<400> SEQUENCE: 88
ttgatgaacg tgagtgattg tcttgaacaa agctgaccgg atagcctaga atatgttcaa       60
atgctgattg attaaagctc tcataaaaga aacctctatc atcaccaaat actcttggct      120
ccagaattag cacatcttca atttcagttc taatcacatt cattaatttg aatccttcgt      180
cattttataa agatactgcc cataattatt ctttattagt ggtacagcta attttcttac      240
ttgctcaaca tcaataaaac ctttacgaaa tgcaatctct tcaggacagg aaaccttcaa      300
tccctggcgc tcttcaattg tcgcaataaa attacttgct tctatcagac tctgatgagt      360
ccccgtgtcc agccacgcgt agccacgccc catcatcgcg acagacgac gtccctgctc       420 aagataaata cggttaatat ctgtaatttc taactcacca cgtgcagacg gcttcaagtt      480
tttcgccatc tgaaccacgt cgttatcata aaagtacaga cctgtaacgg cgtaattact      540
ctttggttct aacggttttt cttccagact gattgccgta ccgtttttat caaactcaac      600
gacaccatag cgttctggat cattaacgtg ataggcaaat accgttgcac cactttcttt      660
gttaacagcg gcctccatta gcttcggcag atcgtgaccg taaagatat tatcaccaag      720 aaccaaagca caatcatcac caccaataaa ctcttcaccg atgataaatg cctgcgcgag      780
gccatctggg ctaggttgca cttttgtactg aagattcagg ccccactggc taccgtcacc      840
cagcaattgt tgaaaacgag gagtatcctg aggtgtactg ataatcaaaa tatcgcgaat      900
acccgccaac atcagtgtag agagcgggta atagatcatc ggtttatcat aaataggtaa      960
tagctgttta ctgacagcca tagtcacagg ataaagacgt gtaccagaac cacccgctaa      1020
aataatacct ttacgcattt tcat                                             1044

<210> SEQ ID NO 89
<211> LENGTH: 1050
<212> TYPE: DNA
<213> ORGANISM: Artificial Sequence
<220> FEATURE:
<223> OTHER INFORMATION: gene editing homology arm pool_4_b2039_right

<400> SEQUENCE: 89
ttcatcattc cttttaattc atcttgctcc accatcacga acaagatgca aaaactatta       60
```

```
aattgctgta gtcgtaaata attcattgag cattcgtttc acgccaacct gccagtcagg    120
caagacaagc gcaaagttct gctgaaattt ttctgtatta aggcgagagt tatgtggacg    180
acgagctggt gtaggatagg ctgttgttgg tactgcgttg agcttgttga gtgcaagggg    240
aatgcctgct ttgcgcgcct cttcaaaaac cagcgcagca taatcgtacc aggttgtggt    300
accactggct accaaatggt acaagcctgc gacatccggt ttattcagtg cgacacgaat    360
ggcatgtgct gtacaatcag ccagcagttc agcacctgtt ggcgcaccaa actgatcgtt    420
aataaccgct aattcttcac gctcttttgc cagacgtaac atcgttttgg cgaagttatt    480
tccttttcct gcatagaccc agctggtccg gaaaataaga tgcttcgcgc aatattcctg    540
taacgctttt tctccggcta acttggtttc accgtaaaca tttagtggtg cggttgcatc    600
cgtctccagc catggcatat cgccatttcc agggaagacg taatcagtcg agtaatggat    660
aacccaggct ccaacttcat tgctgctttt cgcaatcgct tcgacacttg ttgcgttaat    720
taattgtgca aactccggtt ctgattctgc tttgtctact gcggtgtgag cggctgcatt    780
gacaataata tccggccgaa tgcttcttac ggtttcagct acaccttcag gattactaaa    840
atcaccgcaa taatcagtag agtgaacatc aaaagcaatc aaattaccca aggtgccag    900 agcacgctgt agttcccaac ctacctgccc tgttttgcca aaaaggagga tattcattac    960
tggcggccct catagttctg ttcaatccac gattgatagg caccacttt cacattatca    1020 acccattttg tattggacag gtaccattcc    1050

<210> SEQ ID NO 90
<211> LENGTH: 1050
<212> TYPE: DNA
<213> ORGANISM: Artificial Sequence
<220> FEATURE:
<223> OTHER INFORMATION: gene editing homology arm pool_4_b4473_left

<400> SEQUENCE: 90
catcacccgc ccatagtgag cgttggattg gtgcagcacc gcgccagcgt ggcagcagtg    60
aaccatgaac gttgatacag ccaagacgcg gcatctccag cactgctttc ggcagaatta    120
aaccataggc gacgacgacc ataacatcag cctgcagttc ggcgaccagt tgctggtttt    180
cttgtggacg cagggaaaca ggttgaaaaa cgggcagacc ttttttcctca gccagaactt    240 taaccgggct gggcatcagt ttttttaccgc gtcctgccgg tcggtctggc tgggtgaaca    300
cgccaacgac gttatgacca gaagacaaca gcgcgtcgag atgacgcgct gcaaagtcag    360
gtgtacccgc aaaaataata cgtagtgatt ctgacacgtt agttcttatc cttaagcccg    420
ggctttcaga cgatccagtt tttcaacttt ctgacgaata cgttgttgtt tcagcggtga    480
cagataatcc ataaacagtt tgccgaccag gtgatccatc tcatgctgaa tacagatggc    540
taacagaccg tctgcttcca gttcaaatgg tttaccgtcg cggtcaaggg cgcgaatttt    600
aactttctct gcgcgcggca ctaaagcacg ttgttcaggg atcgacaggc aaccttcttc    660
aatgcctgtt tcgccgcttt tttctaaaag ctctggattg attaacacta gccgttcgtc    720
acggttttcc gaaacatcaa taacaatgat acgttgatgg atatcaacct gggttgccgc    780
caggccaata ccttcttctg cgtacatcgt ctcgaacata tcatcgacga tacgctgaat    840
ttctgcattc acttcttcta ccggtttagc aactttgcga agccgctcgt ccggaatatg    900
taacacttgc aaaactgaca taaatctcca gagatgtgtt caggagttag aaagattatt    960
tcttctattc tagacaaatc cccctctgat tgacagcatc actgaccaat cgcaaagatt   1020
```
gctaaggctg cttatggcag ggagataagg                                  1050

<210> SEQ ID NO 91
<211> LENGTH: 1050
<212> TYPE: DNA
<213> ORGANISM: Artificial Sequence
<220> FEATURE:
<223> OTHER INFORMATION: gene editing homology arm pool_4_b4473_right

<400> SEQUENCE: 91
atggtcgata cagaaatttg ctgcgttta atgagtatca gcagcttgta cggcgatgat    60
atggtccgta tcgctcactg ggtggcaaaa cagtcgcata ttgatgcggt tgtattgcag   120
caaacagggc ttacattgcg gcaggcacaa cgctttcttt catttccacg aaagagtatc   180
gaaagctcac tttgttggtt ggagcaaccc aaccatcatt taattcctgc ggacagcgaa   240
ttttatcctc ctcaacttct ggcgacgaca gattaccccg gcgcactgtt tgttgaagga   300
gaactgcacg cgctgcattc atttcagctt gccgtagtgg ggagtcgggc gcattcatgg   360
tatggcgagc gatggggacg attattttgc gaaactctgg cgacgcgtgg agtgacaatt   420
acgagtggac tggcgcgtgg aatcgatggt gtagcgcata aagcagcctt acaggtaaat   480
ggcgtcagca ttgctgtatt ggggaatgga cttaatacca ttcatccccg ccgtcatgcc   540
cgactggctg ccagtctgct tgaacagggg ggcgctctcg tctcggaatt tcccctcgat   600
gttccacccc ttgcttacaa tttcccacga gaaatcgca ttatcagtgg tctaagtaaa   660
ggtgtactgg tggtggaagc ggctttgcgt agtggttcgc tggtgacagc acgttgtgcg   720
cttgagcagg ggcgagaagt ttttgccttg ccaggtccaa tagggaatcc gggaagcgaa   780
gggcctcact ggttaataaa acaaggtgcg attcttgtga cggaaccgga agaaattctg   840
gaaaacttgc aatttggatt gcactggttg ccagacgccc ctgaaaattc attttattca   900
ccagatcagc aagacgtggc attgccattt cctgagctcc tggctaacgt aggagatgag   960
gtaacacctg ttgacgtcgt cgctgaacgt gccggccaac ctgtgccaga ggtagttact  1020
caactactcg aactggagtt agcaggatgg                                   1050

<210> SEQ ID NO 92
<211> LENGTH: 1046
<212> TYPE: DNA
<213> ORGANISM: Artificial Sequence
<220> FEATURE:
<223> OTHER INFORMATION: gene editing homology arm pool_4_b3510_left

<400> SEQUENCE: 92
aatcaacgcc agttgcaaaa aaatgaaccc ggattactta tttaaccgcc catagcatca    60
acgcttacgg aactctttgt tcactttccc acagcacttt taaaacatta aacctgacta   120
cggaaaatat cagccatgat aatgtttgaa atggctaatt tgccatagag tgaaaaaaat   180
tagatgaaat tcagtaggtt gaaataatca ctagcaggta attatttcaa tgatagtgcg   240
caattgatct acaacactgc gtagcggaga gagtattaat cggatcatag tcacatcaag   300
tgactatgat ccgggtgaca accggggtaa ttattgctgc ttaacgaaca aactggcgaa   360
gctgaacagg ctggcggcgc taaatatcag ttcaattccc accagtgtgg aaaccagcgt   420
tacagacacc atcggcgttg caccaaggaa tatccaggca atgacgatat ccagcacacc   480
aataacgagc tgtagccagc tgcctttcat tgaacgctga cgataccaac tcatcaggcg   540
ataaccccct gcaacacaga acaaaccggc aataaatgcc gcaatggcaa aaatgcccag   600
ctccggtgcg cggatgaaga aatagccgat caataaatag gcgactgcga cgaggaaacc   660

```
ggataatacc ggccagaaat tatgactgcg gttgctgaat aacccgacaa taagcgcaat    720
acccgagcag attaataatg cacccactac tgtgcttaaa atatcgccag agacgaacgg    780
gaaactgata cacagcaacc cgacgataaa cagcagcacg gcaataaact ggattgctct    840
gcgatgtttt ttaagcatct ccagatcaaa cttcaaaatt gttgccttat ctatatataa    900
catagaacca ccctataaaa ttaagaagaa atcccctgc tatcaatcta tgccaaaaac     960
gcgtctaaga atgcagtcga tttaataaaa atttcctaat tgcagtatct gatgcatctg   1020
taactcattg tattgaaata aaaata                                        1046
```

<210> SEQ ID NO 93
<211> LENGTH: 1045
<212> TYPE: DNA
<213> ORGANISM: Artificial Sequence
<220> FEATURE:
<223> OTHER INFORMATION: gene editing homology arm pool_4_b3510_right

<400> SEQUENCE: 93

```
atgaaaaaag tattaggcgt tattcttggt ggtctgcttc ttctgccagt tgtgagcaat     60
gcagcggatg cgcaaaaagc agctgataac aaaaaaccgg tcaactcctg gacctgtgaa   120
gatttcctgg ctgtggacga atccttccag ccaactgcag ttggttttgc tgaagcgctg   180
aacaacaaag ataaaccaga agatgcggtt ttagatgttc agggtattgc aaccgtaacc   240
ccagctatcg ttcaggcttg tactcaggat aaacaagcca actttaaaga taaagttaaa   300
ggcgaatggg acaaaattaa gaaagatatg taattccggg aatgcgttac atcgtacttc   360
cttgcatatt gaacaggccg gaatatcttc tttaaaagca gctattcctc ctgttcatat   420
ataatctcta tattgaatgg gttacaaaat gaatatttca tctctccgta aagcgtttat   480
ttttatgggc gctgtagcgg ctttgtcact ggtgaacgca caatctgcgt tggcagccaa   540
tgaatccgct aaagatatga cctgccagga atttattgat ctgaatccaa aagcaatgac   600
cccggttgca tggtggatgc tgcatgaaga aacagtatat aaaggtggcg ataccgttac   660
tttaaatgaa accgatctca ctcaaattcc taaagtgatc gaatactgta agaaaaaccc   720
gcagaaaaat ttgtatacct tcaaaaatca agcatctaat gacttgccga attaatgagg   780
tgcaagtaaa aaggagtagc aagttgagcc atcttgctgc tcctttttgc attttatat    840 gacagcagaa tttattatac gtcttatact cgcggcaatt gcctgtggcg ctattggcat   900
ggaaaggcaa atgcgcggca aaggagcagg gttacgcaca catgtattaa ttggcatggg   960
aagcgccctg tttatgattg tttcgaaata tggttttgct gacgtgctgt ctttagatca  1020
cgtcggactc gacccccagcc gtatt                                       1045
```

<210> SEQ ID NO 94
<211> LENGTH: 1050
<212> TYPE: DNA
<213> ORGANISM: Artificial Sequence
<220> FEATURE:
<223> OTHER INFORMATION: gene editing homology arm pool_4_b1007_left

<400> SEQUENCE: 94

```
tcattaccgc catccagcta tcaaaggccg aagccgatac actttcact gcgataggcg      60 ctaagttcag gccaatcgcc atcaccaccg cacccgtcac caccggcggc atcagtcgtt    120
caatccagcg cgtaccgatt ttcatcacca ccaggccaat gacggtataa accagcccac    180
aggcgataat cccgcccagc gcaatgctga tattcgggtt aatgccctga ccgttaaagc    240
```

| | |
|---|---|
| ccgtcgcggc gatcaccacg ccgacaaaag ccgcgctgga gccgagataa ctggggacgc | 300 |
| gcccgccggt aataaagaaa aacagtaacg tgccgatccc cgacattaaa atggaaagat | 360 |
| tgggatccag ccccatcaga atcggcatta acaccgtcgc gccaaacatc gccaccgcgt | 420 |
| gttgaacgcc cattactgcc gtctgagcaa acggcaatcg ttcatccggc gcgaccacgc | 480 |
| cgctctctgt agaggtcgat tttaactgcc agtgaggaaa accgaacatt gccatcagct | 540 |
| gtctccttaa ggaggttaac aagcagggcg catcagcgcg tgataactgc gatcgaacca | 600 |
| caccagcccg tagggtgtgg tgtgacgatg aatcgcttcg atggcgcaaa acagaatgtc | 660 |
| gtgggtgccg acgctcacca cctggctgat acggcagtca aacgaaacca gagcctcttc | 720 |
| cagttgcggg catccggtca cccccgtctg ccagcgggcg cggcaaagc ggtgttccat | 780 |
| gggcgttttg ccgccaaaaa ggtttgaaag cggctcctgc ccggcgctaa gtgtatttac | 840 |
| acacagcgtt cgattttcat tgaatgccgg ccagacggac gccccacgat tcaggcacac | 900 |
| cagtaatgtg ggcggcgtat cggtcacact gcagacggcg ctggcggtga acccggcgcg | 960 |
| cccggctgga ccgtccgtgg tgataatatt gaccgccgcg cccatgcagg acatcgcatc | 1020 |
| gcgaaaagtt tgttgatcga caatgttcat | 1050 |

<210> SEQ ID NO 95
<211> LENGTH: 1049
<212> TYPE: DNA
<213> ORGANISM: Artificial Sequence
<220> FEATURE:
<223> OTHER INFORMATION: gene editing homology arm pool_4_b1007_right

<400> SEQUENCE: 95

| | |
|---|---|
| agtttgctcc ttacaacagc ccgcaggctt cttcaaagga cagacgtggc aggcgcgcat | 60 |
| aaagcttgct gctatcgcca tagccgatat taatcagcag attgctcttc agcgtgctgc | 120 |
| ccgtaaaaaa ggcgtcgtcc acgtgttgac ggtcaaagcc cgacatcggg ccggtatcca | 180 |
| gtcccagcgc ccggcaggcg acgatcagat aggccgcctg catggaactg ttgcgaaacg | 240 |
| ctgtttcttc ggcaagttgt gggctggagg taaaccaact gcgggcatca ccgtggggaa | 300 |
| acagtagtgg taaccgttca taaaattcac tgtcccaggc gacgatagcg gtgacgggcg | 360 |
| cggtcagggt ttttttgcaga ttgccgctgg aaagtgccgg gcgcagacgt tcttttcctt | 420 |
| ctgccgtgcg ggtaaacacg atccgtgccg gagaacagtt agctgatgtc ggcccccatt | 480 |
| tcatcagggc ataaatctcc cgtaacgtct catcgctgac gggtgtctcc cgccagccgt | 540 |
| tgtgagtgcg ggcatcggtg aacagggtgc taagcgcacc tgggctaacg gcttcgttca | 600 |
| tagcaattcc ttacagggcg gcttcacggt gatgtaacag gctggcaagc ccgttgagta | 660 |
| acagagcatt aaacgtttcg ggatcggtca cgttgcaggc gtgtccgcca tagggcatca | 720 |
| ccattttctg gctatcgggc agggcggcat gaagttcact ggaacatgct gttggcacca | 780 |
| gcagatcatc actggcgcag atgatttgca ccgggcagcg gatgcgatcc gcatggtgac | 840 |
| taaagtcagc gcgtttgagg gcgttaagtc gacgcagtaa attattttg ccctgaaaat | 900 |
| gcgccagtgc cagcgcgtct tctgcctcca ggcgaggtgc gcgggccgcc atccagtcgg | 960 |
| cgggatagag gaacaacggc tgcgcttcca cccatgcctg cgcgccgccg ctatacagta | 1020 |
| atcgttcgcg aacctgaaaa cagcggcgc | 1049 |

<210> SEQ ID NO 96
<211> LENGTH: 1050
<212> TYPE: DNA
<213> ORGANISM: Artificial Sequence
<220> FEATURE:
<223> OTHER INFORMATION: gene editing homology arm pool_4_b3058_left

<400> SEQUENCE: 96

| | | |
|---|---|---|
| ggaacgaaaa ctcggaagca gcgtaacggc tcaccccat cagcatccca cctgaaatgg | 60 |
| tcgcccccgga acgggagaaa cccggccaca gcgccagaca ctggaaacag ccaatcataa | 120 |
| atgcctgacg ataggtcata tcatcaagac ccggcgcacg cggctctttc ggcttcaggc | 180 |
| attcggcggc aatcagcaac aaaccgccaa cgaccagcgc atacatcaca tttatcgggt | 240 |
| taaacaatga cttaatcgtg tcgtggaaca acagccccaa taccaccgcc ggaatcatcc | 300 |
| ccagcaaaat gtggatcagc gttaaacgac ctttgctttc accttcgtgc tgcaacgggc | 360 |
| ggccaaagtg gatgccaatc aggccaaaca gacgccgcca gaacatcact actaccgcca | 420 |
| gaattgatcc taactggatc acaacttcaa aggttttcgc cgtgtcgccc tcaaacccca | 480 |
| acaagtgacc gacaataatc atatggcccg tgctggatac cggcagaaat tctgtcaatc | 540 |
| cttcgaccac acccaatatt gccgctatca gcagcgagtg catatcgctc atcaataaac | 600 |
| ccctaaatta ttaaaatgta ccgcttgtcc gaactactgc gtatgaccag gttataaccg | 660 |
| tttggtttaa cagctgtaaa attaattatt ttctttcaga ttattgccac gctcaatgat | 720 |
| tacgccaaca ttcgccgccc gcgccactgc gcctggcttg ctgagtttga tacgcaccca | 780 |
| cggcgagttg aagcgtgcta acagcagctc cgccacctct tcagccacgc gttccaccag | 840 |
| cgcaaaacgc gccccctcga cgtggctgac caccgtttct gcaatgtcag cgtaactgag | 900 |
| gcaatccgcc acatcatcac ttttcgccgc tttacggtta tcccacgcca tttcgatatc | 960 |
| gaacactaac ttctgttcga tggtctgttc ccagtcgtaa acaccaatag tggtgattac | 1020 |
| cgaaagttgc tctataaata caatatccat | 1050 |

<210> SEQ ID NO 97
<211> LENGTH: 1050
<212> TYPE: DNA
<213> ORGANISM: Artificial Sequence
<220> FEATURE:
<223> OTHER INFORMATION: gene editing homology arm pool_4_b3058_right

<400> SEQUENCE: 97

| | | |
|---|---|---|
| cacgtcctgc ctgcttttg gctaaccgga taccacttcc ggcgaaatgt gcgtattatc | 60 |
| cacagattca tcgttgaaca cgaatttca aaacggaaca gcttatgagt gcaatcgcgc | 120 |
| ctggaatgat cctcatcgcg tacctctgcg gctccatttc cagtgccatt ctggtttgcc | 180 |
| gcttgtgtgg gctgcccgat ccgcgaacca gcggctccgg caatccaggc gcaaccaatg | 240 |
| tgttacgtat cggtggcaag ggagcagccg tagcagtact gatttcgac gttctgaaag | 300 |
| gaatgttgcc cgtctggggc gcgtatgaat taggtgtcag ccccttctgg ctaggcttaa | 360 |
| ttgccatcgc cgcctgtctt ggacacatct ggcccgtttt cttcggattt aaaggaggaa | 420 |
| aaggcgttgc taccgctttt ggtgccatcg cacccattgg ctgggatctc accggagtaa | 480 |
| tggcgggaac ctggttactg accgtgctat tgagcggata ctcgtcgctg ggagcgattg | 540 |
| tcagtgcact gattgctccg ttttatgtct ggtggtttaa gccacaattc accttcccgg | 600 |
| tttcgatgct ctcttgcctg atcctgctgc gtcatcatga caacatccaa cgtctgtggc | 660 |
| gtcgtcagga gacaaaaatc tggacgaaat tcaaagaaa gcgcgaaaag gatcccgagt | 720 |
| gatttctggt ggatctacat gacctgatag ccttcatcgg gcttgcccag ccgttgctgg | 780 |
| caccatgccg ccagaaattc cacgcagaca cgtaattca tgctgcgata gagcggctcc | 840 |

```
cggtaaacag cccagatatt ggcgctttgt gcatactctg gcaatacttg caccagtttg    900
ccactctcca gaaacggcaa cacatcccac tcggaacgca gcataatccc tttgccctcc    960
agcgcccatt gcagcacaat ctcgccgcta ttggaggaaa gatgcccgct taccttcacc   1020 gatttttct cctgaccgtt ccccaactcc                                     1050

<210> SEQ ID NO 98
<211> LENGTH: 1050
<212> TYPE: DNA
<213> ORGANISM: Artificial Sequence
<220> FEATURE:
<223> OTHER INFORMATION: gene editing homology arm pool_4_b2688_left

<400> SEQUENCE: 98
gaggaatcgc acctgctgtt catctacacc aatcggcgag aacgggttga tgtccagcga     60
acgcacttca atatattcaa tgccgccacg taacagcgca tcagaaggcg actcgccgct    120
gcgggtaacg cgttttggac gaatcggcgc gtacagttcg ttttcaatct gcaacacgtt    180
gctgttgatt tgcagcctct taccgtcttt ctcaatacca atcttcgcgt actcttccga    240
tggcgttttg attgcctgtt taaggcccgc tacgtactcg taaagatcgt tgaaggtaat    300
accaagattg ctttgcgatt tattggtata gccgagatcg ctcaaacgaa gagaggtcgc    360
atacggcagg taatacatac cgcactcggt tttctcaaac ggcagcgacg ttggttttcc    420
ttgcaggaaa gaagaacaaa tcgccggaga tgcaccaaac agataaggaa tgacccaacc    480
gaaacgatag taattgcgga taacgcggaa atagcccgca gaatttttct ctttggcatc    540
agcgcccgag atatcaccgc acttcgcttg ccagaatgcc attggcaaag agaaattgta    600
gtgcacgccg gaaatggttt gcatcagcgc gccgtagcga ttttcagcc cttcacgata    660 cagcgtttta aagcgtccgg tgttagaagt gccgtactgt gccagttcga tgtcctgacc    720
ttctgcgatg tagcatggca tacttaacgg ccacatccgc tcatcgccca tattgcgcgc    780
cgtataacga tgcagatcgc gcataaaggt cagcatatgt tcaatatcac catccactgg    840
tgtaatgaat tccagcaatg cttccgcaaa atcggtagta atccatttgt gcgtcagtgc    900
ggaacctaat gcttcaggat gacctgttgt tgccagtgtg ccatcagcat taacacgcaa    960
agtttcgcgc tccagcccac gctgtatccc ctttaacgcc tgaggatgtt tttccagcca   1020
ggccagcgcc tgtgatacgt ccgggatcaa                                    1050

<210> SEQ ID NO 99
<211> LENGTH: 1039
<212> TYPE: DNA
<213> ORGANISM: Artificial Sequence
<220> FEATURE:
<223> OTHER INFORMATION: gene editing homology arm pool_4_b2688_right

<400> SEQUENCE: 99
attgacctcc cgcctgtcaa aatcgttta attagcataa ctgtaatggt gaccatatgt     60
gcaggcctac aattagtgcc accacatcat gccctgaacg gtcgctgctg caactgcaac    120
atagcgtaac gctttaccaa ggcacaaaaa aaagattacc ggtccccacg agatgcgcat    180
ccatcccgct aacagacaca gtaaatcgcc aaccacgggc atccagctta ataatagcgt    240
gactgcacca tagcgtttca gccagccggt agctttctct tgccagcgcg atgttttacg    300
caatggaaag aaacgcccaa ggataacgtt agttaaccct ccaaggctat tacccattgt    360
tgctgttaaa actaaaaccc agggatgact gatcccggaa agcaacattg ccaccagcac    420
gacttcggag ttgccgggta atagtgtagc gctgagaaaa ctactggcaa caacgagaa    480
```

```
aagcgataac gcttcactca cagcaagcga acatccacgg cgtccatgcc tgctgcacgg    540
gccgcctgaa taccgaaatc ggcatcttca aagaccacac actgcgtcgg ttgcacgccc    600
atacgctgcg cgcacaacaa aaatgtgtct ggcgcgggtt tatggtgttt gacgtgatcg    660
gcagcgacga cggcgtcaaa ataatggcgt aatcccaggt gcgccagcaa tgcctcagcg    720
atggcgcttt cactcccgt tcctacagcc attgggcgac gaccatgcca acttttcacc    780
acatcaacaa gaggaagcgg ttcgacgcta tccagcagca tacttcttac tgcttctgtt    840
ttttcacgcg ctaacgcatg cgggtcgaga tcggcctgat tcagctcaat aattgcctga    900
gcaatacgcc aggtgggcga tccattaagc gcaatcatcg cctgaatatc gtactgaaga    960
ccgtagtgcc ctaatacttc gcgccacgct ttacggtgcg taggctccgt atccaggatt    1020
gtgccatcca tatcaaaaa                                                  1039

<210> SEQ ID NO 100
<211> LENGTH: 1050
<212> TYPE: DNA
<213> ORGANISM: Artificial Sequence
<220> FEATURE:
<223> OTHER INFORMATION: gene editing homology arm pool_4_b1716_left

<400> SEQUENCE: 100
agcgctttcc agttccgctt tacgcgcatt cagcgcctgc tgaacctgct ctttcgcttc    60
gttgataacc gcaccagctg ccggacgctc ttctggcggc agctcacgca gggtcgtcat    120
ctgaagggtt aagtgccctt ttttacccaa atattcgacg cgcacattat ctaacgcggc    180
aacatctgac gcctggctaa tggccgcctt cgcactggca accagttctg cgagatgtga    240
catggttttc ctcattgtgt cagtggtgac actggttcgt tggacttaga gcctatccca    300
tcaggctatt ttacttgcca ttttggtccc gggctgtgct cgaaattctc acgtacttaa    360
atacgctccg gtttctccgc gctggccgtg tccagtctgg ctgcgacaat tacacctgat    420
gagacaggct ttttattttt caaaacgcgc atacaaaaaa agcctccact gggaggcttt    480
caggcgctgt tttccgtttc tcttctcacg cgctagcctc ctggattcag gtgctaaagt    540
aaaaaaagaa gcggaaaata gcagcattca ttgcttgcgt tacctttttgg tactcttcaa    600 aagacccttta ttgaaaaggc tacggcgata aaagtcaatg ttttgatggc gttgaaacga    660
aaagagggag actagctccc tctttcaact ggcttatgcc agagctgctt tcgctttttc    720
aaccagagcg gtgaacgcta ctttgtcgaa tactgcgata tcagccagga tcttacggtc    780
gatttcaaca gaggcttttt tcaggccatt gatgaatttg ctgtaagaaa taccgttctg    840
acgtgctgct gcgttgatac gcgcaatcca cagttgacgg aactgacgct tacgttgacg    900
acggtcacgg taagcatact gaccagcttt gataacagcc tggaaggcaa cgcggtatac    960
gcgagaacgc gcaccgtagt agcctttagc ttgtttcaaa attttcttgt gacgtgcacg    1020
tgcaataaca ccacgtttta cgcgagccat                                      1050

<210> SEQ ID NO 101
<211> LENGTH: 1049
<212> TYPE: DNA
<213> ORGANISM: Artificial Sequence
<220> FEATURE:
<223> OTHER INFORMATION: gene editing homology arm pool_4_b1716_right

<400> SEQUENCE: 101
ttatgcgtac ggcaggcacg cgattaccag gcccagatcg cctttggaaa ccatggcttt    60
```

```
cggacgcagg tgacgtttac gtttggtcgc ttttttggtc agaatgtgac gcaggttagc      120
gtgcttgtgc ttaaaaccac ctttaccggt tttttgaag cgcttagcag caccgcgtac        180
ggtcttaatt tttggcattt taataacttc cacttcgcat tgttaataaa cgaaacaaag      240
gcgaacaaag cctgtgaagc ccgaaggctc cacagacagt gctacttgaa ggccttactg      300
tttcttctta ggagcgagca ccatgatcat ctggcggcct tcgatcttcg ttgggaagga      360
ttcgaccact gccagttctt gcaaatcgtc tttcacgcga ttaagcactt ccataccgat      420
ttgctggtgc gccatctcac gaccgcggaa acgcagcgtg attttggctt tatcaccctc      480
ttcgagaaag cgaatcaggc tgcggagttt tacctgatag tcgccttcat ctgtaccagg      540
acggaattta atttccttaa cctggataac ttttttgcttt ttcttctgtt ccttagaaga      600
cttgctcttt tcatagagga atttgccgta atccattata cgacaaaccg gcggctcggc      660
gttagggctg atctcgacta agtctactcc ggcttcttct gctttctcca gagcttctct      720
cagactcaca ataccaagct gctcgccttc cagacctgtt aagcgaactt cctgggcgcg      780
aatttcgcca ttgatacggt tagggcgcgc cgtttgaact cgttttccgc ctttaatacc      840
ttattcctcc aattgtttaa gactgcggct gcgaatctct tgttgcagct tctcgatcac      900
ttcatttacg tccatgcttc ccaggtcttt accacgcgg gtgcgaacgg caactttgcc      960
tgattccacc tctttatcac cacagaccag catatatggg acgcgacgca aagtgtgctc      1020 gcggattta aagccaatct tctcattct                                            1049

<210> SEQ ID NO 102
<211> LENGTH: 1050
<212> TYPE: DNA
<213> ORGANISM: Artificial Sequence
<220> FEATURE:
<223> OTHER INFORMATION: gene editing homology arm pool_4_b3071_left

<400> SEQUENCE: 102
gtcgctggtt caagtccagc aggggccacc agatatagca aaggctgacg agaaatcgtc      60 agccttttc tttttatata tcagttactt tgcgtgccag taagccgctg cacgtacccg      120
ctgtgggtca tactgttccg cttcaaagcg gcggcttaaa ttcttaacga ctttaccttc      180
gccggttatc cagatgaagt aatcatcggc agggatttgc atctgcgcca gacgcgcatc      240
taccgcctgc tcatcatgtg ccagccattc gatattaaaa ccatcaaggt gcgcgagata      300
atcctgacag gcgttatccc gcacgctaac cagcgcacta acttgcggtt taacggcaag      360
tttgctcaac gtttccaggc ggcggcgcaa tgcaggcatt ccggattcat cgcagacata      420
cagctgatac gcgtaatctt ccggcaccac cagcgaaccg cgcggacctg ccaccgtaag      480
tttatcgccc ggttgcgcct gcatcgccca gccgctggcg accccaccgt cgtgaataaa      540
gaaatcaatc gccagttcat ggcgtagttc gtcatacagc ggcgtatagt cacgcgacgg      600
tgggcgtggt ccttccggcc agacgatgcc ctcttccgtt accgttggcg gcacaaagtg      660
agcgtcaggt tgaggaaaga agagtttgct gtgatcgtca aagccacgcg atgtaaaacc      720
gtccagcgcc tcgccgccga ggacaatgcg ctgaaaaccg cgctgatgc gctcaacgcg      780 taacacagtc agttcacgga agcgcagatc attgcgaacg cgctgcgggt agcgggggt      840 gttattcatt gttatcgcct tcgtgatggt aatcagatat atctaaataa aactcgcaaa      900
tgataatgat tgttaatcat gataaatgca agcgatttgt agaactgata tgtctatagt      960
ctgataagac gaaccgcctc ttctcaggca tcattactca acgccggatg cggcgtgaac      1020
gccttatccg gcctacgtgt gagatgagtc                                           1050
```

<210> SEQ ID NO 103
<211> LENGTH: 1050
<212> TYPE: DNA
<213> ORGANISM: Artificial Sequence
<220> FEATURE:
<223> OTHER INFORMATION: gene editing homology arm pool_4_b3071_right

<400> SEQUENCE: 103

```
atgagccatc atcacgaagg gtgttgtaaa catgaaggcc agccacgcca tgagggctgc     60
tgcaaaggtg agaagtcaga acacgagcac tgcggacacg gtcaccagca tgaacacggt    120
caatgctgcg gtggtcgcca cggtcgcggc ggcggtcgtc ggcaacgttt ctttggtcac    180
ggtgaattac gtctggtgat tctggatatt ctctcgcgcg atgacagcca cggttacgaa    240
ttgattaaag cgattgagaa tctaacccag gggaattaca ccccaagccc gggcgtcatc    300
tacccaacgc tggatttttct gcaggagcag tcgctgatta ccatccgcga agaggaagga    360
ggtaagaagc agattgcgct gaccgaacaa ggcgcgcagt ggctggaaga aaaccgcgaa    420
caggtggaga tgattgaaga acgcatcaaa gcgcgttgcg ttggcgcggc gctgcgccag    480
aacccgcaaa tgaagcgggc gctggataat tttaaagcgg tgctggattt acgcgtcaac    540
cagagcgata tcagtgatgc acaaataaaa aagatcattg cggtgatcga ccgcgccgct    600
tttgatatta cgcaactgga ttaatcgccg catccgccag tggcgcggtg caattgccgg    660
atgcgacgct tgacgcgcct tatccggcct acacccgcta cacccccgc aggcctgata    720
agatgcgcca gcatcgcatc aggcattgtg ctccaaccgc cggatccggc ataccgatta    780
atgcagtacc gtcaccgcgt cttccagtcg gctggcgcgg tgtttcacca tcgccgacac    840
ctgcgcactc tcttccacca gctcggcatt tttctgggtg atcaggttaa gctcatccac    900
tgcacgggtc aggctggaaa gcccatcggc ctgttccagc gttgaatggc taatctgggc    960
gatcaactgg gtgacgtttt tcacctgtgc cacaatatct tccatcgtcc gtccggcggc   1020
gtgtacctgc tgcgaaccgg attgcacctt                                    1050
```

<210> SEQ ID NO 104
<211> LENGTH: 1050
<212> TYPE: DNA
<213> ORGANISM: Artificial Sequence
<220> FEATURE:
<223> OTHER INFORMATION: gene editing homology arm pool_4_b2139_left

<400> SEQUENCE: 104

```
cttttgcgat atcgagattg gcgttaagac gaccactatc gaaaatgggt agcgtcaggc     60
ctgccgtaac gcccatttgc tgcgcggaat gacggaacag atcgcttaag tgcaacgcat    120
cctgttgcag gaaggccatc aggttgatgt caggataaaa tgccgctttt gccgcatcaa    180
tggtgcttag cgatgactca acgtaccagt gcgccgcctg caaatctgcc cgccgggcca    240
gtaaggagta ccccagttca tcaggaagct ggcttgccac tttcggcaac gcgaccggtt    300
taagcttcaa tgactttgtc tggttatttg taagtgcgct taaccgtgcc tcaataattt    360
tcattttccc cgcgacatcg ttgagctgct gccgggtttt gctggcatta atatcggttt    420
ccacaccttc aactgaagaa gtaatcccgt tctgatatag ctggcgatcg gtcgcgataa    480
tggtgttctg ctcttttttct atttgctgca agaccgtgtt taacgccgcc tgggtttgcc    540
actcccagta caggcgggct acgctgccag ccagcaattg gcgggtttgc tcgcgttccg    600
ccgcccgtgc tttaaccgta cccaggcggg cagtaacctc cgcccgattc tttccccaga    660
```

```
tatcgagatg ccagcccgcc gttaagccaa aagtaccgtt ggtgtaccac gggccggtcg      720
tacctgcggc cggatcgttc agagcaaacg gccccattaa gccttctgcc gacattttt      780 gccgctccat atccgccgaa aagtcgatct gcggaccatc ctgagtggca actgccttcg      840
cctgggcttc agctagctga atgcgctgtt cagccacctg catatccggt gcgttctgta      900
gtgcattgtt aattaaggaa gtgagttgat tatcgtgata ctccagccac cattggctgt      960
ctggccaacc attttcagcg ccgtgggtaa tgcggtgtca acttgtgcag cgggcgtttg     1020
ctggcttaac gcctggcggg tttcatgcat                                      1050
```

<210> SEQ ID NO 105
<211> LENGTH: 1047
<212> TYPE: DNA
<213> ORGANISM: Artificial Sequence
<220> FEATURE:
<223> OTHER INFORMATION: gene editing homology arm pool_4_b2139_right

<400> SEQUENCE: 105

```
aggcgcacac ccggccagca tcagtaacag cggaaaacag gcgatggctg gataaaagga       60
atcacgattc atgggggaat aatcaggtaa gaaaaggtgc gcggagatta ccgtgtgttg      120
cgatatattt tttagtttcg cgtggcaata catcagtggc aataaaacga catatccaga      180
aaaatataca ctaagtgaat gatatcttcc gatttatctt aatcgtttat ggataacggc      240
aaagggcttc gttttttcct atacttattc agcactcaca aataaaggaa cgccaatgaa      300
aattatactc tgggctgtat tgattatttt cctgattggg ctactggtgg tgactggcgt      360
atttaagatg atatttttaaa attaattaat gtcatcaggt ccgaaaataa cgagaatatt      420
tcagtctctc atcctgttgc gctcctgtca tgtgcattgc ttcatataat cactggcgca      480
aggagcgcgc aggggggcggc caatcgccgc cgccccctgc accccgggc tctggcgaac      540 aaaatcgccg ctgcgcggtg ccctcggctt atcccttacg gctaccgggt cgggcgcgag      600
gtaacatccc tgtaaaacgc gccctcagcc cacatccatg tgggctgccc cggccttcag      660
ggaacgcctc ggcaattttg acgccaccaa acaaccgtgc ggcctattga taaagagcta      720
acacattgtc aaaaaacatc actatggttt tttagagttt ctcgatatca attgcctgaa      780
tagcccttgc aatatcaggg gaattattca acacccgaac atgctgaaat aattccgttg      840
cttcatcgta ttcttttacgc aaataactca accactgttt aatccgcgca acgtgatata      900
acccggtatc gccctgcttt tccagacggg tatatttttg cagcaaagca accacctccg      960
gccacggcat tcgcggttcg ttatattta ccacccggct caggttggga atattgagcg     1020
ccccgcgacc aatcatcact gcgtcgc                                         1047
```

<210> SEQ ID NO 106
<211> LENGTH: 1050
<212> TYPE: DNA
<213> ORGANISM: Artificial Sequence
<220> FEATURE:
<223> OTHER INFORMATION: gene editing homology arm pool_5_b2434_left

<400> SEQUENCE: 106

```
tcgctcactt tggtggacga cccaaaccag ttccacgggt tagcggcaga ccagttaact       60
gacgacatcg tggaacagcc ggtcagcatc aatggcatag cgcataacat taaacgcagc      120
gatttcatgt cacttccttt ggttattcaa taacgttgct tggagtgcaa attcaccaaa      180
aagtgccgtt attcttttac ttcataaaaa caagcgcgta aacgtcgatt ggtcagcagc      240
cagattaacg ccacaatatc cgccactacc agcgccagac cgataccgct aacggattca      300
```

```
ccgttcagcc acagccacgg ttgccagcaa agtaaaacca cctgcgccaa cagcaacaga      360
aaatagagta cacgccaggt gcgaggaaac gtagcccgcc gaccgctcaa caaaaacgcc      420
agcaccgccg gaatgccagg aatcagcccc agccagaaat tatcgtgatc gggataaaac      480
agatttagca gcgcagtacc ctgctcgcgc gacgcaccgg caatgacaaa cagcacccag      540
gttcgcgcct gaagcaatag cacaagccag aagagcaagg gtaaacgcag gcgaccgtgc      600
gcatcataat ggacaggatg aaactcagta ctcttcatct tcaatcaaac gcttacccag      660
actcagcacg tcggcgtgtt catatcccag gcgttcatac attccgagca ccatgtcgtt      720
atcttccggc acattgatct gaattttcgg gcagccacga gcaatcagct ttttctccag      780
ccgattaagc aacgcattgg caatcccacg cccacgaaac tctggatgca cgccaagata      840
ataagcagac ccgcgatgcc cgtcataacc gcccatcacc gttccgacca cgtcaccgtt      900
tacctcagcg accaaaaaca aactgacgtc atggttcatc ttacgctcga tgtccatttc      960
cggatcgttc cacggacgca gcaagtcgca acgctcccaa agggtgatga cctcttcgaa     1020
atcttcctgg cgaaatacgc gtatctccat                                      1050

<210> SEQ ID NO 107
<211> LENGTH: 1050
<212> TYPE: DNA
<213> ORGANISM: Artificial Sequence
<220> FEATURE:
<223> OTHER INFORMATION: gene editing homology arm pool_5_b2434_right

<400> SEQUENCE: 107
ggtattcgtt acctttttgc gggttaaaag gctgattatg gcgtgaacgg tcgaattagc       60
caatatctga cgaaaatcgg ttgaaaaagt ggcataatgg ggagttgtca actattgaaa      120
tgaaaagtaa aacaattctc aacagcaaac cgtcgtaacg gattacgcga tacgatataa      180
catctggaac tttattatta caactcaggc cgtatgagca cttttaaacc actaaaaaca      240
ctcacttcgc gccgccaggt gctgaaagcc ggtttggctg ccctgacgtt gtcaggaatg      300
tcgcaagcca tcgccaaaga cgaactttta aaaaccagca acggacacag caagccgaaa      360
gccaaaaaat ctggcggcaa acgtgtcgtt gttctcgatc caggtcacgg cggaattgat      420
accggagcga tcgacgcaa cggttcgaaa gaaaaacatg tggtgctggc gattgctaaa      480
aacgtccgtt ccatttttgcg taatcatggg attgatgcgc gtttaacgcg ttctggcgat      540
acgtttatcc cactttacga tcgcgttgaa atcgcccata acatggcgc agatctgttt      600 atgtcaattc atgccgatgg ctttaccaac ccgaaagctg ccggtgcttc ggtatttgcc      660
ctctctaacc gtggggcaag tagcgcaatg gcgaaatacc tgtctgaacg cgaaaaccgc      720
gccgatgaag ttgccggtaa aaaggcgact gacaaggatc accattgca caagtgctg      780 tttgatctgg tgcaaacaga taccattaaa aatagtctga cgctcggctc gcatattctg      840
aagaagatta agccggtgca taaactgcac agccgcaaca ccgaacaagc ggcatttgtg      900
gtgttgaaat caccgtcggt tccttcggtg ctggtggaaa cctcgtttat caccaacccg      960
gaagaagaac ggctgttagg cacggcggcg tttcgtcaga aaatcgccac agcgattgct     1020
gaaggcgtga tcagttattt ccactggttc                                      1050

<210> SEQ ID NO 108
<211> LENGTH: 1028
<212> TYPE: DNA
<213> ORGANISM: Artificial Sequence
<220> FEATURE:
```

<223> OTHER INFORMATION: gene editing homology arm pool_5_b2037_left

<400> SEQUENCE: 108

```
aatgaaataa gaaaaggcag aggcgatata atcattagca caatcactgc attatcatat      60
cccggcccta tacttatttt tactagtata gatgcaccca agagcagaat taatgaaaaa     120
gcaccaccaa tcaaactcaa gcaggtcaat gatttttttaa ttaaaatcac acccttcaca    180
cgattaagaa caagcgtact tgatattctt gggtatattg cttgggtgat aggatttaat    240
agcccttgaa gcgcgtttct tatagtattg gccgcattaa aattccctac ggacgttggt    300
ccagatataa atcccaggat aataactatt cccgtagaat ataaactaat agcagatgtg    360
gaaataaaaa catgaaaacc gtctgctaaa gatcgacgca cattatgtaa tgatagcgta    420
actttaccaa tccaaccttc atgaacaacg atagctagtg caataattcc agcaaccaga    480
tttgcacttg actgaataaa accggcaatt gctatatctg actttgtgtt cacaaaaata    540
aatgttagag ggataatagc caagcgggat aaaatactac ttaaagtcag ccatttcatt    600
ttttcttttc cctgaaacag ccagataggg tagattaaat tcccgactaa tgcaggaaca    660
aacgaccata taattacggc atgcttgtta tattcaggaa caagcaaggt catcgacgtt    720
aagaaaatca atgtaatgac gataagaact atttttgaaa atatcaccgc ccaaaaaata    780
gacgttactt tatctttact atctgctgct ttggcaatac tctgagttgc tgtgagattg    840
aaaccatatt caacaaacat tatcatatat agcatagtcg cttggcaaaa accgaatata    900
ccgaaatttt caggaccaag tgttcttaca agatatggaa atgtaagcaa tggtaaaaga    960
taattgctac cttgaacgac agccagatat ataacgtttc ttcttaaaga taatttattc   1020
gtattcat                                                             1028
```

<210> SEQ ID NO 109
<211> LENGTH: 1050
<212> TYPE: DNA
<213> ORGANISM: Artificial Sequence
<220> FEATURE:
<223> OTHER INFORMATION: gene editing homology arm pool_5_b2037_right

<400> SEQUENCE: 109

```
gcaattaatt ttaatctgat aagctcatct aacgtaaaga gcctttcatc ttttggcgaa      60
aggattaacc ctgatgtttg gggccaatca attgcaatgc gttcatcatt ccaacatatt    120
ccacaatcgc tttcaggatg ataatagttt gtagttttat attgaaattc agcgatatca    180
gacagaacca aaaagccatg agcaaaccct tttggtatcc acaactgctg cttattatca    240
gctgaaagca gaacaccaac ccatttacca aaggataccg aattgggtcg aatatcaaca    300
gcaacatcaa aaactgctcc atgagtgcag cgtacaagtt tatcttgtgc gtactcgccg    360
cgttgaaagt gaaggcctct gagtacattt tttgatgaac gtgagtgatt gtcttgaaca    420
aagctgaccg gatagcctag aatatgttca aatgctgatt gattaaagct ctcataaaag    480
aaacctctat catcaccaaa tactcttggc tccagaatta gcacatcttc aatttcagtt    540
ctaatcacat tcattaattt gaatccttcg tcatttttata aagatactgc ccataattat    600
tctttattag tggtacagct aattttctta cttgctcaac atcaataaaa cctttacgaa    660
atgcaatctc ttcaggacag gaaaccttca atccctggcg ctcttcaatt gtcgcaataa    720
aattacttgc ttctatcaga ctctgatgag tccccgtgtc cagccacgcg tagccacgcc    780
ccatcatcgc gacagacaga cgtccctgct caagataaat acggttaata tctgtaattt    840
ctaactcacc acgtgcagac ggcttcaagt ttttcgccat ctgaaccacg tcgttatcat    900
```

```
aaaagtacag acctgtaacg gcgtaattac tctttggttc taacggtttt tcttccagac   960
tgattgccgt accgttttta tcaaactcaa cgacaccata gcgttctgga tcattaacgt  1020
gataggcaaa taccgttgca ccactttctt                                   1050
```

<210> SEQ ID NO 110
<211> LENGTH: 1050
<212> TYPE: DNA
<213> ORGANISM: Artificial Sequence
<220> FEATURE:
<223> OTHER INFORMATION: gene editing homology arm pool_5_b2451_left

<400> SEQUENCE: 110

```
cagatccgtt tcatcaatcg ggatcgccac cggcaaattg cgcagcggca gttgtacgcc    60
ctcaagccag attgtgctgc cagagagcga aagggtatgc gcgcccgcgc caatcaccgt   120
ggcgcgcacg gtttgcgccg gaaactgtac gttcatctca cgcaggcgcg gatggtcatg   180
cagcgcagtt gccagcagcg ggccaatatc ggcaaaacag aacgggtcgg cgggctggtg   240
gcgataacat tcgcccacgc cgccagaaag cgtaatgatt tcgggcgtaa cacctgcggg   300
cagcaaaccg gtttgcatca atgcctgcgc gagcggtgag agcgttccgt caatcacttc   360
gacaatcagt tctgccatcc gccgggtcac ctgcaccagc tgcgcgccgg tcagcgaacg   420
ggcgtcggtg cctgcaccga agcactcatc acaatcatc tgcccggtt tatgagcgta   480
aaccacgcgc ccgtggctgt cggtttccag caggcgacca ccgacgttga ggcaggcagt   540
gccgctgatt tttccggcat cgaacagggc gtagttcgcg gtgccaccgc cgatgtcgat   600
attcagtacc cgacacagcc gttgttcaga aagggtttgt gccccggctc cgtgaccggc   660
gatcacggat tcgaggtgcg gcccggcgct ggcaacgaca aaatcgccca gcgactgaga   720
gagcgccatc accgccgggc gagcattgcg gttttcgcg ctttcaccgg tgatgatgat   780
ggcaccagaa tcaacgcttt ccggctcaat cccgcagca tgatattgct cgagtattaa   840
ggttttcagt tccgcttctt ttaaaccgcc ctgtttatcg acaggggtaa agaacaccgg   900
actttgccag ctaatttcgc gtttaatgaa ttcgtagcgc ggcacctgcg acaccgccgc   960
acggttaacc agctccagcc gggagaaaat cacctgggtg gtggtggtgc cgatatcgat  1020
accgacgctc aatagctggc gagtgttcac                                   1050
```

<210> SEQ ID NO 111
<211> LENGTH: 1046
<212> TYPE: DNA
<213> ORGANISM: Artificial Sequence
<220> FEATURE:
<223> OTHER INFORMATION: gene editing homology arm pool_5_b2451_right

<400> SEQUENCE: 111

```
gattgtgcct ccgcttcggt tttagtcgcg gtcgcgtctt cttttggcac cagcatcatc    60
gccacgccaa tcgccgttac gccgccgatc aacttgccga caatcatcgg gaagatcatg   120
gcgttcatgt tggcagcggc gaagcctaag tggtcgccca gggcgaaagc agcggaaacg   180
gcgaaggcgc agttgatgac tttgccgcgg gtatccatct gcttcatcat gccgaacatc   240
gggatgttgt tggcaagcgt tgccaccatg ccggctgccg cgatgttgtt catattcagt   300
actttaccga cgctcatcag cggttttttca aaccagcgag tcagcagcag caccatcgga   360
tacgcccta acagaacgca ggagatagaa ccgataactt caatggcgcg catcacctca   420
ccgggtttat cgccagggc cataaagata ggatccagac cggggatcag ttcccagcca   480
```

| | |
|---|---|
| agcaggaatt tcactaccgc agcggcaaga ccgagggtga tcaatgcaac gaggaatttg | 540 |
| gcgaagatct ggaagccgtt gatcattttt tccgggatga atttcagccc cagcgccacc | 600 |
| agaatcgcaa caatgatcac cgggatcatg ttcatcagga tcagggcgaa agtgaattcc | 660 |
| accggctggc cgttgatctg cacaccggag tacatagcaa ccagaccacc agcgatacaa | 720 |
| ccaatcggaa tggtcacaat gcccgccagc acgccgagcg ccagataacg acggtcagaa | 780 |
| ggttcgataa tgccgagcgc caccggaatg gaaaacacaa tcgttggccc catcatcgac | 840 |
| ccgagaatta acccagagta tagccacgcg gctacgtcgc cgcccgccag ctctttggcg | 900 |
| aggaagaagc cgcccatatc gcacgccagc agtgttccgg cgaacatcga tgggttagcg | 960 |
| ccgagcattt cgtaaaccgg aataattacc ggcccgagaa cgtgagccag taccggtgcc | 1020 |
| agcgcggtca taccgaccat cgccag | 1046 |

```
<210> SEQ ID NO 112
<211> LENGTH: 1050
<212> TYPE: DNA
<213> ORGANISM: Artificial Sequence
<220> FEATURE:
<223> OTHER INFORMATION: gene editing homology arm pool_5_b1902_left

<400> SEQUENCE: 112
```

| | |
|---|---|
| acatcccagc cacgtttctg catctcttta tacagttcct ggccctgacg ttcgccaatt | 60 |
| ttagtcgccg ccatcatcac cagcggaacg gtatccattg gcttaccttt ggcgttaaca | 120 |
| aactggtcat ccacggcaat gactttcata tcgtagccac gcgctttcgc gacgatggca | 180 |
| gagccgagtt tggggtccgg agtacaaata acgaaacctt ttgcgccact ggcagccagg | 240 |
| ctgtcgatcg cgttcaatgt ttttttcgcca tccggcacgg caatcttaat aacctcaaac | 300 |
| cctaaatcct tccggctttt atcggcaaac ttccattcgg tctggaacca cggctcttcc | 360 |
| ggttgcttca ccagaaaacc gagcttcagg ttctccgcca tagcggattg tgacataacg | 420 |
| gctgccagac caatggctgc cagggcttta gtaaatttgt gcatggttct ctccagcttt | 480 |
| agtgtcgttt tgtgtagggc aaaaacgaat gacattcgtt aaattaatcg gaaaacaaag | 540 |
| cattaccttt taactaaaag ataagtgact gtgttgacat agttttagcg agaaattaat | 600 |
| tctccatagg agagcaatat cacatcgcag aattacagtg agaacgtgca taaatttagc | 660 |
| gggaaaagac ataagggaaa gccaatttgt cagacaaatt gtcgaatgca cagcagatta | 720 |
| atccataaga ttagcctgga atccttgtt gtctttggta cccatgcggg atgtcttctt | 780 |
| tttaaccagt caataggccg cattacctgg cgttgagttt ttgaaatggt gtaataaccg | 840 |
| caactcaaag atgtggaaaa tgcacgtcat tcatttcgtc attaattatc actgtgctca | 900 |
| ttaattaaca gaacacgtat aatgagagcc atctcgcaaa aatgaaaaaa cgttttataa | 960 |
| aatcatcact tcatcatgaa ttcaaattca ttgattaata tcaacaagat acaaaaagca | 1020 |
| ctatcattaa aattcattgc agttacattg | 1050 |

```
<210> SEQ ID NO 113
<211> LENGTH: 1048
<212> TYPE: DNA
<213> ORGANISM: Artificial Sequence
<220> FEATURE:
<223> OTHER INFORMATION: gene editing homology arm pool_5_b1902_right

<400> SEQUENCE: 113
```

| | |
|---|---|
| atggcaaccg ctggaatgct tctcaaactc aactctcaaa tgaaccgcga gttttacgca | 60 |
| tccaatctct accttcacct gagtaactgg tgttctgaac agagtctgaa cggcaccgcc | 120 |

```
actttccttc gcgcccaggc acagagtaat gtgacccaaa tgatgcgcat gtttaacttt      180
atgaagagtg tcggcgctac ccccatcgtt aaagccattg atgttccgg tgaaaaactg      240 aactctctgg aagaactgtt ccaaaaaacg atggaagaat acgagcaacg ttctagtacg      300
ttggcacagt tagccgatga agcgaaagaa ctgaatgatg attcaaccgt caatttcctg      360
cgcgatctgg aaaagaaca gcagcatgat ggtctgttgc tgcaaaccat tcttgatgaa      420
gtgcgcagtg cgaaacttgc gggtatgtgc cctgtgcaga ccgaccaaca tgttctgaat      480
gtcgtgtcac accagctgca ttgatcatca tcggcgctaa tgcattgcgc cgatgaaggt      540
tttgagaaac cgctgcctca tctgtttgaa gcagcggttt ttttaatggg attcaccctg      600
tggggtaaac ttgagttcaa taagcgcgat ggcttttgg attgcccgca tggtgaccgg      660
gtctgcggcg cgggatggt tagtaaagtc gatattcttc agctgactgg acattttttc      720
acgaacttca acgggcgcga ttacatcgag aacatccaga atttgtttga taaccaactg      780
gcaagcaacc acatcagaaa ccaattcctg atcggcattc agcggctggg acatcgtaaa      840
ctcctgatag cattttgaaa gccgttatag tagcgacttc acatcttcag cgatagtcac      900
atccaccgtc atcaggacac aaaaaaacct gccggagcag gttttttgtt atcggaacat      960
attgcctggc ggtacgtctt tgaacgtctt gcaatagtta ttgaacatac ttttcaggat     1020
tttgcgcagt tcatcgcgg cactccga                                         1048

<210> SEQ ID NO 114
<211> LENGTH: 1049
<212> TYPE: DNA
<213> ORGANISM: Artificial Sequence
<220> FEATURE:
<223> OTHER INFORMATION: gene editing homology arm pool_5_b4310_left

<400> SEQUENCE: 114
gctttgccgc ctgcagtttc accgccaata atcaatagac tattattcca gggcaatgat       60
actccgtagg ccccgaccttg cgataattca cccgatttat cccatttccc gttatgccaa     120
agatgaatat cagtgctata tgatttttc aggccttcat gcgcatagtt cttaccgttc      180
tggtaatttt ctcgtgaacc tttgaatccg gcccctccgg caaatataag agaatcattg     240
cttatccccg caaaaccgcc agctacgcca tctggtgatg agacgggagc aagcttattc     300 catttaaat tattaccggt gaaatcaagt tcaaatacgg catccgttcg caatcctggt      360
ttggcttcgc cattaataag ccaggtttta tcacctttat tcacaaccgc cgcaccagcc     420
gttccgtacc agggcgattc gccagcgtaa ctccattgct gtgttgaggg atcaaaagac     480
aacagaaact tattgaagaa ataatcttct gcttttttgt caaaatagtg agcattgatt     540
ttatctatag cggttgaatc ttttccagcc tcgttgagat cttcaaaata gccattgaag     600
atattctggt taacaccacc agtaacataa gccttgccgt tgtgtacaaa agtcacatgg     660
cccgccatgc ccatcggcgc gtgcgacatc aatttaaccc aactattggt tttgggtgtt     720
tatttgtgta cgtcattaaa tacctgagtc aagccctcgc tgtttttgcc aatgccgcca     780
aacacataca gattgccatc aataaatgca gaggttgctt gatctcttgg tccgccaggg     840
aatgcagcta acgctgtcca tttttattct ttggcctgtg tatccagctt gtaccatgcc     900
gtacctgcgc tacctaaacc aatgtagaca gtgtcgttat caattgctcc ggtaccactt     960
ttaaatggca caggagtttc cggtaataca gacgcgtttg cggcaaatga agccatcatg    1020
atagcaagcg ccgttattgt tttattcat                                      1049
```

<210> SEQ ID NO 115
<211> LENGTH: 1021
<212> TYPE: DNA
<213> ORGANISM: Artificial Sequence
<220> FEATURE:
<223> OTHER INFORMATION: gene editing homology arm pool_5_b4310_right

<400> SEQUENCE: 115

| | | | | | |
|---|---|---|---|---|---|
| tgtgactgtc | tcctgtctac | tacagtttaa | atgacacacc | aatgcgataa | ctgttttccg | 60 |
| ataaattatc | tctgccgttg | taaacaccct | gacggtcaag | gtagtcatat | tctatgtatg | 120 |
| gcgtaatatc | gggcgtcata | tggtattgta | gaacaaatgc | attttccgtc | gcccatttct | 180 |
| tatggtttgc | atagcgataa | tcgttctgtt | tgctgtatag | cgtcgtttgc | catgcgaagg | 240 |
| tgaaatcact | attaatatgg | taagtgacat | atccatccca | acgatgaacg | ttatcacgag | 300 |
| acatatcacc | ggataagtct | tgttgtcggt | aagctttcca | gtcgtaacga | tagcgaatgc | 360 |
| caaaattaag | atcttttgtc | gcgtcccagg | acagttttac | gtagggtccg | tagcgtgtgc | 420 |
| cgttgctgct | aaaatgcgtt | aacattcccg | ggcgcaccgt | ccattgatca | tcaagtttaa | 480 |
| tcgcgtaatt | aacttcaacc | tgaacatcat | tgagtgcggc | attttccttt | ttattatcat | 540 |
| gaatggtatt | ccaggtatta | cttttccatgc | ttgcccacca | tccatttttgc | catccctcac | 600 |
| tgactttgag | tcgagtctca | taggcgtggc | ttccactacg | atatccacca | cgtacgtcca | 660 |
| gtgtcgcagc | ctgagaaatt | aatggggacg | aaaagcacag | taataatacg | ccagaaagta | 720 |
| ttttagcctt | tttcataaat | ttcactcatt | tgtaggatac | agaaagcaat | acaaagcccg | 780 |
| cataaacaat | tagcatttat | gttgtgtaat | attttttttgc | caggcttata | gtgtctttgg | 840 |
| caaccggtag | ctgtattta | tatttttttg | tataaggtct | cctgtgaaaa | atctcttttc | 900 |
| acattattta | aataaacaga | gatccagatt | aaatacctga | gtataaaatc | tcttctgatg | 960 |
| tttaattgat | ttgaatgttc | gtaagctata | tcacttactc | aatccatttt | acccagagtc | 1020 |
| a | | | | | | 1021 |

<210> SEQ ID NO 116
<211> LENGTH: 1050
<212> TYPE: DNA
<213> ORGANISM: Artificial Sequence
<220> FEATURE:
<223> OTHER INFORMATION: gene editing homology arm pool_5_b0676_left

<400> SEQUENCE: 116

| | | | | | |
|---|---|---|---|---|---|
| cactttatcg | gcttcggtga | tttcaccggc | aataacaatt | ttttgcggat | taaataagtt | 60 |
| gatagcaatg | gcgatggttt | tacccagatg | acgaccgaca | tactcaatta | cttccgacgc | 120 |
| cagactatcg | cctttgttcg | cggctttgca | gatagttttg | atggtgcagt | cgtccagcgg | 180 |
| cacgcggctc | tggtagccct | gctttaacag | attcaacacc | cgttgttcaa | tggcagcgtt | 240 |
| ggcagcgata | gtttccaggc | agccaaagtt | gccgcagtgg | cagcgttcac | ccagcggttc | 300 |
| gacctgaata | tggccaattt | caccgacgtt | gccgttgcgg | ccaataaaaa | tgcgcccgtt | 360 |
| agagataatc | ccggccccgg | ttccgcgatg | gacacgcacc | agaatggagt | cttcgcaatc | 420 |
| ctgacttgca | ccgaagtagt | gctccgccag | cgccagacta | cggatatcgt | gaccaacgaa | 480 |
| acaggtcact | ttaaaacgtt | cttccagagc | ttctaccagc | ccccagtttt | ctacctgaat | 540 |
| atgcggcatg | taatgaattt | tgccgctgtc | cgggtcaaca | agccctggca | ggatcaccga | 600 |
| aatcgcgatc | agctcgcgca | gtttgcgctg | gtagctatca | ataaactgag | caatggcatt | 660 |
| caacagggca | tgttccagcg | tttgctgggt | acgttccggc | agcgggtaat | gttcttctgc | 720 |

```
cagcactttg ctgctgagat caaacagagt gatggtggcg tcatgacgac caagccgtac    780
gccgattgcg tggaaattgc gggtttcggt gacgatggaa atagcgcggc ggcccccggt    840
ggaggcctgc tgatcaactt ctttgatcag cccgcgttcg ataagctgac gcgtaatttt    900
ggttacgctg gcggggcaa gctggctttg ctcggcaatc tgaatccgcg agattggccc     960
gtactggtca atcaggcgat aaaccgccgc gctgttaagc tgttttacga gatcaacatt   1020
acctatctga gcttgtccgc ctggtgtcat                                     1050

<210> SEQ ID NO 117
<211> LENGTH: 1050
<212> TYPE: DNA
<213> ORGANISM: Artificial Sequence
<220> FEATURE:
<223> OTHER INFORMATION: gene editing homology arm pool_5_b0676_right

<400> SEQUENCE: 117
actttctctt attgagttac gacctcgtta ccgttaacga tggtcttggt gattttaaaa     60
tcaggtgtga atgcagtcag gttggctact ttacctgcgg cgagtgtgcc gagacgtttc    120
tcaacgccaa tcgcacgcgc cggatagagc gtcgccatac gtagcacttc atccagtgcg    180
ataccgcaat gttcgaccag attacgcacg ccttcaatca tggttaagga tgaaccgctt    240
aacgtaccgt tctcatccac acaaagtccg ttacggtagt atattgtttt acccgcaaaa    300
atgaactgtt caatgttggc acctgctggc gcggtggcgt cagtaaccag acacagtttg    360
tcgcctttca gacgtttagc gttgcgaatg ttggcgtaat caacatgcag gccatcagca    420
ataataccgc aataaatgtc agcttcgtcg aggatcgcgc ccgccaggcc aggttcacga    480
ccggtaatat acggcatcgc gttgtacaga tgggtggcaa aggtaatccc cgcgcggaaa    540
ccggcttttg cttctttcaa cgtcgcgttg gagtgaccgg cagaaaccac aatcccggca    600
tttgccagtt tgctgatgac ttccgcagga accatttccg gtgccagggt cactttggta    660
atgacgtcgg cgttttcaca caggaaatcg accagcgcgg catcaggctt acgcacaaaa    720
ttcggattat gggtgccttt ttttaccaga ttcagccacg gaccttccag atgcagacct    780
aacgcctgat tcgatgtttt gccaggtac tcgcgcataa cgcgcacgcc ctgtttcatc     840
agctcatcgc tggtggtgat aagcgtcggc agatagttag tacagcctga tttctcattg    900
gctttctgca tgatttccag cgtttccacg ctgaccgctt cagcggtgtc gttaaactgt    960
acgccgccgc agccgtttaa ctgcacatcg ataaaaccgg gggagagaat ggccccgttc   1020
agtgaacgtt gttcgatctc tggcggcagt                                    1050

<210> SEQ ID NO 118
<211> LENGTH: 1007
<212> TYPE: DNA
<213> ORGANISM: Artificial Sequence
<220> FEATURE:
<223> OTHER INFORMATION: gene editing homology arm pool_5_b1497_left

<400> SEQUENCE: 118
actttagtaa tacgatgctt aggacaaccg ccattgcaga taggtttata tgcacattgc     60
tgacatttcg ctggaatccg ttttttttgc gctgtcagtt gtacactgtt catcgttttg    120
agttcagatt tattaatgtt tccaattttg tactgtggat agacaaaatg gtcgcattcg    180
taaatgtctc cattactttc aacaaccaga ttatccttgc aggactcctg gaaaatacaa    240
ctggtatgcc cattccccaa aaaacggctg acaaagcttc caaactgacg gatgaaaatt    300
```

```
tcacccacat cgttttttaac ccattgcata aaaatggttg acataaactt gccataagcc    360
gtgggaggca cagaaaaatc aatgatacgg aatgtgttct cactatgacc actgaaatca    420
atattcggcg tcccggtttc tagcaattcg ataaattgca tatgtttact gccgatagat    480
tttaaaaaat gataaacctc aagagggtaa tggacattaa cgttattaat gacggttaac    540
gtattaaact ctacttgata tgatttcaga cgctcgatgg ctgctatcac ttttgcaaaa    600
gtaccgttac ctgaattact gcgtctgtaa cggtcatgta actcctgggg gccatcgatc    660
gagataccaa ccagaaattc atgttctttg agaaaggcac accattcatt attcaataaa    720
atgccattcg tttgtaatgc attaaaaata cgttttttggc ctgcatagcg ttgttgatag    780
tgaataactt tacggaaaaa atccaggcca gccagagtgg gttcaccgcc ttgccaggta    840
aaatagacct gattgccaga cgctgcgata tattgtttga tgaactcttt cagagtgctg    900
tcatccatcc attttcatg agtaaactgc gactcttttt caaggtaaaa acagtaatca    960
catttgagat tacattgaaa actggagggc ttggctgtaa cgtgcat                1007
```

<210> SEQ ID NO 119
<211> LENGTH: 1050
<212> TYPE: DNA
<213> ORGANISM: Artificial Sequence
<220> FEATURE:
<223> OTHER INFORMATION: gene editing homology arm pool_5_b1497_right

<400> SEQUENCE: 119

```
cgctatctcg ctcaataagg cggcggaaaa atccgccgca tgaaggttta gttatttcgc     60
ttcgcttagt gctttcttga tattgttaaa cttctcctga tttacctcgc taagcggtgg    120
ctggctgctg tcgataaact ctcttaccac gccttgcatc tctttaacga cctgcggatt    180
ggcggcggca aggttatctt tttgctgtag atccgtcagt tgtagagac ctaactgatt     240 gttttctact gtatagacaa gcgaataatc gttatttctc accgtataag agaattggct    300
taagtcctca gtgttggggt tatgcgggta atcgtctgac tgatggcgaa caaatttgtg    360
gtaattatcc cagaatggaa tattttcctc gtcaaaccag tgagaataag aggttatcca    420
ggtcagattt ttatgtggct cgccttgttt cttatcttgc aaccagggca gcaaggaaac    480
gccatccagc ttaaggtctt ttggaatgct gatatcggct gcatcaagag ctgtcgggta    540
gaaatccatt gcggaaatca gcttgtcata attaccgggt tgaagttttc ctttccacca    600
cataaacatt ggggtgtgag taccgccagg ataggtctga ctcttatagc cttttttgcgc   660 cccgttcagc ggcagaggac catcgataac cgcaccatta tcggaggtaa agagaataat    720
tgtattgtca tactgtccgt tttttcttcag ttgttcgaga atgcgtttta caccctgatc   780
aacagaataa acgaagcgt agtagttatc tgctgtttga ctaccggtat taaattgctt    840
ctgatattga tccggtgcag gattatcatt tggcaggtgc ggagcattat aagccaggta    900
aagcataaaa ggctggtcaa gtgttttggc acgatcaaca acgccaattg cctcatcggt    960
taactgatcg ctgatataac cttttgcggg gacacgttca cgattttga acagtgaagg   1020 ggagttgtaa tatgccgttc ctgcagcgtg                                    1050
```

<210> SEQ ID NO 120
<211> LENGTH: 1045
<212> TYPE: DNA
<213> ORGANISM: Artificial Sequence
<220> FEATURE:
<223> OTHER INFORMATION: gene editing homology arm pool_5_b0183_left

<400> SEQUENCE: 120

```
ccaacgcccg ctttgttggt gttgccgggc cacgaatgca ggctgaaggc tgcgaagcct      60
ggtacgaaat ggaagaactg gcggtgatgg gcattgttga agtgctcggt cgtctgcgtc     120
gcttactgca tattcgtgcc gatctgacaa agcgttttgg cgaactgaag ccagatgttt     180
ttgttggtat tgatgcgcct gacttcaata ttactcttga aggtaacctc aaaaagcagg     240
gtatcaaaac cattcattac gtcagtccgt cagtctgggc gtggcgacag aaacgtgttt     300
tcaaaatagg cagagccacc gatctggtgc tcgcatttct gcctttcgaa aaagcgtttt     360
atgacaaata caacgtaccg tgccgcttta tcggtcatac catggctgat gccatgccat     420
tagatccaga taaaaatgcc gcccgtgatg tgctggggat ccctcacgat gcccactgcc     480
tggcgttgct accggggagc cgtggtgcag aagttgaaat gcttagtgcc gatttcctga     540
aaacggccca gcttttgcgc cagacatatc cggatctcga aatcgtggtg ccactggtga     600
atgccaaacg ccgcgagcag tttgaacgca tcaaagctga agtcgcgcca gacctttcag     660
ttcatttgct ggatgggatg ggccgtgagg cgatggtcgc cagcgatgcg cgcgctactgg    720 cgtcgggtac ggcagccctg gagtgtatgc tggcgaaatg cccgatggtg gtgggatatc     780
gcatgaagcc ttttaccttc tggttggcga agcggctggt gaaaactgat tatgtctcgc     840
tgccaaatct gctggcgggc agagagttag tcaaagaatt attgcaggaa gagtgtgagc     900
cgcaaaaact ggctgcggcg ctgttaccgc tgttggcgaa cgggaaaacc agccacgcga     960
tgcacgatac cttccgtgaa ctgcatcagc agatccgctg caatgccgat gagcaggcgg    1020
cacaagccgt tctggagtta gcaca                                          1045

<210> SEQ ID NO 121
<211> LENGTH: 1040
<212> TYPE: DNA
<213> ORGANISM: Artificial Sequence
<220> FEATURE:
<223> OTHER INFORMATION: gene editing homology arm pool_5_b0183_right

<400> SEQUENCE: 121
atgatcgaat tgtttatcc gcacacgcag ctggttgcgg gtgtggatga agtcggacgc       60
gggccgttag ttggcgcggt cgtcaccgct gcggtgatcc ttgacccggc gcgcccgatt     120
gccgggctga atgattccaa aaagctgagc gaaaaacgcc gtctggcgct ctatgaagag     180
atcaaagaga aagcgttgag ctggagtctg ggccgcgcgg aacccacga atcgacgag      240 ctgaacattc ttcatgcgac catgctggcg atgcagcgtg ccgtcgctgg gctgcatatt     300
gcgccggaat atgtgttgat tgatggtaac cgctgcccga attaccgat gcctgcgatg    360 gctgtggtga aggcgatag ccgcgtaccg gaaatcagtg ccgcgtctat cctggcgaaa     420
gtgacgcgtg acgccgaaat ggcggcgctg atattgttt cccgcaata tggttttgcc     480 caacacaaag ggtacccaac cgcttttcat ctggaaaaac tggctgaaca cggcgcgacc     540
gaacaccatc ggcgcagctt tgggcctgtc aaacgcgcac tgggacttgc gtcctgattc     600
ttgtgtcgag attaagtaaa ccggaatctg aagatgtctg aaccacgttt cgtacacctg     660
cgggtgcaca gcgactactc gatgatcgat ggcctggcca aaaccgcacc gttggtaaaa     720
aaggcggcgg cgttgggtat gccagcactg gcgatcaccg atttcaccaa cctttgtggt     780
ctggtgaagt tctacggagc gggacatggc gcagggatta agcctatcgt cggggcagat     840
tttaacgtcc agtgcgacct gctgggtgat gagttaaccc acctgacggt actggcggcg     900
aacaataccg gctatcagaa tctgacgttg ctgatctcaa aagcgtatca gcgcgggtac     960
```

```
ggtgccgccg ggccgatcat cgatcgcgac tggcttatcg aattaaacga agggttgatc      1020
cttctttccg gcggacgcat                                                  1040

<210> SEQ ID NO 122
<211> LENGTH: 1047
<212> TYPE: DNA
<213> ORGANISM: Artificial Sequence
<220> FEATURE:
<223> OTHER INFORMATION: gene editing homology arm pool_5_b3631_left

<400> SEQUENCE: 122
aatcctggtc ataaagatgc gatatcatgg ggatatgtta ttaactactc ctgtcatcag        60
tacgctcaag cagaattatc ctgatgcaaa atcgatatg ctgctttatc aggacaccat       120
ccctattttg tctgaaaacc cggaaattaa tgcgctctat gggataagca ataaaggtgc       180
gggaactttc gataaaatta aaaatgtgct ttcgttgata aaaactctgc gtgcgaataa       240
ttatgacctg gtcattaatc ttacggatca gtggatggtg gcgctgctgg tacgttgttt       300
acctgcacgg atgaaaatat cgcaacttta tggtcatcgg cagcatggta tttggaaaaa       360
aagcttcaca cacttagcgc caatacacgg tacacatatt gttgagcgta atttatcggt       420
ccttgagcca ttaggtatta ccgatttcta caccgacaca acaatgagtt acgccgaaga       480
ttgctggaag aagatgcgcc gggaattaga tgccctgggc gtaaaagatc attatgttgt       540
catccaaccg acagcgcgtc agatatttaa gtgttgggat aacgtaaat tttctaaggt       600 tatcgatgcg ctgcaacagc gaggctatca ggttgtgcta acctgtgggc cctcggcaga       660
tgatctcgct tgtgtagatg agattgcacg aggttgcgaa acaaaaccca ttactggcct       720
tgcaggtaaa acacgttttc ctgaactggg tgcattaatt gatcatgcag tgcttttat       780 tggtgtggat tctgcgccgg gacatattgc agcggcagtg aaaacgccag tcattagtct       840
atttggtgca acggatcacg tattctggcg tccctggacc gagaatatta ttcaattctg       900
ggcggggaat tatcagaaaa tgccgacccg gcatgaactt gaccgcaaca aaaaatatct       960
ttctgttatc ccagcggagg atgtgatcgc cgctacggaa aagctgttgc cagaagatgc      1020
cccttcagct gacaggaatg cacaatt                                          1047

<210> SEQ ID NO 123
<211> LENGTH: 1041
<212> TYPE: DNA
<213> ORGANISM: Artificial Sequence
<220> FEATURE:
<223> OTHER INFORMATION: gene editing homology arm pool_5_b3631_right

<400> SEQUENCE: 123
atgatcgtgg cgttttgttt atataaatat tttccatttg gtgggcttca acgtgactt        60 atgcgcattg catcaacagt tgccgcacgg ggccaccatg ttcgggtata tacacagtcg       120
tgggaaggcg attgcccgaa agcatttgag cttattcagg tgccagttaa gtcccatacc       180
aaccatggac gcaatgcaga atattatgcc tgggtacaaa atcatctcaa agagcatccc       240
gcagatcgcg ttgttgggtt taataagatg cctggcctgg atgtttattt tgccgctgat       300
gtttgttacg ccgagaaagt tgcgcaagaa aaaggttttt tatatcgttt aacatcacga       360
tatcgccatt atgccgcatt tgagcgagcg actttcgagc agggtaaatc gacgaaactt       420
atgatgctga ccgataagca aatcgccgat ttccagaagc attatcaaac tgaacctgaa       480
cgttttcaaa ttcttcctcc cggtatttat ccggacagaa aatacagtga gcaaatccca       540
aacagccgtg aaatttatcg ccagaaaaat ggcataaaag agcaacaaaa cttattactg       600
```

```
caggttggat cagatttggg ccgtaaaggt gtagatcgct caattgaagc tttggcatcg      660
ttaccggaat cattacgtca caatacgctt ttatttgttg ttggtcagga taagccgcga      720
aaatttgaag cgctggcaga aaaactcggc gtgcggagca atgtgcattt cttctccggt      780
cgcaatgatg tgtcagaatt aatggcagcc gctgatttat tactgcatcc cgcttatcag      840
gaagccgcgg gtatcgttct tctagaagcg atcactgctg ggttacctgt tttaacaaca      900
gcggtatgtg ggtacgcgca ttatattgcg gatgccaatt gtggaacggt catcgctgaa      960
cctttctctc aggaacaatt aaatgaagtt ttacgtaaag cgttaactca gtcgccattg     1020
cgaatggcct gggcggagaa t                                               1041

<210> SEQ ID NO 124
<211> LENGTH: 1047
<212> TYPE: DNA
<213> ORGANISM: Artificial Sequence
<220> FEATURE:
<223> OTHER INFORMATION: gene editing homology arm pool_5_b3791_left

<400> SEQUENCE: 124
gcgctcgctc tctttggtgg tgtagcgatc ttcaccgtgg aactcaccaa agtgttcccc       60
cgcagggcaa ccgtgcagcg gaatgtaatg aaacaccgcc atgatttccg cttctttcag      120
aaagttaatc aacgcgctcc ggtcatcaat atcccgcagt ttaatgtaga acatatgcgc      180
gttctgcacg cagccatcgg gaatcgacgg cagctcgata cgcccggctt tcgccagagg      240
cgctaacgca tcgtagtagt tttgccacag cgccagacgt tgctggttga tacgatccgc      300
tgcttccagt tgcgcccaca ggtatgcagc ttgcagatcg gacatcaaat agctggagcc      360
aatatcgcgc caggtatatt tatcgacctg accacggaag aactggctgc ggttagtgcc      420
cttttcacgg atgatctcgg ctcgttcgat taacgcttta tcgttaatca gcgtcgcgcc      480
gccttcaccg cccgccgtgt agttttttggt ttcatggaag ctaaagcagc caatatgacc      540
aatggttccc agtgcacgcc ctttgtaagt ggacatcacg ccctgagcgg catcttctac      600
cacaaacaaa ttatgctttt tcgccaacgc cataatggtg tccatttcgc aggccacacc      660
cgcgtaatgg accggcacga taacgcgcgt tttgtcggtg atcgccgctt caatcagcgt      720
ttcgtcgatg ttcatggtgt ccgggcgaac atccacaaaa acgattttg cgccacgcag       780 cacaaaggca ttggcggtgg agacaaaggt gtagctcggc atgatcactt catcgccagg      840
ctggatatcg agcagcagcg ccgccatctc cagcgaagcg gtgcaggacg gcgtcagtaa      900
cactttggcg ctgccaaaac gttgctccag ccactgctgg cagcgacggg taaaaccgcc      960
atcgccacac agtttgccgc tacccattgc cgactgcata tagtcgagtt cggttcccac     1020
caccggcggt gcgttaaatg gaatcat                                         1047

<210> SEQ ID NO 125
<211> LENGTH: 1048
<212> TYPE: DNA
<213> ORGANISM: Artificial Sequence
<220> FEATURE:
<223> OTHER INFORMATION: gene editing homology arm pool_5_b3791_right

<400> SEQUENCE: 125
gtgatcacct gtataaccag tacgcggtgc tttctacatt cgcaccactt tgtatgtatc       60
gtttaagcgc ggcggtgttg cccatttggg tcgccaccog caaagttgtt ttaccgcgag      120
catacgccca gtttagcgcc gtttgcatca gctcagcacc tgcaccgcgt ccagccagca      180
```

```
ggccaattcg cgcatctgtc gcattgagtt cccgtaaaga gacatagccg cgaatatcgc         240
cggacgccgc acgtaaaatc agacattgat gatcaaaggt gccgcgcacg gcattttcaa         300
tccactgtgc ataaaagcga ctgctggcgt caggcgcata ccacggcgca cgaaaacggc         360
tttgcgcaaa tgcggcgctg gctaactgac gtaatgcggg aatatcggtc tcttgtgcca         420
ctacagcacc gctatcactg gcattgttca cgggtagcgc caaatcaact tcaccttcta         480
ccagggagaa tcccagctgt tgcagggcat ccagttcacc cgtatttgat gccgcaattt         540
tggcctgcac ccgtgaccac ggcgctaacg cgtctggcgt caggagcggt gcttcagacg         600
taatgcgcac gatggcgctg ttaacaccaa agaaggcgtt ttcccaggtt agtggctcaa         660
tactggcgcg gacgggcacg aagtaactcc agcagatatt ggccgtagcc agttttcgct         720
aatgaactgg cagcacgctt cacccctcg tcatcgagcc agccgttacg ccaggcaatc          780
tcttccaggc aggcaatctt aaagccctgg cgttttttcca ccgtctgtac aaaggtgctg        840
gcttcaatca ggctgtcgtg agtgccgta tccagccagg caaatccgcg cccgagcagt         900
tcaacggtca ggttgcccgc tcgaggtac atctggttga tggaggtaat ctccagttca         960
ccacgctccg acggcttcac ctgctttgcg tactccacga ctttactgtc gtagaaataa        1020
agcccggtca ccgcccagtt tgacttcg                                          1048
```

<210> SEQ ID NO 126
<211> LENGTH: 1045
<212> TYPE: DNA
<213> ORGANISM: Artificial Sequence
<220> FEATURE:
<223> OTHER INFORMATION: gene editing homology arm pool_5_b0438_left

<400> SEQUENCE: 126

```
gtgactgaaa aagaaaccac tttcaacgag ctgatgaacc agcaggcgta atttacgcag          60
cataacgcgc taaattcgca caaaggcccg tcaccgccag gtggtgggct tttttttgtc         120
atgaattttg catggaaccg tgcgaaaagc ctctttcggt gttagcgtaa caacaaaaga         180
ttgttatgct tgaaatatgg tgatgccgta cccataacac agggactagc tgataatccg         240
tccataaggt tacaatcggt acagcaggtt ttttcaattt tatccaggag acggaaatgt         300
catacagcgg cgaacgagat aactttgcac cccatatggc gctggtgccg atggtcattg         360
aacagacctc acgcggtgag cgctcttttg atatctattc tcgtctactt aaggaacgcg         420
tcatttttct gactggccag gttgaagacc acatggctaa cctgattgtg gcgcagatgc         480
tgttcctgga agcggaaaac ccagaaaaag atatctatct gtacattaac tcccaggcg         540 gggtgatcac tgccgggatg tctatctatg acaccatgca gtttatcaag cctgatgtca         600
gcaccatctg tatgggccag gcggcctcga tgggcgcttt cttgctgacc gcaggggcaa        660
aaggtaaacg ttttttgcctg ccgaattcgc gcgtgatgat tcaccaaccg ttgggcggct        720
accagggcca ggcgaccgat atcgaaattc atgcccgtga aattctgaaa gttaaagggc        780
gcatgaatga acttatggcg cttcatacgg gtcaatcatt agaacagatt gaacgtgata        840
ccgagcgcga tcgcttcctt tccgcccctg aagcggtgga atacggtctg gtcgattcga        900
ttctgaccca tcgtaattga tgccagaggc gcaactgtgc cgctatactt atccagggcg        960
gcacaacgct gtaagcggct tgcgcctgag aatggcattt gcgtcgtcgt gtgcggcaca       1020
aagaacaaag aagaggtttt gaccc                                            1045
```

<210> SEQ ID NO 127
<211> LENGTH: 1050

```
<212> TYPE: DNA
<213> ORGANISM: Artificial Sequence
<220> FEATURE:
<223> OTHER INFORMATION: gene editing homology arm pool_5_b0438_right

<400> SEQUENCE: 127
atgacagata aacgcaaaga tggctcaggc aaattgctgt attgctcttt ttgcggcaaa        60
agccagcatg aagtgcgcaa gctgattgcc ggtccatccg tgtatatctg cgacgaatgt      120
gttgatttat gtaacgacat cattcgcgaa gagattaaag aagttgcacc gcatcgtgaa      180
cgcagtgcgc taccgacgcc gcatgaaatt cgcaaccacc tggacgatta cgttatcggc      240
caggaacagg cgaaaaaagt gctggcggtc gcggtataca accattacaa acgtctgcgc      300
aacggcgata ccagcaatgg cgtcgagttg gcaaaagta acattctgct gatcggtccg       360
accggttccg gtaaaacgct gctggctgaa acgctggcgc gctgctgga tgttccgttc       420
accatggccg acgcgactac actgaccgaa gccggttatg tgggtgaaga cgttgaaaac      480
atcattcaga agctgttgca gaaatgcgac tacgatgtcc agaaagcaca gcgtggtatt      540
gtctacatcg atgaaatcga caagatttct cgtaagtcag acaacccgtc cattacccga      600
gacgtttccg gtgaaggcgt acagcaggca ctgttgaaaac tgatcgaagg tacggtagct     660
gctgttccac cgcaaggtgg gcgtaaacat ccgcagcagg aattcttgca ggttgatacc      720
tctaagatcc tgtttatttg tggcggtgcg tttgccggtc tggataaagt gatttcccac     780
cgtgtagaaa ccggctccgg cattggtttt ggcgcgacgg taaaagcgaa gtccgacaaa      840
gcaagcgaag cgagctgct ggcgcaggtt gaaccggaag atctgatcaa gtttggtctt       900
atccctgagt ttattggtcg tctgccggtt gtcgcaacgt tgaatgaact gagcgaagaa      960
gctctgattc agatcctcaa agagccgaaa aacgccctga ccaagcagta tcaggcgctg     1020
tttaatctgg aaggcgtgga tctggaattc                                       1050

<210> SEQ ID NO 128
<211> LENGTH: 1050
<212> TYPE: DNA
<213> ORGANISM: Artificial Sequence
<220> FEATURE:
<223> OTHER INFORMATION: gene editing homology arm pool_5_b1981_left

<400> SEQUENCE: 128
ggtgtcagga gttattgcga tataagcatc ttttatgatt gctgctgaac gtttaatcga        60
gggtggtaag gataaacggt agacattatt ataacaatcc actaatgccc tggctttatc      120
ttcacctttg ggtccatgaa cgatcactat tggtatatct gtttcacttt aaattttgc       180
tattagattt tctgcaatcg ataatgaaaa tgtacgttcc tgcgagctac cttctaaatt      240
gaacgcaatg taagatccta acgatcgcat ttcctcgcgc acctcatcga gtacatcctc      300
acttagtggc aattcatata ttggcctgac tgctggaaaa cccgcctcac gcatcataaa      360
tgcccatgtc ataggtacgg gagcccggag tttctgatcc atactggacg cgttcttgca      420
caaaggggag aagcaattca tggttatacc aacaacctga aaattcgttt ttgctttcaa      480
ctgactgata ataacatcg ttttcaggtt cttttttacgc atcccctcaa tgcaaagatc       540
cggcgtaccg tattgctgtg ttatgttctt tgctaaatct tttatttctt ttaatgttgc      600
gtgatcctgc atagtcattg tgactaatgt taatttagtc tgttcaagtt taagcgcatt      660
aaagacttct aaattaattg tcgacgttac aattaaaaga tgcttaattt tatgcaattc      720
aagcgcccga ataacaggaa agatggccat agcatcgcca atctgatcgg gaatatggat      780
```

| | |
|---|---|
| gacaacaaag tctgttttt caatattgaa attataagct ttataatcgt agtaactaaa | 840 |
| tgcaatacgt ctcaacaatg atgctaaaaa catacctaac ctcgcctccc tactggttat | 900 |
| aatgcaatgc agtctatcag actcatcagg gtgccatttt gtgcatatgc ggactttat | 960 |
| gtttcatatc tctaacctgt gggtcctctg cttaatcctt aaacaacacc agcaactcct | 1020 |
| gcgctttcat cttccatcga attttcatg | 1050 |

<210> SEQ ID NO 129
<211> LENGTH: 1036
<212> TYPE: DNA
<213> ORGANISM: Artificial Sequence
<220> FEATURE:
<223> OTHER INFORMATION: gene editing homology arm pool_5_b1981_right

<400> SEQUENCE: 129

| | |
|---|---|
| atggactcca cgctcatctc cactcgtccc gatgaaggga cgctttcgtt aagtcgcgcc | 60 |
| cgacgagctg cgttaggcag cttcgctggt gccgtcgtcg actggtatga tttttactc | 120 |
| tatggcatca ccgccgcact ggtgtttaat cgcgagtttt tcccgcaagt aagcccggcg | 180 |
| atgggaacgc tcgccgcatt tgctacctt ggcgtcggat ttcttttccg tccgctcggc | 240 |
| ggtgtcattt tcggtcactt tggcgaccga ctgggacgta agcgcatgtt aatgctgacc | 300 |
| gtctggatga tgggcatcgc gacagccttg attggtattc ttccttcatt ctcgaccatt | 360 |
| gggtggtggg cacctatttt gctggtgaca ctgcgtgcca ttcagggatt tgcagtcggc | 420 |
| ggcgaatggg gaggcgcggc gttgctttcc gttgaaagtg caccgaaaaa taaaaaagcc | 480 |
| ttttacagta gcggtgtaca agttggctac ggtgtaggtt tactgctttc aaccggactg | 540 |
| gtttcattga tcagtatgat gacgactgac gaacagtttt taagctgggg ctggcgcatt | 600 |
| cctttcctgt ttagcatcgt actggtactg ggagcattgt gggtgcgcaa tggcatggag | 660 |
| gagtccgcgg aatttgaaca acagcaacat tatcaagctg ccgcgaaaaa acgcatcccg | 720 |
| gttatcgaag cgctgttacg acatcccggt gctttcctga agattattgc gctacgactg | 780 |
| tgcgaattgc tgacgatgta catcgttact gcctttgcac ttaattattc aacccagaat | 840 |
| atggggctac cgcgcgaact tttccttaat attggtttgc tggtaggtgg attaagctgc | 900 |
| ctgacaattc cctgttttgc ctggcttgcc gatcgttttg gtcgccgtag ggtttatatc | 960 |
| acaggtacgt taatcggaac gttgagcgca tttcctttct ttatggcgct tgaagcacaa | 1020 |
| tctatttct ggatag | 1036 |

<210> SEQ ID NO 130
<211> LENGTH: 1050
<212> TYPE: DNA
<213> ORGANISM: Artificial Sequence
<220> FEATURE:
<223> OTHER INFORMATION: gene editing homology arm pool_5_b1709_left

<400> SEQUENCE: 130

| | |
|---|---|
| cgaaacgatc gcgcatcgtc acaaccacaa atcccgaaca gtccacaccg cgccgcgtca | 60 |
| tgccaccata acgatacggc gtgccatgcc agctttgtag ctggtcgttc aaaccggcaa | 120 |
| taacggtaat cgaatcagaa agtctggcat ttggcggcgg tgctttatgg tggctacacc | 180 |
| cggccagaag cagtgctgtg atcaaaataa ggcagaaacg cattccgtac ggttcctctg | 240 |
| ttttttattc ttgcattaat ttagcgtcgt aattacccga ttttcaagat actaatgaaa | 300 |
| tcagatggtc gaaatcagca ttctgtgacc ttcgatatcc agacggcgaa aattcatccc | 360 |
| ataggcctgc gccagatttg gcggcgtgag cacctcttcc ctgcgtccac tggccagcat | 420 |

```
tttccacct tttagcaacc acgcccgatg cgcatgacgc aatgtgtggt tgagatcgtg      480
actgctcatc acaatcgcca gtccttgctg acacagcgcg ctcagaattt tgtctaacgc      540
actttgttgc gcaacatcaa gactgttcat cggctcatca agaagcagca attggcctgc      600
gggattggct tgtggtgtga tttgcaacac caccgcagca agacgtacgc gttgccattc      660
accgccggaa agttgattgg tgctacgtcc gagtttgtca tcaagagcca gcgcccctgc      720
gacatcattc agtagttcgg tacgcgtttt atcgtgctga tgcagtgtca ggtagtgcca      780
gaccggcgtt gcaaacggcg gcgtctgctg ttgtgaaaga taggcgcgat gcagcgcgag      840
ttttgttgcg gaccatgctt ccagtggttg ccccgcgaac tgaatgcttc ccttaccgct      900
ggtcattccg gccattcgcg ccagtaaggt actcttaccc gcgccattcg gccccaccag      960
gtgcaggatc tccccagccc gaacctcgcc agaaagcggc cccaggcggg tagattccgc     1020
aacatcttgt aactgcatca caatagacat                                      1050
```

<210> SEQ ID NO 131
<211> LENGTH: 1050
<212> TYPE: DNA
<213> ORGANISM: Artificial Sequence
<220> FEATURE:
<223> OTHER INFORMATION: gene editing homology arm pool_5_b1709_right

<400> SEQUENCE: 131

```
tattttgcca acgccagttt aatgctttcc atcacaatgg gatcttccgg cgtcatatcc       60
ggggaaaaac gctggatgac ttttccgtcc ctgccaacca ggattttttc aaaattccat      120
aaaatatcat ccgggtacag cggtgcacgg cctttgctga ccatacgggc atagaatccg      180
ctctcttccg gcgcgactgc ggtcggcgct gcggcaatca attttttgata cagcggatgg      240 cgtccttcgc cattaacttc aatcttactg aacatcggga acgtcacccc ccatgtggtg      300
gtacagtaag ttttaatctc ttcatcgctg cccggttctt gttccagaaa ctggttgcac      360
gggaatccca gcaccataaa acctcgatcg acccaggctt tctgaatatt ctccaactgc      420
tcatattgcg gcgttaagcc acactttgag gcgacattga caatcaacag cacattaccg      480
gcgaacttct ccagcgtggt cacttcaccg tcgatatctt tcactacggt cgtcagaatg      540
gaatcttgca tcgtttctcc tgggtgtggt cagtaaaaat cttagctttt aatcatagac      600 cgtcttttttg cggctaacgt cctgctttta acaataacca gataaacacc ggcgcaccta      660
acgttgcggt gaccacgcca ataggcagct ctgcggcagc taatgccagg cgcgctacaa      720
tatcggccag cagcaatgcg ctcgcccctg ccagcgcgca gccgggaagt aatacgcgat      780
gatcggttaa accacacaac cggagaatat ggggatcac cagaccaata aagccgatag      840
cacccgccag cgccacactg acgccaacca tccagccggt cgctgccacc agcacattgc      900
gccagaacca caggggtaaa cccagttgcc gcgccgagat ctcgccaagt gctaacatat      960
tcatcggcct ggactgacaa cagatccaca acaacgggg gatcaatgcc agcatcagcc     1020
agctttgccg ccagtctacg ccgccaaaac                                      1050
```

<210> SEQ ID NO 132
<211> LENGTH: 1050
<212> TYPE: DNA
<213> ORGANISM: Artificial Sequence
<220> FEATURE:
<223> OTHER INFORMATION: gene editing homology arm pool_5_b2176_left

<400> SEQUENCE: 132

```
atggattgca tgcgtttcac tcaattgtac tttaattgac caaccccgct tattaacttt    60
ctgtatcact ttttcttata aaaaatcatg taaaaccgct cgccaagacc gcaccaatcg   120
ggtaatctcg aactcgtttt gcctcggcgg tagattatcc tcacagcata taattttgtg   180
cgttagtcca cagatttggc cttaaggaat tgtttcaaca tgcccaggta attagtctcg   240
tgtcgcttgg catttttta taacgatatt tgtcgttaag gacttcaagg gaaaacaaac   300
aacatggtca atctcaacc gatttgaga tatatcttgc gcgggattcc cgcgattgca    360
gtagcggttc tgctttctgc atgtagtgca ataacaccg caaagaatat gcatcctgag   420
acacgtgcag tgggtagtga acatcatca ctgcaagctt ctcaggatga atttgaaaac   480
ctggttcgta atgtcgacgt aaaatcgcga attatggatc agtatgctga ctggaaaggc   540
gtacgttatc gtctgggcgg cagcactaaa aaaggtatcg attgttctgg tttcgtacag   600
cgtacattcc gtgagcaatt tggcttagaa cttccgcgtt cgacttacga acagcaggaa   660
atgggtaaat ctgtttcccg cagtaatttg cgtacgggtg atttagttct gttccgtgcc   720
ggttcaacgg gacgccatgt cggtatttat atcggcaaca atcagtttgt ccatgcttcc   780
accagcagtg gtgttattat ttccagcatg aatgaaccgt actggaagaa gcgttacaac   840
gaagcacgcc gggttctcag ccgcagctaa taaaccgttt ggatgcaatc ccttggctat   900
cctgacgagt taactgaaag cactgcttag gcagtgcttt tttgttttca ttcatcagag   960
aaaatgatgt ttccgcgtct tgatccaggc tatagtccgg tcattgttat cttttaaatg  1020
ttgtcgtaat ttcaggaaat taacggaatc                                  1050

<210> SEQ ID NO 133
<211> LENGTH: 1050
<212> TYPE: DNA
<213> ORGANISM: Artificial Sequence
<220> FEATURE:
<223> OTHER INFORMATION: gene editing homology arm pool_5_b2176_right

<400> SEQUENCE: 133
atgttcatac gcgctcccaa ttttggacgt aagctcctgc ttacctgcat tgttgcaggc    60
gtaatgattg cgatactggt gagttgcctt cagttttag tggcctggca taagcacgaa   120
gtcaaatacg acacactgat taccgacgta caaaagtatc tcgataccta ttttgccgac   180
ctgaaatcca ctactgaccg gctccagccg ctgaccttag ataccctgcca gcaagctaac   240
cccgaactga ccgcccgcgc agcgtttagc atgaatgtcc gaacgtttgt gctggtgaaa   300
gataaaaaaa cattctgttc atctgcgacc ggtgagatgg acattccact caatgaattg   360
attccggcgc tcgacattaa taaaaacgtc gatatggcga tcttacccgg cacgccgatg   420
gtgccgaaca aacccgcaat cgtcatctgg tatcgcaacc ctttgctgaa aaatagcggc   480
gtctttgccg ctctgaatct caacctgacg ccttcactct tttatagttc acggcaggaa   540
gattacgatg gcgtcgccct cattattggc aatactgcgc tatctacctt ttcttcacgt   600
tgatgaacg ttaacgaatt aaccgacatg ccagtccgtg aaactaaaat tgcgggcatt   660
cctctgaccg ttcggctta tgcagatgac tggacatgga acgatgtgtg gtacgcattt   720
ttactgggcg gcatgagtgg aactgtcgtt ggcctgctct gctattacct gatgagcgta   780
cgtatgcgcc ccggcagaga atcatgacc gccatcaagc gcgaacaatt ttacgtggcg   840
tatcaaccgg tggtggatac acaagctttg cgagtaacgg gcctggaagt actgctacgc   900
tggcggcatc ctgtcgcggg agaaattccc ccgatgcct tcattaactt tgccgaatcg   960
caaaagatga ttgtgccgct gactcagcac ctgtttgagt taattgcccg cgatgccgca  1020
```

```
gaattagaaa aagtgctgcc ggtaggcgtc                                    1050
```

<210> SEQ ID NO 134
<211> LENGTH: 1050
<212> TYPE: DNA
<213> ORGANISM: Artificial Sequence
<220> FEATURE:
<223> OTHER INFORMATION: gene editing homology arm pool_5_b2168_left

<400> SEQUENCE: 134

```
agttttgctt ttcgcgccgc cgcgcccagc agggtcttcg ccatataggc gcgtgcctga      60
ccgagattag cgtcaataat cagcagcgtt ttcattatgc ctctcctgct gtcagttaaa     120
aggttgtaag tcgacgcgcg ccatcattgc ggccaactgc ggacgatcgg taatacccac     180
attgctttga cttaccgcca gggctgcaac agctgtcgcc agacgcagtg tgtgttcact     240
ggattcacgc atcagcaagc cataaatcag gccaccaacc atagaatccc ctgcgccaac     300
ggtgcttacg acatcgactg acggtggttt ggcgatccat tcgccggagg cattaaccca     360
aagcgcgcct tcggcaccca gtgaaataac aacatgcgcg atgccttgtt cacgtagcgc     420
atgtgcagct tcaatcacat ctttcatttc aggcagttta cggcctgccc agatttccag     480
ctcgcggcgg ttaggtttca ccagccacgg tgccgctttc aaacctgcta ctaacgcttc     540
acggctacta tcaaagataa tgcaaggaca ctgactacgc aggcgagtca tccagtcggt     600
gaacgcttcc gggctgacgc ctgacggtaa gcttccgctg acacagacca tatcgaactg     660
accgagccag ctcagagaat cagtcacaaa gcgttcccag tcggcggggg tgacttcaaa     720
acccgagaag ttgaagtcgg tcacttcgcc gtctttttcc gtcagcttaa cgttaattcg     780
ggtgcgcccc tgtacaacct ggaaacggtt ggcaatgccc agctcgctga acagttgctg     840
aaaaccatcc tgattgtctt tacccaggaa gccgccaacg gtgacatcaa ttcccaggtc     900
ttttaatact ttggccacgt tgatgccttt acccgccgca tgcagaccgg tggttttcac     960
caggttcact tcgccgcgtt caatttccgg gcagaaacca acaaggtcat aagccggatt    1020
aagggtgata gtagcaacac gtctgctcat                                    1050
```

<210> SEQ ID NO 135
<211> LENGTH: 1046
<212> TYPE: DNA
<213> ORGANISM: Artificial Sequence
<220> FEATURE:
<223> OTHER INFORMATION: gene editing homology arm pool_5_b2168_right

<400> SEQUENCE: 135

```
tatgcgccct ccccaagacc agcagcgata gcgtcgccga ttgctttcag cgcctgttca      60
gcatctgcac cctgggcggt aaagcgtagg cgatgacctt tcttaacgcc aagtgccaca     120
actttcatca gactacgtcc gtttgccggt ttgccggtac catcaaggtt tgtcacggta     180
atatcactgt taaattgttt aatggtattg accagcatgg tacctggacg agcatgcagg     240
ccgtgttcat tgcgcaccac aaactccgcg cttaacacgt cgtcggtcgg cgcatcatcg     300
ctggtcagca gcgccagcaa cgttgccgca tccgctttca gcaagcggtc agctttattg     360
tcgagcaata aatcagcgag acgcttaaga accgcgatgg gctgatcgtc attcatcgcc     420
acactcacca gcatggctgc cgtttcgccg tccacatcaa aagcatttgc cgcacggctt     480
accgcaatcg cgctacgcag attgccttcg gcgctatcgc tcagccagat accctgtccg     540
agattcagcg gttgttcatt gatggctttg gtgacgaaag tggcgtcaac tgcccccgcc     600
```

| | |
|---|---|
| tctttcagac gcgcagcgtt cagcgcctga agagtcagca gatcgctggc gacgatatcc | 660 |
| agtgtcagca tttcgttgtc gagcttcagc tgctcactct gcttttcgcc catcagtaat | 720 |
| gcgcgaagtt cttctgctgt tgttgctgac ttcagttgtt cagcaacgga atcatcgctc | 780 |
| agtacgtggg tcagctggcg tagcaggccc agatgttcat ccgagctggc agcaataccg | 840 |
| attgccacgt acgctacctg accgtcaccc caggtgacgc cttccgggaa ctgaaatacc | 900 |
| tgaacgccgg ttttcagcac ctgatcgcgg gtgtcggtag tgccgtgtgg aatagcaata | 960 |
| ccattgccga ggaacgttga ggtttgctgt tcgcgcgcca gcatgccatt gacgtagcct | 1020 |
| tctgctacat taccggcctg caccag | 1046 |

<210> SEQ ID NO 136
<211> LENGTH: 1050
<212> TYPE: DNA
<213> ORGANISM: Artificial Sequence
<220> FEATURE:
<223> OTHER INFORMATION: gene editing homology arm pool_5_b1872_left

<400> SEQUENCE: 136

| | |
|---|---|
| catcagcatt gtgcgattcg ccgccatcag ttcagcgagt ttgactatct gcgcttccgg | 60 |
| tacgccagta atttccgccg cccagaccgc gctcttcggc gtattatcgc tcttacctgt | 120 |
| cagatactct tcaaactgcg gatacccggt agtgtatttt tcaaggaaca ctttatcgtg | 180 |
| tttgccttgt gtcatcaggg tatgcgcaat ccctaacatc agtgccacgt cggtgcccat | 240 |
| attcggcgcg atccaggtgg cattatcgtc aaagaattcg atggtttcgg agcggatagg | 300 |
| atcaatggca atcactggtt tgccagattt tttcagctga tggaagtatt ccagcccttg | 360 |
| ctcatcggta ctgctccagg caattttttaa ggtattcagc gggttcattc cccacagcac | 420 |
| cacaacctgc tgttttcca gaatcagcgg ccaggaggtc tgctgttcat acacctctac | 480 |
| agaaccgacc acatgcggca tgatcacctg tgctgccccg gttaataat cgccgctatg | 540 |
| cccggaataa ccgcccgcca ggttcatata acgttgcagt aaggtttgcg ctttatgcaa | 600 |
| cacgccagaa gagcgccagc cgtaagatcc ggcaaaaatg gccgatggtc cgttagcttt | 660 |
| acgaatacga tcatgttgct catgaatcag ttttaatgcc tgttcccagc tcacctgtac | 720 |
| ataggtatct tcgccacgac ctttcgccgg ttgcagtgga ttatcgagat agctttttct | 780 |
| caccatcgga tgctgaatac gcgccgtggt gtgtacctga tccgccgccg tagactgtaa | 840 |
| ggaattcggt atggttttcg ccagcgcgcc tgttgaagaa acaatcttgc cgtccttcac | 900 |
| ttctacgttc atcgctcccc aacgtcccgc ggtgaggatt ttaccgccct tctcttctgc | 960 |
| ccatgcgggg agcggtgctg ccgatgtcac caccagcgct ccagcggcaa taccgctgtg | 1020 |
| tttaataaat tcacgtcttg ttaatgtcat | 1050 |

<210> SEQ ID NO 137
<211> LENGTH: 1050
<212> TYPE: DNA
<213> ORGANISM: Artificial Sequence
<220> FEATURE:
<223> OTHER INFORMATION: gene editing homology arm pool_5_b1872_right

<400> SEQUENCE: 137

| | |
|---|---|
| aacttcctcc ctgatcaacg aggatcactg tttctcggta atatctttgg cgttgtactg | 60 |
| gaaataccgc gttaaaatgt ccagttcgtt ttcgctcatg ctggttcgtg cccccattcc | 120 |
| tttggcaatg gacggccacg cattgacggt gtaatggtcg gcgcaatag ggcatgaca | 180 |
| accagcgcaa taggtatcgt caagtttttc agcgtattgc catagcggtt tacggtccgc | 240 |

```
taatgcggga tcggtaagcg caccctgtaa agacgcctga cgccattgat tgccgtattc    300
gtcagcctgc cattcccgt ttacagtgag cgccttgata ccttcttcac ttaatgtggc    360
tagcgccagc cgttgacctg ccgccaggta gagcgtgttt tcactgccct gcatttgata    420
accctgcaac agaacgatcg gctgtttgcc actggcatca acgacggtga atcggttcc    480 aggattcacg gtagccagct cgcctatgtg agaagttttg aaaggataaa tatgtgcgcc    540
attagtaact gaagtagcgg cctgactttc cagctcatgc gccgcgttgt catccatttt    600
tatttctggc ggaaaatggg caatgccttt atgacaatcg atacaggttt cgctgtcctt    660
ttgtgctttg ttatgcattt tctgcgcaga ttcactttgc gaggcaatat ccatggcatc    720
aaaagaatgg caactacggc acgttgcaga gtcagtggct tttaattctt tccatactgt    780
ttcggccatt tcctggcgat gagcttcgaa cttatcgtca ctgtctattt tgccgctaac    840
aaattcatga taaatatctt tagatgcctt taatttagca aataaataat ccatccctga    900
ctttggaata tggcaatcgg cacattccgc acgtatccct ttctggttcg aaaagtggac    960
agttccctga tattcctcaa aaggtttact catcgagtgg caggaaaggc aaaatgctgt    1020
atccgacgtt ttatgtaaga cttttttgcgc                                    1050
```

<210> SEQ ID NO 138
<211> LENGTH: 1050
<212> TYPE: DNA
<213> ORGANISM: Artificial Sequence
<220> FEATURE:
<223> OTHER INFORMATION: gene editing homology arm pool_5_b1203_left

<400> SEQUENCE: 138

```
gatgtaatct ttaccttctg cacgcatttt gcctgcttct ttcgcgcctt gttcacctttt    60 gtaagtgatg aaatcttcaa acgagatggt ttgtgcacgg ataaagcctt tttcaaaatc    120
agtatggatt ttgcccgctg cctgcggcgc ggttgctcca accggaatgg tccatgcacg    180
cacttctttc accccagcgg tgaagtaagt ttgcaggttc agcagtttat aaccggcacg    240
gatcacacgg ttcaggcccg gctcttccag cccaagctcc tgcataaact cgtcacgttc    300
ttcgtcgtcc agttcggcaa tgtctgcttc aacagcagca caaaccggaa ccacaacaga    360
accttctttc gccgcgattt cacgcacctg gtcaagatat gggttgtttt caaaaccgtc    420
ttcgttgacg ttggcgatgt acattgttgg tttcagcgtc aggaagctca ggtaacgaat    480
agccgctttc tcttcagcgc ttaaatccag cgcgcgcagc atacctgcat tttccaactg    540
gggcaggcat ttttccagga ccgccagctc agctttcgcg tctttatcgc cacctttggc    600
tttcttctgt acgcgatgaa tcgcacgttc gcaggtgtcg aggtctgcca gcgccagttc    660
ggtgttgata acttcaatat cgtcagccgg gttaactttg ccggaaacgt gaatgatgtt    720
gtcattttca aagcagcgaa caacgtgacc gatcgcttcg gtttcacgga tgttggtcag    780
gaactggtta cccagaccctt cgcctttcga tgcgcctttt accagaccgg cgatatcgac    840
aaattccatg gtcgtgggaa gcgtacgctg cggttttacg atttcagcca gttgatccag    900
gcgaggatca ggcattggta cgacgcctgt gttcggctca atggtgcaga atggaaagtt    960
ggccgcttca ataccggctt tggtcagcgc gttgaacagg gtagatttcc cgacgttggg    1020
caaaccgacg ataccgcatt tgaatcccat                                      1050
```

<210> SEQ ID NO 139
<211> LENGTH: 1036
<212> TYPE: DNA

<213> ORGANISM: Artificial Sequence
<220> FEATURE:
<223> OTHER INFORMATION: gene editing homology arm pool_5_b1203_right

<400> SEQUENCE: 139

```
ttattgcgct ttaaaggcgt gcaatcggtt cgttgctttg gtcaagccat ctgtaaacca      60
catttcagta caacgcgccg cttcgtcaat ggcttcatca attaacttct gttcactaac     120
aggcggtttg cctaacacaa aaccgacaac tttatttta tcgcccggat gaccgattcc      180
gatgcgtaaa cggtgaaagt tagggttatt acccaattta ctgatgatgt ctttcagtcc     240
attgtgacca ccatggccac cgcccaattt aaatttggcg acgccaggag gcagatccag     300
ttcgtcgtgg gccaccagaa tttcgtccgg attaatgcgg aaaaaactgg ccatcgccgc     360
aacggctttg ccgctgagat tcataaatgt agtcgggact aacaggcgga catcttcgcc     420
tccaagagtg actcgcgaag tataaccaaa gaatttagcc tcttcgcgca gcggagcgcg     480
caaacgctct gccagtaagt caacgaacca ggcaccagca ttatgtcgcg ttgcggcgta     540
ttcagcaccg gggttcgcca ggccgacaat caatttaatc gtcacgtttt tttgtcctga     600
gtgtgtacat aactggcgcg tagtttactg gttgcggccc cgcttgacaa aaaactgcgt     660
atcaaatgca gataacgtaa taattgcctg agtggactat tagaaagtca aggtgttcag     720
gcgtttattt gtaaagtttt gttgaaataa gggttgtaat tgtgatcacg cccgcacata     780
acccactggg tgttgtctat actttacaca taaggaagag gggtattccc tgttacaacc     840
cagaaagttc cggaggtgac atatgaaacg caaaaacgct tcgttactcg gtaacgtgct     900
catggggttg ggtctggtgg taatggtggt cggcgtgggg tattcaatcc tcaaccagtt     960
accacagttt aatatgcccc agtatttcgc acatggtgca gtgctaagta ttttcgtcgg    1020
tgccattctc tggctg                                                    1036
```

<210> SEQ ID NO 140
<211> LENGTH: 1050
<212> TYPE: DNA
<213> ORGANISM: Artificial Sequence
<220> FEATURE:
<223> OTHER INFORMATION: gene editing homology arm pool_5_b2231_left

<400> SEQUENCE: 140

```
gatgtctttc aggttcatga tcttcggctg accatggtgc aatgccacca tgttgatacc      60
gaaagaaacc tgcaactggg tctgggagta gaggttgttg agcacaactt caccgaccgc     120
atcgcgtttc acttcaatca cgatgcgcat accgtctttg tcagactcgt cacgcagcgc     180
gctgatgcct tccacgcgtt tttctttac cagttccgca atcttctcga tcaggcgcgc     240
tttgtttacc tgatacggaa tttcgtggac gataatggtt tcacgaccgg ttttggcgtc     300
aacttccact tctgcgcgag cgcggatata caccttgccg cgaccggtac ggtaagcttc     360
ttcataccg cgacgaccgt taatgattgc cgccgtcggg aagtccggcc ccggatgtg      420
ttccatcagc ccttcaatgc tgatgtcttc atcatcaata tacgccagac aaccgttgat     480
gacttccgtc aggttgtgcg gcgggatgtt ggttgccata cctacggcga taccggaaga     540
accgttcacc agcaggttag gaattttggt tggcatgacg tccggaattt tttcgtgcc     600
gtcatagtta tcaacgaaat cgaccgtctc tttttcgaga tcggccatca gttcatgggc     660
aattttcgcc agacggattt ccgtataacg cattgccgcc gcagagtcgc cgtcgataga     720
accgaagtta ccctgaccgt ctaccagcat ataacgcagc gagaatggct gcgccatgcg     780
gacgatcgtg tcatagaccg ccgagtcacc atggggatgg tatttaccga ttacgtcacc     840
```

```
aacgacacgg gcagattttt tataggcttt gttccagtca ttgcctagta cgttcatggc      900
gtaaagtacg cgacggtgta ccggcttcag gccatctcgg acatctggca gcgcacggcc      960
aacaatgacc gacatcgcat aatccagata ggagctcttc agctcttcct caatgttgac     1020
cggtgtaatt tctctcgcaa ggtcgctcat                                       1050

<210> SEQ ID NO 141
<211> LENGTH: 1048
<212> TYPE: DNA
<213> ORGANISM: Artificial Sequence
<220> FEATURE:
<223> OTHER INFORMATION: gene editing homology arm pool_5_b2231_right

<400> SEQUENCE: 141
aatgcctgat atactcgttt gtcttgccaa ttacggagta gaagtgccaa tgaatgccga       60
aaaatcgccg gtaaaccata acgtagacca cgaagagatc gctaaatttg aagccgtcgc      120
ctcccgctgg tgggatctgg aaggtgagtt caaaccgctg caccgcatta acccgctgcg      180
tctgggctat attgccgagc gtgctggcgg tttatttggc aaaaaggtgc tcgatgtcgg      240
ttgtggcggc ggcattctgg ccgagagtat ggcgcgcgaa ggcgcgacgg tgaccggtct      300
ggatatgggc tttgagccat gcaggtggc aaaactgcac gcactggaaa gcggcattca      360
ggtggattac gtgcaggaaa ccgtggaaga gcacgcggca aaacatgccg ggcagtatga      420
tgtggtgacc tgcatggaga tgctggagca cgtccccgat ccgcagtcag tggtcagagc      480
ctgtgcgcaa ctggtgaaac caggcggcga tgtcttttc tcgacactta accgcaacgg      540
caagtcatgg ctgatggcgg tggttggtgc ggaatatatt ttgcgcatgg tgcccaaagg      600
cacgcatgat gtgaagaagt ttattaaacc ggcagaattg ctgggctggg tggatcagac      660
cagtttaaaa gagcggcata tcactgggct gcattacaac ccgatcacta atacttttaa      720
actcggcccc ggcgtggatg tgaactatat gctgcacacg cagaataagt gaggttgatg      780
tttggccgcg ccaatgcctg atgcgacgct tgccgcgtct tatcaggcct acaaatgctc      840
cccgtaggcc ggataaggcg tttacgccgc atccggcaac cgtgccgact agacagtgat      900
taccatttca ccgtcatcga caaaaaccct gccgtctggg caaaatcatc actcccttc       960 tgccacgcca cgctgccgcg cagggacact cgctgactga tattgcccgt gactcccact     1020
tttatttcac cccgttgctt caccgcat                                        1048

<210> SEQ ID NO 142
<211> LENGTH: 1050
<212> TYPE: DNA
<213> ORGANISM: Artificial Sequence
<220> FEATURE:
<223> OTHER INFORMATION: gene editing homology arm pool_5_b1622_left

<400> SEQUENCE: 142
attatctcct cgctggtgat gggccttgtc ggcctggtga ttccattagt ctggccgatt       60
ttcgccatgg gtattagcgg cttgggccat atgataaaca gcgcgggtga tttcggaccg      120
atgctgtttg gtaccggtga acgtctgctg ttgccgtttg gtctgcatca cattctggtg      180
gcattaattc gctttaccga cgcaggcggc acgcaggaag tctgcggtca aaccgtcagc      240
ggcgcactga ccatcttcca ggcgcaattg agttgcccga ccactcacgg ttttttctgaa     300 agcgccacgc gtttccttc gcaaggtaaa atgcctgcgt ttctcggcgg tctgccaggt      360
gcagcgttag ctatgtatca ctgcgcgcgc ccggaaaatc gccataaaat taaaggtctg      420
```

```
ctgatttctg gcctgatcgc ctgcgtcgtt ggcggcacta ccgaaccgct ggaattcctg    480
ttcctgttcg tagcgccagt tctgtatgtc atccacgcgc tgttaaccgg cctcggcttc    540
accgtcatgt ctgtgctcgg cgtcaccatc ggtaataccg acggcaatat catcgacttc    600
gtggtgttcg gtattttgca tggtctgtca accaagtggt acatggtgcc agtggtggcg    660
gcaatctggt ttgtcgttta ctacgtcatc ttccgtttcg ctatcacccg cttcaatctg    720
aaaaccccgg ggcgcgatag cgaagttgcc agctcaatcg aaaaagccgt tgccggtgcg    780
ccgggtaaat caggttacaa cgttcctgca atcctcgaag cattaggcgg tgccgacaat    840
attgtcagcc tcgataactg cattacccgt ctgcgtttgt ctgtgaaaga tatgtcgctt    900
gttaatgtgc aggcactgaa ggacaatcgg gcaattggcg tagtacaact taatcaacat    960
aacctgcagg ttgttatcgg gccacaagtt cagtcagtaa aagatgaaat ggccggtctg   1020
atgcatactg tccaggcata aggataagat                                   1050
```

<210> SEQ ID NO 143
<211> LENGTH: 1050
<212> TYPE: DNA
<213> ORGANISM: Artificial Sequence
<220> FEATURE:
<223> OTHER INFORMATION: gene editing homology arm pool_5_b1622_right

<400> SEQUENCE: 143

```
atgttcgatt tttcaaaggt cgtggatcgt catggcacat ggtgtacaca gtgggattat     60
gtcgctgacc gtttcggcac tgctgacctg ttaccgttca cgatttcaga catggatttt    120
gccactgccc cctgcattat cgaggcgctg aatcagcgcc tgatgcacgg cgtatttggc    180
tacagccgct ggaaaaacga tgagtttctc gcggctattg cccactggtt ttccacccag    240
cattacaccg ccatcgattc tcagacggtg gtgtatggcc cttctgtcat ctatatggtt    300
tcagaactga ttcgtcagtg gtctgaaaca ggtgaaggcg tggtgatcca cacacccgcc    360
tatgacgcat tttacaaggc cattgaaggt aaccagcgca cagtaatgcc cgttgctttc    420
gagaagcagg ctgatggttg gttttgcgat atgggcaagt tggaagccgt gttggcgaaa    480
ccagaatgta aaattatgct cctgtgtagc ccacagaatc ctaccgggaa agtgtggacg    540
tgcgatgagc tggagatcat ggctgacctg tgcgagcgtc atggtgtgcg ggttatttcc    600
gatgaaatcc atatggatat ggtttggggc gagcagccgc atattccctg gagtaatgtg    660
gctcgcggag actgggcgtt gctaacgtcg ggctcgaaaa gtttcaatat tcccgccctg    720
accggtgctt acgggattat agaaaatagc agtagccgcg atgcctattt atcggcactg    780
aaaggccgtg atgggctttc ttccccttcg gtactggcgt taactgccca tatcgccgcc    840
tatcagcaag gcgcgccgtg gctggatgcc ttacgcatct atctgaaaga taacctgacg    900
tatatcgcag ataaaatgaa cgccgcgttt cctgaactca actggcagat cccacaatcc    960
acttatctgg catggcttga tttacgtccg ttgaatattg acgacaacgc gttgcaaaaa   1020
gcacttatcg aacaagaaaa agtcgcgatc                                    1050
```

<210> SEQ ID NO 144
<211> LENGTH: 1050
<212> TYPE: DNA
<213> ORGANISM: Artificial Sequence
<220> FEATURE:
<223> OTHER INFORMATION: gene editing homology arm pool_6_b1857_left

<400> SEQUENCE: 144

```
agcgacggcc agagtaagaa cggtgagcga ccccaacata acgcggtgtg gtcgcggtaa     60
```

```
attattaaac gccagggcga cagagcgggc tatctgttgc acgtaatcac ttcctcatta      120
atctcctttc aggcagctcg catactggtt ggctaattga ctcaggaatt ctgaatagct      180
tgttttaccc agtttgatat tcgtccccag gggatccaac gttcccatac gaacggatgt      240
ccctcgtgcg acgctctcaa cgaccgctgg cctgaactgt ggctcagcaa aaacgcaggt      300 tgcttttttgc tcaaccaact gtgttcttat ttcatgtaaa cgctgcgcgc caggttgaat     360
ctcagggtta acgtaaaat gaccaagcgg tgtcagtcca aactgttttt cgaaatagcc       420
gtaagcatcg tgaaaaacga ataaccttt ccccttgagc ggcgcgagct cgttaccaac       480
ctgcgtttcg gttgaggcta attgtgcctc aaaatccttc aggttggcgt caagtttggc      540
tcgactttgc ggcataagtt ccactaattt tccatggatt gcaaccgctg tagcccgcgc      600
tatctctggg gaaagccaaa gatgcatgtt gaaatcgccg tgatggtgat cttcgtcact      660
tttttccgcg tggtcgtgat catcatcatc gccgtgaata cttttcatca gtagcggttt      720
cacatcttca agctgcgcaa tcgttacctg cttcgctcct ggtaatttgc ttaccggttt      780
ttgcataaac gcttccatct ccgggccaac ccaaacgact aagtccgcgt tctgtaagcg      840
ttttacatcc gatgggcgca gtgaataatc atgttctgaa gcgccgtcag gaagtaaaac      900
ctctgtttct gttaccccat cagcaatggc agaagcgatg aacccaacgg gtttaagcga     960
agcgacaacg gcggcatctg cggcctgtgt tgcacctccc cagagagcgg cggataatgc    1020
tgcgaaaaga agcgtttttt tatgtaacat                                     1050
```

<210> SEQ ID NO 145
<211> LENGTH: 1031
<212> TYPE: DNA
<213> ORGANISM: Artificial Sequence
<220> FEATURE:
<223> OTHER INFORMATION: gene editing homology arm pool_6_b1857_right

<400> SEQUENCE: 145

```
aatgcgacca ataatcgtaa tgaatatgag aagtgtgata ttataacatt tcatgactac       60
tgcaagacta aaattaacat gacaagtctg gtttccctgg aaaatgtctc ggtttctttt      120
ggccaacgcc gcgtcctctc tgatgtgtcg ctggaactta aacctggaaa aattttgact      180
ttacttgggc caaatggcgc aggtaagtcg acactggtac gggtagtgct cgggctggta      240
acacccgatg aaggggttat caagcgcaac ggaaaactgc gcatcggcta tgtaccgcag      300
aagctgtatc tcgacaccac gttgccactg accgtaaacc gttttttacg cttacgccct      360
ggtacacata aagaagatat tttgcctgca ctgaaacgtg tccaggccgg gcacctgatt      420
aacgcaccga tgcaaaagct ctctggtggc gaaacgcagc gtgtactatt agcgcgagca      480
ttgttaaatc gcccgcaatt attagtgctg gatgaaccca tcaaggcgt ggatgtaaat       540 ggccaggtgg cgttatatga ccttattgac caactgcgtc gtgaactgga ttgtggcgtt      600
ttaatggttt ctcacgatct gcatctggtg atggcaaaaa ccgatgaagt gctgtgcctg      660
aatcaccaca tttgttgttc cggcacaccg gaagttgttt ccctgcatcc ggagtttatt      720
tcaatgtttg gtcctcgtgg tgctgaacaa ctgggtatct atcgccatca tcataaccat      780
cgtcacgatt tacagggacg aattgttttg cgtcggggaa atgatcgctc atgattgaat     840
tattatttcc cggttggtta gccgggatca tgctcgcctg tgccgcgggt ccgctgggtt     900
cgtttgtagt ctggcgtcgt atgtcttatt tcggtgatac gctggctcat gcctcattac    960
ttggcgtcgc gtttggtttg ttgctggacg tgaatccatt ctatgcggtg attgccgtta   1020
```
cgctgctgct g                                                          1031

<210> SEQ ID NO 146
<211> LENGTH: 1050
<212> TYPE: DNA
<213> ORGANISM: Artificial Sequence
<220> FEATURE:
<223> OTHER INFORMATION: gene editing homology arm pool_6_b4024_left

<400> SEQUENCE: 146
tgccacgctc acttctgacg tggtgattaa gtctaccgaa atattatgcc gcgcgaggat      60
gccgaaaact tccgcgagga aaccgcgaga atgcagcata ttcaggctgt gcaaagtgag     120
cagagtctga ttgcgacgaa gcgccagagc gcggaacagc ggcggatttt cagttttatt     180
gcacaccagc gtaccacctg cgcgtgggtc tttgctggag ccgacaaaga ccgggatatc     240
gctgcgtact gcgggtagca acgttgccgg atgcagtact tttgcaccaa aagttgccat     300
ctctgccgct tcggcaaacg cgatttcatc aatgcgtttt gctgcggaaa ctacgcgtgg     360
atcggtggtg tagatgcccg ggacgtcggt ccagatatca cacgagatg cgtgtaaagc      420
ctccgccagc aaggctgccg tataatcgct gcctccacgg ccaagcgtcg ttgtacgacc     480
tttatttcg ctaccgataa atccctgggt gatcactaag ccttcattga cgtgggag        540
cagctgcagc gcggccagtt ccgccagcgc ggctatatct ggctctgcac gaccaaatcg     600
gtcgttggta cgcatcactt tacgtacatc aaaccactgt gcctgaacat cgcgttcgcg     660
caggatctca acaaacagca gggtcgacat cagctcgccg tggctgacca gctcatctgt     720
cagcgccgga gacgttgcca gcgccgccgc ttctgccaga acagtaatgt tctccagcag     780
acgttcaatc tcttcacgga taacgttcgg gtaacgcaga cgttccagaa tggcaaactg     840
gatgttgcgg atagcgtcga gttttttcgaa tcgctcgcca ggttccagtc cttcagctaa     900
agcgaccagc agattagtga taccagcaga agccgagagg acaactaaac gcacgttggc     960
atcagaaagc acaatatcag cgctgcggtt catggcgtca aaatcagcta cgctggtacc    1020
gccaaatttg gagacaacaa tttcagacat                                     1050

<210> SEQ ID NO 147
<211> LENGTH: 1050
<212> TYPE: DNA
<213> ORGANISM: Artificial Sequence
<220> FEATURE:
<223> OTHER INFORMATION: gene editing homology arm pool_6_b4024_right

<400> SEQUENCE: 147
aactacctcg tgtcagggga tccattttca gccttggcac aagggaagag cggaagacgg      60
gtgggcgcag agcgatactt cgctactatt ttcacccaga agtgctccac cacttgcgaa     120
acgcccgact gcgaacgctt ctggtgacaa cccaggggat tcagccctg tagccgatga      180
tgaacgtggc cagccgttca atcacctcgg cgatgcaccc cctcaggtgt tatcacagga     240
ctggctcctc caacaccgtt acttgggcaa cgcgcctctt ctggcctgcg ctagcgcagg     300
tagtacattt ataaataaag ggtgagcggg gcggttgtca acgatggggt catgcggatt     360
tttcatccac tcctggcggt cagtagttca gctaataaat gcttcactgc gctaagggtt     420
tacactcaac attacgctaa cggcactaaa accatcacat ttttctgtga ctggcgctac     480
aatcttccaa agtcacaatt ctcaaaatca gaagagtatt gctaatgaaa acatcaatc      540
caacgcagac cgctgcctgg caggcactac agaaacactt cgatgaaatg aaagacgtta     600
cgatcgccga tctttttgct aaagacggcg atcgtttttc taagttctcc gcaaccttcg     660

```
acgatcagat gctggtggat tactccaaaa accgcatcac tgaagagacg ctggcgaaat    720
tacaggatct ggcgaaagag tgcgatctgg cgggcgcgat taagtcgatg ttctctggcg    780
agaagatcaa ccgcactgaa aaccgcgccg tgctgcacgt agcgctgcgt aaccgtagca    840
ataccccgat tttggttgat ggcaaagacg taatgccgga agtcaacgcg gtgctggaga    900
agatgaaaac cttctcagaa gcgattattt ccggtgagtg gaaaggttat accggcaaag    960
caatcactga cgtagtgaac atcgggatcg gcggttctga cctcggccca tacatggtga   1020
ccgaagctct gcgtccgtac aaaaaccacc                                   1050
```

<210> SEQ ID NO 148
<211> LENGTH: 1029
<212> TYPE: DNA
<213> ORGANISM: Artificial Sequence
<220> FEATURE:
<223> OTHER INFORMATION: gene editing homology arm pool_6_b3942_left

<400> SEQUENCE: 148

```
gctgcgggtc tgtacccact catacttgaa caggttctcg aagaaatagt tgctccactg     60
ggtcggcgtc tgggtccaga ctacttccag accagaggta atggcatctg cgccaacgcc    120
gctgccgtaa gtgctcgccc aacctaaacc ttgttcttca atcggtgcag cttctggatc    180
aggacctaca tttgatgtcg gaccggcacc gtgggtttta cccagcgtat gaccacccgc    240
aatcagcgcc acggtttctt cgtcgttcat gcccatgttg ccgaaggtcg cgcggatagc    300
tgctgccgca gaaagcggtt cgccgctgtg atcgggcct tccggttaa cgtaaatcag     360 acccatctcg gttgcaccca gcggtgcttt cgccagcgct tccggatgac ggtgagtcag    420
ccaggctttt tcatcacccc agttaacatc cagatccggt tcccagacgt cttcacgacc    480
ggcaccaaaa ccgaaggtac ggaagccgga gttttctagc gccacgttac ccgcgaggat    540
aaacaggtcg gcccaggaga ttttctgacc atatttctgt ttgattggcc acaacaggcg    600
acgcgcttta tcgaggctta cgttatccgg ccaggagttc agcggtgcaa aacgttgctg    660
accacgaccc gcgccaccgc gtccatcgat tgaacggtaa gtccccgcgc cgtgccaggc    720
catacgaata aacagaccgg cgtaactgcc ccagtcggct ggccaccacg gttgagattc    780
tgtcaacagg gctttcagat cttttttcag gccgtagtaa tctaatttgc tgaattcttt    840
gcggtagtca aagtcctcac ccagtgggtt agaacgatta gaatgttggt ttaacaggtc    900
aacacgaagt tgatttggcc accagtcgcg agtggttgtg cccgcccccg cactctggtc    960
gtgaccgccc tgatggaacg ggcatttgcc agtggctgtg gtgttatgga tatcgtctga   1020
cgtgctcat                                                          1029
```

<210> SEQ ID NO 149
<211> LENGTH: 1045
<212> TYPE: DNA
<213> ORGANISM: Artificial Sequence
<220> FEATURE:
<223> OTHER INFORMATION: gene editing homology arm pool_6_b3942_right

<400> SEQUENCE: 149

```
agttgagatc ttacatattg ttggttaaag agatgtagat caaattgatc ttaattaagc     60 tttttttgatt atgtccgaat tcggacaaat gctttataaa aagggttttt agcttcatat    120
ccttcaagta atgagggaga aaacaaggct gataacctta ttttcccgcc ctcatttcga    180
ggcagcattt tgtgctctgt ttaaaatttg tgatcactgt gtgattttca caaaagccac    240
```

```
actatttata aaccaggtcg aacccccagc gtatggcaaa tcgcgtaact catttcagca      300
cggttaagcg tatagaagtg gaaatctttc actccttcac ggcttaaaat cttcaccata      360
tccatggcaa tattcgcgcc aaccagtttg cgggtttcgg catcatcatc cagaccgtcg      420
aacatttgcg ccatccacgc cggaatacgc acgttggtca tatcggcaaa tttcttcgcc      480
tgtttaaagt tagataccgg caaaattccc ggaataattt ccacatcaat gcccgccgat      540
acacagcggt cacgaaaacg caggtagctt tcgacatcga agaagaactg agtaatcgcg      600
cggttggctc cggcatccac tttgcgtttc agattaagca aatccgcctg agcgcttttt      660
gcttccgggt gaacttccgg atacgccgcc acggagatat cgaaatctgc cacttctttt      720
aacagcgtca ccaggtcaga agcatacatt tctggcttac cacttcccgg cggcagatcg      780
ccacgcagcg ccacgatatg acgaataccg ttattccagt agtcgcgtgc aatggtgcgc      840
agctcgtcgg gcgtcgcatc aatgcaagta agatgcggtg ccgcttccag accagtgcga      900
tctttaatgc ctttaataat gctgtgcgta cggtcgcgct cgccggagtt cgcgccatag      960
gtcaccgata caaacttcgg tttcaggctg ctaaggcgat cgatggagtt ccacagggtc     1020
tgctccattt cactggtacg cggcg                                           1045
```

<210> SEQ ID NO 150
<211> LENGTH: 1050
<212> TYPE: DNA
<213> ORGANISM: Artificial Sequence
<220> FEATURE:
<223> OTHER INFORMATION: gene editing homology arm pool_6_b0592_left

<400> SEQUENCE: 150

```
ttgattatcg gcgtgttgtt attgctggtg ctggtggagt tgcgacattt tcgccagacg       60
ccgccgcagg tgacagcgtc cgacagttaa tgcttaaaac agcgccttaa gcctatccag      120
cacttgcatg gcgctgtagt aatccagacg gaacgtctcg gttcccagcg cataaacctg      180
cttgttttgt actgcaggca ggtgcgcgag cagcggatta gcataaatag catcggcatc      240
tttctgatca ccggcgaaca ggaatagtga ctcgccattt aaccctgcag ccagattttc      300
cccaccaagc tgaatgatgt catggcgttt accctgactt ggctggcat ttaaccctgc       360 gggtaacttc gccagcgtaa agccgagttg ttccagcatc tgcccttgtg ctgattctgg      420
cgtccagaga ttggcactgt gtgcagcggc agtatagaca atggcagtga ccggctgcgg      480
cggtaatttg atttgctctt cgccgccgc cagttgctta tcaaactgcg caatccgctc       540
tgccgcttgt ttctcatgcc cggtaatttc gccaagttgc gttaacagcg actgccagct      600
tttgtcgtcg taattgatga ttaatgtcgg ggcgatggtg gaaagctgat catacagtgc      660
cagcgccgaa tccccgccgg ttgcgctaat taaaatcaga tccggcattt gcgcggcaac      720
ggcttcggcg ctcggttcgc cgatatagag ccgttgcagt ttgcgttctt tcgccacctt      780
gctccactgg cgtaaaaagc cctggtcatc cgcgacgcgg ttattcggcg tggtcgcgcc      840
gctggcgatc accggagcat caatcgccag cagtgagccg gtcagggtga cgctggtgga      900
aacaatacgc tgcggctggc tttccagtgt atgtgtgcca cggctgtcag taatctgacg      960
cggccagtca gcggcctgaa ctgcggctat tcctgaaagc aaaagtcctg ttaatagaag     1020
ggcgttgcgg tagagcgggg cgagtctcac                                      1050
```

<210> SEQ ID NO 151
<211> LENGTH: 1050
<212> TYPE: DNA
<213> ORGANISM: Artificial Sequence
<220> FEATURE:
<223> OTHER INFORMATION: gene editing homology arm pool_6_b0592_right

<400> SEQUENCE: 151

| | |
|---|---|
| aaatcagctt cctgttatta ataaggttaa gggcgtaatg acaaattcga caaagcgcac | 60 |
| aatccgtccc ctcgcccctt tggggagagg gttagggtga ggggaacagc cagcactggt | 120 |
| gcgaacatta accctcaccc cagccctcac cctggaaggg agaggggggca gaacggcgca | 180 |
| ggacatcaca ttgcgcttat gcgaatccat caataatgct tctcattttc attgtaacca | 240 |
| caaccagatg caaccccgag ttgcagattg cgttacctca agagttgaca tagtgcgcgt | 300 |
| ttgcttttag gttagcgacc gaaaatataa atgataatca ttattaaagc ctttatcatt | 360 |
| ttgtggagga tgatatggat acgtcactgg ctgaggaagt acagcagacc atggcaacac | 420 |
| ttgcgcccaa tcgcttttc tttatgtcgc cgtaccgcag ttttacgacg tcaggatgtt | 480 |
| tcgcccgctt cgatgaaccg gctgtgaacg gggattcgcc cgacagtccc ttccagcaaa | 540 |
| aactcgccgc gctgtttgcc gatgccaaag cgcagggcat caaaaatccg gtgatggtcg | 600 |
| gggcgattcc cttcgatcca cgtcagcctt cgtcgctgta tattcctgaa tcctggcagt | 660 |
| cgttctcccg tcaggaaaaa caagcttccg cacgccgttt cacccgcagc cagtcgctga | 720 |
| atgtggtgga acgccaggca attccggagc aaaccacgtt tgaacagatg gttgcccgcg | 780 |
| ccgccgcact taccgccacg ccgcaggtcg acaaagtggt gttgtcacgg ttgattgata | 840 |
| tcaccactga cgccgccatt gatagtggcg tattgctgga acggttgatt gcgcaaaacc | 900 |
| cggttagtta caacttccat gttccgctgg ctgatggtgg cgtcctgctg ggggccagcc | 960 |
| cggaactgct gctacgtaaa gacggcgagc gttttagctc cattccgtta gccggttccg | 1020 |
| cgcgtcgtca gccggatgaa gtgctcgatc | 1050 |

<210> SEQ ID NO 152
<211> LENGTH: 1024
<212> TYPE: DNA
<213> ORGANISM: Artificial Sequence
<220> FEATURE:
<223> OTHER INFORMATION: gene editing homology arm pool_6_b1415_left

<400> SEQUENCE: 152

| | |
|---|---|
| gcatttcctt aaaagatatg tcaggcttgc ggagtggcgg ttaaggacat acgatttcct | 60 |
| cctttcagag tgctccgctt ctcactatta tctcacgcag tattcttaag ggaacgataa | 120 |
| ggaggaacca tgaacattac cccgtttccg acgctttcgc cggcaactat agatgccata | 180 |
| aatgttatcg gacagtggct ggcgcaggat gatttctccg gtgaggtgcc gtatcaggcc | 240 |
| gattgcgtga tccttgcagg caatgcggtt atgccgacta tcgatgcggc atgtaagatt | 300 |
| gcccgcgatc agcaaattcc tttactgatt agtggtggta tcggtcactc gacaactttt | 360 |
| ttgtatagcg ccatcgcaca gcatccgcac tacaacacta tccgcaccac tggcagagca | 420 |
| gaagcgacca tcctggcgga tatcgctcat cagttctggc acattccgca tgaaaaaatc | 480 |
| tggattgaag accagtcaac aaactgcggt gaaaacgcac gctttagcat cgcgctattg | 540 |
| aatcaggccg tagaacgagt tcatacggct atcgttgttc aggaccccac catgcagcgg | 600 |
| cgcacgatgg cgacgttccg ccgtatgact ggggacaatc ccgatgcacc acgctggtta | 660 |
| agttatcccg gattcgttcc tcagttagga aataacgcag acagtgtaat ctttattaat | 720 |
| cagttacaag gattatggcc agttgagcgt tatctctcac tactcactgg cgagctgccg | 780 |
| cgtttacgcg atgatagcga tggctacggt ccccgcgggc gagatttat cgttcacgtt | 840 |

| | |
|---|---|
| gattttccgg cagaagtcat ccatgcatgg caaacgctga acatgatgc ggtgctcatc | 900 |
| gaggcgatgg aaagtcgctc gttacgttaa aaattgcccg tttgtgaacc acttgtttgc | 960 |
| aaacgggcat gactcctgac ttttatttct gccttttatt ccttttacac ttgttttat | 1020 |
| gaag | 1024 |

<210> SEQ ID NO 153
<211> LENGTH: 1050
<212> TYPE: DNA
<213> ORGANISM: Artificial Sequence
<220> FEATURE:
<223> OTHER INFORMATION: gene editing homology arm pool_6_b1415_right

<400> SEQUENCE: 153

| | |
|---|---|
| atgtcagtac ccgttcaaca tcctatgtat atcgatggac agtttgttac ctggcgtgga | 60 |
| gacgcatgga ttgatgtggt aaaccctgct acagaggctg tcatttcccg catacccgat | 120 |
| ggtcaggccg aggatgcccg taaggcaatc gatgcagcag aacgtgcaca accagaatgg | 180 |
| gaagcgttgc ctgctattga acgcgccagt tggttgcgca aatctccgc cgggatccgc | 240 |
| gaacgcgcca gtgaaatcag tgcgctgatt gttgaagaag ggggcaagat ccagcagctg | 300 |
| gctgaagtcg aagtggcttt tactgccgac tatatcgatt acatggcgga gtgggcacgg | 360 |
| cgttacgagg gcgagattat tcaaagcgat cgtccaggag aaaatattct tttgtttaaa | 420 |
| cgtgcgcttg gtgtgactac cggcattctg ccgtggaact cccgttctt cctcattgcc | 480 |
| cgcaaaatgg ctcccgctct tttgaccggt aataccatcg tcattaaacc tagtgaattt | 540 |
| acgccaaaca atgcgattgc attcgccaaa atcgtcgatg aaataggcct tccgcgcggc | 600 |
| gtgtttaacc ttgtactggg gcgtggtgaa accgttgggc aagaactggc gggtaaccca | 660 |
| aaggtcgcaa tggtcagtat gacaggcagc gtctctgcag gtgagaagat catggcgact | 720 |
| gcggcgaaaa acatcaccaa agtgtgtctg gaattggggg gtaaagcacc agctatcgta | 780 |
| atggacgatg ccgatcttga actggcagtc aaagccatcg ttgattcacg cgtcattaat | 840 |
| agtgggcaag tgtgtaactg tgcagaacgt gtttatgtac agaaaggcat ttatgatcag | 900 |
| ttcgtcaatc ggctgggtga agcgatgcag gcggttcaat tggtaaccc cgctgaacgc | 960 |
| aacgacattg cgatggggcc gttgattaac gccgcggcgc tggaaagggt cgagcaaaaa | 1020 |
| gtggcgcgcg cagtagaaga aggggcgaga | 1050 |

<210> SEQ ID NO 154
<211> LENGTH: 1048
<212> TYPE: DNA
<213> ORGANISM: Artificial Sequence
<220> FEATURE:
<223> OTHER INFORMATION: gene editing homology arm pool_6_b1762_left

<400> SEQUENCE: 154

| | |
|---|---|
| caggcgttta tgagtattta acggatgatg ctccccacgg aacatttctt atgggccaac | 60 |
| ggcatttctt actgtagtgc tcccaaaact gcttgtcgta acgataacac gcttcaagtt | 120 |
| cagcatccgt taactttctg cgatagcagc agatatgcca gtaaagaaat cccatttgac | 180 |
| tatttttttg ataatcttct tcgctttcga caaactcgtg cgcctttcga gaagcaagca | 240 |
| ttatataatg ccaggccagt tcttcttcaa ttgtcccgtt ttgaaaagct gtgcttgata | 300 |
| tcgagatcat ccatgataat tccgccgccc atattagctt cgccgaggat ttaccggagc | 360 |
| tatgattagc gcaatcagag atatagtctg agggaaaaac agcaaattta ttcaacaagg | 420 |
| cgataaccctg ctctggggct tcctccatgt ttgctttaaa ggtattggct ccatggtcgc | 480 |

```
cagaaagaaa atgctccatt aaggcacaat aactttcgct atcttcgata ccccattgat      540
cctctaaaga ctcgcgtctt ttacttatga tatcgatcga gtcaaaagga agcacatgat      600
attggaaggt atctttgcca ggttcaggct ttcgcggcca gaactccagc gtttcagacc      660
attgcttatg atagaatcga taaggtgcga tcaattgtag cgcctgtaac ttctcgatac      720
tgagcggctc aatacccttta gcctgataat aatgcagttg ttctttttt gctttaaaac       780 cggcccgaac aataagcccc atcataatta atagataaag aaaagagcat cccgcgtaa       840 tcaggcctct ttcattcaaa ccgttggatg ttatcgctgc gaacacaaac attacagcga      900
caacacatgt taaataaaac ccccacttac aaagcagcat ggccttattt tctttaatca       960
tccgttcaaa attactatta aatatttccc agccattaaa agaatacttc tcgctcccag      1020
gatggttttg taataaaact tttttcat                                        1048

<210> SEQ ID NO 155
<211> LENGTH: 1050
<212> TYPE: DNA
<213> ORGANISM: Artificial Sequence
<220> FEATURE:
<223> OTHER INFORMATION: gene editing homology arm pool_6_b1762_right

<400> SEQUENCE: 155
tcagaatatg actcgaatag cacgaaagat tcactcgctt acgctatcgc cccgcttccg        60
acttcatctg ctggcggact ttttttcgca ctacgtttac gcggtgcagc ctttttctta      120
tcagcactgc caccactgcc cggagccaca atgccgcgaa actgccgcac cggcgtacgt      180
ttggcttgat caataagctg atatagcgtc cccaccagcg gctgcataaa gtcctgatag      240
cgacactgct tttcgctgat ttgcgtcagc accgattccc agtgcgcggt catgtccggt      300
cgcgtcgcca tctccggcag cgaatggaat agcgcttttc cggcgtcggt ggagtggata      360
tagcgccctt ttttggtcag gaaaccacgc ttgaacaaca gttcaataat cccggcacgc      420
gttgcctctg tccccagacc atcggtcgca cggaggatct ttttcagatc tttatcctgc      480
acaaagcgcg cgatcccggt catcgccgaa agcagtgttg catcggtaaa atggcgcggc      540
ggctgggttt gccgctctac cacttcacct ttttcacaca gcaactcatc gcctttcgcc      600
accacaggca gtggcgtgcc gtcgttttct tcatcgcgct ctttgctgcc taacagcgtg      660
cgccagcctt cttcagcaag aaaacgcgct ttagcgacaa atttgccttt ggcaatgtcc      720
agttcgataa cacacttgcg gaacaccgca tccgggcaga attgcatcag atactgacgg      780
gcaatcaggt tatagacctt cgcttcgttc tccgtcaggt tgatcgcaga actccgtgcg      840
gtcggaatga tggcgtggtg cgcatcgacc ttttttgtcat cccaacagcg gttgcgtata      900
tctggatcta ccactggctg cggcaacaga tccggtgcat gaacactgat ggcattcatc      960
accgcgtggc gtccggcaaa atgttcttct ggcaaatagc gacaatcaga acgcggataa     1020
gtgattagct tgtgcgtttc gtacagtttc                                     1050

<210> SEQ ID NO 156
<211> LENGTH: 1050
<212> TYPE: DNA
<213> ORGANISM: Artificial Sequence
<220> FEATURE:
<223> OTHER INFORMATION: gene editing homology arm pool_6_b3414_left

<400> SEQUENCE: 156
gcattaatcc aacagcaagc gccacgagga cgagagcgat gaagccgttc attttgaagc        60
```

```
ggatcatcag gagcaacaac aagattacac cgatagcaac aatgactaat ggcatgattt    120
acctggcctt tcatttgtta tgggtaacgt caattttctg acgacaaact ctaattatcc    180
caatcgggaa cagagatatt gcggcaccac gactgatacc cactaaaact aattattgta    240
gtcagatgtc aggagtatgt ttggtaccca tgtgaatgat acgggtaaca tctggcgttt    300
gagaatcacc agagcggggt aaatttaaat tatgagaggt tggtcatatt atcgcgggga    360
aacgaaccga ggatttgaca aagcaatgct gcgccaacgt ctggcacatg ttcaacgtag    420
gcccgaaatg acgctttagc gtcgcatcgg gcaatctaca aaagagggga taacttagta    480
gtaggagtgt tcgccgcgct ggtgttcggt gagatcgcgc acacctttca gctccgggaa    540
ttcgttcagc agctgcttct cgatcccttc tttcagcgtc acatcgacca tggaacaacc    600
gttacagccg ccgccaaatt gcagaatggc gtaaccgtct tcggtgattt ccatcagcga    660
aacgcgacca ccgtgaccag caagctgtgg gttgatctgc gactgcagca tatactccac    720
gcgctccatc agcggtgcat cgtctgccac tttacgcatt ttggcgttcg ggctttcag    780
cgttaactgg gaacccaact ggtcggtaac aaaatcgatc tctgcatctt ccaggtatgg    840
tgcgcttaac tcatcaacat acgcggtcag caggtcaaat ttcagggctg tgtcggtggc    900
ttccacagcg tccggcggac aataagaaac gccacattca gcgttaggcg tgccagggtt    960
aatcacaaat acgcggattt gtgtcccttc ttcctgattt gccagcagtt tggcaaagtg   1020
cgcttgtgca gcatcggaaa tacggatcat                                    1050
```

<210> SEQ ID NO 157  
<211> LENGTH: 1032  
<212> TYPE: DNA  
<213> ORGANISM: Artificial Sequence  
<220> FEATURE:  
<223> OTHER INFORMATION: gene editing homology arm pool_6_b3414_right

<400> SEQUENCE: 157

```
agtaatggcc taatagttga ctattttagt tggttataat acgcccatca tcgaggctct     60
acaaggttcg acaaaggcac cagacctgga cagccgccgc accattgcgt aaaagcaact    120
gcgcaatctc tgcgacggta cttccggtgg taacgacatc atccacaatc accatatggc    180
gaccttgcac gggcaattca agacgaaagg cattttcag gttgcgcttg cgcagccggg    240
cactgagaaa atgctgggtc gcagtggccc gtgtacgtgt gacggcttcg ctatcccatt    300
ggcagtgcaa ccagcgtgat aacggctgac acagcaaatc gctctgatta atccccgac    360
gccagtgacg ccgctgccat aacgaacgc tgacgatgcg atccggcaat tgcaacccgg    420
tggtgcgacg agcgtgtaag acttccaata gtaacagacg tgacagggcg ctggcgattt    480
cactgcgccg ggaaaattta agctggtgga taagcggact taacggcggc gcatagtcgg    540
caaccgtgac cagtctttgc cagggcggcg ttttttgcag gcagcgaccg cagggaagat    600
gggagtgtgt ggcgggtaat ccacattgtg ggcataacgt tttatctgtg cgggtggcgc    660
gtgaacagac cgaacaaatc ccccaatgac ctaacgccag tggcattcgg catagccagc    720
ataatcccgg tactgttagc atatgttcat ccttgtaagt caaaagagaa caatagcgga    780
tgaataacat ctggtggcag accaaaggtc aggggaatgt tcatcttgtg ctgctgcacg    840
gatggggact gaatgccgaa gtgtggcgtt gcattgacga ggaacttagc tcgcatttta    900
cgctgcacct tgttgacctg cccggcttcg ggcgtagccg gggatttggt gcgctgtcac    960
ttgctgtatat ggccgaagcc gtgctgcaac aggcacctga taaagccatt tggttaggct   1020
ggagtctggg cg                                                       1032
```

<210> SEQ ID NO 158
<211> LENGTH: 1049
<212> TYPE: DNA
<213> ORGANISM: Artificial Sequence
<220> FEATURE:
<223> OTHER INFORMATION: gene editing homology arm pool_6_b4374_left

<400> SEQUENCE: 158

```
gcgggcaggt catcctgtaa gtctccggca aacagaatac ggctttgttc gaaatcatca      60
ctgtgacgca gcaagacttc acttgccggg gtaaatgcag acatggaatg ctcctcaatt     120
gatactggcg gcgattatag ccatatgttg gcgcggtatc gacgaatttg ctatatttgc     180
gccccctgaca acaggagcga ttcgctatga catcccgacg agactggcag ttacagcaac     240
tgggcattac ccagtggtcg ctgcgtcgcc tggcgcgtt gcaggggag attgccattg      300
cgatcccggc acacgtccgt ctggtgatgg tgcaaacga tcttcccgcc ctgactgatc     360
ctttagtgag cgatgttctg cgcgcattaa ccgtcagccc cgaccaggtg ctgcaactga     420
cgccagaaaa aatcgcgatg ctgccgcaag gcagtcactg caacagttgg cggttgggta     480
ctgacgaacc gctatcactg gaaggcgctc aggtggcatc accggcgctc accgatttac     540
gggcaaaccc aacggcacgc gccgcgttat ggcaacaaat ttgcacatat gaacacgatt     600
tcttccctcg aaacgactga tttaccggcg gcttaccaca ttgaacaacg cgcccacgcc     660
tttccgtgga gtgaaaaaac gtttgccagc aaccagggcg agcgttatct caactttcag     720
ttaacgcaaa acggcaaaat ggcggcgttt gcgattacgc aagtggtgct ggatgaagct     780
acattgttca atattgcggt cgatcctgac tatcagcgtc agggattggg aagggcgctg     840
ctggaacatc tgatcgacga actggaaaaa cgcggcgtgg cgacactatg ctggaagtc     900
cgtgcttcaa acgctgccgc cattgccctg tacgaaagtt taggctttaa cgaggcgacg     960
attcgccgca attactaccc caccacggac ggtcgcgaag acgccatcat catggcgttg    1020
ccaatcagta tgtaatacaa ggtggaata                                       1049
```

<210> SEQ ID NO 159
<211> LENGTH: 1037
<212> TYPE: DNA
<213> ORGANISM: Artificial Sequence
<220> FEATURE:
<223> OTHER INFORMATION: gene editing homology arm pool_6_b4374_right

<400> SEQUENCE: 159

```
atgaagtggg actggatttt ctttgatgcc gatgaaacgc tgtttacctt tgactcattc      60
accggcctgc agcggatgtt tcttgattac agcgtcacct ttaccgctga agattttcag     120
gactatcagg ccgttaacaa gccactgtgg gtggattatc aaaacggcgc gatcacttca     180
ttacagcttc agcacgggcg gtttgagagc tgggccgaac ggctgaacgt cgagccaggt     240
aaactcaacg aagcctttat taatgcgatg gcggaaatct gcacgccgct gccgggcgcg     300
gtttctctgc ttaacgccat tcgtggcaac gccaaaatcg gcatcatcac caacggcttt     360
agtgccttgc aacaggtgcg tctggaacgc acgggcctgc gtgattactt cgatttgctg     420
gtgatttccg aagaagttgg cgttgccaaa ccgaataaga aaattttcga ttatgcgctg     480
gaacaggcgg gcaatcctga ccgttcacgc gtgctgatgg ttggcgacac tgccgagtcc     540
gatattctcg gtggcatcaa cgccgggctt gcgacctgct ggctgaatgc acaccatcgc     600
gagcaaccag aaggcatcgc gcccacctgg accgtttctt cgttgcacga actggagcag     660
```

```
ctcctgtgta aacactgatt gcctccccc cgttgatggg taaaatagcc gcaattttc      720 gttttcaaca agcgcggcgc gatgccgctt actcaagaag aaagaattat gacgttgtct      780
ccttatttgc aagaggtggc gaagcgccgc acttttgcca ttatttctca cccggacgcc      840
ggtaagacta ccatcaccga gaaggtgctg ctgttcggac aggccattca gaccgccggt      900
acagtaaaag gccgtggttc caaccagcac gctaagtcgg actggatgga gatggaaaag      960
cagcgtggga tctccattac tacgtctgtg atgcagtttc cgtatcacga ttgcctggtt     1020
aacctgctcg acacccc                                                   1037
```

<210> SEQ ID NO 160
<211> LENGTH: 1050
<212> TYPE: DNA
<213> ORGANISM: Artificial Sequence
<220> FEATURE:
<223> OTHER INFORMATION: gene editing homology arm pool_6_b2917_left

<400> SEQUENCE: 160

```
acgtgaacga ggatttgagc gcgcggcaca aaagctgtgc attacacaat cagccgtctc       60
acagcgcatt aagcaactgg aaaatatgtt cgggcagccg ctgttggtgc gtaccgtacc      120
gccgcgcccg acgaacaag gcaaaaact gctggcactg ctgcgccagg tggagttgct       180
ggaagaagag tggctgggcg atgaacaaac cggttcgact ccgctgctgc tttcactggc      240
ggtcaacgcc gacagtctgg cgacgtggtt gcttcctgca ctggctcctg tgttggctga      300
ttcgcctatc cgcctcaact tgcaggtaga agatgaaacc cgcactcagg aacgtctgcg      360
ccgcggcgaa gtggtcggcg cggtgagtat tcaacatcag gcgctgccga ttgtcttgt       420 cgataaactt ggtgcgctcg actatctgtt cgtcagctca aaaccctttg ccgaaaaata      480
tttccctaac ggcgtaacgc gttcggcatt actgaaagcg ccagtggtcg cgtttgacca      540
tcttgacgat atgcaccagg cctttttgca gcaaaacttc gatctgcctc caggcagcgt      600
gccctgccat atcgttaatt cttcagaagc gttcgtacaa cttgctcgcc agggcaccac      660
ctgctgtatg atcccgcacc tgcaaatcga gaaagagctg gccagcggtg aactgattga      720
cttaacgcct gggctatttc aacgacggat gctctactgg caccgctttg ctcctgaaag      780
ccgcatgatg cgtaaagtca ctgatgcgtt actcgattat ggtcacaaag tccttcgtca      840
ggattaatcc atcaaataat gcctgatagc acatatcagg cgttgtcctc acttctttt       900 gtattccttg aatcacatca caaaatagac aaatctcagg cggcaaaaaa cgacgtctga      960
atgcattttt tttgctggcg acaaacccac gtaaaagct caccgtaggc gcaaataccc      1020
tcattttgat tgcgttttac ggagcaaata                                     1050
```

<210> SEQ ID NO 161
<211> LENGTH: 1033
<212> TYPE: DNA
<213> ORGANISM: Artificial Sequence
<220> FEATURE:
<223> OTHER INFORMATION: gene editing homology arm pool_6_b2917_right

<400> SEQUENCE: 161

```
atgtctaacg tgcaggagtg gcaacagctt gccaacaagg aattgagccg tcgggagaaa       60
actgtcgact cgctggttca tcaaaccgcg gaagggatcg ccatcaagcc gctgtatacc      120
gaagccgatc tcgataatct ggaggtgaca ggtaccttc ctggtttgcc gccctacgtt       180
cgtggcccgc gtgccactat gtataccgcc caaccgtgga ccatccgtca gtatgctggt      240
ttttcaacag caaagagtc caacgctttt tatcgccgta acctggccgc cgggcaaaaa      300
```

```
ggtctttccg ttgcgtttga ccttgccacc caccgtggct acgactccga taacccgcgc    360
gtggcgggcg acgtcggcaa agcgggcgtc gctatcgaca ccgtggaaga tatgaaagtc    420
ctgttcgacc agatcccgct ggataaaatg tcggtttcga tgaccatgaa tggcgcagtg    480
ctaccagtac tggcgtttta tatcgtcgcc gcagaagagc aaggtgttac acctgataaa    540
ctgaccggca ccattcaaaa cgatattctc aaagagtacc tctgccgcaa cacctatatt    600
tacccaccaa aaccgtcaat gcgcattatc gccgacatca tcgcctggtg ttccggcaac    660
atgccgcgat ttaataccat cagtatcagc ggttaccaca tgggtgaagc gggtgccaac    720
tgcgtgcagc aggtagcatt tacgctcgct gatgggattg agtacatcaa agcagcaatc    780
tctgccggac tgaaaattga tgacttcgct cctcgcctgt cgttcttctt cggcatcggc    840
atggatctgt ttatgaacgt cgccatgttg cgtgcggcac gttatttatg agcgaagcg    900 gtcagtggat ttggcgcaca ggacccgaaa tcactggcgc tgcgtaccca ctgccagacc    960
tcaggctgga gcctgactga acaggatccg tataacaacg ttatccgcac caccattgaa   1020
gcgctggctg cga                                                      1033

<210> SEQ ID NO 162
<211> LENGTH: 1047
<212> TYPE: DNA
<213> ORGANISM: Artificial Sequence
<220> FEATURE:
<223> OTHER INFORMATION: gene editing homology arm pool_6_b0346_left

<400> SEQUENCE: 162
tcgtataacg ttactggttt cacattcacc accctgaatt gactctcttc cgggcgctat     60
catgccatac cgcgaaaggt tttgcgccat tcgatggtgt caacgtaaat gcatgccgct    120
tcgccttccg gccaccagaa tagcctgcga ttcaaccct tcttcgatct gttttgctac    180
ccgttgtagc gccggaagat gcttttccgc tgcctgttca atggtcattg cgctcgccat    240
atacaccaga ttcagacagc caatcacccg ttgttcactg cgcagcggta cggcgataga    300
ggcgatcttc tcctcctgat cccagccgcg gtagttctgt ccgtaaccct ctttgcgcgc    360
gcgcgccaga atggcttcca gctttaacgg ttcccgtgcc agttgatagt catcaccggg    420
gcgggaggct aacatttcga ttaattcctt gcggtcttgt tccgggcaaa aggccagcca    480
ggtcaggccc gaggcggttt tcagaagcgg caaacgtcgc ccgaccattg cccggtgaaa    540
ggataagcgg ctgaaacggt gagtggtttc gcgtaccacc attgcatcaa catccagcgt    600
ggacacatct gtcggccata ccacttcgcg caacagatcg cccagcagtg gggccgccag    660
tgcagaaatc cactgttcgt cacgaaatcc ttcgcttaat tgccgcactt tgatggtcag    720
tcgaaaacta tcatcggagg ggctacgcg gacatatccc tcttcctgca gcgtctccag    780
cagtcgccgc acagtggtgc gatgcaggcc gctgagttcc gccagcagcc cgacgctggc    840
accgccatca agtttattta acatatttaa taacattaga ccgcgggtta agccgcgcac    900
ggttttgtat tccgtctgct cattgttctg catattaatt gacatttcta tagttaaaac    960
aacgtggtgc acctggtgca cattcgggca tgttttgatt gtagccgaaa acacccttcc   1020
tatactgagc gcacaataaa aaatcat                                       1047

<210> SEQ ID NO 163
<211> LENGTH: 1049
<212> TYPE: DNA
<213> ORGANISM: Artificial Sequence
<220> FEATURE:
```

<223> OTHER INFORMATION: gene editing homology arm pool_6_b0346_right

<400> SEQUENCE: 163

```
cgtgaggtac tgaaatggca atacaacacc ctgacatcca gcctgctgtt aaccatagcg      60
ttcaggtggc gatcgctggt gccggcccgg ttgggctgat gatggcgaac tatctcggcc     120
agatgggcat tgacgtgctg gtggtggaga aactcgataa gttgatcgac tacccgcgtg     180
cgattggtat tgatgacgag gcgctgcgca ccatgcagtc ggtcggcctg gtcgatgatg     240
ttctgccgca cactacgccg tggcacgcga tgcgttttct caccccgaaa ggccgctgtt     300
ttgctgatat tcagccaatg accgatgaat ttggctggcc gcgccgtaac gcctttattc     360
agccgcaggt cgatgcggtg atgctggaag gggtgtcgcg ttttccgaat gtgcgctgct     420
tgttttcccg cgagctggag gccttcagtc agcaagatga cgaagtgacc ttgcacctga     480
aaacggcaga agggcagcgg gaaatagtca agcccagtg gctggtagcc tgtgacggtg      540
gagcaagttt tgtccgtcgc actctgaatg tgccgtttga aggtaaaact gcgccaaatc     600
agtggattgt ggtagatatc gccaacgatc cgttaagtac gccgcatatc tatttgtgtt     660
gcgatccggt gcgcccgtat gtttctgccg cgctgcctca tgcggtacgt cgctttgaat     720
ttatggtgat gccgggagaa accgaagagc agctgcgtga gccgcaaaat atgcgcaagc     780
tgttaagcaa agtgctgcct aatccggaca atgttgaatt gattcgccag cgtgtctaca     840
cccacaacgc gcgactggcg caacgtttcc gtattgatcg cgtactgctg gcgggcgatg     900
ccgcgcacat catgccggta tggcaggggc agggctataa cagtggtatg cgcgacgcct     960
ttaacctcgc atggaaactg gcgttggtta tccaggggaa agcccgcgat gcgctgctcg    1020
atacctatca acaagaacgt cgcgatcac                                      1049
```

<210> SEQ ID NO 164
<211> LENGTH: 1050
<212> TYPE: DNA
<213> ORGANISM: Artificial Sequence
<220> FEATURE:
<223> OTHER INFORMATION: gene editing homology arm pool_6_b3966_left

<400> SEQUENCE: 164

```
ctcaacataa cctgtacccg cgtcgtagt ctgtttctgc cagtcgacac ccgcaccaat       60
actaccgtga ccaacgatga cattgtttgc ccactggacg gtgtattgct tcatctcatc    120
gagcgtcgcc gacgaatcat aacgaccata atggggatcg tagttgtaat ctttgctatg    180
gctatagctg gtaatgagtt gtgatttaat cagttcgccg ttatagcgca gcccggcgtc    240
ccaactttgg ctatagagtt tacgggtatc gagcaacggt gaaccgggag aataatacgc    300
gtcataattg gtacggttat catagccata gccgcgcaca aagccgctcc aggcatcagt    360
aaagttatgc tccagcgcgc cataaagcgt tttacttaaa aaaccatcgt tatctgtctg    420
cgcttgcgtt ccggtattac cataggcaac aacatcataa ccatgagtat gggcataatc    480
gcccaacagc gttacccgtg tcttatcccc cagttgttgc tgcgtagaga catcatagtt    540
ctgataacta ttgcttcccc accctgctga aatttccgtt ccgggttcat cgcgcgtcgt    600
gatgatattc accacccgc ctattgcatc ggaaccataa acagcggagc gcggcccacg    660
gatatattca acacgctgga caagcgcaat agggaactgg ctaaggtcgg cagaaccact    720
cacccccgcc agattcaggc gtacgccatc aattaacacc aacacatgac tggcatttgt    780
accgcgaata aaaatagatg agagctgacc tgaaccgccg ttttgggtga tatcgacgcc    840
cggaagacgg cgcagcacat cattgaccga ggtcgactgc cagcggtcga tatcctgacg    900
```

```
ggtcacaacg gtggttggtg caagcacagt gctgcgcggc tgttcaaaac ggttagcagt    960
aacgacgaga gtatccgggc tggtatcctg tgcccaagcg gaaaatgccg tgacggaaca   1020
cgccgtcagc agcgaagctt ttttaatcat                                    1050
```

<210> SEQ ID NO 165
<211> LENGTH: 1050
<212> TYPE: DNA
<213> ORGANISM: Artificial Sequence
<220> FEATURE:
<223> OTHER INFORMATION: gene editing homology arm pool_6_b3966_right

<400> SEQUENCE: 165

```
tgtaaagcat ccacaataga agaaggatgc cgcaggtttc atcaatatta cgcgatgatg     60
agaaccagat gcgacgttgg ccggcaggtc ttcgggcttg gaggggtatc taagatacta    120
agagatgatg acttcccacc gaatggcagt gtccgcataa cgcaatcatc gcacctttcc    180
ttaccgctgc cgcgtcagctc cagattcgca ctggattccc tattaactca caggaccggc   240
aagtggatgc tacaggttgt aacaagttac tgtccagacg tagctcacaa ataggaattc    300
atcaagatct ggacatctga tgagcaatcc ctacaatcgc cgcgtacttt aattttcag    360 gatacatcat gacccccgaa caccttccaa cagaacagta tgaagcgcag ttagccgaaa    420
aagtggtacg tttgcaaagt atgatggcac cgttttctga cctggttccg gaagtgtttc    480
gctcgccggt cagtcattac cggatgcgcg cggagttccg catctggcac gatggcgatg    540
acctgtatca catcattttc gatcaacaaa ccaaaagccg catccgcgtg gatagcttcc    600
ccgccgccag tgaacttatc aaccagttga tgacggcgat gattgcgggt gtgcgtaata    660
atcccgttct cgcccacaag ttgttccaga ttgattacct cactacactg agtaatcagg    720
cggtggtttc cctgctatac cataagaagc tggatgatga gtggcgtcag gaagcggagg    780
ccctgcgcga tgcactgcgc gcgcagaatc tgaatgtgca tctgattggt cgggcaacga    840
aaaccaaaat cgagctggat caggattaca tcgatgaacg tctgccggtc gcagggaaag    900
agatgatcta ccgtcaggta gaaaacagct ttacccagcc gaacgcggcg atgaatattc    960
agatgctgga atgggcgctg gacgtaacca aaggctcaaa aggcgattta ctggagctgt   1020
actgcggcaa cggtaacttt tcattagcgc                                    1050
```

<210> SEQ ID NO 166
<211> LENGTH: 1050
<212> TYPE: DNA
<213> ORGANISM: Artificial Sequence
<220> FEATURE:
<223> OTHER INFORMATION: gene editing homology arm pool_6_b0406_left

<400> SEQUENCE: 166

```
gtcgtttact gtcgctggac gggccgacgg gcgcgctgac gcacggtact ttcaccgatt     60
tacttgataa gctcaacccc ggcgatcttc tggtttttaa taatacccgc gtgatcccgg    120
cgcgcctgtt tgggcgtaaa gccagcggcg gcaagattga agtgctggtt gaacggatgc    180
tcgacgacaa acgcattctt gcgcatattc gcgcctcgaa agcgccaaaa cctggcgcag    240
aactgctgct gggcgatgac gaaagtatta acgcaacaat gaccgcgcgc acggcgcac    300 tgtttgaagt cgaatttaat gatgaacgct cggtgctgga tattctcaac agcatcggcc    360
atatgccgct gccgccgtat atcgaccgtc cggacgaaga cgctgaccgc gaactttatc    420
aaaccgttta tagcgaaaaa ccgggcgcgg ttgcagcccc gaccgcaggt ctgcatttg    480
```

```
acgagccttt gctggaaaaa ttgcgcgcca aaggcgtgga gatggcgttt gtgacgttgc      540
acgttggtgc gggcaccttc cagccggtgc gcgtcgacac cattgaagat cacatcatgc      600
actcggaata cgctgaagta ccgcaggatg tggtagacgc ggtactggcg gcgaaagcgc      660
gcggtaaccg ggtgattgcg gttggcacca cttcagtacg ttcgctggaa agcgcggctc      720
aggcagcgaa aaacgatctc attgaaccgt tcttcgacga tacccaaatc tttatctatc      780
cgggcttcca gtacaaagtg gtcgatgcgc tggtgacgaa cttccacttg ccagagtcga      840
cgctgattat gctggtttcg gcctttgccg gttatcaaca caccatgaac gcctataaag      900
cagcggtaga agagaaatat cgcttttttta gttacggtga tgcgatgttt atcacgtaca      960
atccgcaggc aattaatgag cgcgtcgggg agtaattccg cggcgctggt ttaaaacgtt     1020
ggactgtttt tctgacgtag tggagaaaaa                                     1050

<210> SEQ ID NO 167
<211> LENGTH: 1050
<212> TYPE: DNA
<213> ORGANISM: Artificial Sequence
<220> FEATURE:
<223> OTHER INFORMATION: gene editing homology arm pool_6_b0406_right

<400> SEQUENCE: 167
atgaaatttg aactggacac caccgacggt cgcgcacgcc gtggccgcct ggtctttgat       60
cgtggcgtag tggaaacgcc ttgttttatg cctgttggca cctacggcac cgtaaaaggg      120
atgacgccgg aagaagttga agccactggc gcgcaaatta cctcggcaa caccttccac      180 ctgtggctgc gcccgggcca ggaaatcatg aaactgcacg gcgatctgca cgattttatg      240
cagtggaagg ggccgatcct caccgactcc ggcggcttcc aggtcttcag ccttggcgat      300
attcgtaaaa tcaccgaaca gggcgtgcac ttccgtaacc cgatcaacgg cgatccgatt      360
ttcctcgatc ctgaaaaatc aatggagatt cagtacgatc ttggttcgga tatcgtcatg      420
atctttgatg agtgtacgcc gtatcctgct gactgggatt acgcaaaacg ctccatggag      480
atgtctctgc gttgggcgaa gcgtagccgt gagcgttttg acagtctcgg aaacaaaaat      540
gcgctgtttg gtatcatcca gggcagcgtt tacgaagatt tacgtgatat ttctgttaaa      600
ggtctggtag atatcggttt tgatggctac gctgtcggcg gtctggctgt gggtgagccg      660
aaagcagata tgcaccgcat tctggagcat gtatgcccgc aaattccggc agacaaaccg      720
cgttacctga tgggcgttgg taaaccagaa gacctggttg aaggcgtacg tcgtggtatc      780
gatatgtttg actgcgtaat gccaacccgc aacgcccgaa atggtcattt gttcgtgacc      840
gatggcgtgg tgaaaatccg caatgcgaag tataagagcg atactggccc actcgatcct      900
gagtgtgatt gctacacctg tcgcaattat tcacgcgctt acttgcatca tcttgaccgt      960
tgcaacgaaa tattaggcgc gcgactcaac accattcata accttcgtta ctaccagcgt     1020
ttgatggcgg gtttacgcaa ggctattgaa                                     1050

<210> SEQ ID NO 168
<211> LENGTH: 1040
<212> TYPE: DNA
<213> ORGANISM: Artificial Sequence
<220> FEATURE:
<223> OTHER INFORMATION: gene editing homology arm pool_6_b0652_left

<400> SEQUENCE: 168
ccgcctgcta ccggaatatc ggtgcgatta agcaaggtca gcatacgcag aacattgcgt       60
aaggtttttt ctggtgtctg gtttccggcg gaagacgtaa ttgctttgac atcaagctct      120
```

```
ggtgaggcga gggcgagaac tattgcgata gcgtcgtcat gacctgggtc gcaatctaac      180
agaattggca gtgccattgt tgctccttgt tgtgtgcttc tttgcgacaa gggtaacgcc      240
aggatgtaac agatacgagg ggcgaaacga taaagcgtga gatggcgcgc aattgggtat      300
gcgcgccaga gtgattaatg caggattttc gcgaggaagt cttttgcgcg gtccgatttc      360
ggatcatcga agaaagcgtc tttcggcgag tcttcgacaa ttttaccctc gtccataaag      420
atcacccgat tcgccacttt acgggcaaag cccatttcgt gggtcaccac catcatggtc      480
attccttcgt tcgccagttc caccatcacg tccagtactt cgttgatcat ctccggatcc      540
agcgccgatg tcggttcgtc aaacagcatc gcaataggat ccatacacaa cgcgcgagcg      600
attgccacac gctgctgctg accgccggaa agctgcgccg gaaacttatt ggcgtgagca      660
gaaagcccga cacgctccag cagtttcagg gcttttttcac gagccggcgc tttatcgcgt      720
ttaagcactt tcacctgcgc cagggtcagg ttttcgataa tcgacagatg agggaacagc      780
tcgaaatgct ggataccat cccgacgcgg aacgcagct ttgccagatc ggttttcttg       840
tcgttaacca cgataccatc gacggtgatt tcaccttgct gcaccggttc gaggccgttg      900
acggttttaa tcagcgttga tttgccgaa ccagacgggc cgcaaaccac caccacttcg       960
ccttttttca cttcggttga gcagtcggtc agcacctgaa agtgaccata ccatttgaa     1020 acatttttca gggtaatcat                                                1040
```

<210> SEQ ID NO 169
<211> LENGTH: 1041
<212> TYPE: DNA
<213> ORGANISM: Artificial Sequence
<220> FEATURE:
<223> OTHER INFORMATION: gene editing homology arm pool_6_b0652_right

<400> SEQUENCE: 169

```
tatgctgtcc ttcttttcaa gtagctgacc aacaacgacg cgctaagact aataacgaaa       60
taaacaaatc cggcaaacag gatcatctca acctgcgtac catcacgctc accaatggtt      120
gaggcggtac ggaagaaatc ggccagggat aacacataca ccagtgaggt atcctggaac      180
agtacgatgc cctgagtgag cagcagcggc accatcgcgc ggaacgcctg cggcagaata      240
atcagtttca tcgactgcca gtgagtcatt cccaacgcca gcgggcgct cgattgacca       300 cgagaaatac tttgaatacc agcacggata atctctgaat agtaggccgc ttcaaacatc      360
gaaaacgcca ccatcgccga aattaaacgg atatcatttt ttggcgataa tcccagcacg      420
ttttgcagaa aacccggcac gatcaggtaa aaccacagca aaaccataac taaaggaatc      480
gagcggaata cgttaacgta ggctttggca aaccacgcca cgggcgcaaa gctggataaa      540
cgcatcaccg ccagcatcgt gccccacaaa ataccaatca ctaccgccgt gacggtgatt      600
ttcagggtga tcaccagccc gtcgagcaga tatggcaggg aagggacaat ggaactccag      660
tcaaactcgt acattatttg cccccatgt tgccaggcag cgaactttta cgttcaacca      720
gcgtcatcac cagcatgata aaagcgttaa tcaacacata cgccagcgta atggcggtaa      780
acgactccca ggcatgggct gagtaatcga gcaatttacc cgcctgcgcc gccatatcca      840
ccagaccgat agtcgaggcg atggcggagt ttttcaccag gttcatcatc tctgaggtca      900 tggcgggac gataacgcga taagcattag gcagcagtac gtatcgataa gcctgcggta      960
gcgtcaggcc catcgccagc gcggcatttt tttgccctcg cggcagcgac tgaatcgcgg     1020
cgcgtacctg ttcgcaaaca c                                               1041
```

<210> SEQ ID NO 170
<211> LENGTH: 1050
<212> TYPE: DNA
<213> ORGANISM: Artificial Sequence
<220> FEATURE:
<223> OTHER INFORMATION: gene editing homology arm pool_6_b1493_left

<400> SEQUENCE: 170

```
ggcaacctgg taagaggcgt tctgtacttt ggtatagcct tcacgaccga ggcgcaggaa      60
ttcatagtac tgtgcaatta cctgacccgc cgggcgggag aagttgatgg caaaagtacc     120
aatttgacca cccaggtagt caacgttgaa caccagttcc tgcggcagcg cttcttcgtc     180
acgccagata acccagccgc agcccagcgg agccagaccg aatttatggc ctgaagcact     240
gatcgatttc acacgcggca ggcggaagtc ccagacgata tccggggcga cgaacggtgc     300
caggaagcca ccgctggcag cgtcgatgtg catgtcgatg tcgataccgg tatcggcctg     360
gaatttatcc agcgcatcgt gcagcggttg tgggaactca tagttaccag tgtaggtcac     420
gccgaaagtc ggcaccacgc cgatggtgtt ttcgtcacag gcttcaatca tgcgtttcgg     480
gtccataaac aactgaccgg ggcgcatagg gatctcacgc agctccacat cccagtagcg     540
ggcgaattta tgccagcaga tttgtaccgg accgcacacc aggtttggtt tatccgttgg     600
tttgcctgca gcttccatac gcttcgcgcca acgccatttc atcgccatcc cgccgagcat     660
acaggcctcg gaagaaccaa tggtgttggt gccaacggcc tgaccatttt tcggcgcagg     720
cgcatgccac agatcggcaa ccatatttac gcaacgcagg tcgatggctg cggattgcgg     780
atattcttct ttgtcgatcc agttttttgtt aatggataaa tccatcaatt tgtggacatt     840
ttcgtcgtcc caggtctggc agaaagtggc caggttctga cgagcgttgc catcaagata     900
taattcgtca ttgataatct ggaatgcgac atcgtcgcgc atttcgtgca gcggaaaacg     960
ttttgattct gcgatagtgg aaatagactt cgcaccaaaa cgtgaatcga gtagttccga    1020
ccttaaaatcc gttacttgct tcttatccat                                    1050
```

<210> SEQ ID NO 171
<211> LENGTH: 1046
<212> TYPE: DNA
<213> ORGANISM: Artificial Sequence
<220> FEATURE:
<223> OTHER INFORMATION: gene editing homology arm pool_6_b1493_right

<400> SEQUENCE: 171

```
acaaaatcct aatgttattt atcgtgagat attacgcgaa taatattttt tcattgaaaa      60
acaatacaat atgaaattct tgggtggtgg taaggtgttt tatgctgtta tttttatgcg     120
cattctgtgt ctcctgaatt atcacgtaaa aatcagacct taaatatca ctattagtac     180
ttgattatta ttttgaacgc atttataaaa ttattacata aaaatagcga atattgctaa     240
aatccccgcc aacgatgtgt tgacggggct gttattattt tggcaataat actccggtat     300
aagtatttac cggatgagaa agatattgtt taacggcagt gttaacattc tctaccgtca     360
tttgtttcaa caattgctcc tgctcagtcc atgctgcagg atcgtcatat tgaataagac     420
tatttacaat agtgttcgct aattgttgaa cgctacgctg ttggatatcg aggctgcgct     480
gaacgttttg ctggtattca ttcagttctt gctcactgat cccttttagcc agacgcttaa     540
ccatcacttc attcgctaac gttaacagtt catcatgtcg ttctggttga caagtaaaag     600
ccagcaaatg actgatatct ttggcctgag gatcaaccga gaggcgagaa gaaacgctgt     660
atgctccaga tgcctgttca cgaatattaa cacgtagatc ttttgccagt gcgacgttaa     720
```

```
aagcatcgag cgccatacgc gtcggcagat taacaggtgt ccgggaatca taacgcttcc    780
actgtgaaac ctgtgccaca ggttcatttt gttcttttac agtaaccgat gcgttgtccg    840
tcgcgcgagt taatggttta cctgcggcta atggcgaatc agagtgtttg attgatccta    900
agtaacgcgt aattaacgcc acgagtttgt cttctgcgac attaccgaca atgacaaacg    960
tgatatccgc tggagatgaa aacaattggc gatcggcagc cagcgcatct gcggcagtaa   1020
actgtgcaat ctgattttct tgcagt                                        1046

<210> SEQ ID NO 172
<211> LENGTH: 1050
<212> TYPE: DNA
<213> ORGANISM: Artificial Sequence
<220> FEATURE:
<223> OTHER INFORMATION: gene editing homology arm pool_6_b4159_left

<400> SEQUENCE: 172
ataacgtaac cgttgcacac gcaactgcgc catttcggta tcaagctgtt gtggtttcgg     60
catttccggc agccgtgcca cctgcgcccg cagcgcttcg ccgagcagat tggacgatcc    120
cagccattgc gactgttcac gcagcgtatt caacgcctgc cggacctgta acgtctggct    180
ggcagcctga cgctgttgcg aggcaacgag atccatccgc tgcgcctgtt gattcaaagc    240
cgccgatagt tcgcggttaa ttttgaattg cgcgacgata tctttcggca aatcggcgct    300
gttttctgcc agcaattcgg tactttccag cgcccgctcc gcctcaagct gacgttggct    360
gtttaattga ttacgcaagg cctgcaaata cgcatccagt tgctggctct cttttccgc    420 cagctctgag cgtaagcgcg ctaattcctg gcggttattg gcagacagct gcgccagctc    480
cagttcatca acgagcgcct taagacgtgc agagtcagac tgcaacgcga aattttgtgc    540
ctgattgagc ggagtattgc cggtaagcgt tcccaggcgg cgctcgatct catttaactg    600
acggcgggcg tcggtttgct gttgcggcag ttgattcagc gaatcggcaa tctcgcgggc    660
gcgctcctgc tcttgctggg cctgacggct tttatccagc aactggctgc tgacctggag    720
aatttcctga ttcagcgcgt cggtagacat tcccggcgac acgctgcgcg gctcgtcacg    780
catgttgttt aattgtgcgc gcagagtagc ggagagtttc ggataattat cgataacttg    840
ctgatattgt ttgatgcgct caagggaacc ttttcgttcc tcaagcgcat ttaaggcaga    900
ctggagcgcc tctacgactt ccggctgtgc gggtttcgcc gcttttgcct gctccagttc    960
ctgagtgatt tgtttgctat cggggccgt cgcggcgtac gcccccaac tgaggcacca   1020 ggccatcaga aaagtgataa tcaggcgcac                                   1050

<210> SEQ ID NO 173
<211> LENGTH: 1050
<212> TYPE: DNA
<213> ORGANISM: Artificial Sequence
<220> FEATURE:
<223> OTHER INFORMATION: gene editing homology arm pool_6_b4159_right

<400> SEQUENCE: 173
gtcagcgttt cctttgatgg attagacctg gtcttttttg tcgtcaacca atgggctggc     60
gtcgtgttct gcttcgatct cttcagcagg aagcggggca ggttcagcgt ctggcgtaac    120
aaaggtttcg gtagatactg ccagcggctg gccaattttc gtgacagaca ggctttccag    180
ttgctcaacc agattcactt tacccggtgc aaacaggttg ataacggtgg aaccgagttt    240
aaagcgaccc atttcctggc ctttcagcag tgccacagaa ccgtcgtttt ccccggcagg    300
```

```
ccaggtccag cgcttgatga taccttcgcg cggcggcgta atggtgcccg cccagaccgt    360
ctcaatgctg ccaacaatcg tcgctccgac cagaatctgc gccattgggc caaattcggt    420
atcgaaaagg caaatcacgc gttcgttacg ggcaaacaga ttcggcacgt tctgagccgt    480
gagatggtta acgagaaga gatcgcccgg cacgtagatc atctcacgca gaataccgtt    540
gcacggcatg tgtacgcggt ggtagtcacg cggggagagg taagtggtca caaacgtacc    600
gttgcggaac aggtccgcca tcagatagtt gcctgccagc agggcttcga ggctgtagtt    660
gtggcctttg gcttgcagga ttttatcttc ttcgatttta cccaactggc tgataacgcc    720
atcggcaggc atgaccagta cattcggatc ggtatcgatt gggcgtactt cgtcacgcag    780
cggacggaca aagaattcgt taaaggtgcg gtagctggcg gtgtccggct tttgcgcctc    840
tttcatgtcg accttgtagt atttaacgaa cagatcgata accagttttg tcagccatcc    900
tgcccgcttg cttgcgcccc aacccgccag gcgagtaagc catagtttcg gcagaatgta    960
ctgtagcgaa agtttaaatg aatttaacaa ggtagcctcc aggccattgt tttgtcgttc   1020
ctgatccggc tacatgccg gatcctgaaa                                     1050

<210> SEQ ID NO 174
<211> LENGTH: 1050
<212> TYPE: DNA
<213> ORGANISM: Artificial Sequence
<220> FEATURE:
<223> OTHER INFORMATION: gene editing homology arm pool_6_b3795_left

<400> SEQUENCE: 174
gttcaggcat gagccaatta gcagaatagc aatagatact gccacacccg caaccggtac     60
gccgtgacgg gaaactttcg ccattgccgc cggtaactga cggttttttcg ccagtgcgta    120 gagcatacgt ccgcaactgt acatgccgct gttacagcca gagagcgcag ccgtcagcac    180
cacaaagttg ataatgcccg ccgctgcggt aataccgatt ttggcaaaag tcagtacgaa    240
cgggctgccg ttgctgccta tttcattcca cgggaagatg gtgacgataa cgaaaatcgc    300
gcctacgtag aaaatcagga tccgccacag caccttgcct acggcactgc gcagcgtcac    360
ctgcggattc ttcgcttcac cggcagtaat gccaatcagc tccacgccct ggtaggacgc    420
caccacaata cacagagcgg tcaggaaccc tttccagcca cccgcaaaga aaccgccatg    480
ctctgtgaga ttgctaaaac caatcgactg cccgccattg ccaaagccaa agaaaatcac    540
gcccaggcca atgacaatca tcacgataat cgtggtgact ttgatcatcg cgaaccagaa    600
ctcgatttcg ccgtacaacc gcaccgccgc cagattcgcc aacgccacca gcgccactgc    660
gatcaatgcg ggtatccact cgccatctc cgggaaccag aactggacat aaacgccaat    720
ggcggtgatt tcagagatcc ccaccgccat ccacataaac cagtaagacc aggcggtgag    780
atagccaaag aacgggctca tataacgatg cgcataaacg gcgaacgaac cggtaaccgg    840
ttcgaggaac aacatttcgc ccattgaacg catgatgaaa aagacgaaca gcccggcgat    900
gatataggcc aacaatacgg atggcccggc ccatttcagg gtactggcgg ccccataaa    960 caggccgacg ccaatggtgc ccccagggc gatgagttcg atatgtcgag cttccagccc   1020
acgctgtagc tctggtttgt tatctgccat                                    1050

<210> SEQ ID NO 175
<211> LENGTH: 1050
<212> TYPE: DNA
<213> ORGANISM: Artificial Sequence
<220> FEATURE:
<223> OTHER INFORMATION: gene editing homology arm pool_6_b3795_right
```

<400> SEQUENCE: 175

```
aaatcctcgt gttgtgtttg catgctttcc ggtgttaccg gttatcgtta tgggtacatc      60
gagtgttgca aatgttttcg taattcagga gaaatggcaa ataaagcatt aaaaatttga     120
atgctttgtg taataaaaaa gcagacaggc gacggagtga ccactccgtc gctttacaaa     180
gagaggaaaa tcataggttg ccggtgtagt gccagcgtaa ataacgcagc aaacgaagct     240
gacgcttaat gcggctcggc tgcgaaagca ggcggtagag ccactccagc cccagcgttt     300
gccagatttt cggtgcgcgt tttacgtgac cggtgaaaac atcgtaagtc cgccaacgc      360
ccatatacag cgcatctgga tgtaccagac ggcagtcgcg catgatgatc tcctgctttg     420
gcgatcccat cgcaacggtg acgatttgcg caccgctggc atgaatgcgt tcaaacagcg     480
cctgacgctg ctcgggttta aaataaccat cctgactgcc aacgatattc acattccact     540
ggttgcgcag tttagcttca gtttgcgcca gcacttcagg tttaccgccc acaagaaata     600
ccggcgtccc ttctttgcct gcgcgcgcca tcagctcttc ccagagatcg gcaccggcaa     660
cgcgggaaac ctgcgcctgc gggtactttt tacgtactga acgtacaacg ctgatgccat     720
ccgcatattt aaattcggca gcgttaatta actccctgac ctcggcgtta tcttcaatag     780
tcagcatttt ttcagcatta atggcaacca gcgttccctg cttaagctgc ccgtcagcaa     840
acagataatc gagggcgtgc tgcatatcac gccaaccaat caactgtaag ccacgcagcg     900
tataggttgg tgccgtggtg ttgttattca ttgttatcct tcaacctgcg tccggagcga     960
tgattttgta cgtttatgaa tgagtccggc gctttcaaaa agccagtaca acagttttgc    1020
gatcatcaga catgcgccga agaccacgat                                     1050
```

<210> SEQ ID NO 176
<211> LENGTH: 1050
<212> TYPE: DNA
<213> ORGANISM: Artificial Sequence
<220> FEATURE:
<223> OTHER INFORMATION: gene editing homology arm pool_6_b4246_left

<400> SEQUENCE: 176

```
aaccagtgcc agtaacgcct ggcgagcgaa atcccgttg cctgcctgct ggaagtacca      60
ggcgtgtggc gttttatcaa catccgtcgc aatctcatca acacgcggca gcggatgcag     120
cactttcata ttggctttgg cgttgtggag atcgctggcg cgaagaacaa actgcgcttt     180
cacgttggcg tactcggacg ggtccagacg ctcttttttgc acgcgggtca tgtacaggat     240
gtctacttcc gccatcactt cttcaataga gctgtgcaga ctccatgcga tcccttttttc     300
atcgagcata tccagaatgt attgcggcat tgccagcgcg tccggcgcga tgaagtaaaa     360
acggttgccc tcgaacttcg ctaacgcctg agtcagggag tgaacggtgc ggccatattt     420
caggtcacca accattgcga cgtggagatt gtccagacgc ccctgggttt cctgaatagt     480
gaataagtcc agcaaggttt gcgtcggatg ttggttggag ccatcaccgg cattcagtac     540
cggtacattg ccggaaaact cggtggccag gcgcgccgca ccttcctgcg gatgacgcat     600
cactatcgca tcgacgtaag tgctgataac cgaaatggta tcggccagcg tttcgccctt     660
tttacccagt gatgtattgg cgctgtcgga gaagcccacc acgctggccc ccaggcggtg     720
catagatgtt tcgaaagaga ggcgggtacg ggtagaggct tcgaagaaac agctggcaat     780
gactttgtgc ttcaacagct ctggttgcgg gtttgctttc agtttcgccg ctgtcgccag     840
caccagatta aggtcatcgc gactaaggtc gtttatggaa atgatatgtt tctgatatag     900
```

```
cggattagcc atcttttatc tcctgacgcc tgggcaaaaa aaagcccctc gattgagggg      960
ctgggaatgg gtgatcaacg ggaagaaaaa cggcaggcca gcgtcttttt tcagacgcgg     1020
taagacaaaa tgtcgaacac actgaaccat                                      1050

<210> SEQ ID NO 177
<211> LENGTH: 1050
<212> TYPE: DNA
<213> ORGANISM: Artificial Sequence
<220> FEATURE:
<223> OTHER INFORMATION: gene editing homology arm pool_6_b4246_right

<400> SEQUENCE: 177
actattgctt actgctcagg gatgcgcgct atcactttaa tttcaaaatc aaagcctgcc       60
agccatgtaa cacccaccgc cgtccagttt ggataaggtg gggcgctaaa tatttcattt      120
ttcaccgtca tgatgtcttc aaattggttt tctggatcgg tatggaagct cgtaacatca      180
atgatatcgt caaaagtgca tcccgcagct gccagggtcg catgcaaatt atcaaatgcc      240
agtctgactt gttgctgaaa tcgggttct ggtgttccgt cctctcgact tcctacttgc       300
ccggaaacaa acagcaaatc gccggaacga atagccgcag aataacgatg ctcagcatat      360
agtgaatgtc ggccagcagg gaaaacagcg gttctttcta ccatttggtt atcctcaaga     420
tttacgacat gaacagaaga tttctcttta ccgggagccg cttttagcgg acgacgtgag      480
taaacaaaac ccagacatca tggataatgg ctgggcttaa ttgagcgtag tcggttatgc      540
gccaaacgcg ccatcaatgg tatgcatcgc gccggtaaca aaactggctt ctggccctgc      600
taaccatgcg accataccag cgacctcttc cggttgccca tgtctttga tagccatcaa       660 actatgcaac atatcgcgca ttggcccgtt ggcgggatta gcgtcggtat caattggccc      720
tggctggacg acgttaatgg tgatcccacg cggtccaaaa tcacgggcca gcccgcgcgc      780
catgccttgc agggcagatt tgctggcggc ataagcagcc atgcctgcaa caggcatacg      840
atcgccattc acggagccga tgattaagat gcgcccgcct tcgggcatct gccgggcggc      900
ttcaacagag gcatgataag gagcatgaat attgattttg aaaaggcgat caatatcgtc      960
ggcatttaat tccagggcct cgccaaagac gccaatacct gcatttacca ccaggatatc     1020
caatgcgccg ctcttacgaa cgacatcaat                                      1050

<210> SEQ ID NO 178
<211> LENGTH: 1050
<212> TYPE: DNA
<213> ORGANISM: Artificial Sequence
<220> FEATURE:
<223> OTHER INFORMATION: gene editing homology arm pool_6_b4440_left

<400> SEQUENCE: 178
atggtggatg ctgcgcacct ttggtgtaga gaaagtgtcg attctggggg gtggacttgc       60
aggctggcag cgcgatgatc tgctgttaga agaaggtgca gtagagctgc cggaaggaga      120
gtttaacgcc gcgtttaatc ctgaagccgt ggtgaaagta accgatgtat tattggcaag     180
ccatgaaaat acggcgcaaa ttattgatgc ccgcccggct gcacgtttta acgcagaagt      240
tgatgaacct cgcccaggtt tacgtcgcgg acatattccc ggagcactga atgttccgtg      300
gacggaactg gtgcgcgaag gcgaactaaa aacgaccgat gaactggatg cgatattttt      360
tggtcgcggc gtcagctacg acaaaccaat tatcgtcagc tgcggctctg gtgtaacggc      420
agccgtggtt ttgttagcac tcgcgacgct ggatgtgcca aacgtgaaac tgtacgacgg      480
cgcatggagt gaatgggcg cgcgggcaga tttaccggtt gagccagtga ataagtatt       540
```

```
ttacaggcaa taaaaaaccg ccgaatttgg cggttttta ttgctagtct ggttcgcggc    600
ctttccagca ggttgacttg tgttacatga gcaacgcagg tgcttcacag caaaacaata    660
ctcaccagta actctctttt tgtcaagcaa aagagagtaa ttattgttta tttagcgtat    720
tatcgacacc ggccctttcc gccgtgttcg gtaataaaat aacctggctt attagtccga    780
attcagacaa atataaataa atcctgctca aaattaaaaa ttctaaccgg taaaagatat    840
tacttaaaca tgtaaattca ctttccttta aaaaacaaaa aaccgccaaa atcaggcggt    900
tttttgttgc tggtccggtt cgcggccttt ccagcaggtt gtattaccgt agtaatgcaa    960
gcgcgtctca gcggagacaa tactcgccag taactctctt tttgtcaagc aaaagagagt   1020
tattattgtt ctgttagtgt attatccact                                    1050

<210> SEQ ID NO 179
<211> LENGTH: 1050
<212> TYPE: DNA
<213> ORGANISM: Artificial Sequence
<220> FEATURE:
<223> OTHER INFORMATION: gene editing homology arm pool_6_b4440_right

<400> SEQUENCE: 179
gcggcccttt ccgccgtctc gcaaacgggc gctggcttta ggaaaggatg ttccgtggcc     60
gtaaatgcag gtgtttcaca gcgcttgcta tcgcggcaat atcgccagtg gtgctgtcgt    120
gatgcggtct tcgcatggac cgcacaatga agatacggtg cttttgtatc gtacttattg    180
tttctggtgc gctgttaacc gaggtaaata ataaccggag tctctccggc gacaatttac    240
tggtggttaa caaccttcag agcagcaagt aagcccgaat gccgcccttt gggcggcata    300
ttttagatta tccgattctg tttaaagtca cgcaaaaaac caccccagcg acgttcatag    360
aatggcgcaa tatgttcggt aataaagtgg ctaattcctt tttccccttt tttcacctga    420
caaatatcga ttggttcatc gccaggtaat gtatcggtcg ctacacttcc cgtcgcctga    480
ataatttctt cgatatcacc atcggcttca atgccaataa gtaaattagg ctgtgcctct    540
tcgttctctt taattgaaca aataaaagca cgcttcaccg gcttaatggt tttaaataag    600
gtggtgagtg aatcaatcat ttgtgctggc ggctctgcga cttccgataa tatcagcgat    660
tcaccgcctt ccaggatttc ctggctgctc agcggatttc cctcttcacc aatcaacaaa    720
ctgatttcac gcggcataaa ttctttaccg gttggcagtt tggcattaag gaagagcgtt    780
tcgccaagtg tcatctcaaa cagcgtgcga acgggcatta cgacaaatgc ctgttcgtct    840
tcaaccgcct gttgaagtgc ttctaacgag gtgaaaaaag gaatgacgct ggtgccgtct    900 tcttttccc agtgctgtaa atcaagcgcg ctatcttcaa ccacagcctc gccctgcgcc    960
gccgtaccag gcacccagac ggtggattcc agtagagtac ggaaaaaggc cgggcggtgc   1020
gccggttcag ttgctgcttt ttccagcagg                                    1050
```